US011819531B2

(12) United States Patent
Charles et al.

(10) Patent No.: US 11,819,531 B2
(45) Date of Patent: *Nov. 21, 2023

(54) MULTIFUNCTIONAL ZWITTERIONIC POLYMER CONJUGATES

(71) Applicant: Kodiak Sciences Inc., Palo Alto, CA (US)

(72) Inventors: Stephen A. Charles, Ravenna, OH (US); D. Victor Perlroth, Palo Alto, CA (US); Lane A. Clizbe, Redwood City, CA (US); Didier G. Benoit, San Jose, CA (US); Wayne To, San Mateo, CA (US)

(73) Assignee: Kodiak Sciences Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/099,234

(22) Filed: Apr. 14, 2016

(65) Prior Publication Data

US 2016/0287715 A1    Oct. 6, 2016
US 2023/0277616 A9    Sep. 7, 2023

Related U.S. Application Data

(63) Continuation of application No. 13/516,173, filed as application No. PCT/US2010/061358 on Dec. 20, 2010, now abandoned, application No. 15/099,234 is a continuation-in-part of application No. 14/265,174, filed on Apr. 29, 2014, now abandoned, which is a continuation of application No. 13/515,913, filed as application No. PCT/US2010/034252 on May 10, 2010, now Pat. No. 8,765,432.

(60) Provisional application No. 61/288,127, filed on Dec. 18, 2009.

(51) Int. Cl.
| | |
|---|---|
| A61K 49/00 | (2006.01) |
| A61K 47/58 | (2017.01) |
| A61K 47/54 | (2017.01) |
| A61K 38/00 | (2006.01) |
| A61K 47/68 | (2017.01) |
| C12N 9/96 | (2006.01) |
| A61K 38/18 | (2006.01) |
| A61K 38/46 | (2006.01) |
| A61K 39/395 | (2006.01) |
| C07K 16/00 | (2006.01) |
| C08F 8/32 | (2006.01) |
| C08F 230/02 | (2006.01) |
| C12N 9/16 | (2006.01) |
| C08F 230/08 | (2006.01) |

(52) U.S. Cl.
CPC .......... *A61K 38/00* (2013.01); *A61K 38/1816* (2013.01); *A61K 38/465* (2013.01); *A61K 39/395* (2013.01); *A61K 47/544* (2017.08); *A61K 47/58* (2017.08); *A61K 47/6805* (2017.08); *A61K 47/6811* (2017.08); *A61K 49/0002* (2013.01); *A61K 49/0043* (2013.01); *A61K 49/0054* (2013.01); *C07K 16/00* (2013.01); *C08F 8/32* (2013.01); *C08F 230/02* (2013.01); *C12N 9/16* (2013.01); *C12N 9/96* (2013.01); *C12Y 301/03001* (2013.01); *C07K 2317/21* (2013.01); *C07K 2317/55* (2013.01); *C08F 230/085* (2020.02); *C08F 2438/01* (2013.01)

(58) Field of Classification Search
None
See application file for complete search history.

(56) References Cited

U.S. PATENT DOCUMENTS

| | | | |
|---|---|---|---|
| 4,634,664 A | 1/1987 | Oestberg | |
| 4,634,666 A | 1/1987 | Engleman et al. | |
| 4,757,006 A | 7/1988 | Toole, Jr. et al. | |
| 4,868,112 A | 9/1989 | Toole, Jr. | |
| 4,892,538 A | 1/1990 | Aebischer et al. | |
| 5,162,218 A | 11/1992 | Schultz | |
| 5,198,349 A | 3/1993 | Kaufman | |
| 5,225,539 A | 7/1993 | Winter | |
| 5,250,421 A | 10/1993 | Kaufman et al. | |
| 5,283,187 A | 2/1994 | Aebischer et al. | |
| 5,336,603 A | 8/1994 | Capon et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |

(Continued)

FOREIGN PATENT DOCUMENTS

| | | |
|---|---|---|
| AU | 2015207898 | 8/2015 |
| AU | 2017201930 | 4/2017 |

(Continued)

OTHER PUBLICATIONS

IUPAC Gold Book, Random copolymer, available at https://goldbook.iupac.org/html/R/R05126.html, accessed Nov. 21, 2017.*

(Continued)

*Primary Examiner* — H. Sarah Park

(74) *Attorney, Agent, or Firm* — Knobbe, Martens, Olson & Bear, LLP

(57) ABSTRACT

The present invention provides random copolymers containing zwitterions and one or more functional agents, and methods of preparing such random copolymers.

21 Claims, 1 Drawing Sheet

Specification includes a Sequence Listing.

(56) References Cited

U.S. PATENT DOCUMENTS

| | | |
|---|---|---|
| 5,661,016 A | 8/1997 | Lonberg et al. |
| 5,663,425 A | 9/1997 | Detroit et al. |
| 5,681,746 A | 10/1997 | Bodner et al. |
| 5,733,743 A | 3/1998 | Johnson et al. |
| 5,733,873 A | 3/1998 | Osterberg et al. |
| 5,741,923 A | 4/1998 | Driver et al. |
| 5,763,548 A | 6/1998 | Matyjaszewski et al. |
| 5,770,429 A | 6/1998 | Lonberg et al. |
| 5,789,487 A | 8/1998 | Matyjaszewski et al. |
| 5,789,650 A | 8/1998 | Lonberg et al. |
| 5,807,937 A | 9/1998 | Matyjaszewski et al. |
| 5,814,318 A | 9/1998 | Lonberg et al. |
| 5,834,597 A | 11/1998 | Tso et al. |
| 5,837,242 A | 11/1998 | Holliger et al. |
| 5,858,657 A | 1/1999 | Winter et al. |
| 5,859,205 A | 1/1999 | Adair et al. |
| 5,871,907 A | 2/1999 | Winter et al. |
| 5,872,218 A | 2/1999 | Wolf et al. |
| 5,874,299 A | 2/1999 | Lonberg et al. |
| 5,877,218 A | 3/1999 | Herzig et al. |
| 5,877,397 A | 3/1999 | Lonberg et al. |
| 5,882,644 A | 3/1999 | Chang et al. |
| 5,919,766 A | 7/1999 | Osterberg et al. |
| 5,945,491 A | 8/1999 | Matyjaszewski et al. |
| 5,981,786 A | 11/1999 | Kitano et al. |
| 6,111,022 A | 8/2000 | Matyjaszewski et al. |
| 6,121,371 A | 9/2000 | Matyjaszewski et al. |
| 6,124,411 A | 9/2000 | Matyjaszewski et al. |
| 6,156,884 A | 12/2000 | Ahlem et al. |
| 6,162,882 A | 12/2000 | Matyjaszewski et al. |
| 6,348,554 B1 | 2/2002 | Roos et al. |
| 6,407,187 B1 | 6/2002 | Matyjaszewski et al. |
| 6,407,213 B1 | 6/2002 | Carter et al. |
| 6,512,060 B1 | 1/2003 | Matyjaszewski et al. |
| 6,538,091 B1 | 3/2003 | Matyjaszewski et al. |
| 6,541,580 B1 | 4/2003 | Matyjaszewski et al. |
| 6,555,593 B1 | 4/2003 | Hoyle et al. |
| 6,583,272 B1 | 6/2003 | Ballon |
| 6,624,262 B2 | 9/2003 | Matyjaszewski et al. |
| 6,627,314 B2 | 9/2003 | Matyjaszewski et al. |
| 6,657,043 B1 | 12/2003 | Guerret et al. |
| 6,703,528 B2 | 3/2004 | Hagiya et al. |
| 6,730,822 B1 | 5/2004 | Ivarie et al. |
| 6,759,491 B2 | 7/2004 | Matyjaszewski et al. |
| 6,781,030 B1 | 8/2004 | Baguisi et al. |
| 6,790,919 B2 | 9/2004 | Matyjaszewski et al. |
| 6,852,816 B2 * | 2/2005 | Lewis ............... C08F 4/40 |
| | | 524/710 |
| 6,881,557 B2 | 4/2005 | Foote |
| 6,887,962 B2 | 5/2005 | Matyjaszewski et al. |
| 6,964,859 B2 | 11/2005 | Rajbhandary et al. |
| 6,979,556 B2 | 12/2005 | Simmons et al. |
| 7,019,082 B2 | 3/2006 | Matyjaszewski et al. |
| 7,049,373 B2 | 5/2006 | Matyjaszewski et al. |
| 7,056,455 B2 | 6/2006 | Matyjaszewski et al. |
| 7,060,271 B2 | 6/2006 | Ramakrishnan et al. |
| 7,064,166 B2 | 6/2006 | Matyjaszewski et al. |
| 7,125,938 B2 | 10/2006 | Matyjaszewski et al. |
| 7,157,530 B2 | 1/2007 | Matyjaszewski et al. |
| 7,169,901 B2 | 1/2007 | Baca et al. |
| 7,200,990 B2 | 11/2007 | Lewis et al. |
| 7,300,990 B2 | 11/2007 | Lewis et al. |
| 7,306,799 B2 | 12/2007 | Wiegand et al. |
| 7,348,424 B2 | 3/2008 | Miyazawa et al. |
| 7,374,757 B2 | 5/2008 | Papadopoulos et al. |
| 7,374,762 B2 | 5/2008 | Amphlett et al. |
| 7,375,193 B2 | 5/2008 | Baca et al. |
| 7,375,234 B2 | 5/2008 | Sharpless et al. |
| 7,491,390 B2 | 2/2009 | Law et al. |
| 7,494,649 B2 | 2/2009 | Amphlett et al. |
| 7,501,120 B2 | 3/2009 | Amphlett et al. |
| 7,514,080 B2 | 4/2009 | Amphlett et al. |
| 7,521,541 B2 | 4/2009 | Eigenbrot et al. |
| 7,569,655 B2 | 8/2009 | Pacetti et al. |
| 7,632,921 B2 | 12/2009 | Pan et al. |
| 7,662,387 B2 | 2/2010 | Law et al. |
| 7,695,716 B2 | 4/2010 | Drachman et al. |
| 7,740,850 B2 | 6/2010 | Zhu et al. |
| 7,745,394 B2 | 6/2010 | Doronina et al. |
| 7,754,208 B2 | 7/2010 | Ledbetter et al. |
| 7,754,681 B2 | 7/2010 | Feng |
| 7,754,855 B1 | 7/2010 | Cox, III et al. |
| 7,759,472 B2 | 7/2010 | Shima et al. |
| 7,855,178 B2 | 12/2010 | Alitalo et al. |
| 7,893,173 B2 | 2/2011 | Matyjaszewski et al. |
| 8,003,097 B2 | 8/2011 | Schroeter et al. |
| 8,008,453 B2 | 8/2011 | Gegg et al. |
| 8,187,597 B2 | 5/2012 | Shima et al. |
| 8,206,707 B2 | 6/2012 | Shima et al. |
| 8,273,353 B2 | 9/2012 | Davis-Smyth et al. |
| 8,455,622 B2 | 6/2013 | McDonagh et al. |
| 8,486,397 B2 | 7/2013 | Bagri et al. |
| 8,492,527 B2 | 7/2013 | Fuh et al. |
| 8,512,699 B2 | 8/2013 | Fuh et al. |
| 8,765,432 B2 | 7/2014 | Charles |
| 8,815,236 B2 | 8/2014 | Burke et al. |
| 8,846,021 B2 | 9/2014 | Charles |
| 9,079,953 B2 | 7/2015 | Harding et al. |
| 9,416,210 B2 | 8/2016 | Emrick et al. |
| 9,840,553 B2 | 12/2017 | Perlroth et al. |
| 10,363,290 B2 | 7/2019 | Perlroth et al. |
| 10,702,608 B2 | 7/2020 | Charles et al. |
| 11,066,465 B2 | 7/2021 | Perlroth et al. |
| 11,071,771 B2 | 7/2021 | Perlroth et al. |
| 11,155,610 B2 | 10/2021 | Perlroth et al. |
| 11,584,790 B2 | 2/2023 | Perlroth et al. |
| 11,590,235 B2 | 2/2023 | Charles et al. |
| 2003/0143596 A1 | 7/2003 | Bentley et al. |
| 2003/0204022 A1 | 10/2003 | Kennedy et al. |
| 2004/0063881 A1 | 4/2004 | Lewis et al. |
| 2004/0253596 A1 | 12/2004 | Pawlak et al. |
| 2005/0009988 A1 * | 1/2005 | Harris ............... C08G 65/33337 |
| | | 525/56 |
| 2005/0112088 A1 | 5/2005 | Zhao et al. |
| 2005/0118651 A1 | 6/2005 | Basi et al. |
| 2005/0123501 A1 | 6/2005 | Lews |
| 2005/0136049 A1 | 6/2005 | Ledbetter et al. |
| 2005/0159556 A1 | 7/2005 | Lewis et al. |
| 2005/0164301 A1 | 7/2005 | Kolkman et al. |
| 2005/0180945 A1 | 8/2005 | Chaikof et al. |
| 2005/0220880 A1 * | 10/2005 | Lewis ............... A61K 9/1075 |
| | | 424/486 |
| 2005/0276796 A1 | 12/2005 | Tomatsu et al. |
| 2006/0069203 A1 | 3/2006 | Lewis et al. |
| 2006/0135714 A1 | 6/2006 | Lewis et al. |
| 2006/0165804 A1 | 7/2006 | Lewis et al. |
| 2006/0167230 A1 | 7/2006 | Koga et al. |
| 2006/0217285 A1 | 9/2006 | Destarac |
| 2006/0234347 A1 | 10/2006 | Harding et al. |
| 2006/0234437 A1 | 10/2006 | Harding et al. |
| 2007/0041967 A1 | 2/2007 | Jung et al. |
| 2007/0111279 A1 | 5/2007 | Rosenberg |
| 2007/0141104 A1 | 6/2007 | Hauenstein |
| 2008/0008736 A1 * | 1/2008 | Glauser ............... C08F 220/26 |
| | | 424/423 |
| 2008/0124450 A1 | 5/2008 | Pacetti |
| 2008/0147175 A1 | 6/2008 | Pacetti et al. |
| 2008/0147178 A1 | 6/2008 | Pacetti et al. |
| 2008/0152661 A1 | 6/2008 | Rozema et al. |
| 2008/0199464 A1 | 8/2008 | Plowman et al. |
| 2008/0214439 A1 | 9/2008 | Grabstein et al. |
| 2008/0241102 A1 | 10/2008 | Hersel et al. |
| 2009/0060906 A1 | 3/2009 | Barry et al. |
| 2009/0061533 A1 | 3/2009 | Minami |
| 2009/0117103 A1 | 7/2009 | Devalaraja et al. |
| 2009/0324679 A1 * | 12/2009 | Ippoliti ............... A61L 31/06 |
| | | 424/423 |
| 2010/0111942 A1 | 5/2010 | Shima et al. |
| 2010/0158850 A1 | 6/2010 | Baker, Jr. et al. |
| 2010/0166700 A1 | 7/2010 | Charles |
| 2010/0322931 A1 | 12/2010 | Harding et al. |
| 2011/0033378 A1 | 2/2011 | Dimasi et al. |
| 2011/0069176 A1 | 3/2011 | Lin et al. |
| 2011/0165648 A1 | 7/2011 | Campange et al. |

(56) References Cited

U.S. PATENT DOCUMENTS

| | | |
|---|---|---|
| 2011/0213105 A1 | 9/2011 | Jakubowski et al. |
| 2012/0100136 A1 | 4/2012 | Patel et al. |
| 2012/0213705 A1 | 8/2012 | Dimasi et al. |
| 2012/0282211 A1 | 11/2012 | Washburn et al. |
| 2012/0322738 A1 | 12/2012 | Behrens et al. |
| 2013/0040889 A1 | 2/2013 | Bolt et al. |
| 2013/0045522 A1 | 2/2013 | Charles et al. |
| 2013/0071394 A1 | 3/2013 | Troyer et al. |
| 2013/0259881 A1 | 10/2013 | Fandl et al. |
| 2013/0334517 A1 | 12/2013 | Hong et al. |
| 2013/0337534 A1 | 12/2013 | Charles |
| 2014/0024776 A1 | 1/2014 | Charles et al. |
| 2014/0170140 A1 | 2/2014 | Bennett et al. |
| 2014/0242082 A1 | 8/2014 | Shima et al. |
| 2015/0050714 A1 | 2/2015 | Charles |
| 2015/0071861 A1 | 3/2015 | Kondo et al. |
| 2015/0093390 A1 | 4/2015 | Bansal |
| 2015/0158952 A1 | 6/2015 | Mao et al. |
| 2015/0376271 A1 | 12/2015 | Perlroth et al. |
| 2016/0008485 A1 | 1/2016 | Marquette et al. |
| 2016/0184445 A1 | 6/2016 | Perlroth et al. |
| 2016/0199501 A1 | 7/2016 | Charles et al. |
| 2016/0346400 A1 | 12/2016 | Emrick et al. |
| 2016/0369005 A1 | 12/2016 | Lippincott et al. |
| 2017/0143841 A1 | 5/2017 | Charles et al. |
| 2017/0190766 A1 | 7/2017 | Perlroth et al. |
| 2018/0244762 A1 | 8/2018 | Perlroth et al. |
| 2018/0334496 A1 | 11/2018 | Perlroth et al. |
| 2019/0270806 A1 | 9/2019 | Jacobson et al. |
| 2020/0000930 A1 | 1/2020 | Charles |
| 2020/0171179 A1 | 6/2020 | Charles et al. |
| 2020/0261590 A1 | 8/2020 | Charles et al. |
| 2020/0262905 A1 | 8/2020 | Perlroth et al. |
| 2021/0107999 A1 | 4/2021 | Ehrlich et al. |
| 2021/0324063 A1 | 10/2021 | Perlroth et al. |
| 2021/0402015 A1 | 12/2021 | Charles et al. |
| 2022/0096643 A1 | 3/2022 | Charles |
| 2023/0173081 A1 | 6/2023 | Charles et al. |

FOREIGN PATENT DOCUMENTS

| | | | |
|---|---|---|---|
| CN | 1486995 | 4/2004 | |
| CN | 101053681 | 10/2007 | |
| CN | 101389690 | 3/2009 | |
| CN | 101575402 | 11/2009 | |
| CN | 103193819 | 7/2013 | |
| CN | 103421039 | 12/2013 | |
| CN | 103492489 | 1/2014 | |
| CN | 106432557 | 2/2017 | |
| CN | 107428824 | 12/2017 | |
| CN | 108712911 A | 10/2018 | |
| CO | 12203725 | 2/2013 | |
| EP | 0306968 | 12/1993 | |
| EP | 1465933 | 8/2007 | |
| EP | 1592719 | 3/2008 | |
| EP | 1988910 | 11/2008 | |
| EP | 1732621 | 12/2009 | |
| EP | 2260873 | 12/2010 | |
| EP | 2363414 | 9/2011 | |
| EP | 2512462 | 10/2012 | |
| EP | 2203180 | 11/2012 | |
| EP | 3222142 | 9/2017 | |
| EP | 3254678 | 12/2017 | |
| JP | H09-504299 | 4/1997 | |
| JP | H10 139832 | 5/1998 | |
| JP | H11 217588 | 8/1999 | |
| JP | 2000-093169 | 4/2000 | |
| JP | 2002-512265 | 4/2002 | |
| JP | 2003-064132 | 3/2003 | |
| JP | 2003-104913 | 4/2003 | |
| JP | 2004-510851 | 4/2004 | |
| JP | 2005-239989 | 9/2005 | |
| JP | 2005-255969 | 9/2005 | |
| JP | 2006-503549 | 2/2006 | |
| JP | 2007-516302 | 6/2007 | |
| JP | 2007-263935 | 10/2007 | |
| JP | 2007-314736 | 12/2007 | |
| JP | 2008-133434 | 6/2008 | |
| JP | 2008-524247 | 7/2008 | |
| JP | 2008-239997 | 10/2008 | |
| JP | 2008-297488 | 12/2008 | |
| JP | 2009-042617 | 2/2009 | |
| JP | 2009-114283 | 5/2009 | |
| JP | 2009-532330 | 9/2009 | |
| JP | 2009-533519 | 9/2009 | |
| JP | 2009-542862 | 12/2009 | |
| JP | 2009-543895 | 12/2009 | |
| JP | 2010-013651 | 1/2010 | |
| JP | 2010-117189 | 5/2010 | |
| JP | 2012-025820 | 2/2012 | |
| JP | 2013-515099 | 5/2013 | |
| JP | 2013-534931 | 9/2013 | |
| JP | 2014-043453 | 3/2014 | |
| JP | 2014-043456 | 3/2014 | |
| JP | 5745009 | 7/2015 | |
| JP | 5846044 | 1/2016 | |
| JP | 2016-040371 | 3/2016 | |
| JP | 2016-530302 | 9/2016 | |
| JP | 2018-87330 | 6/2018 | |
| JP | 2020-183404 | 11/2021 | |
| KR | 10-0808116 | 3/2008 | |
| KR | 2013-0097636 | 9/2013 | |
| KR | 10-1852044 | 4/2018 | |
| MX | 2012006970 | 10/2012 | |
| MX | 2012011876 | 11/2012 | |
| MX | 2016017290 | 8/2017 | |
| WO | WO 91/10741 | 7/1991 | |
| WO | WO 91/17271 | 11/1991 | |
| WO | WO 92/01047 | 1/1992 | |
| WO | WO 93/01221 | 1/1993 | |
| WO | WO 93/12227 | 6/1993 | |
| WO | WO 93/25673 | 12/1993 | |
| WO | WO 1994/016748 | 8/1994 | |
| WO | WO 1994/016749 | 8/1994 | |
| WO | WO 97/14702 | 4/1997 | |
| WO | WO 97/14703 | 4/1997 | |
| WO | WO 98/45331 | 10/1998 | |
| WO | WO 00/37658 | 6/2000 | |
| WO | WO 2000/059968 | 10/2000 | |
| WO | WO 01/24763 | 4/2001 | |
| WO | WO 0141827 | 6/2001 | |
| WO | WO 2003/028929 | 4/2002 | |
| WO | WO 2003/062290 | 7/2003 | |
| WO | WO 2003/074026 | 9/2003 | |
| WO | WO 2003/074090 | 9/2003 | |
| WO | WO 2004/010957 | 2/2004 | |
| WO | WO 2004/020405 | 3/2004 | |
| WO | WO 2004/063237 | 7/2004 | |
| WO | WO 2004/091494 | 10/2004 | |
| WO | WO 2004/113394 | 12/2004 | |
| WO | WO 2005/028539 | 3/2005 | |
| WO | WO 2005/058367 | 6/2005 | |
| WO | WO 2005/117984 | 12/2005 | |
| WO | WO 2006/063055 | 6/2006 | |
| WO | WO 2006/118547 | 11/2006 | |
| WO | WO 2007/005253 | 1/2007 | |
| WO | WO 2007/075534 | 7/2007 | |
| WO | WO 2007/100902 | 9/2007 | |
| WO | WO-2007100902 A2 * | 9/2007 | ............ A61P 35/00 |
| WO | WO 2007/148230 | 12/2007 | |
| WO | WO 2008/003099 | 1/2008 | |
| WO | WO 2008/020827 | 2/2008 | |
| WO | WO 2008/025856 | 3/2008 | |
| WO | WO 2008/098930 | 8/2008 | |
| WO | WO 2008/112257 | 9/2008 | |
| WO | WO 2008/112289 | 9/2008 | |
| WO | WO 2008/144248 | 11/2008 | |
| WO | WO 2008/155134 | 12/2008 | |
| WO | WO 2009/052249 | 4/2009 | |
| WO | WO 2005/047334 | 5/2009 | |
| WO | WO 2009/066746 | 5/2009 | |
| WO | WO 2009/117531 | 9/2009 | |
| WO | WO 2009/134977 | 11/2009 | |
| WO | WO 2009/138473 | 11/2009 | |

(56) References Cited

FOREIGN PATENT DOCUMENTS

| WO | WO 2010/040508 | 4/2010 |
|---|---|---|
| WO | WO 2010/068862 | 6/2010 |
| WO | WO 2010/068864 | 6/2010 |
| WO | WO 2010/111625 | 9/2010 |
| WO | WO 2010/126552 | 11/2010 |
| WO | WO 01/18080 | 3/2011 |
| WO | WO 2011/075185 | 6/2011 |
| WO | WO 2011/075736 | 6/2011 |
| WO | WO 2011/130694 | 10/2011 |
| WO | WO 2013/059137 | 4/2013 |
| WO | WO 2013/093809 | 6/2013 |
| WO | WO 2014/060401 | 4/2014 |
| WO | WO 2014/160507 | 10/2014 |
| WO | WO 2015/035342 | 3/2015 |
| WO | WO 2015/200905 | 12/2015 |
| WO | WO 2016/061562 | 4/2016 |
| WO | WO 2017/117464 | 7/2017 |
| WO | WO 2018/002761 | 1/2018 |
| WO | WO 2018/191548 | 10/2018 |

OTHER PUBLICATIONS

IUPAC Gold Book, Random copolymerization, available at https://goldbook.iupac.org/html/R/R05126.html, accessed Nov. 21, 2017.*
Database WPI Week 200833 (2008) Thomson Scientific, London, GB; AN 2008-E72441 XP-002795732, CN101053681A.*
Yamaguchi, J., et al., Phospholipid polymer hydrogel formed by the photodimerization of cinnamoyl groups in the polymer side chain, Journal of Applied Polymer Science (2007), 104(1), 44-50.*
Chen, X., et al., Polymeric Phosphorylcholine-Camptothecin Conjugates Prepared by Controlled Free Radical Polymerization and Click Chemistry, Bioconjugate Chemistry, 2009, 20, 2331-2341.*
Bontempo, et al., "Cysteine-Reactive Polymers Synthesized by Atom Transfer Radical Polymerization for Conjugation to Proteins," J. Am. Chem. Soc. (2004), 126, pp. 15372-15373.
Chen, et al., "Lubrication at Physiological Pressures by Polyzwitterionic Brushes," Science, (2009), 323, pp. 1698-1701.
Chen, et al., "Polymeric Phosphorylcholine-Camptothecin Conjugates Prepared by Controlled Free Radical Polymerizationand Click Chemistry," Bioconjugate Chem., (2009), 20:12, pp. 2331-2341.
Crowe, et al., "Recombinant human respiratory syncytial virus (RSV) monoclonal antibody Fab is effective therapeutically when introduced directly into the lungs of RSV-infected mice," Proc. Natl. Acad. Sci. USA, (1994) 91 pp. 1386-1390.
Da Pieve, et al., "Conjugation of PolyPEG®, Linear PEG and Branched PEG to a Thiol-Modified Aptamer," Poster, Warwick Effect Polymers Ltd, retrieved from <http:www.wep-ltd.co.uk> (2010).
Da Pieve, et al., "Modification of Thiol Functionalized Aptamers by Conjugation of Synthetic Polymers," Bioconjugate Chem., (2010), 21:1, pp. 169-174.
Dong, et al., "ARGET ATRP of 2-(Dimethylamino)ethyl Methacrylate as an Intrinsic Reducing Agent," Macromolecules, (2008), 41:19 pp. 6868-6870.
Dong, et al., "Well-Defined High-Molecular-Weight Polyacrylonitrile via Activators Regenerated by Electron Transfer ATRP," Macromolecules, (2007), 40:9, pp. 2974-2977.
Haddleton, et al., "Phenolic Ester-Based Initiators for Transition Metal Mediated Living Polymerization," Macromolecules, (1999), 32, pp. 8732-8739.
Heise, et al., "Investigation of the Initiation Behavior of a Dendritic 12-Arm Initiator in Atom Transfer Radical Polymerization," Macromolecules, (2001), 34:11, pp. 3798-3801.
Heredia, et al., "In Situ Preparation of Protein-'Smart' Polymer Conjugates with Retention of Bioactivity," J. Am. Chem. Soc., (2005), 127, pp. 16955-16960.
Hong, et al., "Preparation of Segmented Copolymers in the Presence of an Immobilized/Soluble Hybrid ATRP Catalyst System," Macromolecules, (2003), 36:1, pp. 27-35.

Iwasaki, et al., "Platelet compatible blood filtration fabrics using a phosphorylcholine polymer having high surface mobility," Biomaterials, (2003), 24 pp. 3599-3604.
Janssen, Alzheimer Immunotherapy Research & Development, LLC, AAB-001 in Patients With Mild to Moderate Alzheimer's Diesear, Clinical Trials, gov, NIH, 2005, [retrieved on Aug. 29, 2017], Retreived from the Internet: <http://clinicaltrials.gov/ct2/show/NCT00112073?term=aab-001&rank=3>.
Jakubowski, et al., "Activators Regenerated by Electron Transfer for Atom Transfer Radical Polymerization of Styrene," Macromolecules, (2006), 39:1, pp. 39-45.
Kizhakkedathu, et al., "Synthesis of Well-Defined Environmentally Responsive Polymer Brushes by Aqueous ATRP," Macromolecules, (2004), 37:3, pp. 734-743.
Kwiatdowski, et al., "High Molecular Weight Polymethacrylates by AGET ATRP under High Pressure," Macromolecules, (2008), 41:4, pp. 1067-1069.
Lacciardi, et al., "Synthesis of Novel Folic Acid-Functionalized Biocompatible Block Copolymers by Atom Transfer Radical Polymerization for Gene Delivery and Encapsulation of Hydrophobic Drugs," Biomacromolecules, (2005), 6:2, pp. 1085-1096.
Lena, et al., "Investigation of metal ligand affinities of atom transfer radical polymerization catalysts with a quadrupole ion trap," Dalton Transactions, (2009), 41, pp. 8884-8889.
Lewis, et al., "Crosslinkable coatings from phosphorylcholine-based polymers," Biomaterials, (2001), 22, pp. 99-111.
Lewis, et al., "Poly(2-methacryloyloxyethyl phosphorylcholine) for Protein Conjugation," Bioconjugate Chem., (2008), 19:11, pp. 2144-2155.
Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, (2006), 39:2, pp. 893-896.
Ma, et al., "Synthesis of Biocompatible Polymers. 1. Homopolymerization of 2-Methacryloyloxyethyl Phosphorylcholine via ATRP in Protic Solvents: An Optimization Study," Macromolecules, (2002), 35:25, pp. 9306-9314.
Ma, et al., "Well-Defined Biocompatible Block Copolymers via Atom Transfer Radical Polymerization of 2-Methacryloyloxyethyl Phosphorylcholine in Protic Media," Macromolecules, (2003), 36:10, pp. 3475-3484.
Mantovani, et al., "Design and Synthesis of N-Maleimido-Functionalized Hydrophilic Polymers via Copper-Mediated Living Radical Polymerization: A Suitable Alternative to PEGylation," J. Am. Chem. Soc., (2005), 127, pp. 2966-2973.
Matyjaszewski, et al., "Diminishing catalyst concentration in atom transfer radical polymerization with reducing agents," PNAS, (Oct. 17, 2006), 103:42, pp. 15309-15314.
McRae, et al. "Pentafluorophenyl Ester-Functionalized Phosphorylcholine Polymers: Preparation of Linear, Two-Arm, and Grafted Polymer-Protein Conjugates," Biomacromolecules, 13, 2099-2109 (2012).
Min, et al., "Use of Ascorbic Acid as Reducing Agent for Synthesis of Well-Defined Polymers by ARGET ATRP," Macromolecules, (2007), 40:6, pp. 1789-1791.
Miyamoto, et al., "Effect of water-soluble Phospholipid polymers conjugated with papain on the enzymatic stability," Biomaterials, (2004), 25, pp. 71-76.
Ng, et al., "Successful Cu-Mediated Atom Transfer Radical Polymerization in the Absence of Conventional Chelating Nitrogen Ligans," Macromolecules, (2010), 43:2, pp. 592-594.
Oh, et al., "Preparation of Poly(oligo(ethylene glycol) monomethyl ether methacrylate) by Homogeneous Aqueous AGET ATRP," Macromolecules, (2006), 39:9, pp. 3161-3167.
Palma, et al., "A new bispphosphonate-containing 99mTc(I) tricarbonyl complex potentially useful as bone-seeking agent: synthesis and biological evaluation," J Biol Inorg Chem, 12:667-679, (2007).
Pasut, et al., "Protein peptide and non-peptide drug PEGylation for therapeutic application," Expert Opin. Ther. Patents, 14(6) 859-894 (2004).
Pietrasik, et al., "Synthesis of High Molecular Weight Poly(styrene-co-acrylonitrile) Copolymers with Controlled Architecture," Macromolecules, (2006), 39:19, pp. 6384-6390.

(56) References Cited

OTHER PUBLICATIONS

Ranganathan, et al., "Synthesis of Thermoresponsive Mixed Arm Star Polymers by Combination of RAFT and ATRP from a Multifunctional Core and Its Self-Assembly in Water," Macromolecules, (2008), 41:12, pp. 4226-4234.
Roberts, et al., "Chemistry for peptide and protein PEGylation," Advanced Drug Delivery Reviews, (2002), 54, pp. 459-476.
Ruiz, et al., "Synthesis structure and surface dynamics of phosphorylcholine functional biomimicking polymers," Biomaterials, (1998), 19, pp. 987-998.
Ryan, et al., "Conjugation of salmon calcitonin to a combed-shaped end functionalized poly(poly(ethylene glycol) methyl ether methacrylate) yields a bioactive stable conjugate," Journal of Controlled Release, (2009), 135 pp. 51-59.
Sakaki, et al., "Stabilization of an antibody conjugated with enzyme by 2-methacryloyloxyethyl phosphorylcholine copolymer in enzyme-linked immunosorbent assay," J Biomed Mater Res, (1999), 47, pp. 523-528.
Samanta, et al., "End-Functionalized Phosphorylcholine Methacrylates and their Use in Protein Conjugation," Biomacromolecules, (2008), 9:(10), pp. 2891-2897.
Sayers, et al., "The Reduced Viscosity of PolyPEG® Compared with Linear PEG," Poster, Warwick Effect Polymers Ltd, retrieved from <http:www.wep-ltd.co.uk> on Feb. 11, 2009.
Tao, et al., "α-Aldehyde Terminally Functional Methacrylic Polymers from Living Radical Polymerization: Application in Protein Conjugation 'Pegylation'," J. Am. Chem. Soc., (2004), 126:41, pp. 13220-13221.
Ueda, et al., "Preparation of 2-Methacryloyloxyethyl Phosphocrycholine Copolymers with Alkyl Methacrylates and their Blood Campatability," Polymer Journal, vol. 24, No. 11, pp. 1259-1269 (1992).
Venditto, et al., "Cancer Therapies Utilizing the Camtothecins: A Review of the Vivo Literature," Molecular Pharmaceutics, vol. 7, No. 2, pp. 307-349 (2010).
Wang, et al., "Controlled/'Living' Radical Polymerization. Atom Transfer Radical Polymerization in the Presence of Transition-Metal Complexes," J. Am. Chem. Soc., (1995), 117:20, pp. 5614-5615.
Wang, et al., "Synthesis and Evaluation of Water-Soluble Polymers Bone-Targeted Drug Delivery Systems," Bioconjugate Chem., 14, 853-859 (2003).
Warwick Effect Polymers, PowerPoint presentation, "Polymers for the Healthcare and Specialty Materials Industries," Jan. 2009, pp. 1-29.
Yaseen, et al., "The Structure of Zwitterionic Phosphoacholine Surfactant Monolayers," Langmuir, (2006), 22:13, pp. 5825-5832.
Yusa, et al., "Synthesis of Well-Defined Amphiphilic Block Copolymers Having Phospholipid Polymer Sequences as a Novel biocompatible Polymer Micelle Reagents," Biomacromolecules, 6, 663-670 (2005).
Ambati et al., "Mechanisms of age-related macular degeneration," Neuron, vol. 75, No. 1, pp. 26-39, 2012.
Anderson, W.F., "Human gene therapy," Science, vol. 256, No. 5058, pp. 808-813, May 8, 1992.
Andrae et al., "Role of platelet-derived growth factors in physiology and medicine," Genes & Development, vol. 22, pp. 1276-1312, 2008.
Armulik, A. et al., "Endothelial/Pericyte Interactions," Circulation Research, vol. 97, Issue 6, pp. 512-523, Sep. 16, 2005.
Baluk, P. et al., "Cellular abnormalities of blood vessels as targets in cancer," Current Opinion in Genetics & Development, vol. 15, Issue 1, pp. 102-111, Feb. 2005.
Bates, D.O. et al., "Vascular endothelial growth factor increases microvascular permeability via a Ca(2+)-dependent pathway," American Journal of Physiology, vol. 273, No. 2, pp. H687-H694, Aug. 1, 1997.
Berthold, W. et al., "Protein Purification: Aspects of Processes for Pharmaceutical Products," Biologicals, vol. 22, Issue 2, pp. 135-150, Jun. 1994.

Blong, M. Renee et al., "Tetramerization domain of human butyrylcholinesterase is at the C-terminus," Biochemical Journal, vol. 327, No. 3, pp. 747-757, Nov. 1, 1997.
Bowen-Pope et al., "History of Discovery: Platelet-derived Growth Factor," Arterioscler Thromb Vasc Biol., vol. 31, No. 11, pp. 2397-2401, Nov. 2011.
Brown, D. et al., "Ranibizumab versus Verteporfin for Neovascular Age-Related Macular Degeneration," The New England Journal of Medicine, vol. 355, No. 14, pp. 1432-1444, Oct. 5, 2006.
Capon, D. et al., "Designing CD4 immunoadhesins for AIDS therapy," Nature, vol. 337, pp. 525-531, 1989.
Carmeliet, P., "Angiogenesis in healt and disease," Nature Medicine, vol. 9, pp. 653-660, (2003).
Carmeliet, P., "Synergism between vascular endothelial growth factor and placental growth factor contributes to angiogenesis and plasma extravasation in pathological conditions," Nature Medicine, vol. 7, No. 5, pp. 575-583, May 2001.
Carmeliet, "Mechanisms of angiogenesis and arteriogenesis," Nature Medicine, vol. 6, No. 3, pp. 389-395, 2000.
Casset, F. et al. A Peptide Mimetic of an Anti0CD4 Monoclonal Antibody by Rational Design, Biochemical and Biophysical Research Communications, vol. 307, pp. 198-205, (2003).
Chen et al., "Factors affecting endotoxin removal from recombinant therapeutic proteins by anion exchange chromatography," Protein Expression and Purification, vol. 64, pp. 76-81, 2009.
Chen, Y et al. Selection and Analysisi an Optimized Anti-VEGF Antibody: Crystal Structure of an Affinity-Matured Complex with Antigen, J. Mol. Biol,, vol. 293, pp. 865-881 , (1999).
Chothia, C. et al., "Canonical structures for the hypervariable regions of immunoglobulins," Journal of Molecular Biology, vol. 196, Issue 4, pp. 901-917, Aug. 20, 1989.
Chothia, C. et al., "Conformations of immunoglobulin hypervariable regions," Nature, vol. 342, pp. 877-883, Dec. 1989.
Christy, N.E. et al., "Antibiotic prophylaxis of postoperative endophthalmitis," Annals of Ophthalmology, vol. 11, No. 8, pp. 1261-1265, Aug. 1, 1979.
Cohen, S.Y. et al., "Causes of unsuccessful ranibizumab treatment in exudative age-related macular degeneration in clinical settings," Retina, vol. 32, Issue 8, pp. 1480-1485, Sep. 2012.
Daneshian, M. et al., "In vitro pyrogen test for toxic or immunomodulatory drugs," Journal of Immunological Methods, vol. 313, Issues 1-2, pp. 169-175, Jun. 30, 2006.
De Pascalis, R. et al., "Grafting of "abbreviated" complementarity-determining regions containing specificity-determining residues essential for ligand contact to engineer a less immunogenic humanized monoclonal antibody," J. Immunol., vol. 169, No. 6, pp. 3076-3084, Sep. 15, 2002.
Declaration of Harvey N. Masonson, M.D., under 37 C.F.R., for U.S. Appl. No. 12/465,051, filed May 13, 2009, including Exhibits A, B, and C, signed Jul. 6, 2011, in 50 pages.
Dillon et al., "Structural and functional characterization of disulfide isoforms of the human IgG2 subclass," The Journal of Biological Chemistry, vol. 283, No. 23, pp. 16206-16215, 2008.
Ding, J.L. et al., "A new era of pyrogen testing," Trends in Biotechnology, vol. 19, Issue 8, pp. 277-281, Aug. 1, 2001.
Du et al. "pH-Sensitive Vesicles based on a Biocompatible Zwitterionic Diblock Copolymer" J. Am. Chem. Soc., Dec. 1, 2005, 127, 17982-17983.
Edelman et al., "The covalent structure of an entire yG immunoglobulin molecule," Proceedings of the National Academy of Sciences, vol. 63, pp. 78-85, May 1, 1969.
Engelgau, M et al. Evolving Diabetes Burden in the United States. Ann of Int Med. 140 (11): 945-951, 2004.
"Facts About Diabetic Eye Disease", National Eye Institute, https://nei.nih.gov/health/diabetic/retinopathy, publication reviewed Sep. 2015, accessed Mar. 27, 2018, in 7 pages.
Fares, F.A. et al., "Design of a long-acting follitropin agonist by fusing the C-terminal sequence of the chorionic gonadotropin beta subunit to the follitropin beta subunit," Proc Natl Acad Sci USA, vol. 89, No. 10, pp. 4304-4308, May 15, 1992.
Ferrara, et al. Development of Ranibizumab, An Anti-Vascular Endothelial Growth, as Therapy for Neovascular Age-Related Macular

(56) References Cited

OTHER PUBLICATIONS

Degeneration, Retina, The Journal of Retinal and Vitreous Diseas, vol. 26, Issue No. 8, pp. 859-870, (2006).
Ferrara, et al, "The Biology of VEGF and its Receptors", Nature Medicine, vol. 9 No. 6, pp. 669-676, (2003).
Fiske, M. et al., "Method for reducing endotoxin in Moraxella catarrhalis UspA2 protein preparations," Journal of Chromatography B: Biomedical Sciences and Applications, vol. 753, Issue 2, pp. 269-278, Apr. 5, 2001.
Folkman, J., "Angiogenesis: an organizing principle fordrug discover?" Nature Reviews, Drug Discovery, vol. 6, pp. 273-286, Apr. 2007.
Fontaine et al., "Long-Term Stabilization of Maleimide-Thiol Conjugates," Bioconjugate Chem., vol. 26, pp. 145-152, 2015.
Foster, Graham R., "Pegylated interferons for the treatment of chronic Hepatitis C," Drugs, vol. 70, Issue 2, pp. 147-165, Jan. 2010.
Friedman, D.S. et al., "Prevalence of age-related macular degeneration in the United States," Arch. Ophthalmol., vol. 122, No. 4, pp. 564-572, Apr. 2004.
Greene et al., "Protective Groups In Organic Synthesis," 3rd Edition, John Wiley and Sons, Inc., New York, (1999). In 52 pages which includes only the Title Page and Table of Contents.
Gillies, et al., "Dendrimers and Dedritic Polymers in Drug Delivery," Drug Delivery today, Jan. 2005, vol. 10, No. 1, pp. 35-43.
Haishima, Y et al. Estimation of uncertainty in kinetic-colorimetric assay of bacterial endotoxins, J Pharm Biomed Analysis, 32: 1, pp. 495-503, (2003).
Haupt, H. et al., "Isolierung und physikalisch-chemische Charakterisierung der Cholinesterase aus Humanserum," Blut, vol. 14, Issue 2, pp. 65-75, Nov. 1966.
Heise et al., "Starlike Polymeric Architectures by Atom Transfer Radical Polymerization: Templates for the Production of Low Dielectric Constant Thin Films," Macromolecules, Jan. 17, 2000, 33:2346-2354.
Hirayama, C. et al., "Chromatographic removal of endotoxin from protein solutions by polymer particles," Journal of Chromatography B, vol. 781, Issues 1-2, pp. 419-432, Dec. 5, 2002.
Hoffmann, S. et al., "International validation of novel pyrogen tests based on human monocytoid cells," Journal of Immunological Methods, vol. 298, Issues 1-2, pp. 161-173, Mar. 2005.
Holash, J et al. VEGF-Trap: A VEGF Blocker with Potent Antitumor Effects, PNAS, vol. 9, No. 17, pp. 11393-11398, (2002).
Huang, Y-S. et al., "Engineering a pharmacologically superior form of granulocyte-colony-stimulating factor by fusion with gelatin-like-protein polymer," European Journal of Pharmaceutics and Biopharmaceutics, vol. 74, Issue 3, pp. 435-441, Mar. 2010.
Humphreys et al., "Alternative antibody FAB' fragment PEGylation strategies: combination of strong reducing agents, disruption of the interchain disulphide bond and disulphide engineering," Protein Engineering, Design & Selection, vol. 20, No. 5, pp. 227-234, 2007.
Huston, James S., "Protein engineering of single-chain Fv analogs and fusion proteins," Methods of Enzymology, vol. 203, pp. 46-96, 1991.
Ishikawa, K. et al., "Molecular mechanisms of subretinal fibrosis in age-related macular degeneration," Experimental Eye Research, vol. 142, pp. 19-25, Jan. 2016.
Iwasaki, Yasuhiko et al., "Synthesis and Characterization of Amphiphilic Polyphosphates with hydrophilic graft chains and Cholesteryl Groups as Nanocarriers", Biomacromolecules, 2006, 7, 1433-1438.
Jankova, et al., "Star Polymers by ATRP of Styrene and Acrylates Employing Multifunctional Initiators," Journal of Polymer Science Part A: Polymer Chemistry, Mar. 30, 2005, vol. 43, pp. 3748-3759.
Jeon, et al., "Synthesis of High Molecular Weight 3-Arm Star PMMA by ARGET ATRP," Macromolecular, 17:4 pp. 240-244, (2009).
Jo, N. et al., "Inhibition of platelet-derived growth factor B signaling enhances the efficacy of anti-vascular endothelial growth factor therapy in multiple models of ocular neovascularization," American Journal of Pathology, vol. 168, No. 6, pp. 2036-2053, Jun. 2006.

Jones, A., Analysis of Polypeptides and Proteins, Adv. Drug Delivery Rev. 10:, pp. 29-90, (1993).
Junghans, R.P., "Anti-Tac-H, a humanized antibody to the interleukin 2 receptor with new features for immunotherapyin malignant and immune disorders," Cancer Research, vol. 50, pp. 1495-1502, Mar. 1, 1990.
Kabat, E.A. et al., "Sequences of proteins of immunological interest," in 10 pages, 1991 (includes title page and table of contents only).
Kempen, J, et al. The Prevalence of Diabetic Retinopathy Among Adults in the United States, Arch Opthalmol., vol. 122, pp. 532-563, (2004).
Kostelny, S.A. et al., "Formation of a bispecific antibody by the use of leucine zippers," J. Immunol., vol. 148, No. 5, pp. 1547-1553, Mar. 1, 1992.
Kuhnert, F. et al. "Soluble receptor-mediated selective inhibition of VEGFR and PDGFR_ signaling during physiologic and tumor angiogenesis", PNAS, vol. 105, No. 29, p. 10185-10190, (2008).
Kumar et al., "PDGF-DD targeting arrests pathological angiogenesis by modulating GSK3β phosphorylation," JBC Papers in Press, published on Mar. 15, 2010 as Manuscript M110.113787, retrieved on Jun. 18, 2015 from http://www.jbc.org; However, as this item is accessible on the world wide web, it may have been available in some form at an earlier point in time.
Kumar, A. et al., "Platelet-derived growth factor-DD targeting arrests pathological angiogenesis by modulating glycogen synthase kinase-3β phosphorylation," The Journal of Biological Chemistry, vol. 285, No. 20, pp. 15500-15510, May 14, 2010.
Lafaut et al., "Clinicopathological correlation in exudative age related macular degeneration: histological differentiation between classic and occult choroidal neovascularisation," Br J Ophthalmol, vol. 84, pp. 239-243, 2000.
Lin, Weifeng et al., "A novel zwitterionic copolymer with a short poly(methyl acrylic acid) block for improving both conjugation and separation efficiency of a protein without losing its bioactivity". Journal of Materialos Chemistry B. May 21, 2013, vol. 1, No. 19, pp. 2482-2488. See abstract; and p. 2487.
Liu, et al., "Syntheses and Micellar Properties of Well-Defined Amphiphilic AB2 and A2B Y-Shaped Miltoarm Star Copolymers of ε-Caprolactone and 2-(Dimethylamino) ethyl Methacdrylate," Journal of Polymer Science: Part A: Polymer Chemistry, DOI 10.1002/pola, published online in Wiley InterSciences (www.intersience.wiley.com), Sep. 22, 2006; accepted Nov. 23, 2006.
Lucentis ramibizumab (reb) Name of the Medicine, Active ingredient Ranibizumab, Product Information Sheet, in 30 pages, based on CDS dated Aug. 30, 2013.
Mabry, R. et al., "A dual-targeting PDGFRβ/VEGF-A molecule assembled from stable antibody fragments demonstrates anti-angiogenic activity in vitro and in vivo", Landes Bioscience, vol. 2, Issue 2, pp. 20-34 (2010).
Maccallum, R. et al., Antibody-Antigen Interactions: Contact Analysis and Binding Site Toopgraphy, J/. Mol Biol., vol. 262, pp. 732-745, (1996).
Magalhaes et al., "Methods of Endotoxin Removal from Biological Preparations: a Review," J. Pharm Pharmaceut Sci., vol. 10, No. 3, pp. 388-404, 2007.
Marticorena, J. et al., "Sterile endophthalmitis after intravitreal injections," Mediators of Inflammation, vol. 2012, 6 pages, (2012).
Masson, P. et al., "Expression and Refolding of Functional Human butyrylcholinesterase from *E. coli*", Multidisciplinary Approaches to Cholinesterase Functions, New York, pp. 49-52, 1992.
McPherson, D. et al., "Production and Purification of a Recombinant Elastomeric Polypeptide, G-(VPGVG)19-VPGV, from *Escherichia coli*," Biotechnology Process, vol. 8, Issue 4, pp. 347-352, Jul./Aug. 1992.
Meng, X. et al. New Generation Recombinant hBuChe-FC Fusion with In-Vivo Performance Equivilanet to Gold Standard Plasma-Derive hbuChe-A First-in-Class Broad Spectrum Bioscanvenger that is Sustainable, Scalable, and Highly Cost-Effective on a Troop-Equivalent-Dose (TED) Basis.
Mones, Jordi, Inhibiting VEGF and PDGF to Treat AMD, http://www.reviewofophthalmology.com/content/d/retinal_insider/c/29979/#stash.fJePfjQ4.dpuf, Spain, Sep. 9, 2011.

(56) References Cited

OTHER PUBLICATIONS

Morris, G.E., "Epitope mapping protocols in methods in molecular biology," vol. 66, 1996.
Neuberger, M., "Generating high-avidity human Mabs in mice," Nature Biotechnology, vol. 14, pp. 826, 1996.
Ogikubo, Y. et al., "Evaluation of the bacterial endotoxin test for quantification of endotoxin contamination of porcine vaccines," Biologicals, vol. 32, Issue 2, pp. 88-93, Jun. 2004.
Ong, K. et al., "A rapid highly-sensitive endotoxin detection system," Biosensors and Bioelectronics, vol. 21, Issue 12, pp. 2270-2274, Jun. 15, 2006.
Ostberg, L. et al., "Human X (mouse X human) hybridomas stably producing human antibodies," Hybridoma, vol. 2, No. 4, pp. 361-367, 1983.
Padlan, Eduardo A., "A possible procedure for reducing the immunogenicity of antibody variable domains while preserving their ligand-binding properties," Molecular Immunology, vol. 28, Issues 4-5, pp. 489-498, Apr.-May 1991.
Papadopoulos et al., "Binding and neutralization of vascular endothelial growth factor (VEGF) and related ligands by VEGF Trap, ranibizumab and bevacizumab," Angiogenesis, vol. 15, pp. 171-185, 2012.
Paul, W., Fundamental Immunology, 2nd ed. Raven Press, N.Y., (1989).
Petsch, D. et al., "Endotoxin removal from protein solutions," Journal of Biotechnology, vol. 76, Issues 2-3, pp. 97-119, Jan. 21, 2000.
Pennock, S. et al Vascular Endothelial Growth Factor A Competitively Inhibits Platelet-Derived Growth Factor (PDGF)-Dependent Activation of PDGF Receptor and Subsequent Signaling Events and Cellar Responses, Molecular and Cell Biology, vol. 32, No. 2, pp. 1955-1966, (2012).
Pratt, et al. End-Functionalized Phosphorycholine Methacrylate and Their Use in Protein Conjugation, Biomacromlecules, vol. 9, pp. 2891-2897, (2008).
Presta et al., "Humanization of an Anti-Vascular Endothelial Growth Factor Monoclonal Antibody for the Therapy of Solid Tumors and Other Disorders," Cancer Research, vol. 57, pp. 4593-4599, 1997.
Raetz, C.R. et al., "Gram-negative endotoxin: an extraordinary lipid with profound effects on eukaryotic signal transduction," The FASEB Journal, vol. 5, No. 12, pp. 2652-2660, Sep. 1991.
Raica, M. et al., "Platelet-derived growth factor (PDGF)/PDGF receptors (PDGFR) axis as target for antitumor and antiangiogenic therapy," Pharmaceuticals, vol. 3, No. 3, pp. 572-599, (2010).
*Regeneron Pharmaceuticals Inc.* vs. *Bayer Pharma AG* Approved Judgment dated Feb. 21, 2013.
Regillo, C. et al., "Randomized, double-masked, sham-controlled trial of ranibizumab for neovascular age-related macular degeneration: PIER Study Year 1," American Journal of Ophthalmology, vol. 145, Issue 2, pp. 239-248, Feb. 2008.
Roberts, W.G. et al., "Increased microvascular permeability and endothelial fenestration induced by vascular endothelial growth factor," Journal of Cell Science, vol. 108, pp. 2369-2379, (1995).
Rosenfeld, P. et al., "Ranibizumab for neovascular age-related macular degeneration," The New England Journal of Medicine, vol. 355, No. 14, pp. 1419-1431, Oct. 5, 2006.
Rudikoff, S. et al., Single Amino Acid Substituon Altering Antigen-Bidning Specificity, Proc Natl. Acad. Sci. USA, vol. 79, pp. 1979-1983, (1982).
Rycroft, B.W., "Penicillin and the control of deep intra-ocular infection," British J. Ophthalmol, vol. 29, No. 2, pp. 57-87, Feb. 1945.
Schellenberger, V. et al., "A recombinant polypeptide extends the in vivo half-life of peptides and proteins in a tunable manner," Nature Biotechnology, vol. 27, pp. 1186-1190, 2009.
Schlapschy, M. et al., "Fusion of a recombinant antibody fragment with a homo-amino-acid polymer: effects on biophysical properties and prolonged plasma half-life," Protein Eng Des Sel, vol. 20, Issue 6, pp. 273-284, Jun. 1, 2007.
Shim et al., "Structures of a platelet-derived growth factor/propeptide complex and a platelet-derived growth factor/receptor complex," PNAS, vol. 107, No. 25, pp. 11307-11312, 2010.
Songsivilai, S. et al., "Bispecific antibody: a tool for diagnosis and treatment of disease," Clin Exp. Immunol., vol. 79, No. 3, pp. 315-321, Mar. 1990.
Stuttfeld et al., "Structure and function of VEGF receptors," Life, vol. 61, No. 9, pp. 915-922, 2009.
Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.
Tonkinson, J. et al., "New Drugs: Antisense Oligodeoxynucleotides as Clinical Therapeutic Agents," Cancer Investigation, vol. 14, No. 1, pp. 54-65, 1996.
Uutela et al., "PDFG-D induces macrophage recruitment, increased intersitial pressure, and blood vessel maturation during angiogenesis," Blood, vol. 104, No. 10, pp. 3198-3204, Nov. 15, 2004.
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Voynov et al., "Design and application of antibody cysteine variants," Bioconjugate Chemistry, vol. 21, pp. 385-392, Jan. 21, 2010.
Wagner, E. et al., "Transferrin-polycation conjugates as carriers for DNA uptake into cells," Proc. Natl. Acad. Sci. USA, vol. 87, No. 9, pp. 3410-3414, May 1, 1990.
Wu, G.Y. et al., "Receptor-mediated in vitro gene transformation by a soluble DNA carrier system," Journal of Biological Chemistry, vol. 262, pp. 4429-4432, Apr. 5, 1987.
Wu, H et al., Humanization of a Murine Monoclonal Antibody by Simultaneous Optimization of Frameorkand CDR Resiudes, J. Mol. Biol., vol. 294, pp. 151-162, (1999).
Yeh, P. et al., "Design of yeast-secreted albumin derivatives for human therapy: biological and antiviral properties of a serum albumin-CD4 genetic conjugate," Proc Natl Acad Sci USA, vol. 89, No. 5, pp. 1904-1908, Mar. 1, 1992.
Yu, L et al. Internaction Between Bevacizumab and Murie VEGF-A: A Reassessment, Investigative Opthalmology & Visual Science, vol. 49, No. 2, pp. 522-527, (2008).
Zebrowski, B. et al., "Vascular endothelial growth factor levels and induction of permeability in malignant pleural effusions," Clinical Cancer Research, vol. 5, pp. 3364-3368, Nov. 1999.
Zetter, "Angiogenesis and Tumor Metastasis," Annu. Rev. Med., vol. 49, pp. 407-424, 1998.
Zhang, X et al., Prevalence of Diabetic Retinopathy in the United States, 2005-2008, JAMA. vol. 304, No. 6, pp. 649-656, (2010).
Advisory Action dated Jun. 12, 2014 in U.S. Appl. No. 13/959,563.
Advisory Action dated Nov. 29, 2018 in U.S. Appl. No. 14/916,180.
Advisory Action dated Dec. 11, 2018 in U.S. Appl. No. 14/916,180.
Extended European Search Report received in European Patent Application No. 17165316.5 dated Aug. 2, 2017.
Extended European Search Report received in European Patent Application No. 17181272.0 dated Feb. 23, 2018 in.
Extended European Search Report dated Mar. 21, 2016 in EP Application No. 11769715.1, dated Jul. 18, 2016 s.
Extended Search Report received in European Patent Application No. 14841835.3 dated Mar. 14, 2017.
First Examination Report in NZ Application No. 6009449, dated Mar. 14, 2013.
First Examination Report in NZ Application No. 603048, dated Jun. 13, 2013 in 2 pages.
International Preliminary Report on Patentability dated Feb. 11, 2014 in PCT Application No. PCT/US2011/32768.
International Preliminary Report on Patentability (IPRP) dated Jun. 24, 2014, in International Application No. PCT/IB2012/057491, 10 pages.
International Preliminary Report on Patentability (IPRP) dated Jul. 5, 2016, in International Application No. PCT/US2015/038203.
International Preliminary Report on Patentability on dated Jul. 3, 2018 for International Patent Application No. PCT/US2016/069336 filed Dec. 29, 2016.

(56) References Cited

OTHER PUBLICATIONS

International Search Report and Written Opinion dated Feb. 27, 2013 in Internatnional Application No. PCT/US2012/060301.
International Search Report and Written Opinion for PCT/US2018/027378 dated Sep. 27, 2018.
International Search Report and Written Opinion dated Mar. 30, 2017 for International Patent Application No. PCT/US2016/069336 filed Dec. 29, 2016.
International Search Report in PCT Application No. PCT/US2007/005372, dated Aug. 8, 2008.
International Search Report and Written Opinion dated Sep. 9, 2010 in PCT Application No. PCT/US2010/034252.
International Search Report and Written Opinion dated May 9, 2011 in PCT Application No. PCT/US2010/61358.
International Search Report and Written Opinion dated Dec. 16, 2011 in PCT Application No. PCT/US2011/327681.
International Search Report in PCT Application No. PCT/US2014/054622, dated Feb. 27, 2015.
International Search Report and Written Opinion for PCT/US2015/038203, dated Dec. 8, 2015.
International Search Report dated Jun. 4, 2013, in International Application No. PCT/IB2012/057491.
Notice of Allowance dated Aug. 18, 2014 in U.S. Appl. No. 13/959,563.
Notice of Allowance dated Sep. 26, 2018 in Canadian Patent Application No. 2,783,615.
Notice of Allowance dated Jan. 28, 2014 in U.S. Appl. No. 13/515,913.
Notice of Allowance dated Aug. 9, 2017 in U.S. Appl. No. 14/753,824.
Notice of Final Rejection received in Korean Patent Application No. 10-2012-7029878 dated Aug. 28, 2017.
Notice of Final Rejection received in Korean Patent Application No. 10-2012-7029878 dated Oct. 27, 2017.
Notice of Rejection received in Japanese Patent Application No. 2016-159104 dated Jun. 27, 2017.
Notice of Rejection received in Japanese Patent Application No. 2016-159104 dated Feb. 26, 2018.
Notice to File a Response received in Korean Patent Application No. 10-2012-7018788 dated Sep. 13, 2017.
Office Action dated Jun. 21, 2018 in U.S. Appl. No. 15/394,500.
Office Action dated Jan. 7, 2019 in U.S. Appl. No. 15/394,500.
Office Action in U.S. Appl. No. 13/959,563, dated Oct. 10, 2013.
Office Action in U.S. Appl. No. 13/959,563, dated Feb. 20, 2014.
Office Action in U.S. Appl. No. 14/456,875, dated Jun. 9, 2015.
Office Action in U.S. Appl. No. 14/456,875, dated Oct. 5, 2016 in 10 pages.
Office Action in U.S. Appl. No. 14/456,875, dated Apr. 20, 2017.
Office Action in U.S. Appl. No. 14/456,875, dated Dec. 14, 2017.
Office Action in U.S. Appl. No. 14/456,875, dated Aug. 28, 2018.
Office Action dated Feb. 7, 2012 in U.S. Appl. No. 12/281,071.
Office Action in JP Patent Application No. 2008-557399, dated May 25, 2013.
Office Action in CA Application No. 2783615, dated Sep. 16, 2016.
Office Action in CA Application No. 2783615, dated Jan. 9, 2018.
Office Action dated Dec. 14, 2015 in U.S. Appl. No. 14/265,174.
Office Action Received in Chinese Patent Application No. 201080062252.7 dated Apr. 20, 2017.
Office Action Received in Chinese Patent Application No. 201610439969.8 dated Jul. 24, 2018.
Office Action in EP Application No. 10838353.0, dated Oct. 4, 2016.
Office Action in European Patent Application No. 17181272.0 dated Oct. 31, 2018.
Office Action in JP Application No. 2012-544945, dated Jul. 9, 2014.
Office Action dated Feb. 8, 2018 in Indian Patent Application No. 6116/CHENP/2012.
Office Action in KR Application No. 10-2012-7018788, dated Mar. 10, 2017.
Office Action dated Dec. 31, 2013 in U.S. Appl. No. 13/516,173.
Office Action dated Jul. 2, 2014 in U.S. Appl. No. 13/516,173.
Office Action dated Dec. 16, 2014 in U.S. Appl. No. 13/516,173.
Office Action dated Apr. 12, 2018 in Australian Patent Application No. 2017201930.
Office Action dated Jun. 2, 2016 U.S. Appl. No. 13/901,483.
Office Action dated Feb. 9, 2018 in U.S. Appl. No. 15/368,376.
Office Action dated Sep. 10, 2018 in U.S. Appl. No. 15/368,376.
Office Action dated Apr. 6, 2017 Canadian Patent Application No. 2,795,667.
Office Action in CN Application No. 201180028682.1, dated Aug. 21, 2014.
Office Action in CN Application No. 201180028682.1, dated Jan. 26, 2015.
Office Action in CN Application No. 201180028682.1, dated Aug. 11, 2015.
Office Action received in Chinese Patent Application No. 201610446624.5 dated Mar. 12, 2018 in 12 pages.
Office Action received in Chinese Patent Application No. 201610446624.5 dated Nov. 26, 2018.
Office Action received in European Patent Application No. 11769715.1 dated Nov. 9, 2017.
Office Action in JP Application No. 2013-505799, dated Feb. 19, 2015.
Office Action in JP Application No. 2015-165282, dated Aug. 15, 2016.
Office Action in JP Application No. 2015-165282, dated Aug. 1, 2017.
Office Action in JP Application No. 2015-165282, dated Sep. 27, 2018.
Office Action dated Nov. 27, 2018 in Japanese Patent Application No. JP 2017-231724.
Office Action in KR Application No. 10-2012-7029878, dated Mar. 8, 2017.
Office Action dated Mar. 9, 2018 in KR Application No. 10-2017-703456.
Office Action dated Aug. 28, 2018 in KR Application No. 10-2017-703456.
Office Action dated Oct. 26, 2018 in KR Application No. 10-2017-703456.
Office Action received in Mexican Patent Application No. MX/a/2012/011876 dated Jul. 13, 2017.
Office Action dated Jan. 16, 2018 in MX Application No. MX/a/2012/011876.
Office Action dated Jan. 23, 2019 in European Patent Application No. EP 14841835.3.
Office Action dated Jul. 13, 2018 in Japanese Patent Application No. 2016-540916.
Office Action dated Jan. 24, 2018 in U.S. Appl. No. 14/916,180.
Office Action dated Aug. 10, 2018 in U.S. Appl. No. 14/916,180.
Office Action dated Feb. 27, 2017 in U.S. Appl. No. 14/753,824.
Office Action dated Jan. 9, 2019 in U.S. Appl. No. 15/820,325.
Office Action dated Jun. 27, 2018 in Indian Patent Application No. 9476/CHENP/2012 in 5 pages.
Office Action dated Jun. 6, 2018 in Mexican patent Application No. MX/a/2012/011876.
Patent Examination Report No. 1 in AU Application No. 2010330727, dated Nov. 19, 2014.
Patent Examination Report in AU Application No. 2011239434, dated Mar. 19, 2014.
Patent Examination Report in AU Application No. 2015207898, dated Mar. 23, 2016.
Patent Examination Report in AU Application No. 2015207898, dated May 27, 2017.
Restriction Requirement dated Mar. 7, 2018 in U.S. Appl. No. 15/394,500.
Restriction Requirement dated Jun. 20, 2011 in U.S. Appl. No. 12/28071.
Restriction Requirement dated Jul. 15, 2015 in U.S. Appl. No. 14/265,174.
Restriction Requirement dated Aug. 14, 2013 in U.S. Appl. No. 13/515,913.
Restriction Requirement dated Sep. 3, 2013 in U.S. Appl. No. 13/516,173.
Restriction Requirement dated Nov. 3, 2015 U.S. Appl. No. 13/901,483.

(56) References Cited

OTHER PUBLICATIONS

Restriction Requirement dated Aug. 21, 2017 in U.S. Appl. No. 15/368,376.
Restriction Requirement dated Jan. 30, 2017 in U.S. Appl. No. 14/916,180.
Restriction Requirement dated Aug. 16. 2017in U.S. Appl. No. 14/916,180.
Supplemental European Search Report received in European Patent Application No. EP 07752096.3 dated Feb. 19, 2013.
Supplemental European Search Report dated Feb. 2, 2015 in European Patent Application No. EP 10838353.0 dated Feb. 3, 2015.
File History of U.S. Appl. No. 15/952,092, filed Apr. 12, 2018.
File History of U.S. Appl. No. 15/394,500, filed Dec. 29, 2016.
File History of U.S. Appl. No. 14/456,875, filed Aug. 11, 2014.
File History of U.S. Appl. No. 15/368,376, filed Dec. 2, 2016.
File History of U.S. Appl. No. 14/916,180, filed Mar. 2, 2016.
File History of U.S. Appl. No. 15/820,325, filed Nov. 21, 2017.
Chinese Patent Office, Application No. 201610439969.8 Office Action, dated Mar. 13, 2019, in 6 pages.
Office Action issued in Japanese Patent Application No. 2018-189049; dated May 19, 2020; 4 pages.
Japanese Office Action, JP Application No. 2018-189049, dated Nov. 26, 2019, in 11 pages.
Extended European Search Report, EP Application No. 20151266.2, dated Feb. 28, 2020, in 6 pages.
Brazilian Office Action, BR Application No. BR11 2012 014556-8, dated Jun. 12, 2020, in 5 pages.
Chinese Patent Office, Application No. 201610439969.8 Office Action, dated Nov. 18, 2020, in 15 pages.
Japanese Patent Office, Decision to Grant, App. No. JP 2018-189049, dated Sep. 2, 2020, in 7 pages.
Canadian Patent Office, Examination Report, Application No. 3,039,426, dated Oct. 30, 2020 in 4 pages.
Chinese Patent Office, Application No. 201610439969.8; Reexamination Decision; dated Mar. 25, 2021, in 18 pages.
Canadian Patent Office, Application No. 3,039,426, Office Action, dated Apr. 15, 2021, in 4 pages.
"Papain", MilliporeSigma, webpage accessed Aug. 10, 2021 [publication of information on webpage unknown], in 4 pages. URL: https://www.sigmaaldrich.com/US/en/technical-documents/technical-article/research-and-disease-areas/metabolism-research/papain.
Warnecke, A. et al., "Synthesis and Biological Activity of Water-Soluble Maleimide Derivatives of the Anticancer Drug Carboplatin Designed as Albumin-Binding Prodrugs", Bioconjugate Chemistry, Oct. 2004, vol. 15, pp. 1349-1359.
Sletten, E. et al., "Bioorthogonal Chemistry: Fishing for Selectivity in a Sea of Functionality", Angewandte Chemie International Edition, Dec. 2009, vol. 48, pp. 6974-6998 (author manuscript copy).
Cai, Y. et al., "Direct Synthesis and Stimulus-Responsive Micellization of Y-Shaped Hydrophilic Block Copolymers", Macromolecules, vol. 37, No. 26, Dec. 2004, pp. 9728-9737. DOI: 10.1021/ma0487756.
Chakravarthy, R. et al., "Efficacy of extrinsic stain removal by novel dentifrice containing papain and bromelain extracts", J. Young Pharm, 2012, vol. 4(4), pp. 245-249.
Coessens, V. et al., "Functional polymers by atom transfer radical polymerization", Progress in Polymer Science, Apr. 2001, vol. 26, pp. 337-377.
Curriculum Vitae of Didier G. Benoit, filed in U.S. Appl. No. 12/281,071 on Feb. 4, 2013, in 6 pages.
Database WPI Week 200833 Thomson Scientific, London, GB; AN 2008-E72441 XP002795732, & CN 101 053 681 A (Univ Tianjin), Oct. 17, 2007.
Declaration of Didier G. Benoit, filed in U.S. Appl. No. 12/281,071 on Feb. 5, 2013 (signed Jan. 31, 2013), in 8 pages.
Declaration of Stephen A. Charles under 37 CFR 1.132 filed in U.S. Appl. No. 13/959,563, dated Dec. 6, 2013, in 20 pages.
Exhibit D filed in U.S. Appl. No. 12/281,071 on Feb. 4, 2013, in 1 page.
Exhibit E filed in U.S. Appl. No. 12/281,071 on Feb. 4, 2013, in 1 page.
Gauthier, M. et al., "Peptide/protein-polymer conjugates: synthetic strategies and design concepts", Chemical Communications, 2008, pp. 2591-2611.
Geng, J. et al. Site-Directed Conjugation of "Clicked" Glycopolymers to Form Glycoprotein Mimics: Binding to Mammalian Lectin and Induction of Immunological Function, J. Am. Chem. Soc., 2007, 129, p. 15156-15163.
Hermanson, G., *Bioconjugate Techniques*, Academic Press, 2nd ed., 2008, in 1233 pages.
Inada, Y. et al., "Application of Polyethylene glycol-modified enzymes in biotechnological processes: organic solvent-soluble enzymes", Tibtech, Jul. 1986, pp. 190-194.
Ishihara, K. et al, "Photoinduced graft polymerization of 2-methacryloyloxyethyl phosphorylcholine on polyethylene membrane surface for obtaining blood cell adhesion resistance", Colloids Surf B Biointerfaces, Oct. 2000, vol. 18(3-4), pp. 325-335.
Ivens, I.A. et al., "PEGylated therapeutic proteins for hemophilia treatment; a review for haemophilia caregivers", Hemophilia, Jan. 2013, vol. 19, pp. 11-20.
Iwasaki, Y. et al., "Preservation of platelet function on 2-methacryloyloxyethyl phosphorylcholine-graft polymer as compared to various water-soluble graft polymers", Journal of Biomedical Materials Research, Jun. 2001, vol. 57(1), pp. 72-78.
Kobayashi, M et al., "Tribological properties of hydrophilic polymer brushes under wet conditions", The Chemical Record, vol. 10, pp. 208-216.
Lucentis ramibizumab (reb) Product Information Sheet most recent amendment Oct. 22, 2013.
Matyjaszewski, K. et al., "Controlled Radical Polymerization in the Presence of Oxygen", Marcomolecules, 1998, vol. 31(17), pp. 5967-5969.
Mayadunne, R. et al. Living Free Radical Polymerization with Reversible Addition-Fragmentation Chain Transfer (RAFT Polymerization): Approaches to Star Polymers, Macromolecules, vol. 36, pp. 1505-1513, (2003).
Merrifield, R. B., "Solid Phase Peptide Synthesis: I. The Synthesis of a Tetrapeptide", Journal of the American Chemical Society, Jul. 1963, vol. 85, pp. 2149-2154.
Pepinsky et al., "Improved Pharmacokinetic Properties of a Polyethylene Glycol-Modified Form of Interferon-b-1a with Preserved in Vitro Bioactivity", J. Pharmco. Exp. Therp., 2001, vol. 297(3), pp. 1059-1066.
Perruchot, C. et al. "Synthesis of Well-Defined, Polymer-Grafted Silica Particles by Aqueous ATRP", Langmuir, 2001, vol. 17(15), pp. 4479-4481.
Robinson, K. et al. Controlled Polymerization of 2-Hydroxyethyl Methacrylate by ATRP at Ambient Temperature, Macromolecules, vol. 34, pp. 3155-3158, (2001).
Second Supplemental Declaration of Stephen A. Charles filed in U.S. Appl. No. 13/959,563, dated Jul. 22, 2014, in 3 pages.
Seo et al., Conformational Recovery and Preservation of Protein Nature from Heat-Induced Debaturation by Water-Soluble Phospholipid Plymer Conjugation, Biomaterials, vol. 30, 2009, pp. 4859-4867.
Strandman, S. et al., "Effect of ligand on the synthesis of star polymers by resorcinarene-based ATRP initiators", Journal of Polymer Science Part A: Polymer Chemistry, Aug. 2005, vol. 43, pp. 3349-3358.
Supplemental Declaration of Stephen A. Charles filed in U.S. Appl. No. 13/959,563, dated May 20, 2014, in 3 pages.
Takahara, et al., Int. Symp. Nano-bio-Interfaces Rel. Mol. Molecular Mobility, Program and Abstracts Book, p. 25-26, https://www.nof.co.jp/business/life/product01.html (2009).
Tao, Lei et al., "Branched polymer-protein conjugates made from mid-chain-functional P (HPMA)", Biomacromolecules, 2009, vol. 10, No. 10, pp. 2487-2851. See abstract; pp. 2847 and 2850; and scheme 2.
Wong, S. S., *Chemistry of Protein Conjugation and Cross-Linking*, CRC Press Inc., Aug. 1991, in 10 pages (Table of Contents only).

(56) References Cited

OTHER PUBLICATIONS

Xiaoying, S. et al. Synthesis and Characterization of a Multiarm Star Polymer, Journal of Polymer Science, vol. 42, pp. 2356-2364, (2004).
Zhang, X et al. Synthesis of Functional Polystyrenes by Atom Transfer Radical Polymerization Using Protected and Unprotected Carboxylic Acid Initiators, Macromolecules, vol. 32, pp. 7349-7353, (1999).
Office Action, BR112012014556-8, dated Nov. 6, 2019, in 7 pages.
Office Action for Brazilian Application No. BR 11 2012 014556-8 with English translation in 6 pages, dated Aug. 5, 2021.
Office Action for Canadian Application No. CA 2,783,615 in 4 pages, dated May 12, 2017.
Office Action dated Dec. 29, 2017 Canadian Patent Application No. 2,795,667.
Office Action for Chilean Application No. CL 01621/2012 in 4 pages, dated Jun. 3, 2014.
Office Action for Chinese Application No. CN 201080062252.7 with English translation in 10 pages, dated May 17, 2013.
Office Action for Chinese Application No. CN 201080062252.7 with English translation in 9 pages, dated Apr. 9, 2014.
Office Action for Chinese Application No. CN 201080062252.7 with English translation in 7 pages, dated Oct. 27, 2014.
Office Action for Chinese Application No. CN 201080062252.7 with English translation in 11 pages, dated Apr. 23, 2015.
Office Action for Chinese Application No. CN 201080062252.7 with English translation in 8 pages, dated Oct. 9, 2016.
Office Action for Chinese Application No. CN 201610439969.8 with English summary in 6 pages, dated Mar. 19, 2019.
Rejection Decision Received in Chinese Patent Application No. 201610439969.8 dated Sep. 20, 2019.
Office Action for Chinese Application No. CN 201610446624.5 with English translation in 18 pages, dated Mar. 15, 2022.
English Summary of Office Action for Columbian Application No. CO 12-119310 in 19 pages, dated Aug. 11, 2014.
Office Action for European Application No. EP 10838353.0 in 8 pages, dated Jun. 10, 2015.
Office Action for European Application No. EP 17181272.0 in 3 pages, dated Mar. 22, 2019.
Notice of Hearing for Indian Application No. IN 6116/CHENP/2012 with English translation in 3 pages, dated Jun. 24, 2019.
Office Action for Japanese Application No. JP 2020-170314 with English translation in 11 pages, dated Dec. 7, 2021.
Office Action for Korean Application No. KR 10-2012-7018788 with English translation in 3 pages, dated Jan. 19, 2018.
Office Action in MX Application No. MX/a/2012/006970, dated Sep. 22, 2014 in 2 pages.
Office Action in MX Application No. MX/a/2012/006970, dated Dec. 15, 2015.
Office Action dated Apr. 5, 2019 in Mexican Patent Application No. MX/a/2016/010818.
Office Action dated Oct. 1, 2019 in Mexican Patent Application No. MX/a/2016/010818.
International Search Report and Written Opinion in PCT Application No. PCT/US2007/005372, dated Aug. 8, 2008.
International Search Report and Written Opinion in PCT Application No. PCT/US2014/054622, dated Feb. 27, 2015 in 19 pages.
International Preliminary Report on Patentability in Application No. PCT/US2010/034252, dated Jun. 28, 2012.
International Preliminary Report on Patentability in Application No. PCT/US2010/061358, dated Jun. 28, 2012.
Notice of Allowance dated Jul. 31, 2014 in U.S. Appl. No. 13/959,563.
Office Action in U.S. Appl. No. 14/456,875, dated Nov. 9, 2015 in 20 pages.
Restriction Requirement in U.S. Appl. No. 15/182,278, dated Feb. 17, 2017.
Office Action dated Oct. 14, 2015 in U.S. Appl. No. 13/516,173.
Boeckman, R. et al., "The Dess-Martin Periodinane: 1,1,1-Traicetoxy-1,1-Dihydro-1,2-Benziodoxol-3(1H)-One", Organic Syntheses, Coll., 2004, vol. 10, in 7 pages.

Chandler, W. et al., "Comparison of Three Methods for Measuring Factor VIII Levels in Plasma", American Journal of Clinical Pathology, Jul. 2003, vol. 120, pp. 34-39.
Fan, Q. et al., "Preclinical evaluation of Hematide, a novel erythropoiesis stimulating agent, for the treatment of anemia", Experimental Hematology, 2006, vol. 34, pp. 1303-1311.
Herd, O. et al., "Palladium catalyzed P-C coupling—a powerful took for the syntheses of hydrophilic phosphines", Catalysis Today, 1998, vol. 42, pp. 413-420.
Kaplanek, R. et al., "Three-fold polyfluoroalkylated amines and isocyanates based on tris(hydroxymethyl)aminomethane (TRIS)", Journal of Fluorine Chemistry, 2007, vol. 128, pp. 179-183.
Lenting, P. et al., "The Life Cycle of Coagulation Factor VIII in View of Its Structure and Function", Blood, Dec. 1998, vol. 92, pp. 3983-3996.
Leong, S. et al., "Adapting pharmacokinetic properties of a humanized anti-interleukin-8 antibody for therapeutic applications using site-specific pegylation", Cytokine, Nov. 2001, vol. 16(3), pp. 106-119.
Mei, B. et al., "Rational design of a fully active, long-acting PEGylated factor VIII for hemophilia A treatment", Thrombosis and Hemostasis, Jul. 2010, vol. 116(2), pp. 270-279.
Sato, A. et al., "Therapeutic peptides: technological advances driving peptides into development", Current Opinion in Biotechnology, 2006, vol. 17, pp. 638-642.
Simakova, A. et al., "Aqueous ARGET ATRP", Macromolecules, Aug. 2012, vol. 45(16), pp. 6371-6379.
Woodworth, B. et al., "Copper Triflate as a Catalyst in Atom Transfer Radical Polymerization of Styrene and Methyl Acrylate", Macromolecules, Oct. 1998, vol. 31, No. 23, pp. 7999-8004.
Yong, R. et al., "Radical copolymerization of maleimide with ethyl α-ethylacrylate and α-ethylacrylic acid via RAFT", Journal of Polymer Science, Aug. 2004, vol. 42, pp. 3828-3835.
Office Action for Australian Application No. AU 2017201930 in 4 pages, dated Mar. 27, 2019.
Office Action, BR112012026118-5, dated Aug. 23, 2019.
Office Action for Brazilian Application No. BR 11 2012 026118-5 with English translation in 11 pages, dated Feb. 28, 2020.
Office Action for Chinese Application No. CN 201180028682.1 with English summary in 5 pages, dated Mar. 3, 2016.
Office Action for Chinese Application No. CN 201610446624.5 with English summary in 8 pages, dated Jun. 14, 2019.
Office Action for Chinese Application No. CN 201610446624.5 with partial English translation in 11 pages, dated Feb. 6, 2020.
Office Action for Chinese Application No. CN 201610446624.5 with English summary in 10 pages, dated Oct. 28, 2021.
English Summary of Office Action for Columbian Application No. CO 12-203725 in 7 pages, dated Mar. 14, 2014.
Office Action for European Application No. EP 11769715.1 in 4 pages, dated Jun. 11, 2018.
Summons to Attend Oral Proceedings for EP Application No. 14841835.3 in 8 pages, dated Sep. 27, 2019.
Result of Consultation for EP Application No. 14841835.3 in 3 pages, dated Feb. 6, 2020.
Partial Search Report, European Patent Office, Application No. EP 19175761.6, dated Aug. 21, 2019, in 20 pages.
Extended European Search Report in EP Application No. 19175761.6, dated Nov. 27, 2019.
Office Action for European Application No. 19175761.6 in 9 pages, dated Nov. 2, 2020.
European Patent Office, Extended European Search Report, Application No. 20188750.2-1109, dated Nov. 5, 2020, in 13 pages.
Notice of Hearing for Indian Application No. IN 9473/CHENP/2012 with English translation in 2 pages, dated Aug. 19, 2019.
Office Action for Japanese Application No. 2008-557399 with English translation in 9 pages, dated Sep. 18, 2012.
Office Action for Japanese Application No. JP 2013-505199 with English translation in 2 pages, dated Oct. 27, 2015.
Office Action, JP 2019-000261, dated Feb. 12, 2020.
Office Action for Japanese Application No. JP 2017-231724 with English translation in 9 pages, dated Jun. 4, 2019.
Office Action for Japanese Application No. JP 2017-231724 with English translation in 6 pages, dated Dec. 24, 2019.

(56) References Cited

OTHER PUBLICATIONS

Office Action for Japanese Application No. JP 2020-077026 with English translation in 12 pages, dated May 11, 2021.
Office Action for Japanese Application No. JP 2020-077026 in 7 pages, dated Mar. 22, 2022.
Office Action for Japanese Application No. JP 2020-117047 with English translation in 10 pages, dated Aug. 31, 2021.
Trial Decision in KR Application No. 10-2012-7029878, dated Jul. 23, 2019.
Office Action for Korean Application No. KR 10-2018-7034569 with English translation in 11 pages, dated May 21, 2019.
Office Action dated Jan. 22, 2020 in Korean Patent Application No. 10-2018-7034569.
Office Action in KR Application No. 10-2018-7034569, dated Apr. 8, 2020 in 8 pages.
Notice of Trial Decision with Partial English Translation in Korean Application No. 10-2018-7034569, dated Apr. 22, 2021.
Final Office Action dated Sep. 24, 2020 in Korean Patent Application No. 10-2020-7016413.
Final Office Action dated Mar. 30, 2021 in Korean Patent Application No. 10-2020-7016413.
Decision to Dismiss an Amendment in Korean Application No. 10-2020-7016413, dated Jul. 16, 2021.
Notice of Final Rejection in Korean Application No. 10-2020-7016413, dated Jul. 16, 2021.
Office Action for Korean Application No. KR 10-2021-7020330 with English translation in 11 pages, dated Oct. 27, 2021.
Notice of Allowance for Korean Application No. KR 10-2021-7020330 with English translation in 3 pages, dated Apr. 27, 2022.
Office Action dated Dec. 17, 2018 in Mexican patent Application No. MX/a/2012/011876.
International Preliminary Report on Patentability in PCT Application No. PCT/US2007/005372, dated Oct. 21, 2008.
International Preliminary Reporton Patentability in PCT Application No. PCT/US2014/054622, dated Mar. 17, 2016.
Office Action in U.S. Appl. No. 14/456,875, dated Mar. 8, 2019.
Restriction Requirement dated Apr. 21, 2020 in U.S. Appl. No. 16/424,265.
Office Action dated Oct. 21, 2020 in U.S. Appl. No. 16/424,265.
Office Action received in U.S. Appl. No. 16/424,265 dated Jun. 17, 2021.
Office Action in U.S. Appl. No. 12/281,071, dated Aug. 2, 2012.
Office Action dated Mar. 11, 2019 in U.S. Appl. No. 15/368,376.
Office Action dated Aug. 2, 2019 in U.S. Appl. No. 15/368,376.
Restriction Requirement dated Nov. 10, 2020 in U.S. Appl. No. 16/779,102.
Office Action dated Feb. 22, 2021 in U.S. Appl. No. 16/779,102.
Office Action dated Nov. 13, 2020 in U.S. Appl. No. 16/781,869 in 10 pages.
Final Office Action dated Mar. 17, 2021 in U.S. Appl. No. 16/781,869 in 10 pages.
Non-Final Office Action for U.S. Appl. No. 16/781,869 in 12 pages, dated Sep. 28, 2021.
Office Action dated Mar. 8, 2019 in U.S. Appl. No. 14/916,180.
Office Action dated Jun. 26, 2019 in U.S. Appl. No. 14/916,180.
Advisory Action dated Sep. 9, 2019 in U.S. Appl. No. 14/916,180.
Notice of Allowance dated Nov. 5, 2019 in U.S. Appl. No. 14/916,180.
Office Action for Canadian Application No. CA 3,039,426 in 4 pages, dated Oct. 7, 2022.
Office Action for Japanese Application No. JP 2020-170314 with English translation in 12 pages, dated Oct. 18, 2022.
Notice of Allowance for Canadian Application No. CA 3,039,426 in 1 page, dated May 5, 2023.
Office Action for European Application No. EP 20151266.2 in 3 pages, dated Jan. 12, 2023.
Reconsideration Report by Examiner before Appeal for Japanese Application No. JP 2020-170314 with English translation in 6 pages, dated May 17, 2023.

\* cited by examiner

Initiation: $I-I' \longrightarrow I\bullet + \bullet I'$

Propagation:

$$I\bullet + \bullet I' \xrightarrow{M^1, M^2} I-M^1-M^2\bullet + \bullet I' \rightleftarrows I-M^1-M^2-I'$$
$$\phantom{I\bullet + \bullet I' \xrightarrow{M^1, M^2}} A \phantom{xxxxxxxx} B$$

Reversible termination:

$$I-M^1-M^2\bullet + \bullet I' \xrightarrow{M^1, M^2} I\text{-}(M^1)_x\text{-}(M^2)_{(y^1-1)}\text{-}M^2\bullet + \bullet I' \rightleftarrows I\text{-}(M^1)_x\text{-}(M^2)_{y^1}\text{-}I'$$
$$\phantom{xxxx}A \phantom{xxxxxxxxxxxxxxxxxxxxx} C \phantom{xxxxxxxxxxxxxxx} D$$

US 11,819,531 B2

MULTIFUNCTIONAL ZWITTERIONIC POLYMER CONJUGATES

CROSS-REFERENCE TO RELATED APPLICATION

The present application is a continuation of U.S. Ser. No. 13/516,173 filed Aug. 27, 2012, now abandoned, which is a US national phase of PCT/US2010/061358 filed Dec. 20, 2010, which claims the benefit of U.S. 61/288,127 filed Dec. 18, 2009. The present application is also continuation-in-part of U.S. Ser. No. 14/265,174 filed Apr. 29, 2014, , now abandoned, which is a continuation of U.S. Ser. No. 13/515,913 filed Aug. 27, 2012, now U.S. Pat. No. 8,765,432, which is a US national phase of PCT/US2010/034252 filed May 10, 2010, which claims the benefit of U.S. 61/288,127 filed Dec. 18, 2009. Each of the applications from which the present application claims priority is incorporated by reference in its entirety for all purposes.

REFERENCE TO A SEQUENCE LISTING

This application includes an electronic sequence listing in a file named 434550CON_SEQLST.txt, created on Apr. 13, 2016 and containing 956 bytes, which is hereby incorporated by reference in its entirety for all purposes.

BACKGROUND OF THE INVENTION

An arms race of sorts is happening right now amongst the pharmaceutical companies who are all trying to deliver 'medically differentiated products'. Current drug formats are inflexible, in that they generally allow for a single activity. For example, a recombinant monoclonal antibody generally is designed and optimized to bind and inhibit a single target protein. For example, a small molecule drug is generally designed and optimized to bind and activate (or inhibit) a single target. In some cases, the drug is not selective and there are multiple activities (for example, a small molecule kinase inhibitor that is designed to bind the ATP binding site of a single kinase but which shows a level of affinity and bioactivity against adjacent kinase family members). But generally drug developers optimize using today's drug formats for single activities and non-selectivity is seen as something to engineer away in the drug development process.

In today's drug development, then, the selection of the single target is the key variable. Drugs, therefore, are developed from a format-centric point of view. But drugs are developed to treat disease. And diseases generally are composed of more than one pathophysiologic mechanism happening in series or in parallel. A mechanism being a pathway or set of intersecting pathways occurring either in a localized cell or tissue or organ or systemically throughout the organism. A pathway being a set of moieties that interact with each other. A more ideal way to engage in drug development is to be able to take a disease-centric or biology-centric approach. For example, based on the sum of academic and corporate and historical research and experience to date, disease x involves pathways a, b, and c. Within pathway a, target protein z is known to be upregulated (and could be bound and inhibited by an antibody fragment). Within pathway b, cell-type y is known to be proliferating inappropriately (and could be impacted by a small molecule anti-proliferative agent). And the pathophysiology of pathway a and b is occurring within tissue subtype x (and which could be targeted or enriched with drug by including on the drug several copies of a small tissue-targeting peptide). It would be ideal to have a drug technology or format that allowed these multiple functions and different types of bioactive moieties (protein, oligonucleotide, small molecule, lipid, etc.) to be integrated into a single, adaptable, multi-functional drug that is a practical best-of-breed and straightforward in its design, implementation, manufacturing, and administration. In addition, the technology should allow for certain of the bioactive moieties to be unstably attached such that they can be released under the desired conditions (time, aqueous pH environment, other). These drugs should demonstrate higher efficacy and safety while providing a higher overall probability of technical, regulatory, and commercial success from early in the drug development process.

Most diseases are complex and multifactorial in origin. Therefore, in applying this biology-centric or disease-centric approach, one could imagine a future ten or fifteen years down the road where a big disease such as rheumatoid arthritis is actually divided through diagnostic (molecular, imaging, biomarker, genetic) or other approaches into, say, ten major subtypes each of which is driven by a particular set of pathophysiologies and which can be targeted using one multi-functional drug such that ten multi-functional drugs are developed in order to treat the ten different disease types.

The present invention describes such a drug technology format that can be the backbone of the next-generation of multi-functional drug development. The technology delivers a polymer backbone which (i) itself delivers fundamental biocompatibility to the drug through the selection of hydrophilic monomer and architecture, and (ii) also forms a core backbone or scaffold for conjugation and/or adsorption to multiple agents of different types (amino acid, small molecule, oligonucleotide, lipid, other, diagnostic agent, imaging agent, therapy monitoring agent), predefined stoichiometries and functions (biocompatibility, spacer, bioactivity, targeting, diagnostic, imaging, other), and (iii) can employ any stable or flexible (under predefined conditions) conjugation linker and chemistries.

Hydrophilic polymers for drug conjugation have been well described and the drug conjugates are generating in excess of $5 billion revenue per annum. What is important for these polymers is the extent to which they bind water molecules and the physical properties of those water binding interactions. This combination of properties drives the fundamental biocompatibility of the polymer. PEG is one example of a hydrophilic polymer, but there are other examples of hydrophilic polymers that bind water to a different extent and with different physical properties and therefore with different fundamental biocompatibility. One such example is phosphorylcholine-based polymers, specifically polymers derived from 2-methacryloyloxyethyl phosphorylcholine, which polymers have been commercialized in various forms in medical devices such as coronary drug eluting stents and contact lenses. In recent years, new methods of controlled radical polymerization have been developed with the promise to enable the manufacture of large, complex-architecture polymers with low cost and high quality.

The present invention integrates a drug technology and format that allows for a new paradigm of drug development, starting with a set of biologies driving disease pathophysiology; integrating biocompatibility moieties, drug moieties of different classes, extended architectures, flexible chemistries, all in a practical package. More simply put, the present invention presents a drug format that allows the user to create a nanoscale biomachine with the goal of creating magic bullets for combating diseases to the benefit of patients.

Efforts to formulate biologically active agents for delivery must deal with a variety of variables including the route of administration, the biological stability of the active agent and the solubility of the active agents in physiologically compatible media. Choices made in formulating biologically active agents and the selected routes of administration can affect the bioavailability of the active agents. For example, the choice of parenteral administration into the systemic circulation for biologically active proteins and polypeptides avoids the proteolytic environment found in the gastrointestinal tract. However, even where direct administration, such as by injection, of biologically active agents is possible, formulations may be unsatisfactory for a variety of reasons including the generation of an immune response to the administered agent and responses to any excipients including burning and stinging. Even if the active agent is not immunogenic and satisfactory excipients can be employed, biologically active agents can have a limited solubility and short biological half-life that can require repeated administration or continuous infusion, which can be painful and/or inconvenient.

For some biologically active agents a degree of success has been achieved in developing suitable formulations of functional agents by conjugating the agents to water soluble polymers. The conjugation of biologically active agents to water soluble polymers is generally viewed as providing a variety of benefits for the delivery of biologically active agents, and in particular, proteins and peptides. Among the water soluble polymers employed, polyethylene glycol (PEG) has been most widely conjugated to a variety of biologically active agents including biologically active peptides. A reduction in immunogenicity or antigenicity, increased half-life, increased solubility, decreased clearance by the kidney and decreased enzymatic degradation have been attributed to conjugates of a variety of water soluble polymers and functional agents, including PEG conjugates. As a result of these attributes, the polymer conjugates of biologically active agents require less frequent dosing and may permit the use of less of the active agent to achieve a therapeutic endpoint. Less frequent dosing reduces the overall number of injections, which can be painful and which require inconvenient visits to healthcare professionals. Conjugation of PEG or other polymers can also modify the core activity of the drug itself—the idea of "additional bioactivities conferred to the drug by virtue of polymer conjugation (for example, the large hydrodynamic radius broadens the scope of inhibition from drug (antibody fragment) inhibits binding to receptor A but polymer-drug conjugate inhibits binding to receptor A plus receptor B as a function of any number of different mechanisms but certainly steric hindrance.

Although some success has been achieved with PEG conjugation, "PEGylation" of biologically active agents remains a challenge. As drug developers progress beyond very potent agonistic proteins such as erythropoietin and the various interferons, the benefits of the PEG hydrophilic polymer are insufficient to drive the increases in solubility, stability and the decreases in viscosity and immunogenicity that are necessary for a commercially successful product that is subcutaneously administered. PEG conjugation may also result in the loss of biological activity. A variety of theories have been advanced to account for loss of biological activity upon conjugation with PEG. These include blockage of necessary sites for the agent to interact with other biological components, either by the conjugation linkage or by the agent being buried within the PEG conjugate, particularly where the polymer is long and may "wrap" itself around some of the active agent, thereby blocking access to potential ligands required for activity.

Branched forms of PEG for use in conjugate preparation have been introduced to alleviate some of the difficulties encountered with the use of long straight PEG polymer chains. While branched polymers may overcome some of the problems associated with conjugates formed with long linear PEG polymers, neither branched nor linear PEG polymer conjugates completely resolve the issues associated with the use of conjugated functional agents. Both linear and branched PEG conjugates can, for example, suffer from rates of degradation that are either too long or too short. A rapid rate of degradation can result in a conjugate having too short of an in vivo half-life, whereas, too slow of a rate of degradation can result in an unacceptably long conjugate half-life in vivo.

In view of the recognized advantages of conjugating functional agents to water soluble polymers, and the limitations of water soluble polymers such as PEG in forming conjugates suitable for therapeutic purposes, additional water soluble polymers for forming conjugates with functional agents are desirable. Water soluble polymers, particularly those which have many of the advantages of PEG for use in conjugate formation, and which do not suffer from the disadvantages observed with PEG as a conjugating agent would be desirable for use in forming therapeutic and diagnostic agents. To this end, polymers containing zwitterionic monomers, in particular, 2-methacryloyloxyethyl-phosphorylcholine are set forth for use in preparing conjugates of biologically active agents.

BRIEF SUMMARY OF THE INVENTION

In one embodiment, the random copolymers of the present invention have formula I:

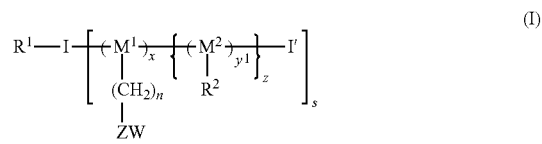

Each monomer $M^1$ and $M^2$ of formula I can independently be an acrylate, methacrylate, acrylamide, methacrylamide, styrene, vinyl-pyridine or a vinyl-pyrrolidone. Moreover, $R^1$ of formula I can independently be H, $L^1$-$A^1$, a linking group $LG^1$ or $L^1$-$LG^1$, and each $R^2$ of formula I is independently H, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, heteroaryl, $A^2$, $L^2$-$A^2$, $LG^2$, $L^2$-$LG^2$, $I^2$ and $L^2$-$I^2$. The group ZW of formula I is a zwitterionic moiety. The groups I is an initiator fragment and I' is a radical scavenger, such that the combination of I-I' is an initiator, $I^1$, for the polymerization of the random copolymer of Formula I. Alternatively, I' can be H or $C_{1-6}$ alkyl. The group $I^2$ is an initiator. In addition, each of the groups $L^1$ and $L^2$ is a linker, each of the groups $A^1$ and $A^2$ is a functional agent, and each of the groups $LG^1$ and $LG^2$ is a linking group. In formula I above, subscripts x and $y^1$ are each independently an integer of from 1 to 1000, subscript z is an integer of from 1 to 10, subscript s is an integer of from 1 to 100, and subscript n is an integer of from 1 to 20, wherein either $R^1$ is $L^1$-$A^1$ or one of $R^2$ is $L^2$-$A^2$.

In other embodiments, the present invention provides a process for preparing a random copolymer of the present invention, the process including the step of contacting a mixture of a first monomer and a second monomer with an initiator, $I^1$, under conditions sufficient to prepare a random copolymer via free radical polymerization, wherein the first monomer comprises a phosphorylcholine, and each of the second monomer and initiator independently comprise at least one of a functional agent or a linking group for linking to the functional agent.

In another embodiment, the random copolymers of the present invention have a first monomer with a zwitterion such as phosphorylcholine, at least one second monomer having a functional agent or a linking group, and an initiator moiety having a functional agent or a linking group, wherein the functional agent is linked to the second monomer or the initiator moiety via a linker.

In another embodiment, the random copolymers of the present invention have a first monomer with a zwitterion such as phosphorylcholine, at least one second monomer having a functional agent or a linking group, said second monomer having a different reactivity ratio than the first monomer allowing the final polymer to be an alternating copolymer, a periodic copolymer, a gradient copolymer, a block copolymer or a statistical copolymer.

In another embodiment, the random copolymers of the present invention have a first monomer with a zwitterion such as phosphorylcholine, at least one second monomer having a functional agent and a tunable linking group, said second monomer having the same reactivity ratio as the first monomer allowing the final polymer to be an alternating copolymer, a periodic copolymer, a gradient copolymer, a block copolymer or a statistical copolymer.

In another embodiment, the random copolymers of the present invention have a first monomer with a zwitterion such as phosphorylcholine, at least one second monomer having a functional agent or a linking group and other monomers that have differing environment affinities allowing for the formation of new topologies by non-covalent binding.

In another embodiment, the random copolymers of the present invention have a first monomer with a zwitterion such as phosphorylcholine, at least one second monomer having a functional agent and a tunable linking group and other monomers that have differing environment affinities allowing for the formation of new topologies by non-covalent binding.

In another embodiment, the random copolymers of the present invention have a first monomer with a zwitterion such as phosphorylcholine, at least one second monomer having a functional agent or a linking group and other monomers of similar environment affinities allows for the formation of new topologies by non-covalent binding (e.g. chelation between carboxylic groups in aqueous environments, or pH sensitive groups).

In another embodiment, the random copolymers of the present invention have a first monomer with a zwitterion such as phosphorylcholine, at least one second monomer having a functional agent and a tunable linking group allowing for the formation of new topologies by non-covalent binding (e.g. chelation between carboxylic groups in aqueous environments, or pH sensitive groups).

In another embodiment, the random copolymers of the present invention have a first monomer with a zwitterion such as phosphorylcholine, at least one second monomer having a tunable linking group allowing for the release of functional agents in response to predefined triggers such as aqueous environments or low pH environments.

BRIEF DESCRIPTION OF THE DRAWINGS

FIG. 1 shows a scheme for the preparation of the random copolymers of the present invention. The initiator I-I' is cleaved into initiator fragment I and radical scavenger I'. The initiator fragment I then reacts with comonomers $M^1$ and $M^2$ to initiate the polymerization process and generate species A. The radical scavenger I' can then reversibly react with species A to form species B. Alternatively, species A can react with additional monomers to continue propagation of the polymer (species C). Concomitantly, the growing polymer chain of species C reversibly reacts with radical scavenger I' to form the random copolymer, species D.

DETAILED DESCRIPTION OF THE INVENTION

I. General

The present invention provides random copolymers having a zwitterion such as phosphorylcholine, and at least one functional agent (as defined herein). A zwitterion such as phosphorylcholine as a highly biocompatible molecule drives fundamental biocompatibility. It also has chaperone type functions, in terms of protecting proteins under temperature or other stress. It also can allow other functions such as reversible cellular uptake. The functional agent can be a bioactive agent such as a drug, therapeutic protein or targeting agent, as well as a detection agent, imaging agent, labeling agent or diagnostic agent. The random copolymers are useful for the treatment of a variety of conditions and disease states by selecting one or more appropriate functional agents. Multiple bioactive agents can be linked to the random copolymer, thus enabling treatment of not just a single disease symptom or mechanism, but rather the whole disease. Furthermore, the bioactive agents can be linked via non-cleavable linkers in a stable manner, or via a variety of cleavable linkers such that different predefined triggers release the respective bioactive agents through the use of prodrug or double prodrug linker and linking group strategies. In addition, the random copolymers are useful for diagnostic and imaging purposes by attachment of suitable targeting agents and imaging agents. The random copolymers can include both therapeutic and diagnostic agents in a single polymer, providing theranostic agents that treat the disease as well as detect and diagnose.

The random polymers can be prepared via a conventional free-radical polymerization or controlled/living radical polymerization, such as atom transfer radical polymerization (ATRP), using monomers that contain the zwitterion such as phosphorylcholine and monomers that contain one or more bioactive agents which may be the same or different, or linking groups that are able to link to the bioactive agents. The initiators used for preparation of the random copolymers can have multiple initiating sites such that multi-arm polymers, such as stars, can be prepared. The initiator can also contain either a bioactive agent, or linking groups, or flexible chemistries that are able to link to bioactive agents.

II. Definitions

For the purpose of the present invention the following terminology will be used in accordance with the definitions set forth below.

"Random copolymer" refers to a polymer having at least two different monomer groups that are distributed randomly throughout the polymer backbone. The monomers of the random copolymer are the chemical moieties that are bonded together to form the polymer. Each distinct chemical moiety is termed a monomer. The random copolymers are prepared from monomers that include, but are not limited to, acrylates, methacrylates, acrylamides, methacrylamides, styrenes, vinyl-pyridine and vinyl-pyrrolidone. Additional monomers are useful in the random copolymers of the present invention. When two different monomers are used, such as in the random copolymers of the present invention, the two monomers are called "comonomers," meaning that the different monomers are copolymerized to form a single polymer.

"Zwitterionic moiety" refers to a compound having both a positive and a negative charge. Zwitterionic moieties useful in the random copolymers can include a quaternary nitrogen and a negatively charged phosphate, such as phosphorylcholine: $RO-P(=O)(O^-)-O-CH_2CH_2-N^+(Me)_3$. Other zwitterionic moieties are useful in the random copolymers of the present invention, and Patents WO 1994/016748 and WO 1994/016749 are incorporated in their entirety herein.

"Initiator" refers to a compound capable of initiating a polymerization using the comonomers of the present invention. The polymerization can be a conventional free radical polymerization or a controlled/living radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. When the initiator is suitable for ATRP, it contains a labile bond which can homolytically cleave to form an initiator fragment, I, being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile.

"Linker" refers to a chemical moiety that links two groups together. The linker can be cleavable or non-cleavable. Cleavable linkers can be hydrolyzable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Nonlimiting examples include those illustrated in Table 1.

"Hydrolyzable linker" refers to a chemical linkage or bond, such as a covalent bond, that undergoes hydrolysis under physiological conditions. The tendency of a bond to hydrolyze may depend not only on the general type of linkage connecting two central atoms between which the bond is severed, but also on the substituents attached to these central atoms. Non-limiting examples of hydrolytically susceptible linkages include esters of carboxylic acids, phosphate esters, acetals, ketals, acyloxyalkyl ether, imines, orthoesters, and some amide linkages.

"Enzymatically cleavable linker" refers to a linkage that is subject to degradation by one or more enzymes. Some hydrolytically susceptible linkages may also be enzymatically degradable. For example esterases may act on esters of carboxylic acid or phosphate esters, and proteases may act on peptide bonds and some amide linkages.

"pH sensitive linker" refers to a linkage that is stable at one pH and subject to degradation at another pH. For example, the pH sensitive linker can be stable at neutral or basic conditions, but labile at mildly acidic conditions.

"Photolabile linker" refers to a linkage, such as a covalent bond, that cleaves upon exposure to light. The photolabile linker includes an aromatic moiety in order to absorb the incoming light, which then triggers a rearrangement of the bonds in order to cleave the two groups linked by the photolabile linker.

"Self-immolative or double prodrug linker" refers to a linkage in which the main function of the linker is to release a functional agent only after selective trigger activation (for example, a drop in pH or the presence of a tissue-specific enzyme) followed by spontaneous chemical breakdown to release the functional agent.

"Functional agent" is defined to include a bioactive agent or a diagnostic agent. A "bioactive agent" is defined to include any agent, drug, compound, or mixture thereof that targets a specific biological location (targeting agent) and/or provides some local or systemic physiological or pharmacologic effect that can be demonstrated in vivo or in vitro. Non-limiting examples include drugs, vaccines, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, DNA, cDNA, antisense constructs, ribozymes, etc). A "diagnostic agent" is defined to include any agent that enables the detection or imaging of a tissue or disease. Examples of diagnostic agents include, but are not limited to, radiolabels, fluorophores and dyes.

"Therapeutic protein" refers to peptides or proteins that include an amino acid sequence which in whole or in part makes up a drug and can be used in human or animal pharmaceutical applications. Numerous therapeutic proteins are known to practitioners of skill in the art including, without limitation, those disclosed herein.

"Phosphorylcholine," also denoted as "PC," refers to the following:

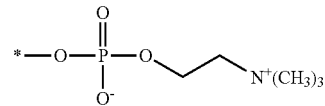

where * denotes the point of attachment. The phosphorylcholine is a zwitterionic group and includes salts (such as inner salts), and protonated and deprotonated forms thereof.

"Phosphorylcholine containing polymer" is a polymer that contains phosphorylcholine. It is specifically contemplated that in each instance where a phosphorylcholine containing polymer is specified in this application for a particular use, a single phosphorylcholine can also be employed in such use. "Zwitterion containing polymer" refers to a polymer that contains a zwitterion.

"Poly(acryloyloxyethyl phosphorylcholine) containing polymer" refers to a polymer of acrylic acid containing at least one acryloyloxyethyl phosphorylcholine monomer such as 2-methacryloyloxyethyl phosphorylcholine (i.e., 2-methacryloyl-2'-trimethylammonium ethyl phosphate).

"Contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

"Water-soluble polymer" refers to a polymer that is soluble in water. A solution of a water-soluble polymer may transmit at least about 75%, more preferably at least about 95% of light, transmitted by the same solution after filtering. On a weight basis, a water-soluble polymer or segment thereof may be at least about 35%, at least about 50%, about 70%, about 85%, about 95% or 100% (by weight of dry polymer) soluble in water.

"Molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average, weight average and peak, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. The polymeric reagents of the invention are typically polydisperse (i.e., number average molecular weight and weight average molecular weight of the polymers are not equal), possessing low polydispersity values of preferably less than about 1.5, as judged by gel permeation chromatography. In other embodiments the polydispersities may be in the range of about 1.4 to about 1.2, more preferably less than about 1.15, still more preferably less than about 1.10, yet still more preferably less than about 1.05, and most preferably less than about 1.03.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

"About" as used herein means variation one might see in measurements taken among different instruments, samples, and sample preparations.

"Protected,", "protected form", "protecting group" and "protective group" refer to the presence of a group (i.e., the protecting group) that prevents or blocks reaction of a particular chemically reactive functional group in a molecule under certain reaction conditions. Protecting group will vary depending upon the type of chemically reactive group being protected as well as the reaction conditions to be employed and the presence of additional reactive or protecting groups in the molecule, if any. The skilled artisan will recognize protecting groups known in the art, such as those found in the treatise by Greene et al., "Protective Groups In Organic Synthesis," 3$^{rd}$ Edition, John Wiley and Sons, Inc., New York, 1999.

"Spacer," and "spacer group" are used interchangeably herein to refer to an atom or a collection of atoms optionally used to link interconnecting moieties such as a terminus of a water-soluble polymer and a reactive group of a functional agent and a reactive group. A spacer may be hydrolytically stable or may include a hydrolytically susceptible or enzymatically degradable linkage.

"Alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2m'+1), where m' is the total number of carbon atoms in such radical. R', R" and R''' each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —$NO_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

"Alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

"Carboxyalkyl" means an alkyl group (as defined herein) substituted with a carboxy group. The term "carboxycycloalkyl" means an cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

"Haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

"Fluoro-substituted alkyl" refers to an alkyl group where one, some, or all hydrogen atoms have been replaced by fluorine.

"Cytokine" in the context of this invention is a member of a group of protein signaling molecules that may participate in cell-cell communication in immune and inflammatory responses. Cytokines are typically small, water-soluble glycoproteins that have a mass of about 8-35 kDa.

"Cycloalkyl" refers to a cyclic hydrocarbon group that contains from about 3 to 12, from 3 to 10, or from 3 to 7 endocyclic carbon atoms. Cycloalkyl groups include fused, bridged and Spiro ring structures.

"Endocyclic" refers to an atom or group of atoms which comprise part of a cyclic ring structure.

"Exocyclic" refers to an atom or group of atoms which are attached but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocycloalkylene" refers to a heterocyclalkyl group, as defined above, linking at least two other groups. The two moieties linked to the heterocycloalkylene can be linked to the same atom or different atoms of the heterocycloalkylene.

"Aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR' C(NH$_2$)=NH, —NH—C(NH$_2$)=NR', —S(O)R', —S(O)$_2$R', —S(O)$_2$NR' R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazol yl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers, alkyl-amines and alkyl-thiols.

As used herein, the term "heteroalkylene" refers to a heteroalkyl group, as defined above, linking at least two other groups. The two moieties linked to the heteroalkylene can be linked to the same atom or different atoms of the heteroalkylene.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Maleimido" refers to a pyrrole-2,5-dione-1-yl group having the structure:

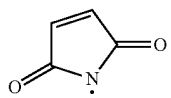

which upon reaction with a sulfhydryl (e.g., a thio alkyl) forms an —S-maleimido group having the structure

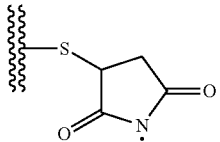

where "●" indicates the point of attachment for the maleimido group and "⌇" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer having a single monomer derived backbone.

"Branched," in reference to the geometry, architecture or overall structure of a polymer, refers to polymer having 2 or more polymer "arms" extending from a single group, such as an L group that may be derived from an initiator employed in an atom transfer radical polymerization reaction. A branched polymer may possess 2 polymer arms, 3 polymer arms, 4 polymer arms, 5 polymer arms, 6 polymer arms, 7 polymer arms, 8 polymer arms or more. For the purpose of this disclosure, compounds having three or more polymer arms extending from a single linear group are denoted as having a "comb" structure or "comb" architecture. Branched can also be achieved through "statistical" structures to create broader dendrimer-like architectures.

"Pharmaceutically acceptable" composition or "pharmaceutical composition" refers to a composition comprising a compound of the invention and a pharmaceutically acceptable excipient or pharmaceutically acceptable excipients.

"Pharmaceutically acceptable excipient" and "pharmaceutically acceptable carrier" refer to an excipient that can be included in the compositions of the invention and that causes no significant adverse toxicological effect on the patient. Non-limiting examples of pharmaceutically acceptable excipients include water, NaCl, normal saline solutions, lactated Ringer's, normal sucrose, normal glucose and the like.

"Patient" or "subject in need thereof" refers to a living organism suffering from or prone to a condition that can be prevented or treated by administration of a pharmaceutical composition as provided herein. Non-limiting examples include humans, other mammals and other non-mammalian animals.

"Therapeutically effective amount" refers to an amount of a conjugated functional agent or of a pharmaceutical composition useful for treating, ameliorating, or preventing an identified disease or condition, or for exhibiting a detectable therapeutic or inhibitory effect. The effect can be detected by any assay method known in the art.

The "biological half-life" of a substance is a pharmacokinetic parameter which specifies the time required for one half of the substance to be removed from an organism following introduction of the substance into the organism.

III. Zwitterion-Containing Random Copolymers

The present invention provides random copolymers having zwitterionic groups, such as phosphorylcholine, and at least one functional agent. In some embodiments, the random copolymers of the present invention have a first monomer with phosphorylcholine, at least one second monomer having a functional agent or a linking group, and an initiator moiety having a functional agent or a linking group, wherein the functional agent can be linked to the second monomer or the initiator moiety via a linker.

In other embodiments, the random copolymers of the present invention have formula I:

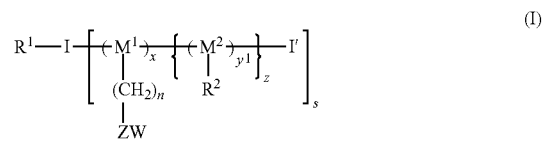

In formula I, the monomer units $M^1$ and $M^2$ are any monomers suitable for polymerization via controlled free radical methods, such as atom-transfer radical polymerization (ATRP). Each of monomers $M^1$ and $M^2$ can have any suitable number of comonomers in the random copolymer, as defined by radicals x and $y^1$, respectively. The $M^1$ monomer is linked to a zwitterionic group ZW, such as phosphorylcholine, via an alkylene chain (as defined by radical n). The random copolymers can include a single comonomer $M^2$ (radical z is 1), or can include several comonomers $M^2$ (z is greater than 1) wherein the different comonomers $M^2$ are the same or different. The comonomers $M^2$ are each linked to an $R^2$ group that can be inert but modifies the properties of the random copolymer (such as alkyl, aryl, etc.), or the $R^2$ groups can be functional such as when the $R^2$ group includes a functional agent A, a linking group LG or an initiator I. When the $R^2$ group includes one of these functional groups, the functional group can optionally be linked to the comonomer $M^2$ via a linker L. The $R^2$ groups can include a variety of functional groups and inert groups to tune the properties and functionality of the random copolymer. For example, several different targeting agents can be included along with several different drugs or therapeutic proteins as functional agents A. The monomers $M^1$ and $M^2$ can be polymerized by an initiator, I-I', that can be cleaved into initiator fragment I and radical scavenger I'. The initiator fragment I can be any group that initiates the polymerization. The radical scavenger I' can be any group that will reversibly terminate the growing polymer chain. The radical scavenger I' can be a halogen such as bromine, allowing the end of the polymer to be functionalized after polymerization. In addition, the initiator fragment I can be (but does not need to be) functionalized with an $R^1$ group that can include a variety of functional groups to tune the functionality of the random copolymer. For example, the $R^1$ group can include a functional agent A or a linking group LG, each optionally linked to initiator fragment I via a linker L. Moreover, the initiator fragment I can have multiple initiating sites such that the product polymer has several polymer arms (radical s greater than 1).

In some embodiments, each monomer $M^1$ and $M^2$ of formula I can independently be an acrylate, methacrylate, acrylamide, methacrylamide, styrene, vinyl-pyridine or a vinyl-pyrrolidone. Moreover, R' of formula I can independently be H, $L^1$-$A^1$, a linking group $LG^1$ or $L^1$-$LG^1$, and each $R^2$ of formula I is independently H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, heteroaryl, $A^2$, $L^2$-$A^2$, $LG^2$, $L^2$-$LG^2$, $I^2$ and $L^2$-$I^2$. The group ZW of formula I is a zwitterionic moiety. The groups I and I' of formula I can each independently be an initiator fragment, such that the combination of I-I' is an initiator, $I^t$, for the polymerization of the random copolymer of formula I. Alternatively, I' can be H or $C_{1-6}$ alkyl. The group $I^2$ is an initiator. In addition, each of the groups $L^1$ and $L^2$ is a linker, each of the groups $A^1$ and $A^2$ is a functional agent, and each of the groups $LG^1$ and $LG^2$ is a linking group. In formula I above, subscripts x and $y^1$ are each independently an integer of from 1 to 1000, subscript z is an integer of from 1 to 10, subscript s is an integer of from 1 to 100, and subscript n is an integer of from 1 to 20, wherein either $R^1$ is $L^1$-$A^1$ or one of $R^2$ is $L^2$-$A^2$.

The random copolymers of the present invention can have any suitable number of repeat units for each of the monomers $M^1$ and $M^2$. Exemplary ranges of repeat units for each comonomer include, but are not limited to, from about 1 to about 10,000, from about 10 to about 5,000, from about 10 to about 2,000, from about 10 to about 1,500, from about 10 to about 1,000, from about 100 to about 1,000, from about 100 to about 900, from about 100 to about 800, from about 100, to about 700, from about 100 to about 600, and from about 100 to about 500. When multiple $M^2$ monomers are present, each $M^2$ monomer can have a different number of repeat units.

The random copolymers of the present invention can have any suitable molecular weight. Exemplary molecular weights for the random copolymers of the present invention can be from about 1000 to about 1,500,000 Daltons (Da). In some embodiments, the random copolymers of the present invention can have a molecular weight of about 5,000 Daltons, about 10,000 Daltons, about 25,000 Daltons, about 50,000 Daltons, about 75,000 Daltons, about 100,000 Daltons, about 150,000 Daltons, about 200,000 Daltons, about 250,000 Daltons, about 300,000 Daltons, about 350,000 Daltons, about 400,000 Daltons, about 450,000 Daltons, about 500,000 Daltons, about 550,000 Daltons, about 600,000 Daltons, about 650,000 Daltons, about 700,000 Daltons, about 750,000 Daltons, about 800,000 Daltons, about 850,000 Daltons, about 900,000 Daltons, about 950,000 Daltons, about 1,000,000 Daltons and about 1,250,000 Daltons.

The random copolymers of the present invention can also have any suitable number of comonomers, $M^2$. For example, the number of comonomers, subscript z, can be from 1 to 10, such as 1, 2, 3, 4, 5, 6, 7, 8, 9 or 10. The number of comonomers, subscript z, can also be from 1 to 5, 1 to 4, 1 to 3, or 1 to 2. In some embodiments, the random copolymer of the present invention can have two different monomers where subscript z is 1, such as in formula II:

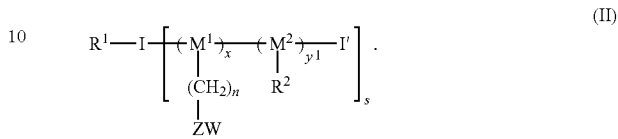

In other embodiments, the random copolymer can have 3 different monomers where subscript z is 2, such as in formula III:

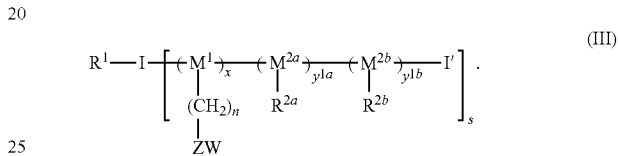

Additional comonomers $M^2$ can be present in the random copolymers of the present invention, such as $M^{2c}$, $M^{2d}$, $M^{2e}$, $M^{2f}$, $M^{2g}$, $M^{2h}$, etc., where each comonomer is present in a same or different $y^1$ value, and each comonomer having a corresponding $R^2$ group attached, $R^{2c}$, $R^{2d}$, $R^{2e}$, $R^{2f}$, $R^{2g}$, $R^{2h}$, etc., respectively. Each $M^2$ group, such as $M^{2a}$, $M^{2b}$, $M^{2c}$, etc., can be as defined above for $M^2$. Each $R^2$ group, such as $R^{2a}$, $R^{2b}$, $R^{2c}$, etc., can be as defined above for $R^2$. Similarly, each $y^1$ group, such as $y^{1a}$, $y^{1b}$, $y^{1c}$, etc., can be as defined above for $y^1$.

In some embodiments, the random copolymer can be of formula III, wherein $R^{2a}$ and $R^{2b}$ are each independently H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, heteroaryl, $A^2$, $L^2$-$A^2$, $LG^2$, or $L^2$ $LG^2$; $M^{2a}$ and $M^{2b}$ are each independently acrylate, methacrylate, acrylamide, methacrylamide, styrene, vinyl-pyridine or vinyl-pyrrolidone; and subscripts $y^{1a}$ and $y^{1b}$ are each independently an integer of from 1 to 1000.

The different monomers of the random copolymers can also be present in any suitable ratio. For example, the $M^2$ monomers, collectively or individually, can be present relative to the $M^1$ monomer in a ratio of 100:1, 50:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:40, 1:50 and 1:100. In addition, each $M^2$ monomer can be present in any suitable ratio relative to the $M^1$ or any other $M^2$ monomer, such as 100:1, 50:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:40, 1:50 and 1:100.

The random copolymers of the present invention can have any suitable architecture. For example, the random copolymers can be linear or branched. When the random copolymers are branched, they can have any suitable number of copolymer arms, as defined by subscript s of formula I, such as 2, 3, 4, 5, 6, 7, 8, 9, 10, 20, 30, 40, 50, 60, 70, 80, 90 and up to 100 arms. In some embodiments, subscript s can be from 1 to 20, 1 to 15, 1 to 10, 1 to 9, 1 to 8, 1 to 7, 1 to 6, 1 to 5, 1 to 4, 1 to 3 or 1 to 2. The random copolymers of the present invention can adopt any suitable architecture.

For example, the random copolymers can be linear, branched, stars, dendrimers, dendrigrafts, combs, etc.

A functional agent of the random copolymers can be linked to either one of the comonomers $M^2$, or to the initiator fragment I, or both. When multiple functional agents are present, a functional agent can be linked to both the comonomer $M^2$ and the initiator fragment I. In some embodiments, the random copolymer has formula IIa:

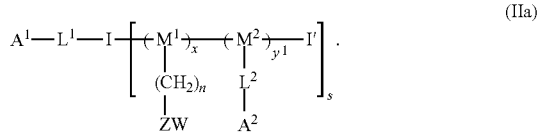
(IIa)

In formula IIa, functional agent $A^1$ can be a drug or therapeutic protein and functional agent $A^2$ can be a targeting agent. Alternatively, functional agent $A^1$ can be a targeting agent and functional agent $A^2$ can be a drug or therapeutic protein. Furthermore, functional agents $A^1$ and $A^2$ can both be therapeutic agents. Functional agents can be chosen to inhibit (or activate) distinct targets in the same molecular pathway, provide inhibition (or activation) of both a primary and compensatory pathway, or inhibit (or activate) the same target at different binding sites to decrease resistance or allow use of lower doses to minimize toxicity. Moreover, the linkers $L^1$ and $L^2$ can be the same or different. For example, linker $L^1$ can be a cleavable linker, such as when attached to a drug or therapeutic protein to facilitate release of the drug or therapeutic protein, while linker $L^2$ can be a non-cleavable linker, such as when attached to a targeting agent. Furthermore, linker $L^1$ can be a non-cleavable linker, while linker $L^2$ can be a cleavable linker. Alternatively, both linkers $L^1$ and $L^2$ can be cleavable linkers or non-cleavable linkers. In addition, the linker attached to the targeting agent can also be a cleavable linker. Alternatively, one or both of $L^1$ and $L^2$ can be self-immolative or double prodrug linkers.

When multiple comonomers $M^2$ are present, each comonomer $M^2$ can have a different functional agent attached. For example, the random copolymer can have formula

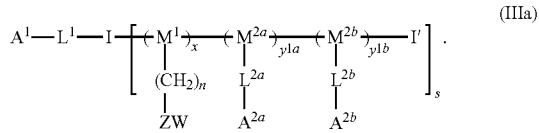
(IIIa)

When multiple comonomers $M^2$ are present, each comonomer $M^2$ can have a different functional agent attached. For example, the random copolymer can have formula IIIa:

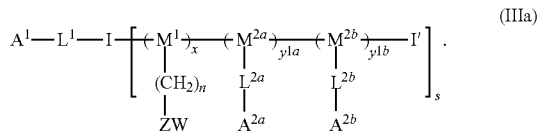
(IIIa)

In formula IIIa, $M^{2a}$ and $M^{2b}$ can be as defined above for $M^2$; $A^{2a}$ and $A^{2b}$ can be as defined above for $A^2$; $L^{2a}$ and $L^{2b}$ can be as defined above for $L^2$; and $y^{1a}$ and $y^{1b}$ can be as defined above for $y^1$. In some embodiments, each of $L^{2a}$ and $L^{2b}$ is a linker; and each of $A^{2a}$ and $A^{2b}$ is a functional agent.

Functional agents $A^{2a}$ and $A^{2b}$ can be the same or different in formula IIIa. Functional agent $A^{2a}$ can be a drug or therapeutic protein and functional agent $A^{2b}$ can be a targeting agent. Alternatively, functional agents $A^{2a}$ and $A^{2b}$ can both be targeting agents, and functional agent $A^1$ can be the drug or therapeutic agent. The functional agents $A^{2a}$ and $A^{2b}$ can also both be a drug or therapeutic agent, while functional agent $A^1$ is the targeting agent. When functional agents $A^{2a}$ and $A^{2b}$ are both a drug or therapeutic agent, each functional agent $A^{2a}$ and $A^{2b}$ can be a different drug or therapeutic agent. In addition, one of functional agents $A^{2a}$ and $A^{2b}$ can be a drug or therapeutic agent and the other can be a targeting agent, where functional agent $A^1$ can be any functional agent.

As described above for formula IIa, the linkers $L^1$, $L^{2a}$ and $L^{2b}$ of formula IIIa can be the same or different. For example, linker $L^1$ can be a cleavable linker when attached to a drug or therapeutic agent to facilitate release of the drug or therapeutic agent, while linkers $L^{2a}$ and $L^{2b}$ can be non-cleavable linkers when attached to targeting agents. Alternatively, linker $L^1$ can also be a non-cleavable linker and linkers $L^{2a}$ and $L^{2b}$ can be cleavable linkers. Furthermore, linkers $L^{2a}$ and $L^{2b}$ can be the same or different, such as where one is a cleavable linker and the other is a non-cleavable linker. Linkers $L^{2a}$ and $L^{2b}$ can also be different cleavable linkers, such as when each is attached to a drug, to provide different release rates for the different drugs.

In some embodiments, there is no functional agent linked to the initiator fragment I, such as in formula IIIb:

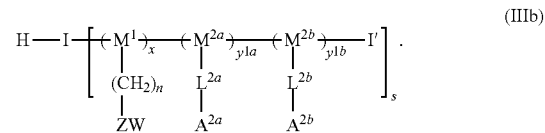
(IIIb)

In formula IIIb, $M^{2a}$ and $M^{2b}$ can be as defined above for $M^2$; $A^{2a}$ and $A^{2b}$ can be as defined above for $A^2$; $L^{2a}$ and $L^{2b}$ can be as defined above for $L^2$; and $y^{1a}$ and $y^{1b}$ can be as defined above for $y^1$. In some embodiments, each of $L^{2a}$ and $L^{2b}$ is a linker; and each of $A^{2a}$ and $A^{2b}$ is a functional agent.

In formula IIIb, functional agents $A^{2a}$ and $A^{2b}$ can be the same or different, as described above, and linkers $L^{2a}$ and $L^{2b}$ can be the same or different. In other embodiments, one of the comonomers $M^2$ can have no functional agent or linking group, such as in formula IIIc:

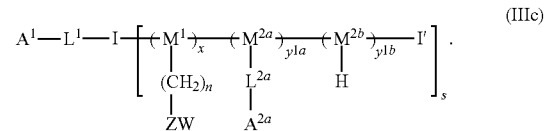
(IIIc)

In formula IIIc, $M^{2a}$ and $M^{2b}$ can be as defined above for $M^2$; $A^{2a}$ can be as defined above for $A^2$; $L^{2a}$ can be as defined above for $L^2$. Similarly, $y^{1a}$ and $y^{1b}$ can be as defined above for $y^1$.

When additional comonomers, $M^2$ are present in the random copolymers of the present invention, the corresponding linkers $L^2$ can be the same or different as linkers $L^1$, $L^{2a}$ and $L^{2b}$, as described above. Moreover, the corresponding functional agents $A^2$ can be the same or different as functional agents $A^1$, $A^{2a}$ and $A^{2b}$, as described above.

In some embodiments, the random copolymers have linking groups LG linked to either or both of the initiator fragment I and the comonomers $M^2$, such as shown in the structures below:

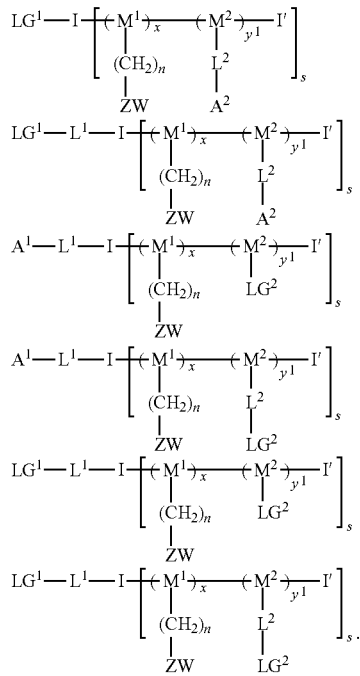

The linking groups $LG^2$ facilitate the "clicking" on or covalent chemical attachment of functional agents and initiator groups following polymerization.

When a plurality of comonomers $M^2$ is present, the comonomers can be linked to either a functional agent or a linking group, for example as shown in the following formula:

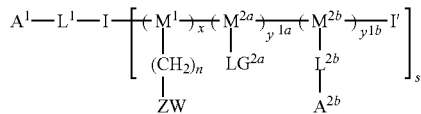

wherein $M^{2a}$ and $M^{2b}$ can be as defined above for $M^2$; $LG^{2a}$ can be as defined above for $LG^2$; $L^{2b}$ can be as defined above for $L^2$; $A^{2b}$ can be as defined above for $A^2$; and $y^{1a}$ and $y^{1b}$ can be as defined above for $y^1$. In addition, the linking group can be present on the initiator fragment I while functional agents $A^2$ are linked to the comonomers $M^2$. Alternatively, when the linking group LG is linked to the initiator fragment I, a second linking group LG can be linked to one of the comonomers $M^2$:

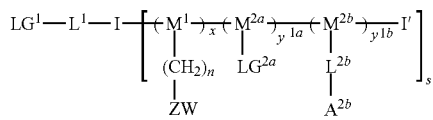

Moreover, a functional agent $A^1$ can be linked to the initiator fragment I while linking groups LG are linked to the comonomers $M^2$, where the linking groups can be the same or different:

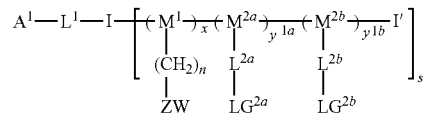

wherein $M^{2a}$ and $M^{2b}$ can be as defined above for $M^2$; $L^{22}$ and $L^{2b}$ can be as defined above for $L^2$; $LG^{2a}$ and $LG^{2b}$ can be as defined above for $LG^2$; and $y^{1a}$ and $y^{1b}$ can be as defined above for $y^1$.

In some embodiments when there are multiple comonomers $M^2$, one of the comonomers $M^2$ can be linked to a group other than a linking group LG, a functional agent A or an initiator I. In other embodiments, at least one $R^2$ group is H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, or heteroaryl. For example, such structures include the following:

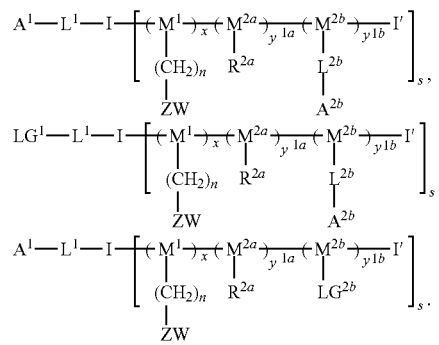

wherein $R^{2a}$ can be H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, or heteroaryl. In other embodiments, $R^{2a}$ can be a species having one or more positive or negative charges, such as aspartic acid, glutamic acid, lysine, histidine, arginine, choline or hyaluronic acid. Other radicals $M^{2a}$, $M^{2b}$, $y^{1a}$, $y^{1b}$, $R^{2a}$ and $LG^{2b}$ can be as defined above.

When $R^2$ of some comonomers $M^2$ is the initiator $I^2$, more complex architectures can be prepared of the random copolymers. For example, comb polymers, hyperbranched polymers, dendrimers, and dendrigrafts can be prepared. When initiator $I^2$ is present on a comonomer $M^2$, polymerization using initiator $I^2$ typically occurs following polymerization using initiator I-I'. In some embodiments, polymerization via I-I' and $I^2$ can be simultaneous. Moreover, the initiator $I^2$ can be linked to the comonomer $M^2$ via a cleavable or non-cleavable linker $L^2$.

In some embodiments, the random copolymers of the present invention can be modified via a subsequent polymerization with one or more additional monomers. For example, in formula III above, monomers $M^1$ and $M^{2a}$ can be copolymerized in a first polymerization, and monomer $M^{2b}$ can be polymerized in a second polymerization. A block copolymer would be formed having two blocks, the first block being a random copolymer of $M^1$ and $M^{2a}$, and the second block a homopolymer of $M^{2b}$. Alternatively, following polymerization of monomers $M^1$ and $M^{2a}$, monomer $M^{2b}$ can be copolymerized with monomer $M^{2c}$, thus forming a block copolymer where the first block is a random copolymer of $M^1$ and $M^{2a}$, and the second block is a random copolymer of $M^{2b}$ and $M^{2c}$. Additional polymer structures can be prepared by copolymerizing monomers $M^1$, $M^{2a}$ and $M^{2b}$ in a first polymerization, followed by copolymerization of monomers $M^{2c}$, $M^{2d}$, and others, in a second copolymerization. Additional blocks can be prepared by yet a third polymerization using additional monomers. Such polymers provide blocks of copolymers that can have different properties, drugs and functional agents.

In other embodiments, the random copolymer has the formula:

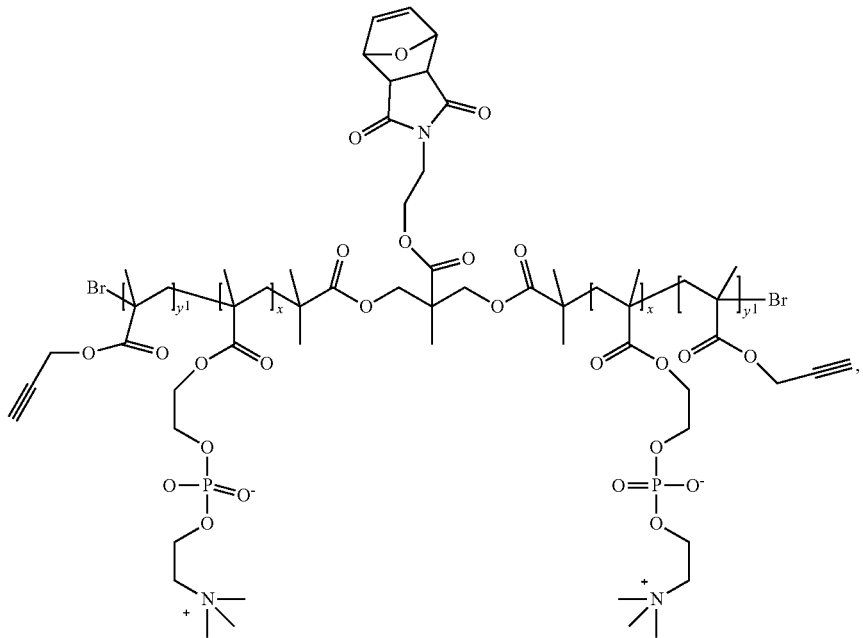

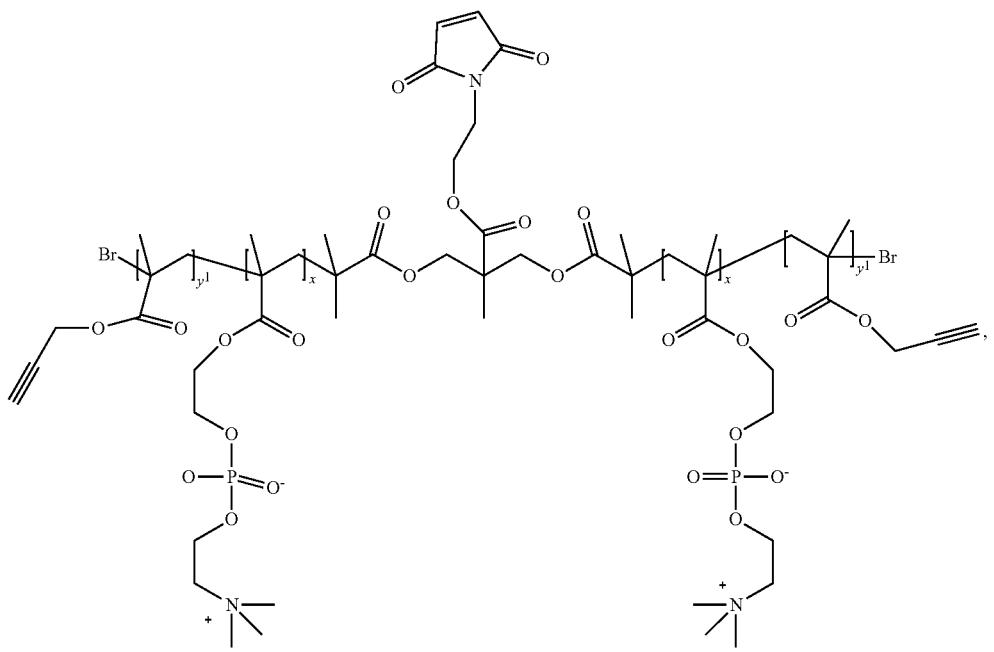

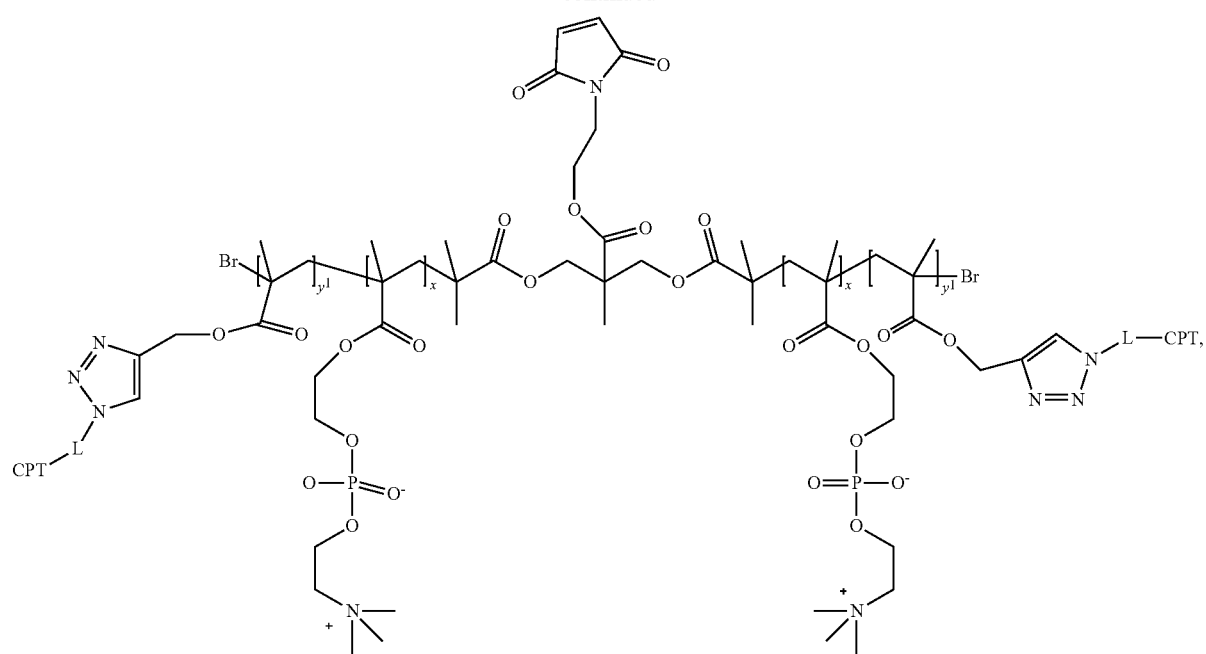
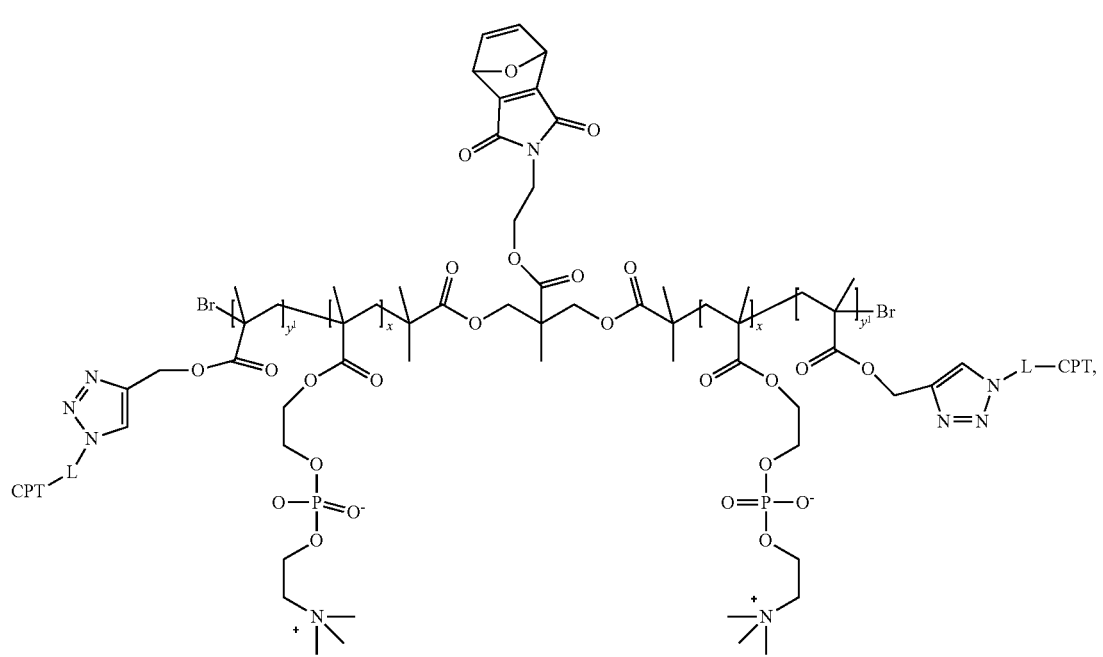

-continued
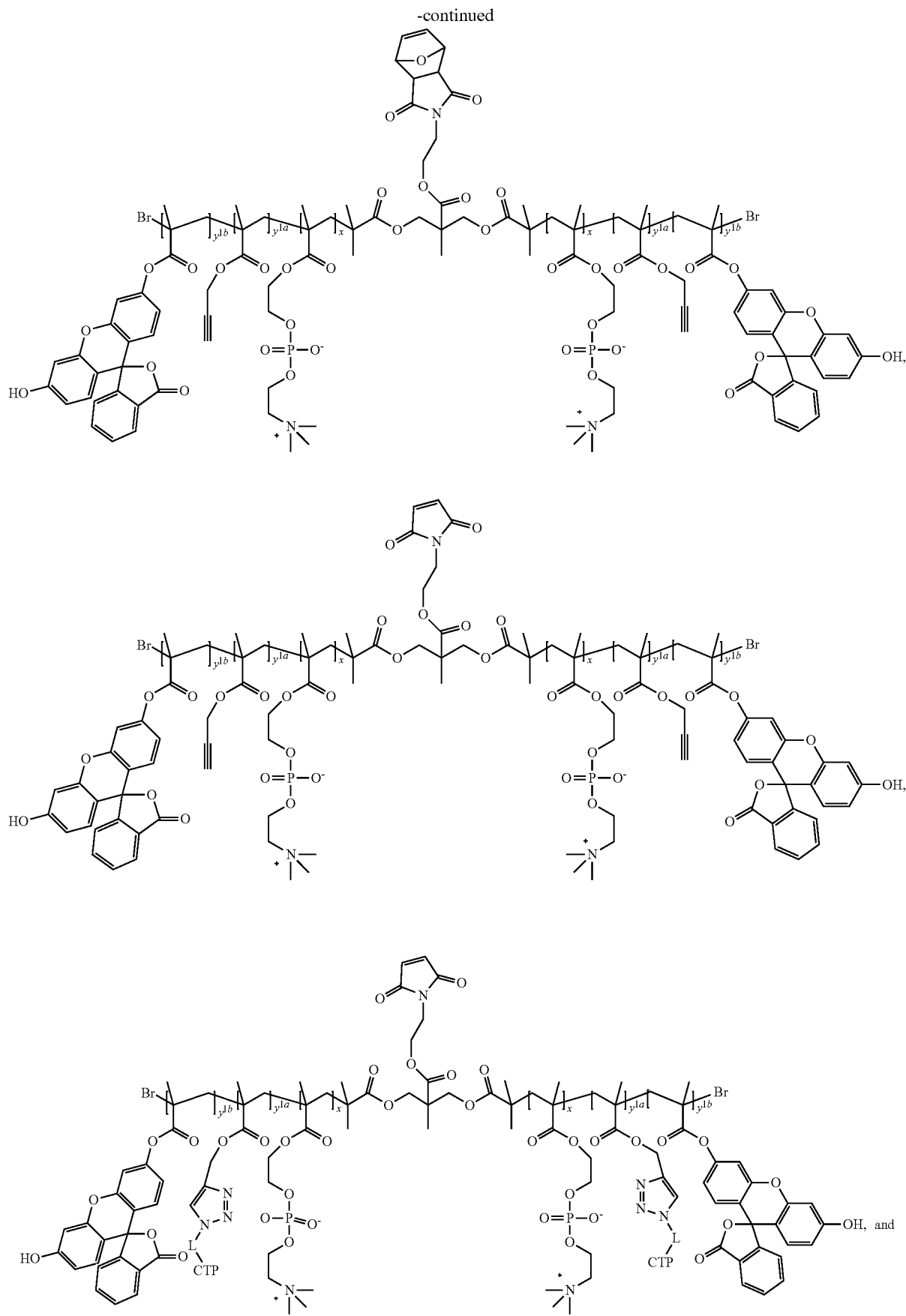

-continued
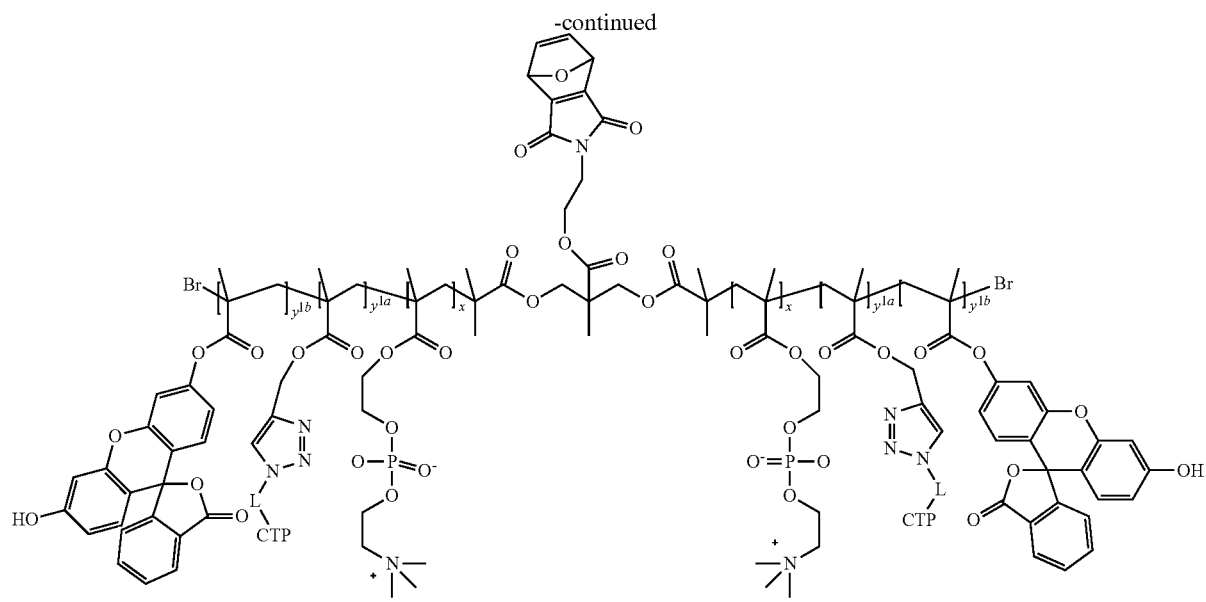
wherein L-CTP has the formula:
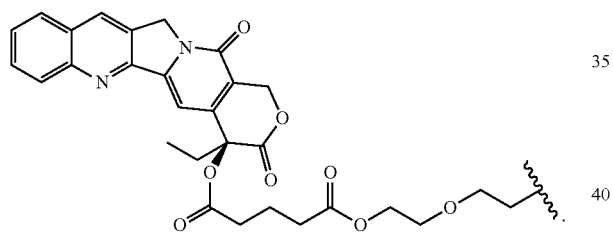
In some other embodiments, the random copolymer has the formula:
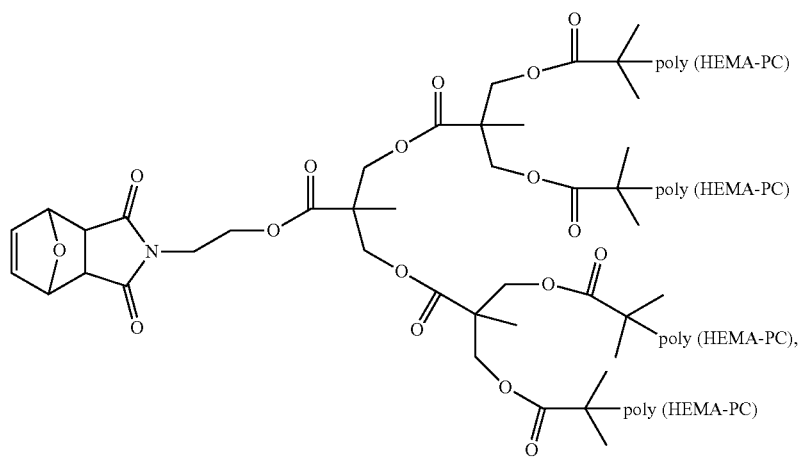

31
-continued
32
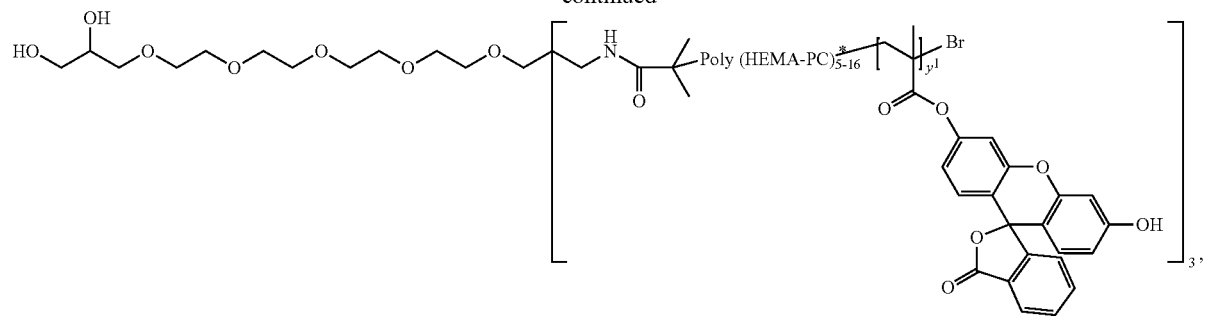
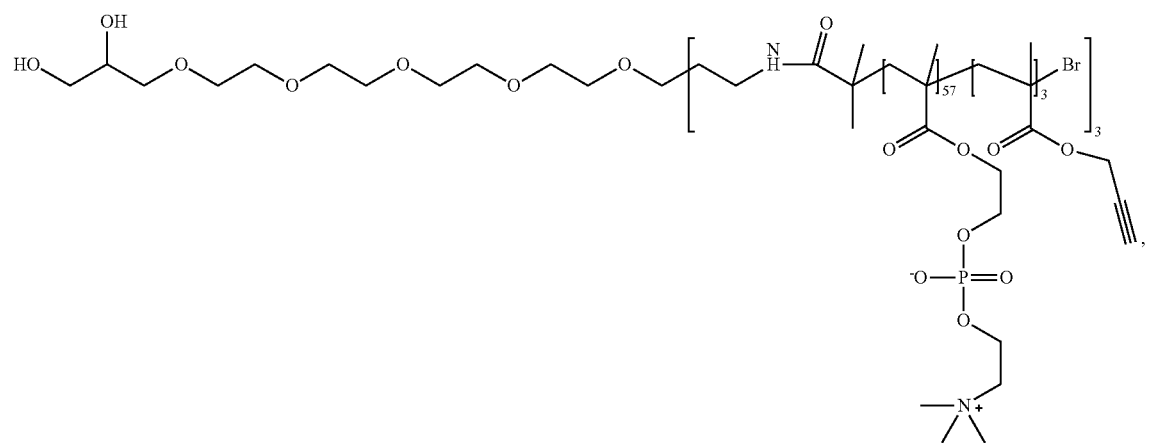
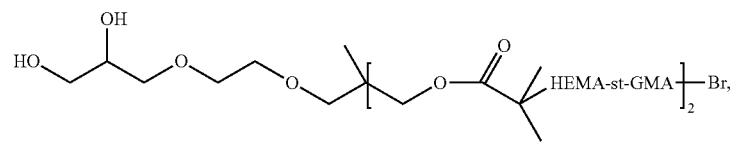
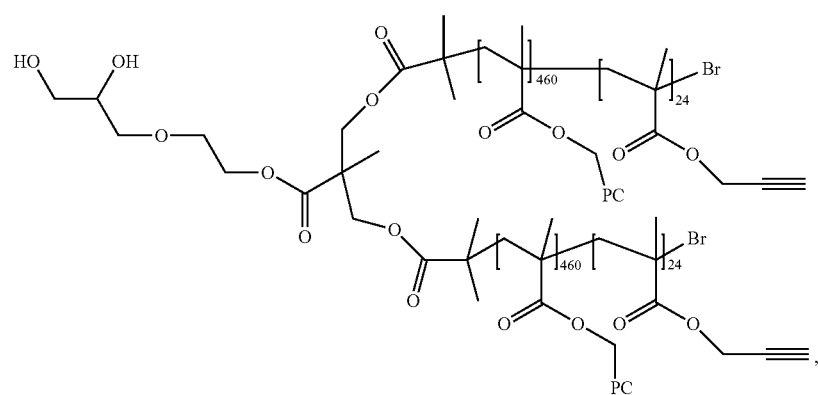

-continued
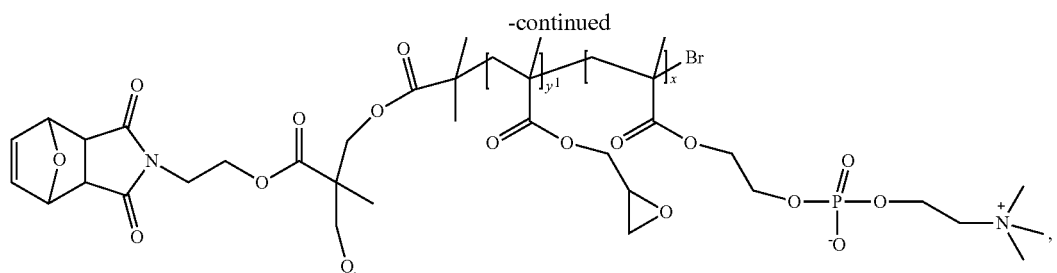
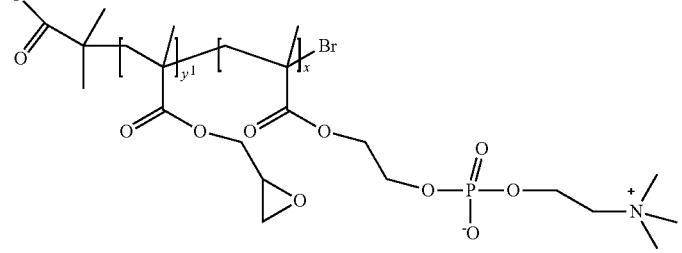
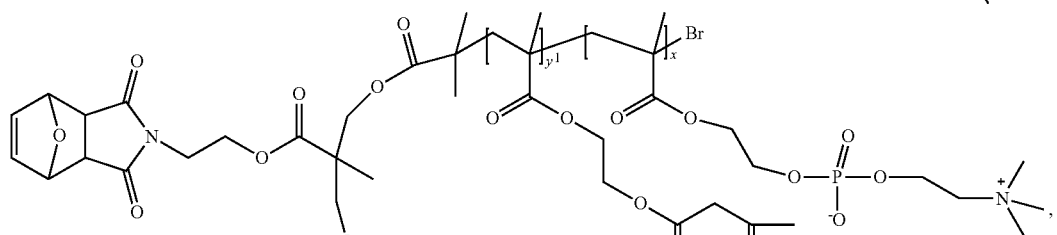
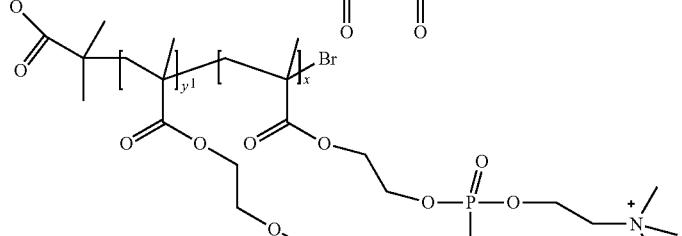
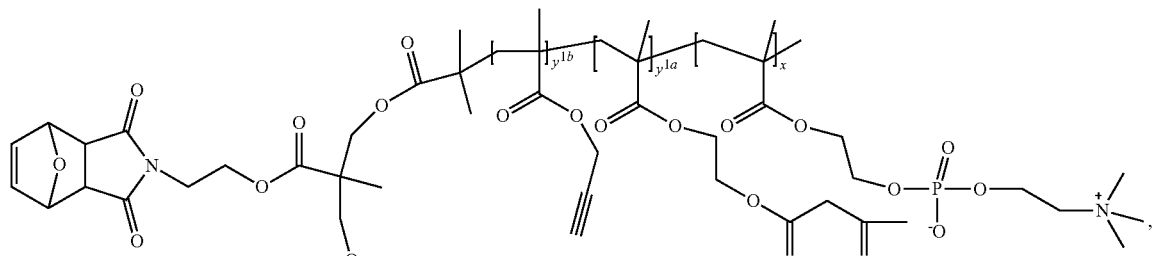
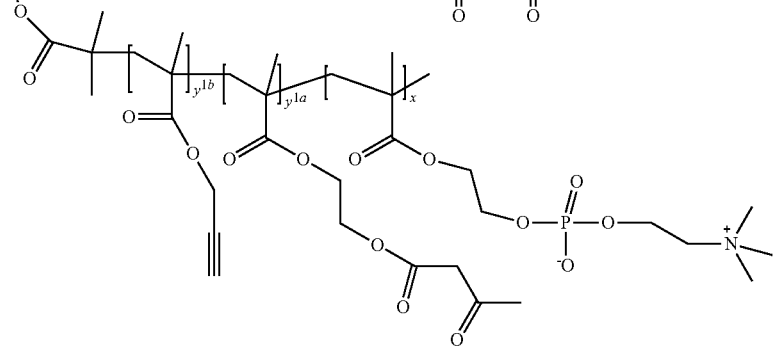

-continued
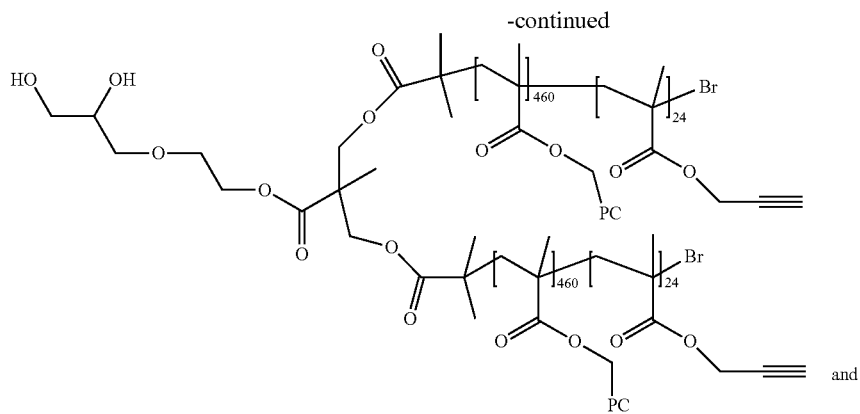
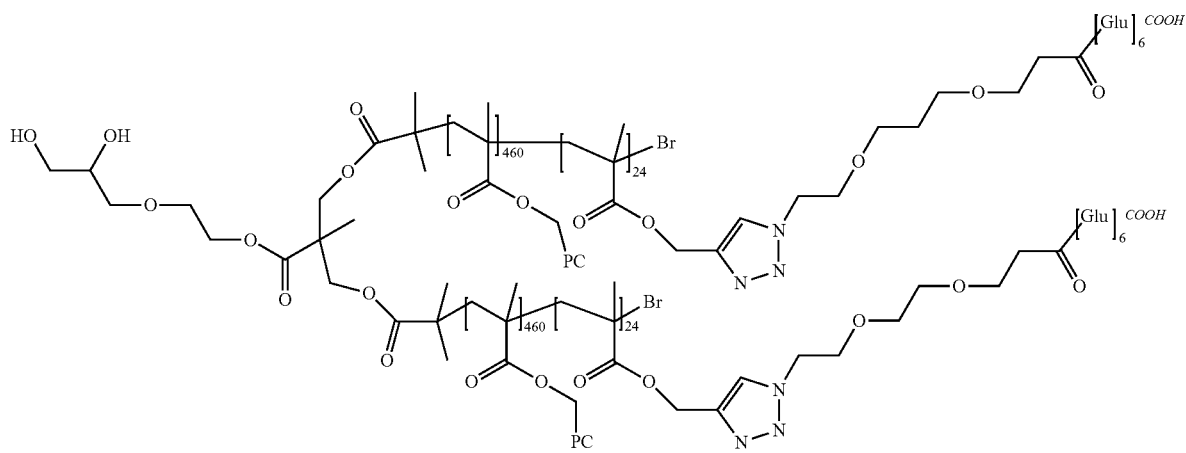
wherein PC is phosphorylcholine; HEMA is hydroxyethyl methacrylate; GMA is glycidyl methacrylate; and Glu is glutamic acid.
In still other embodiments, the random copolymer has the formula:
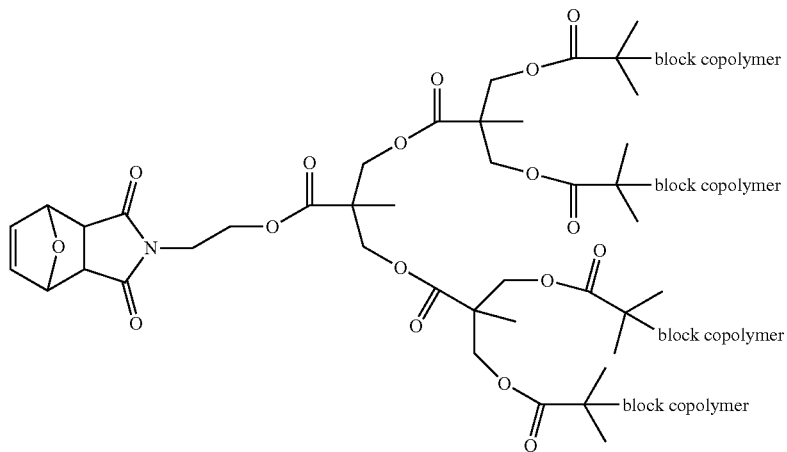

wherein the block copolymer has the formula:

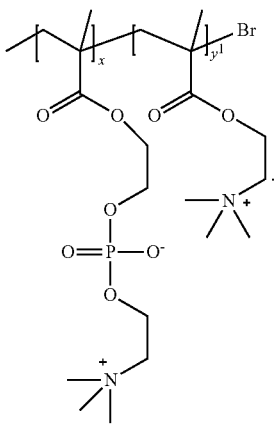

A. Initiators

The random copolymers of the present invention are polymerized using any suitable initiator. Initiators useful in the present invention can be described by the formula: I-(I')$_m$, where subscript m is an integer from 1 to 20. The initiator fragment I can be any group that initiates the polymerization. The radical scavenger I' can be any group that will reversibly terminate the growing polymer chain. The radical scavenger I' can be a halogen such as bromine, allowing the end of the polymer to be functionalized after polymerization. In addition, the initiator fragment I can optionally be functionalized with an $R^1$ group that can include a variety of functional groups to tune the functionality of the random copolymer.

Initiators useful in the present invention can have a single radical scavenger I', or any suitable number of branches such that there are multiple radical scavengers I' each capable of reversibly terminating a growing polymer chain. When the initiator fragment I is branched and is capable of initiating multiple polymer chains, subscript m is greater than one such that there are as many radical scavengers I' as there are growing polymer chains.

The bond between initiator fragment I and radical scavenger I' is labile, such that during the polymerization process monomers $M^1$ and comonomers $M^2$ are inserted between initiator fragment I and radical scavenger I'. For example, during a free radical polymerization, such as ATRP, initiator fragment I and radical scavenger I' dissociate, as shown in FIG. 1, to form radicals of I and I'. The radical of initiator fragment I then reacts with the monomers in solution to grow the polymer and forms a propagating polymer radical (species A and species C of FIG. 1). During the polymerization process, the radical of the radical scavenger I' will reversibly react with the propagating polymer radical to temporarily stop polymer growth. The bond between the monomer and the radical scavenger I' is also labile, such that the bond can cleave and allow the propagating polymer radical to react with additional monomer to grow the polymer. The end result of the polymerization process is that initiator fragment I is at one end of the polymer chain and radical scavenger I' is at the opposite end of the polymer chain.

The radical of initiator fragment I is typically on a secondary or tertiary carbon, and can be stabilized by an adjacent carbonyl carbon. The radical scavenger I' is typically a halogen, such as bromine, chlorine or iodine.

Together, initiator fragment I and radical scavenger I' form the initiators $I^1$ and $I^2$ useful in the preparation of the random copolymers of the present invention.

A broad variety of initiators can be used to prepare the random copolymers of the invention, including a number of initiators set forth in U.S. Pat. No. 6,852,816 (incorporated herein by reference). In some embodiments, the initiators employed for ATRP reactions to prepare random copolymers of the invention are selected from alkanes, cycloalkanes, alkyl carboxylic acids or esters thereof, cycloalkylcarboxylic acids or esters thereof, ethers and cyclic alkyl ethers, alkyl aryl groups, alkyl amides, alkyl-aryl carboxylic acids and esters thereof, and also bearing one radical scavenger I' where unbranched random copolymers are prepared, and more than one radical scavenger I' where branched molecules are prepared.

Radical scavengers I' useful in the present invention include, but are not limited to, halogens, such as Br, Cl and I, thiocyanate (—SCN) and isothiocyanate (—N=C=S). Other groups are useful for the radical scavenger I' of the present invention. In some embodiments, the radical scavenger I' is bromine.

Initiators employed for ATRP reactions can be hydroxylated. In some embodiments, the initiators employed for ATRP reactions to prepare random copolymers of the invention are selected from alkanes, cycloalkanes, alkyl carboxylic acids or esters thereof, cycloalkylcarboxylic acids or esters thereof, ethers, cyclic alkyl ethers, alkyl aryl groups, alkyl amides, alkyl-aryl carboxylic acids and esters thereof, bearing a hydroxyl group, and also bearing one radical scavenger I' where unbranched random copolymers are to be prepared, or alternatively, more than one radical scavenger I' where branched molecules are to be prepared.

Initiators employed for ATRP reactions can bear one or more amine groups. In some embodiments, the initiators employed for ATRP reactions to prepare random copolymers of the invention are alkanes, cycloalkanes, alkyl carboxylic acids or esters thereof, cycloalkylcarboxylic acids or esters thereof, ethers, cyclic alkyl ethers, alkyl-aryl groups, alkyl amides, alkyl-aryl carboxylic acids and esters thereof, bearing an amine group and also bearing one radical scavenger I' where unbranched random copolymers are to be prepared, or alternatively, more than one radical scavenger I' where branched molecules are to be prepared.

Alkylcarboxylic acids, including alkyl dicarboxylic acids, having at least one radical scavenger I', and substituted with amino or hydroxy groups can also be employed as initiators. In some embodiments of the invention where ATRP is employed to prepare random copolymers of the present invention, the initiators can be alkylcarboxylic acids bearing one or more halogens selected from chlorine and bromine.

Alkanes substituted with two or more groups selected from —COOH, —OH and —NH$_2$, and at least one radical scavenger I', can also be employed as initiators for the preparation of random copolymers where ATRP is employed to prepare random copolymers of the present invention.

Initiators can also contain one or more groups including, but not limited to, —OH, amino, monoalkylamino, dialkylamino, —O-alkyl, —COOH, —COO-alkyl, or phosphate groups (or protected forms thereof).

A broad variety of initiators are commercially available, for example bromoacetic acid N-hydroxysuccinimide ester available from Sigma-Aldrich (St. Louis, Mo.). Suitably protected forms of those initiators can be prepared using standard methods in the art as necessary.

Other initiators include thermal, redox or photo initiators, including, for example, alkyl peroxide, substituted alkyl peroxides, aryl peroxides, substituted aryl peroxides, acyl peroxides, alkyl hydroperoxides, substituted aryl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, azo compounds and halide compounds. Specific initiators include cumene hydroperoxide (CHP), tert-butyl hydroperoxide (TBHP), tert-butyl perbenzoate, (TBPB), sodium carbonateperoxide, benzoyl peroxide (BPO), lauroyl peroxide (LPO), methylethyl ketone 45%, potassium persulfate, ammonium persulfate, 2,2-azobis(2,4-dimethyl-valeronitrile), 1,1-azobis(cyclo-hexanecarbonitrile), 2,2-azobis(N,N-dimethyleneisobutyramidine) dihydrochloride, and 2,2-azobis (2-amido-propane) dihydrochloride. Redox pairs such as persulfate/sulfite and Fe (2+) peroxide or ammonium persulfate and N,N,N'N'-tetramethylethylenediamine (TEMED).

Still other initiators useful for preparing the random copolymers of the present invention, are branched. Suitable initiators having a single branch point include the following:

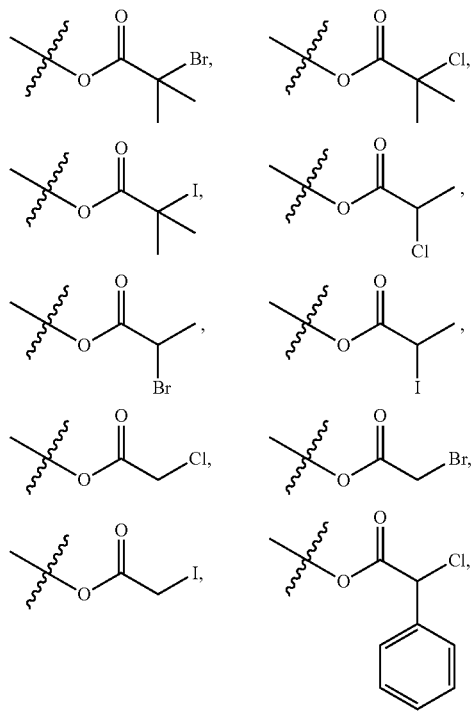

where radical R can be any of the following:

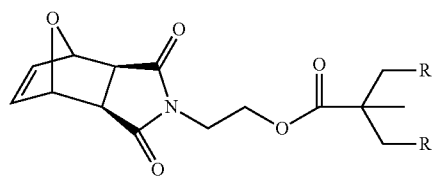

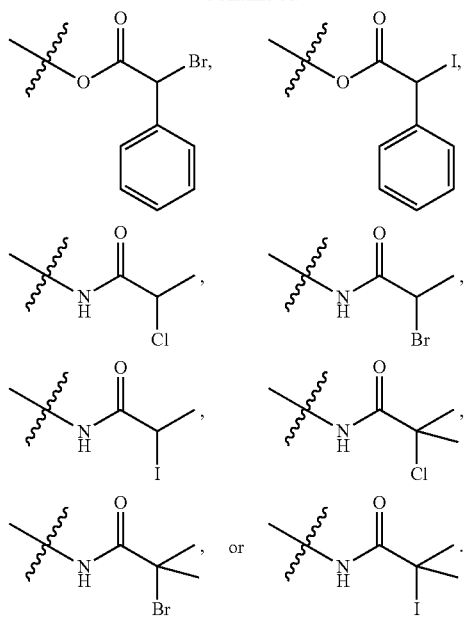

In some embodiments, the initiator can be:

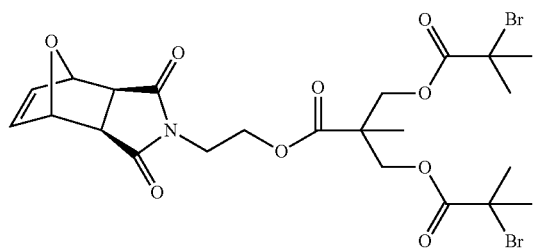 [SMILES: CC(C)(Br)C(=O)OCC(C)(COC(=O)C(C)(C)Br)C(=O)OCCN1C(=O)[C@@H]2C3C=CC(O3)[C@@H]2C1=O]

which is a protected maleimide that can be deprotected after polymerization to form the maleimide for reaction with additional functional groups.

Additional branched initiators include, but are not limited to, the following, where radical R is as defined above:

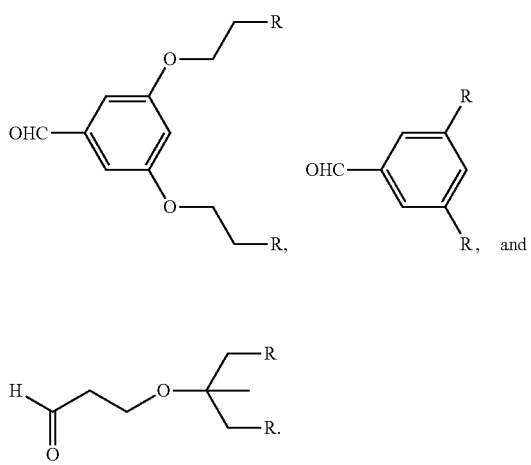

In some embodiments, the branched initiators include, but are not limited to, the following:

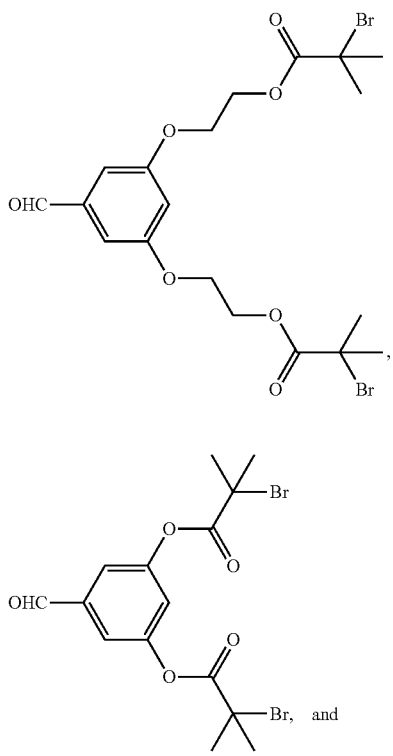

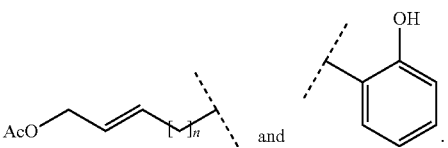

Still other initiators include, but are not limited to, the following:

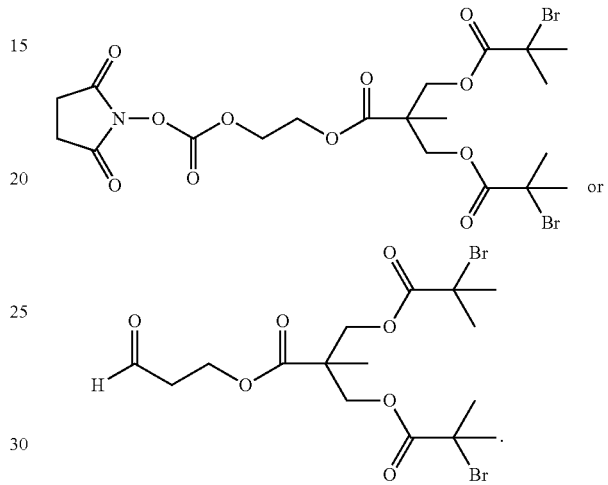

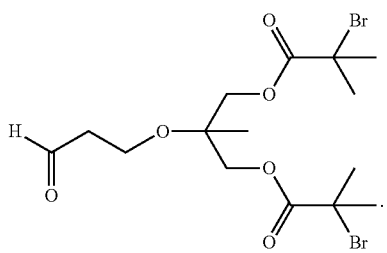

In other embodiments, the initiator can have several branch points to afford a plurality of polymer arms, such as:

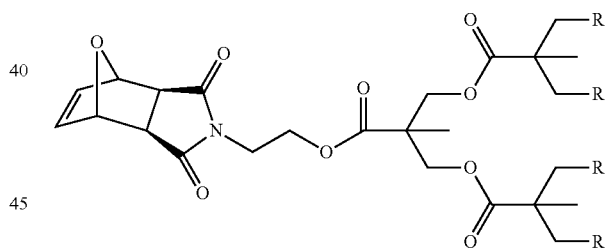

Other branched initiators useful for preparing the random copolymers of the present invention include the following:

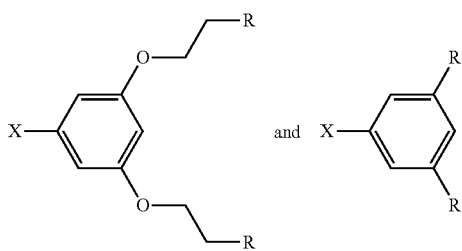

where radical R is as defined above, and radical X can be CHO, $SO_2Cl$, $SO_2CH=CH_2$, $NHCOCH_2I$, $N=C=O$ and $N=C=S$, among others. Additional X groups can include the following:

where radical R is as defined above. In some other embodiments, the initiator can have the following structure:

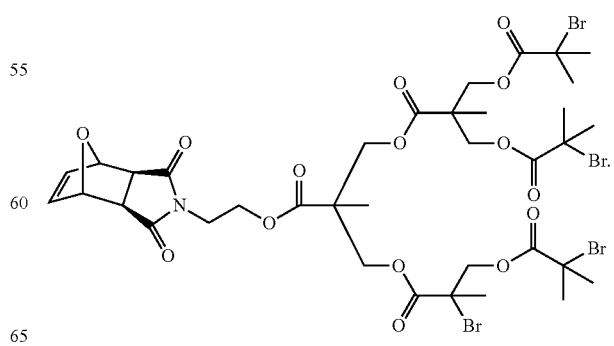

In some other embodiments, the initiator can have the following structures:
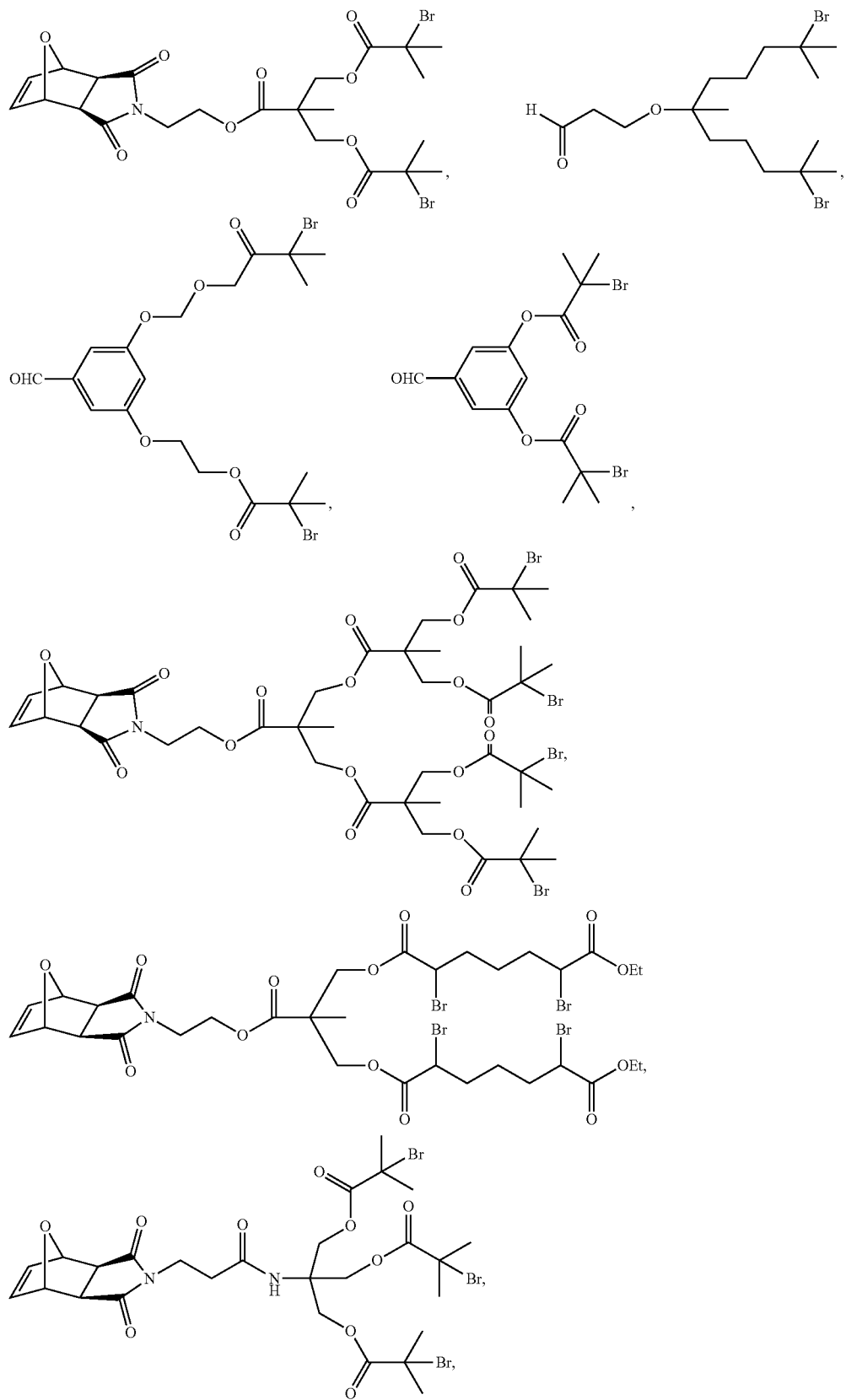

-continued
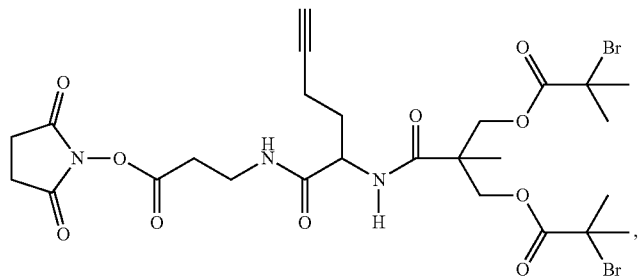
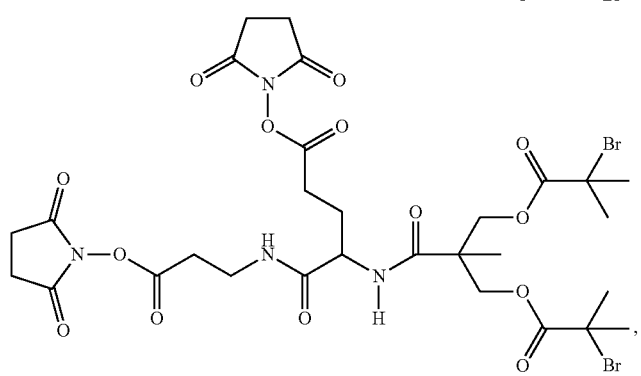
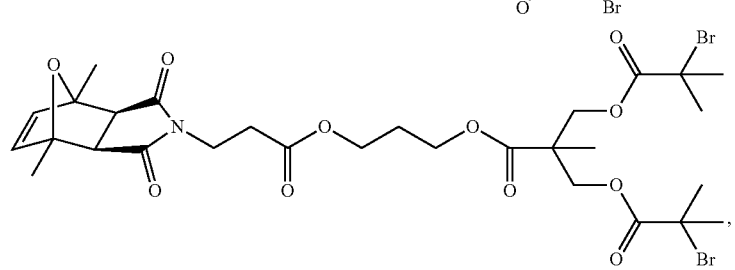
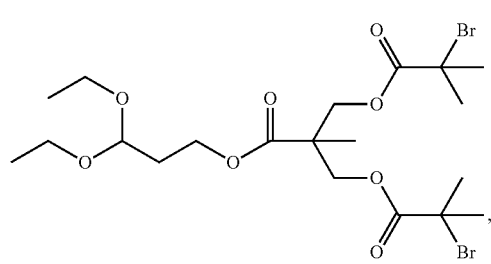
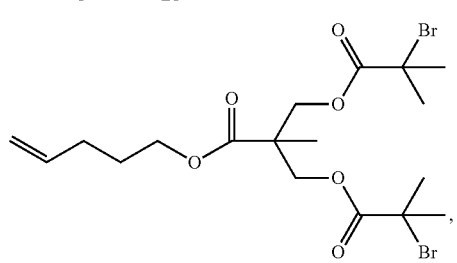
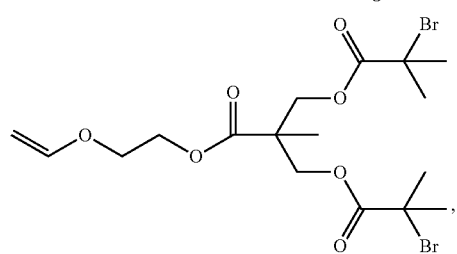
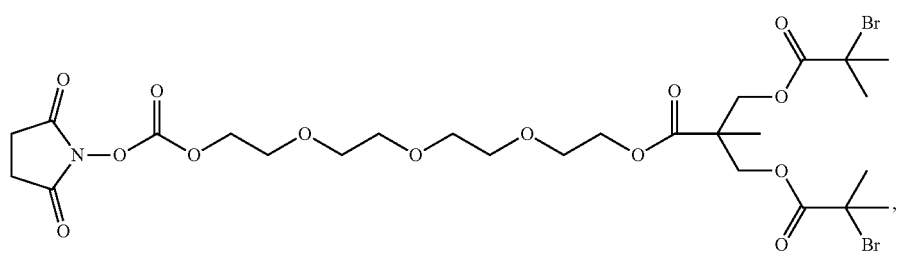

-continued
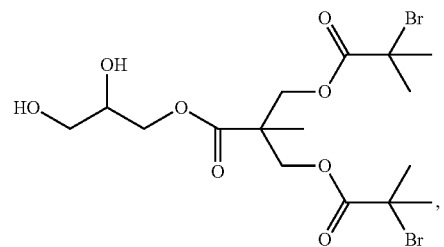
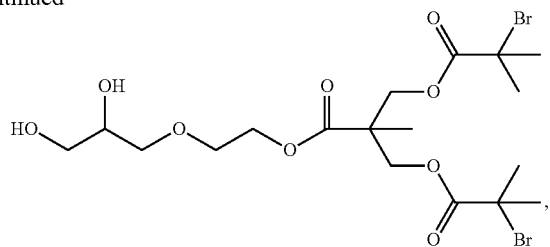
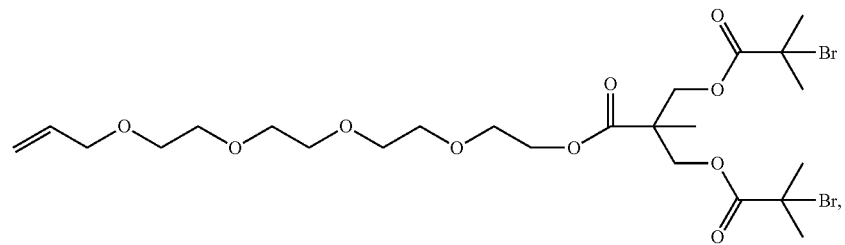
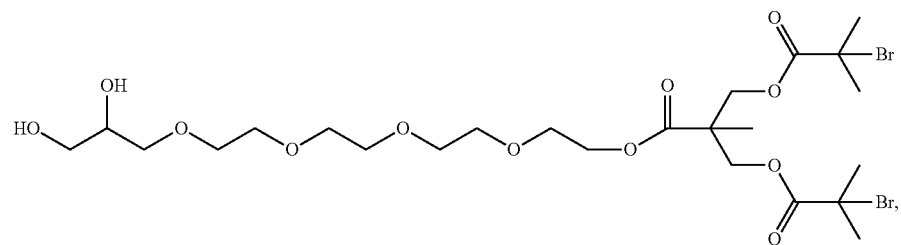
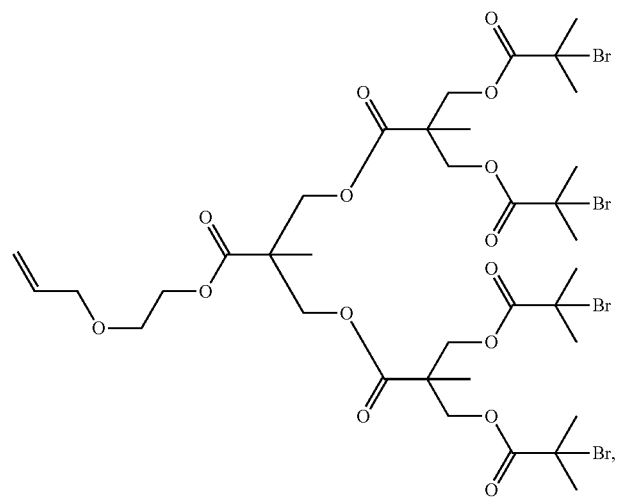
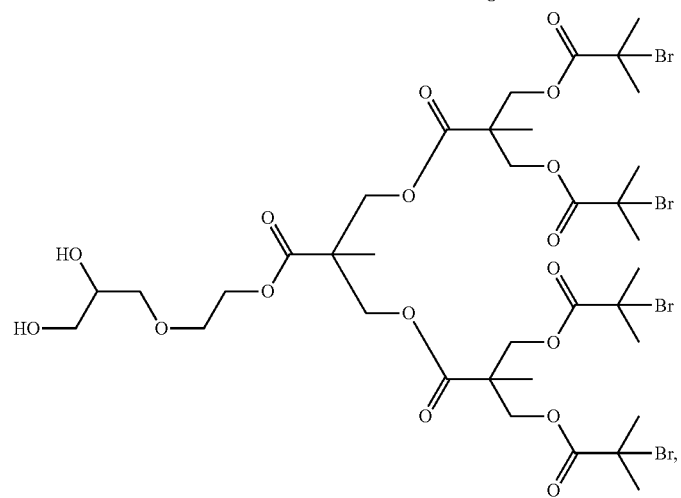

-continued
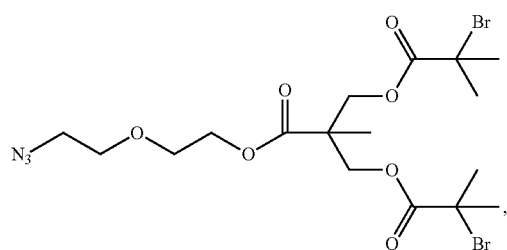
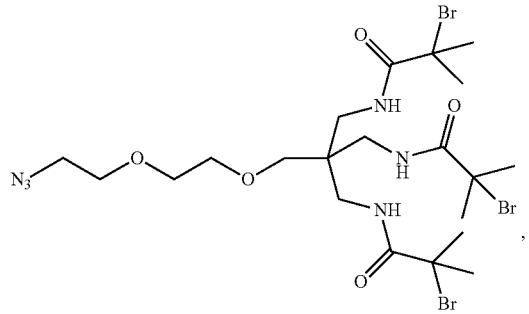
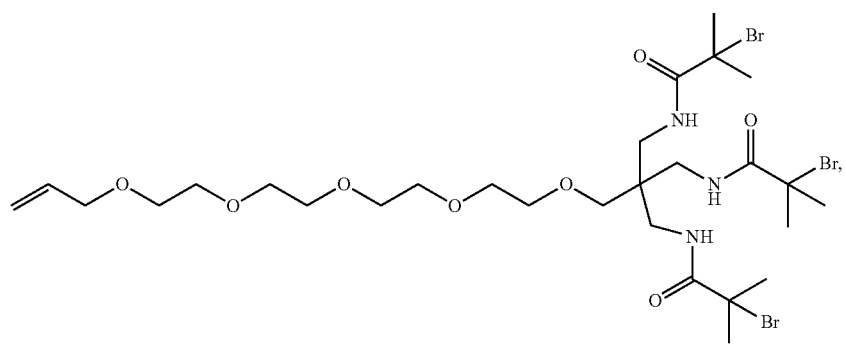
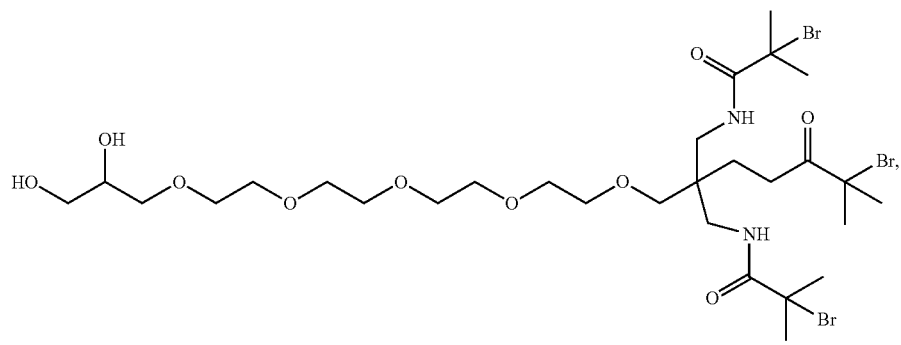
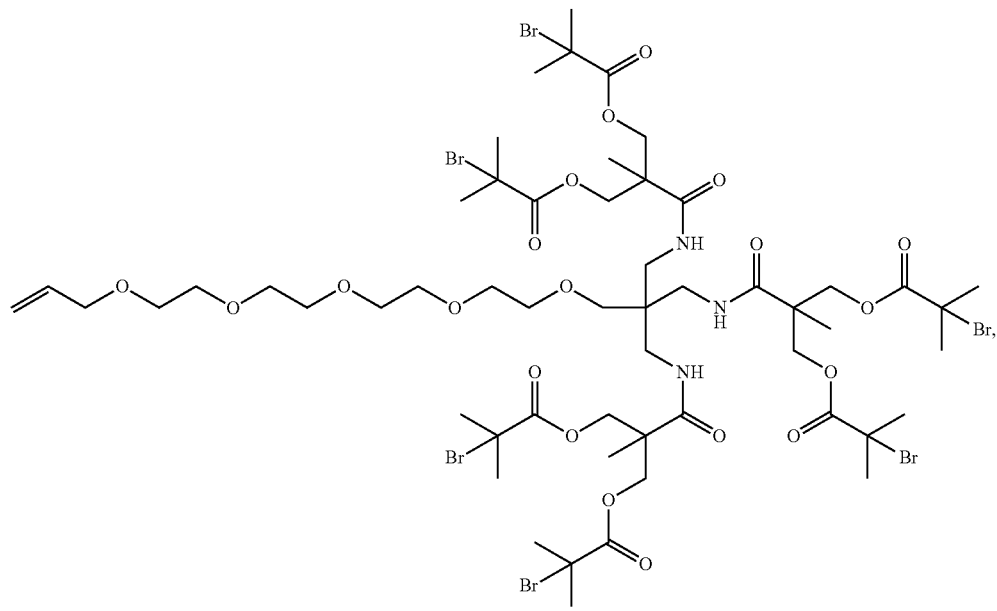

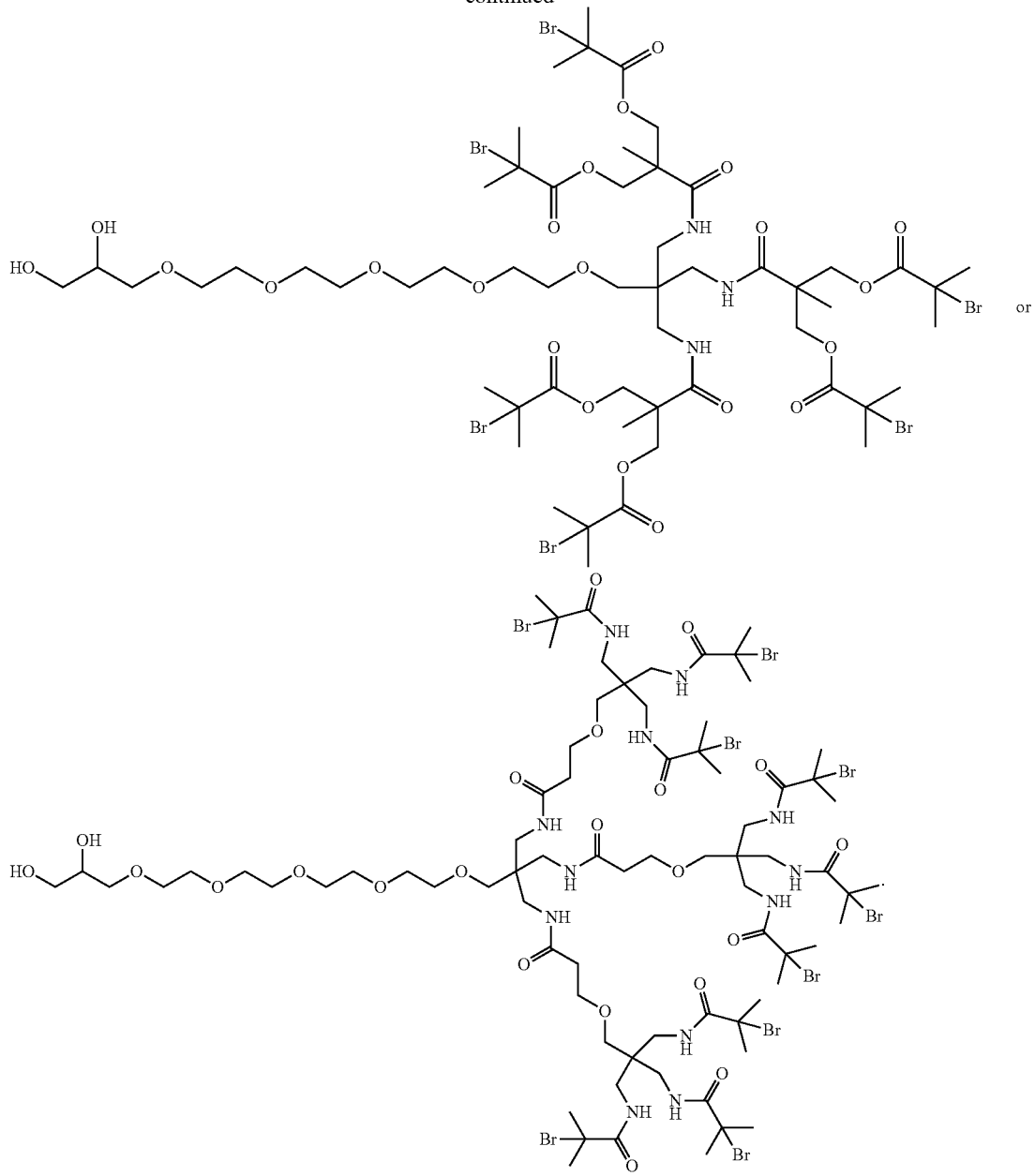

50

As described above, the initiator can be added to the polymerization mixture separately, or can be incorporated into another molecule, such as a monomer (hyperbranched structure) or a polymer fragment (such as graft copolymers). Initiation of the polymerization can be accomplished by heat, UV light, or other methods known to one of skill in the art.

In some embodiments, the initiator I-I' of the present invention has the formula:

$(F)_r\text{-Sp}^1\text{-C-Sp}^2\text{-I}'$ where the initiator fragment I corresponds to F-Sp$^1$-C-Sp$^2$. Each radical F is a functional group for reaction with a functional agent or linking group of the present invention. Radical r is from 1 to 10. Radicals Sp$^1$ and Sp$^2$ are spacers and can be any suitable group for forming a covalent bond, such as $C_{1-6}$ alkyl, aryl or heteroaryl. Radical C can be any core providing one or a plurality of points for linking to one or more spacers, Sp$^2$ (which can be the same or different), and one or more radical scavengers, I', and providing one or a plurality of points for linking to one or more spacers, Sp$^1$ (which can be the same or different), and one or more functional groups, F (which can be the same or different). Core C can be any suitable structure, such as a branched structure, a crosslinked structure including heteroatoms, such as silsesquiloxanes, and a linear, short polymer with multiple pendant functional groups. In addition, core C can be attached to the one or more Sp$^1$ and Sp$^2$ spacers by any suitable group for forming a covalent bond including, but not limited to, esters, amides, ethers, and ketones. Radical scavenger I' is a radically transferable atom or group such as, but not limited to, a halogen, Cl, Br, I, OR$^{10}$, SR$^{11}$, SeR$^{11}$, OC(=O)R$^{11}$, OP(=O)R$^{11}$, OP(=O)(OR$^{11}$)$_2$, O—(R$^{11}$)$_2$, S—C(=S)N($R^{11}$)$_2$, CN, NC, SCN, CNS, OCN, CNO, N$_3$, OH, O, C1-C6-alkoxy, (SO$_4$), PO$_4$, HPO$_4$, H$_2$PO$_4$, triflate, hexafluorophosphate, methanesulfonate, arylsulfonate, carboxylic acid halide. $R^{10}$ is an alkyl of from 1 to 20 carbon atoms or an alkyl of from 1 to 20 carbon atoms in which each of the hydrogen atoms may be replaced by a halide, alkenyl of from 2 to 20 carbon atoms, alkynyl of from 2 to 10 carbon atoms, phenyl, phenyl substituted with from 1 to 5 halogen atoms or alkyl groups with from 1 to 4 carbon atoms, aralkyl, aryl, aryl substituted alkyl, in which the aryl group is phenyl or substituted phenyl and the alkyl group is from 1 to 6 carbon atoms, and $R^1$ is aryl or a straight or branched $C_1$-$C_{90}$ alkyl group or where an N($R^{11}$)$_2$ group is present, the two $R^{11}$ groups may be joined to form a 5-, 6- or 7-member heterocyclic ring. Spacer $Sp^1$ covalently links functional group F and core C while spacer $Sp^2$ covalently links core C and radical scavenger I'.

In other embodiments, the initiator of the present invention has the formula:

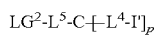

wherein each I' is independently selected from halogen, —SCN, or —NCS. $L^4$ and $L^5$ are each independently a bond or a linker, such that one of $L^4$ and $L^5$ is a linker. C is a bond or a core group. $LG^2$ is a linking group. And subscript p is from 1 to 32, wherein when subscript p is 1, C is a bond, and when subscript p is from 2 to 32, C is a core group. In some other embodiments, the initiator has the formula:

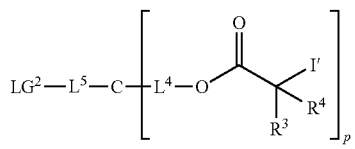

wherein each $R^3$ and $R^4$ is independently selected H, CN or $C_{1-6}$ alkyl.

B. Monomers

Monomers useful for preparing the random copolymers of the present invention include any monomer capable of radical polymerization. Typically, such monomers have a vinyl group. Suitable monomers include, but are not limited to, acrylate, methacrylate, acrylamide, methacrylamide, styrene, vinyl-pyridine and vinyl-pyrrolidone monomers. Monomers, $M^1$, containing the zwitterionic moiety, ZW, include, but are not limited to, the following:

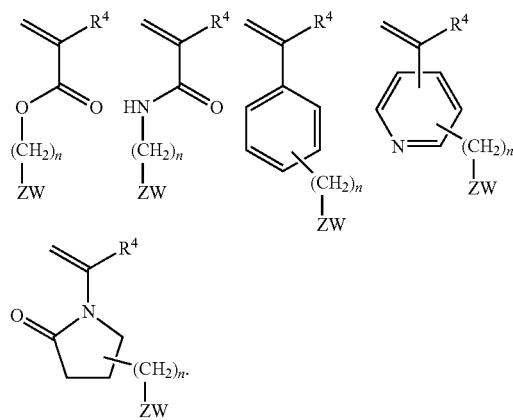

Monomers, $M^2$, containing the linking group or functional agent include, but are not limited to, the following structures:

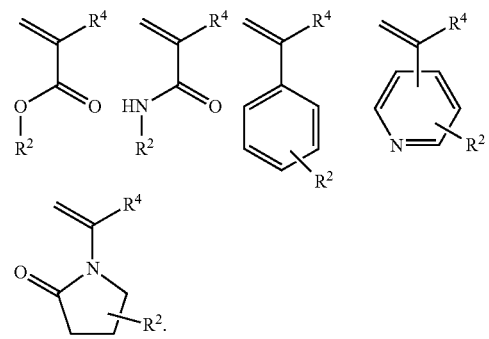

Other monomers are well-known to one of skill in the art, and include vinyl acetate and derivatives thereof.

In some embodiments, the monomers are acrylate or methacrylate monomers. In other embodiments, the random copolymer has the formula:

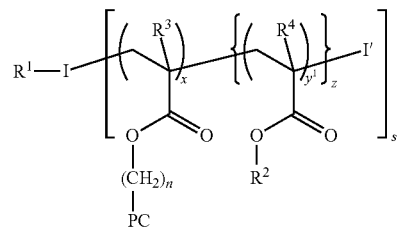

wherein each of $R^3$ and $R^4$ are independently H or $C_{1-6}$ alkyl; and PC is phosphatidylcholine.

In some other embodiments, the random copolymer has the formula:

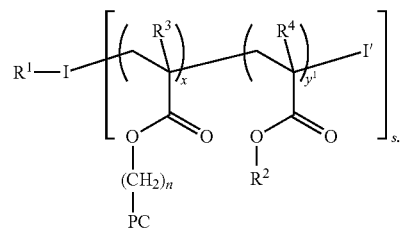

In other embodiments, the random copolymer has the formula:

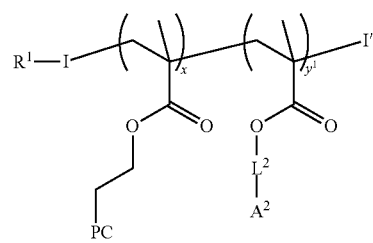

wherein $A^2$ is camptothecin.

In still other embodiments, the random copolymer has the formula:

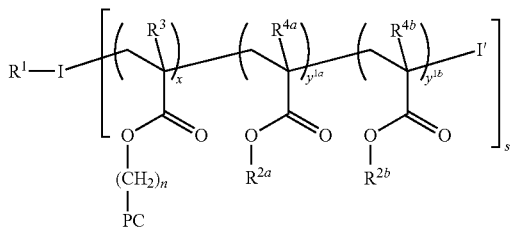

wherein $R^{4a}$ and $R^{4b}$ can be as defined above for $R^4$; $R^{2a}$ and $R^{2b}$ can be as defined above for $A^2$; and $y^{1a}$ and $y^{1b}$ can be as defined above for y'. In some embodiments, $R^{2a}$ and $R^{2b}$ are each independently H, $C_{1-20}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, heteroaryl, $A^2$, $L^2$-$A^2$, $LG^2$, or $L^2$-$LG^2$; each of $R^3$, $R^{4a}$ and $R^{4b}$ are independently H or $C_{1-6}$ alkyl; subscripts $y^{1a}$ and $y^{1b}$ are each independently an integer of from 1 to 1000; and PC is phosphatidylcholine.

In still yet other embodiments, the random copolymer can have any of the following formulas:

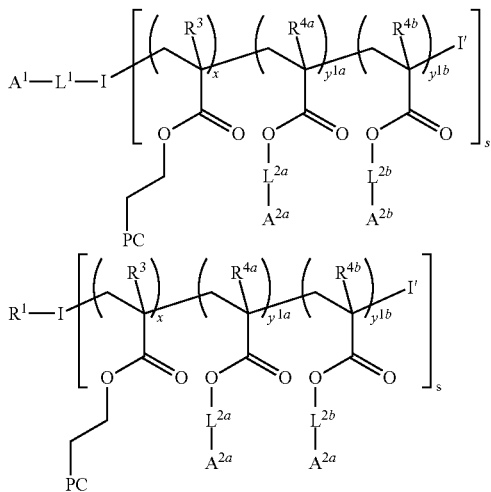

wherein $R^{4a}$ and $R^{4b}$ can be as defined above for $R^4$; $L^{2a}$ and $L^{2b}$ can be as defined above for $L^2$; $A^{2a}$ and $A^{2b}$ can be as defined above for $A^2$; and $y^{1a}$ and $y^{1b}$ can be as defined above for $y^1$. In some embodiments, each of $L^{2a}$ and $L^{2b}$ is a linker; and each of $A^{2a}$ and $A^{2b}$ is a functional agent.

C. Zwitterions

The zwitterions of the present invention include any compound having both a negative charge and a positive charge. Groups having a negative charge and suitable for use in the zwitterions of the present invention include, but are not limited to, phosphate, sulfate, other oxoanions, etc. Groups having a positive charge and suitable for use in the zwitterions of the present invention include, but are not limited to, ammonium ions. In some embodiments, the zwitterion can be phosphorylcholine.

D. Linkers

The random copolymers of the present invention can also incorporate any suitable linker L. The linkers provide for attachment of the functional agents to the initiator fragment I and the comonomers $M^2$. The linkers can be cleavable or non-cleavable, homobifunctional or heterobifunctional. Other linkers can be both heterobifunctional and cleavable, or homobifunctional and cleavable.

Cleavable linkers include those that are hydrolyzable linkers, enzymatically cleavable linkers, pH sensitive linkers, disulfide linkers and photolabile linkers, among others. Hydrolyzable linkers include those that have an ester, carbonate or carbamate functional group in the linker such that reaction with water cleaves the linker. Enzymatically cleavable linkers include those that are cleaved by enzymes and can include an ester, amide, or carbamate functional group in the linker. pH sensitive linkers include those that are stable at one pH but are labile at another pH. For pH sensitive linkers, the change in pH can be from acidic to basic conditions, from basic to acidic conditions, from mildly acidic to strongly acidic conditions, or from mildly basic to strongly basic conditions. Suitable pH sensitive linkers are known to one of skill in the art and include, but are not limited to, ketals, acetals, imines or imminiums, siloxanes, silazanes, silanes, maleamate-amide bonds, ortho esters, hydrazones, activated carboxylic acid derivatives and vinyl ethers. Disulfide linkers are characterized by having a disulfide bond in the linker and are cleaved under reducing conditions. Photolabile linkers include those that are cleaved upon exposure to light, such as visible, infrared, ultraviolet, or electromagnetic radiation at other wavelengths.

Other linkers useful in the present invention include those described in U.S. Patent Application Nos. 2008/0241102 (assigned to Ascendis/Complex Biosystems) and 2008/0152661 (assigned to Mims), and International Patent Application Nos. WO 2004/010957 and 2009/117531 (assigned to Seattle Genetics) and 01/24763, 2009/134977 and 2010/126552 (assigned to Immunogen) (incorporated in their entirety herein). Minis linkers useful in the present invention include, but are not limited to, the following:

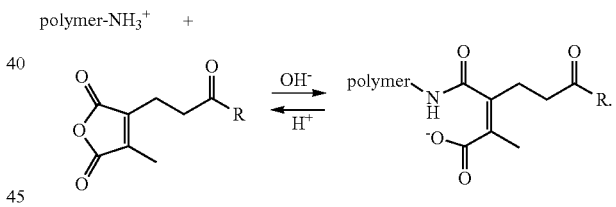

Other linkers include those described in Bioconjugate Techniques, Greg T. Hermanson, Academic Press, 2d ed., 2008 (incorporated in its entirety herein), and those described in Angew. Chem. Int. Ed. 2009, 48, 6974-6998 (Bertozzi, C. R. and Sletten, E.M) (incorporated in its entirety herein).

In some embodiments, linkers $L^1$ and $L^2$ can have a length of up to 30 atoms, each atom independently C, N, O, S, and P. In other embodiments, the linkers $L^1$ and $L^2$ can be any of the following: —$C_{1-12}$ alkyl-, —$C_{3-12}$ cycloalkyl-, —($C_{1-8}$ alkyl)-($C_{3-12}$ cycloalkyl)-($C_{0-8}$ alkyl)-, —$(CH_2)_{1-12}$O—, (—$(CH_2)_{1-6}$—O—$(CH_2)_{1-6}$—)$_{1-12}$—, (—$(CH_2)_{1-4}$—NH—$(CH_2)_{1-4}$)$_{1-12}$—, (—$(CH_2)_{1-4}$—O—$(CH_2)_{1-4}$)$_{1-12}$—O—, (—$(CH_2)_{1-4}$—O—$(CH_2)_{1-4}$—)$_{1-12}$O—$(CH_2)_{1-12}$—, —$(CH_2)_{1-12}$—(C=O)—O—, —$(CH_2)_{1-12}$—O—(C=O)—, -(phenyl)-$(CH_2)_{1-3}$—(C=O)—O—, -(phenyl)-$(CH_2)_{1-3}$—(C=O)—NH—, —($C_{1-6}$ alkyl)-(C=O)—O—($C_{0-6}$ alkyl)-, —$(CH_2)_{1-12}$—(C=O)—O—$(CH_2)_{1-12}$—, —CH(OH)—CH (OH)—(C=O)—O—CH(OH)—CH(OH)—(C=O)—NH—, —S-maleimido-$(CH_2)_{1-6}$—, —S-maleimido-($C_{1-3}$ alkyl)-(C=O)—NH—, —S-maleimido-($C_{1-3}$alkyl)-($C_{5-6}$ cycloalkyl)-($C_{0-3}$alkyl)-, —($C_{1-3}$ alkyl)-($C_{5-6}$ cycloalkyl)-($C_{0-3}$alkyl)-(C=O)—O—, —($C_{1-3}$ alkyl)-($C_{5-6}$ cycloalkyl)-($C_{0-3}$ alkyl)-(C=O)—NH—, —S-maleimido-($C_{0-3}$alkyl)-phenyl-($C_{0-3}$alkyl)-, —($C_{0-3}$ alkyl)-phenyl-(C=O)—NH—, —($CH_2$)$_{1-12}$—NH—(C=O)—, —($CH_2$)$_{1-12}$—(C=O)—NH—, -(phenyl)-($CH_2$)$_{1-3}$—(C=O)—NH—, —S—($CH_2$)—(C=O)—NH-(phenyl)-, —($CH_2$)$_{1-12}$—(C=O)—NH—($CH_2$)$_{1-12}$—, —($CH_2$)$_2$—(C=O)—O—($CH_2$)$_2$—O—(C=O)—($CH_2$)$_2$—(C=O)—NH—, —($C_{1-6}$ alkyl)-(C=O)—N—($C_{1-6}$ alkyl)-, acetal, ketal, acyloxyalkyl ether, —N=CH—, —($C_{1-6}$ alkyl)-S—S—($C_{0-6}$ alkyl)-, —($C_{1-6}$ alkyl)-S—S—($C_{1-6}$ alkyl)-(C=O)—O—, —($C_{1-6}$ alkyl)-S—S—($C_{1-6}$ alkyl)-(C=O)—NH—, —S—S—($CH_2$)$_{1-3}$—(C=O)—NH—($CH_2$)$_{1-4}$—NH—(C=O)—($CH_2$)$_{1-3}$—, —S—S—($C_{0-3}$ alkyl)-(phenyl)-, —S—S—($C_{1-3}$-alkyl)-(phenyl)-(C=O)—NH—($CH_2$)$_{1-5}$—, —($C_{1-3}$ alkyl)-(phenyl)-(C=O)—NH—($CH_2$)$_{1-5}$—(C=O)—NH—, —S—S—($C_{1-3}$-alkyl)-, —($C_{1-3}$-alkyl)-(phenyl)-(C=O)—NH—, —O—($C_1$-$C_6$ alkyl)-S($O_2$)—($C_{1-6}$ alkyl)-O—(C=O)—NH—, —S—S—($CH_2$)$_{1-3}$—(C=O)—, —($CH_2$)$_{1-3}$—(C=O)—NH—N=C—S—S—($CH_2$)$_{1-3}$—(C=O)—NH—($CH_2$)$_{1-5}$—, —($CH_2$)$_{1-3}$—(C=O)—NH—($CH_2$)$_{1-5}$—(C=O)—NH—, —($CH_2$)$_{0-3}$-(heteroaryl)-($CH_2$)$_{0-3}$—, —($CH_2$)$_{0-3}$-phenyl-($CH_2$)$_{0-3}$—, —N=C(R)—, —($C_{1-6}$ alkyl)-C(R)=N—($C_{1-6}$ alkyl)-, —($C_{1-6}$ alkyl)-(aryl)-C(R)=N—($C_{1-6}$ alkyl)-, —($C_{1-6}$ alkyl)-C(R)=N-(aryl)-($C_{1-6}$ alkyl)-, and —($C_{1-6}$ alkyl)-O—P(O)(OH)—O—($C_{0-6}$ alkyl)-, wherein R is H, $C_{1-6}$ alkyl, $C_{3-6}$ cycloalkyl, or an aryl group having 5-8 endocyclic atoms.

In some other embodiments, linkers $L^1$ and $L^2$ can be any of the following: —$C_1$-$C_{12}$ alkyl-, —$C_3$-$C_{12}$ cycloalkyl-, (—($CH_2$)$_{1-6}$—O—($CH_2$)$_{1-6}$—)$_{1-12}$—, (—($CH_2$)$_{1-4}$—NH—($CH_2$)$_{1-4}$)$_{1-12}$—, —($CH_2$)$_{1-12}$O—, (—($CH_2$)$_{1-4}$—O—($CH_2$)$_{1-4}$)$_{1-12}$—O—, —($CH_2$)$_{1-12}$—(CO)—O—, —($CH_2$)$_{1-12}$—(CO)—NH—, —($CH_2$)$_{1-12}$—O—(CO)—, —($CH_2$)$_{1-12}$—NH—(CO)—, (—($CH_2$)$_{1-4}$—O—($CH_2$)$_{1-4}$)$_{1-12}$—O—($CH_2$)$_{1-12}$—, —($CH_2$)$_{1-12}$—(CO)—O—($CH_2$)$_{1-12}$—, —($CH_2$)$_{1-12}$—(CO)—NH—($CH_2$)$_{1-12}$—, —($CH_2$)$_{1-12}$—O—(CO)—($CH_2$)$_{1-12}$—, —($CH_2$)$_{1-12}$—NH—(CO)—($CH_2$)$_{1-12}$—, —($C_3$-$C_{12}$ cycloalkyl)-, —($C_1$-$C_8$ alkyl)-($C_3$-$C_{12}$ cycloalkyl)-, —($C_3$-$C_{12}$ cycloalkyl)-($C_{1-8}$alkyl)-, —($C_{1-8}$alkyl)-($C_3$-$C_{12}$ cycloalkyl)-($C_{1-8}$alkyl)-, and —($CH_2$)$_{0-3}$-aryl-($CH_2$)$_{0-3}$—.

In still other embodiments, each of linkers $L^1$ and $L^2$ is a cleavable linker independently selected from hydrolyzable linkers, enzymatically cleavable linkers, pH sensitive linkers, disulfide linkers and photolabile linkers.

Other linkers useful in the present invention include self-immolative linkers. Useful self-immolative linkers are known to one of skill in the art, such as those useful for antibody drug conjugates. Exemplary self-immolative linkers are described in U.S. Pat. No. 7,754,681.

E. Linking Groups LG

The linkers and functional agents of the present invention can react with a linking group on the initiator fragment I or the comonomers $M^2$ to form a bond. The linking groups LG of the present invention can be any suitable functional group capable of forming a bond to another functional group, thereby linking the two groups together. For example, linking groups LG useful in the present invention include those used in click chemistry, maleimide chemistry, and NHS-esters, among others. Linking groups involved in click chemistry include, but are not limited to, azides and alkynes that form a triazole ring via the Huisgen cycloaddition process (see U.S. Pat. No. 7,375,234, incorporated herein in its entirety). The maleimide chemistry involves reaction of the maleimide olefin with a nucleophile, such as —OH, —SH or —$NH_2$, to form a stable bond. Other linking groups include those described in Bioconjugate Techniques, Greg T. Hermanson, Academic Press, 2d ed., 2008 (incorporated in its entirety herein).

Some non-limiting examples of the reaction of the linking groups and some groups typically found or introduced into functional agents are set forth in Table I.

TABLE I

| Illustrative Groups that may react with a linking group (LG) | Exemplary Reactive Linking Groups (shown as appended to —X) | Product Y—X |
|---|---|---|
| Y—COOH | HO—X (hydroxyl or activated forms thereof (e.g., tresylate, mesylate etc.)) | Y—C(=O)O—X |
| Y—COOH | HS—X | Y—C(=O)S—X |
| Y—SH | (thiol) | Y—S—S—X |
| Y—SH | R'—S—S—X (disulfide) | Y—S—S—X |
| Y—SH | (pyridyl)-S—S—X (dithiopyridyl) | Y—S—S—X |
| Y—$NH_2$ | H(O=)C—X aldehyde | Y—N=CH—X or Y—NH—$CH_2$—X following reduction |
| Y—$NH_2$ | (HO)$_2$HC— aldehyde hydrate | Y—N=CH—X or Y—NH—$CH_2$—X following reduction |
| Y—$NH_2$ | (R'O)$_2$CH—X or 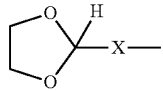 acetal | Y—N=CH—X or Y—NH—CH—X following reduction |

TABLE I-continued

| Illustrative Groups that may react with a linking group (LG) | Exemplary Reactive Linking Groups (shown as appended to —X) | Product Y—X |
|---|---|---|
| Y—NH$_2$ | R'OCH(OH)—X or hemiacetal | Y—N=CH—X or Y—NH—CH—X following reduction |
| Y—NH$_2$ | R'(O=)C—X ketone | Y—N=CR'—X or Y—NH—C(R')H—X following reduction |
| Y—NH$_2$ | (R'O)$_2$C(R')—X or 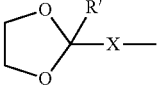 ketal | Y—N=C(R')—X or Y—NH—C(R')H—X following reduction |
| Y—NH$_2$ | R'OC(R')(OH)—X hemiketal | Y—N=C(R')—X or Y—NH—C(R')H—X following reduction |
| Y—NH$_2$ | R'(S=)C—X ketone thione (thioketone) | Y—N=C(R')—X or Y—NH—C(R')H—X following reduction |
| Y—NH$_2$ | (R'O)(R'S)C(R')—X or 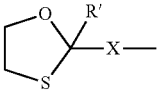 monothioketal | Y—N=C(R')—X or Y—NH—C(R')H—X following reduction |
| Y—NH$_2$ | R'SC(R')(SH)—X or dithiohemiketal | Y—N=C(R')—X or Y—NH—C(R')H—X following reduction |
| Y—NH$_2$ | (R'S)$_2$C(R')—X or 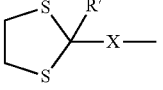 dithioketal | Y—N=C(R')—X or Y—NH—C(R')H—X following reduction |
| Y—SH Y—OH Y—COOH (anion) Y—NHR" | 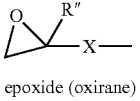 epoxide (oxirane) | Y—S—CH$_2$—C(OH)(R")—X— Y—O—CH$_2$—C(OH)(R")—X— Y—C(=O)O—CH$_2$—C(OH)(R")—X— Y—NR"—CH$_2$—C(OH)(R")—X— |
| Y—SH Y—OH Y—COOH (anion) Y—NHR" | 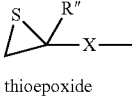 thioepoxide | Y—S—CH$_2$—C(SH)(R")—X Y—O—CH$_2$—C(SH)(R")—X— Y—C(=O)O—CH$_2$—C(SH)(R")—X— Y—NR"—CH$_2$—C(SH)(R")—X— |
| Y—SH Y—OH Y—NHR" Y—SH Y—OH Y—NHR" | HO—(C=O)—X carboxyl (alcohol)-(C=O)—X carboxylic acid ester (alcohol indicates an esterified suitable alcohol leaving group e.g., p-nitrophenyl) | Y—S—(C=O)—X Y—O—(C=O)—X Y—N(R")—(C=O)—X Y—S—(C=O)—X Y—O—(C=O)—X Y—NR"—(C=O)—X |

TABLE I-continued

| Illustrative Groups that may react with a linking group (LG) | Exemplary Reactive Linking Groups (shown as appended to —X) | Product Y—X |
|---|---|---|
| Y—NH$_2$ | N-hydroxysuccinimide ester (succinimide with N—O—R'''—X) | Y—NH—R'''—X |
| Y—SH | maleimide N—X, R = H, CH$_3$ | Y—S— (succinimide) N—X, R = H, CH$_3$ |
| Y—NH$_2$ | 1-benzotriazole ester (benzotriazole-N—O—R'''—X) | Y—NH—R'''—X |
| Y—NH$_2$ | CH$_3$—((CH$_2$)$_{1-3}$)—O(C=NH)—X (imidoester) | Y—NH—(C=NH)—X (amidine) |
| Y—(C=NH)—O—((CH$_2$)$_{1-3}$)—CH$_3$ (imidoester) | H$_2$N—X | Y—(C=NH)—HN—X (amidine) |
| Y—COOH | H$_2$N—X | Y—(C=O)—NH—X |
| Y—(C=O)—R" | amine | Y—(R")C=N—X or Y—(R")CH—NH—X following reduction |
| Y—COOH | H$_2$N—(C=O)—NH—X | Y—(C=O)—NH—(C=O)—NH—X |
| Y—(C=O)—R" | urea | Y—(R")C=N—(C=O)—NH—X or Y—(R")CH—NH—(C=O)—NH—X following reduction |
| Y—COOH | H$_2$N—(C=O)—O—X | Y—(C=O)—NH—(C=O)—O—X |
| Y—(C=O)—R" | carbamate | Y—(R")C=N—(C=O)—O—X or Y—(R")CH—NH—(C=O)—O—X following reduction |
| Y—COOH | H$_2$N—(C=S)—NH—X | Y—(C=O)—NH—(C=S)—NH—X |
| Y—(C=O)—R" | thiourea | Y—(R")C=N—(C=S)—NH—X or Y—(R")CH—NH—(C=S)—NH—X following reduction |
| Y—COOH | H$_2$N—(C=S)—O—X | Y—(C=O)—NH—(C=S)—O—X |
| Y—(C=O)—R" | thiocarbamate | Y—(R")C=N—(C=S)—O—X or Y—(R")CH—NH—(C=S)—O—X following reduction |
| Y—(C=O)—R" | H$_2$N—HN—X | Y—(R")C=N—HN—X hydrazone |
| Y—NH—NH$_2$ | R"—(O=C)—X | Y—NH—N=C(R")—X hydrazone |
| Y—NH$_2$ | O=C=N—X | Y—NH—(C=O)—NH—X |
| Y—OH | isocyanate | Y—O—(C=O)—NH—X |
| Y—NH$_2$ | S=C=N—X | Y—NH—(C=S)—NH—X |
| Y—OH | isothiocyanate | Y—O—(C=S)—NH—X |
| Y—SH | H$_2$C=CH—(C=O)—X or H$_2$C=C(CH$_3$)—(C=O)—X alpha-beta unsubstituted carbonyls | Y—S—CH$_2$CH$_2$—(C=O)—X Y—S—CH$_2$—CH(CH$_3$)—(C=O)—X |
| Y—SH | H$_2$C=CH—(C=O)O—X alpha-beta unsubstituted carboxyl | Y—S—CH$_2$CH$_2$—(C=O)O—X |

TABLE I-continued

| Illustrative Groups that may react with a linking group (LG) | Exemplary Reactive Linking Groups (shown as appended to —X) | Product Y—X |
|---|---|---|
| Y—SH | $H_2C=C(CH_3)-(C=O)-O-X$ alpha-beta unsubstituted carboxyls (methacrylates) | $Y-S-CH_2CH(CH_3)-(C=O)O-X$ |
| Y—SH | $H_2C=CH-(C=O)NH-X$ alpha-beta unsubstituted amides (acrylamides) | $Y-S-CH_2CH_2-(C=O)NH-X$ |
| Y—SH | vinylpyridine-X (2- or 4-vinylpyridine) | $Y-S-CH_2-CH_2$-(pyridyl)-X |
| Y—SH | $H_2C=CH-SO_2-X$ (vinyl sulfone) | $Y-S-H_2C-CH_2-SO_2-X$ |
| Y—SH | $ClH_2C-CH_2-SO_2-L$ (chloroethyl sulfone) | $Y-S-H_2C-CH_2-SO_2-X$ |
| Y—SH | (halogen)-$CH_2$—(C=O)—O—X<br>(halogen)-$CH_2$—(C=O)—NH—X<br>(halogen)-$CH_2$—(C=O)—X<br>(halogen is preferably I or Br) | $Y-S-CH_2-(C=O)-O-X$<br>$Y-S-CH_2-(C=O)-NH-X$<br>$Y-S-CH_2-(C=O)-X$ |
| Y—O(C=O)—$CH_2$— (halogen)<br>Y—NH(C=O)—$CH_2$— (halogen)<br>Y—(C=O)—$CH_2$— (halogen)<br>(halogen is preferably I or Br) | HS—X | $Y-O(C=O)-CH_2-S-X$<br>$Y-NH(C=O)-CH_2-S-X$<br>$Y-(C=O)-CH_2-S-X$ |
| Y—SH | (halogen)-$CH_2$(C=O)O—X<br>(halogen)-$CH_2$(C=O)NH—X<br>(halogen)-$CH_2$(C=O)—X<br>(halogen is preferably I or Br) | $Y-S-CH_2(C=O)O-X$<br>$Y-S-CH_2(C=O)NH-X$<br>$Y-S-CH_2(C=O)-X$ |
| Y—$N_3$ | HC≡C—X | triazole product (Y—N triazole—X) |
| Y—$N_3$ | 2-(diphenylphosphino)phenyl carbonate-X | $Y-NH-C(O)-X$ |
| Y—$N_3$ | (diphenylphosphino)methyl thiocarbonate-X | $Y-NH-C(O)-X$ |
| Y—SH | aziridine-X | $Y-S-CH_2-CH(NH_2)-X$ |
| Y—$NH_2$ | $(F_5-Ph)-OC(O)-X$ | $Y-NH-C(O)-X$ |

R' is $C_{1-6}$ alkyl, $C_{3-6}$ cycloalkyl, or an aryl group having 5-8 endocyclic atoms;

R" is H, $C_{1-6}$ alkyl, $C_{3-6}$ cycloalkyl, or an aryl group having 5-8 endocyclic atoms;

R'" is a carbonyl derivative *—(C=O)—, *—(C=O)—$(CH_2)_{1-8}$—S—S—, *—(C=O)—$(CH_2)_{1-8}$—(C=O)—O—, *—(C=O)—$(CH_2)_{1-8}$—O—(C=O)—, *—(C=O)—$(CH_2)_{1-8}$—(C=O)—NH—, or *—(C=O)—$(CH_2)_{1-8}$—NH—(C=O)—, or alternatively, R'" is carbonyl derivative of the form *—(C=O)—O—$(CH_2)_{1-8}$—S—, *—(C=O)—O—$(CH_2)_{1-8}$—(C=O)—O—, *—(C=O)—O—$(CH_2)_{1-8}$—O—(C=O)—, *—(C=O)—O—$(CH_2)_{1-8}$—(C=O)—NH—, or *—(C=O)—O—$(CH_2)_{1-8}$—NH—(C=O)—, where "*" indicates the point of attachment to succinimidyl or benzotriazolyl groups;

X and Y are each the active agent, linker, monomer or initiator fragment I.

$C(O)NR^{1a}R^{1b}$, —$NR^{1a}R^{1b}$, $C_{1-6}$ alkyl-$NR^{1a}R^{1b}$, —$N(R^{1a})C(O)R^{1b}$, —$N(R^{1a})C(O)OR^{1b}$, —$N(R^{1a})C(O)NR^{1a}R^{1b}$, —OP(O)(OR$^{1a}$)$_2$, —S(O)$_2$OR$^{1a}$, —S(O)$_2$NR$^{1a}$R$^{1b}$, —CN, —NO$_2$, cycloalkyl, heterocycloalkyl, aryl and heteroaryl.

F. Functional agents

Functional agents useful in the random copolymers of the present invention include any biological agent or synthetic compound capable of targeting a particular ligand, receptor, complex, organelle, cell, tissue, epithelial sheet, or organ, or of treating a particular condition or disease state. Of particular interest, is a combination of bioactive agents that together target mechanisms common to a particular disease. For example, a first bioactive agent (stably attached) that is a biopharmaceutical agent that binds to a protein upregulated in a disease; a second bioactive agent (stably attached) that is a peptide that binds to an extracellular matrix tissue constituent such as heparin sulfate; a third bioactive agent (unstably attached) that is a small molecule drug that releases over time and exerts a local, intracellular effect, for example, an anti-proliferative effect. In some embodiments, the bioactive agent is a drug, a therapeutic protein, a small molecule, a peptide, a peptoid, an oligonucleotide (aptamer, siRNA, microRNA), a nanoparticle, a carbohydrate, a lipid, a glycolipid, a phospholipid, or a targeting agent. The ratio of comonomers is chosen based on predefined stoichiometry (for example, to match a biological avidity; to match a biological stoichiometry; to impart a 'gearing' effect). Other functional agents useful in the random copolymers of the present invention include, but are not limited to, radiolabels, fluorophores and dyes.

The functional agents can be linked to the initiator fragment I or the comonomers M$^2$, or both, of the random copolymers. The functional agents can be linked to the initiator fragment I or the comonomers M$^2$ either before or after polymerization via cleavable, non-cleavable, or self-immolative linkers described above. The functional agent can also be physisorbed or ionically absorbed to the random copolymer instead of covalently attached.

The preparation of the random copolymers of the present invention linked to a functional agent can be conducted by first linking the functional agent to a linking group attached to a monomer and subjecting the coupled functional agent to conditions suitable for synthesis of the inventive random copolymers. In those cases, a suitable linking group can be an initiator (e.g., iodinated, brominated or chlorinated compound/group) for use in ATRP reactions. Such a reaction scheme is possible where the functional agent is compatible with the polymer polymerization reactions and any subsequent workup required. However, coupling of functional agents to preformed random copolymers can be used where the functional agent is not compatible with conditions suitable for polymerization. In addition, where cost makes the loss of an agent to imperfect synthetic yields, oftentimes encountered particularly in multistep synthetic reactions, coupling of functional agent to preformed random copolymers of the present invention can be employed.

Where a functional agent is not compatible with the conditions employed for polymerization reactions, it can be desirable to introduce the functional agent subsequent to the polymerization reaction.

Bioactive agents, A, can be broadly selected. In some embodiments the bioactive agents can be selected from one or more drugs, vaccines, aptamers, avimer scaffolds based on human A domain scaffolds, diabodies, camelids, shark IgNAR antibodies, fibronectin type III scaffolds with modified specificities, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, microRNA, DNA, cDNA, antisense constructs, ribozymes, etc., and combinations thereof). In one embodiment, the bioactive agents can be selected from proteins, peptides, polypeptides, soluble or cell-bound, extracellular or intracellular, kinesins, molecular motors, enzymes, extracellular matrix materials and combinations thereof. In another embodiment, bioactive agents can be selected from nucleotides, oligonucleotides, polynucleotides, and nucleic acids (e.g., mRNA, tRNA, snRNA, RNAi, DNA, cDNA, antisense constructs, ribozymes, etc., and combinations thereof). In another embodiment, bioactive agents can be selected from steroids, lipids, fats and combinations thereof. For example, the bioactive agent can bind to the extracellular matrix, such as when the extracellular matrix is hyaluronic acid or heparin sulfate proteoglycan and the bioactive agent is a positively charged moiety such as choline for non-specific, electrostatic, Velcro type binding interactions. In another embodiment, the bioactive agent can be a peptide sequence that binds non-specifically or specifically.

Bioactive agents can be designed and/or selected to have a full activity (such as a high level of agonism or antagonism). Alternatively, a multifunctional bioactive agent can be selected to modulate one target protein's activity while impacting fully another.

Just as mosaic proteins contain extracellular binding domains or sub-domains (example, VEGF and Heparin Binding Epidermal Growth Factor), sequences from these binding sites can be replicated as a bioactive agent for polymer attachment. More broadly, mosaic proteins represent strings of domains of many functions (target binding, extracellular matrix binding, spacers, avidity increases, enzymatic). The set of bioactives chosen for a particular application can be assembled in similar fashion to replicate a set of desired functional activities.

Other functional agents, A, include charged species such as choline, lysine, aspartic acid, glutamic acid, and hyaluronic acid, among others. The charged species are useful for facilitating ionic attachment, to vitreous for example.

Therapeutic Proteins and Antibodies

In one particularly useful embodiment, the functional agent is a therapeutic protein. Numerous therapeutic proteins are disclosed throughout the application such as, and without limitation, erythropoietin, granulocyte colony stimulating factor (G-CSF), GM-CSF, interferon alpha, interferon beta, human growth hormone, and imiglucerase.

In one embodiment, the functional agents can be selected from specifically identified polysaccharide, protein or peptide bioactive agents, including, but not limited to: agalsidase, alefacept, alkaline phosphatase, aspariginase, amdoxovir (DAPD), antide, becaplermin, botulinum toxin including types A and B and lower molecular weight compounds with botulinum toxin activity, calcitonins, cyanovirin, denileukin diftitox, erythropoietin (EPO), EPO agonists, dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, N-Acetylgalactosamine-6-sulfate sulfatase, collagen, cyclosporin, alpha defensins, beta defensins, desmopressin, exendin-4, cytokines, cytokine receptors, granulocyte colony stimulating factor (G-CSF), thrombopoietin (TPO), alpha-1 proteinase inhibitor, elcatonin, granulocyte macrophage colony stimulating factor (GM-CSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, parathyroid hormone, parathyroid hormone related peptide, OP-1; acidic fibroblast growth factor, basic fibroblast growth factor, Fibroblast Growth Factor 21, CD-40 ligand, heparin, human serum albumin, low molecular weight heparin (LMWH), interferon alpha, interferon beta, interferon gamma, interferon omega, interferon tau, consensus interferon, human lysyl oxidase-like-2 (LOXL2); interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-17, interleukin-21, interleukin-23, p40, interleukin-13 receptor, interleukin-17 receptor; lactoferrin and lactoferrin fragments, luteinizing hormone releasing hormone (LHRH), insulin, pro-insulin, insulin analogues, leptin, ghrelin, amylin, C-peptide, somatostatin, somatostatin analogs including octreotide, vasopressin, follicle stimulating hormone (FSH), imiglucerase, influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF) (e.g., TNF-α and TNF-β), TNF receptors (e.g., TNF-α receptor and TNF-β receptor), CTLA4, CTLA4 receptor, monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-484, CDP-571, CDP-791, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, I$^{131}$tositumomab, trastuzumab, tuvirumab, visilizumab, and fragments and mimetics thereof. Functional agents also include agents which bind to these specifically identified polysaccharide, protein or peptide bioactive agents.

In one embodiment, the bioactive agent is a fusion protein. For example, and without limitation, the bioactive component can be an immunoglobulin or portion of an immunoglobulin fused to one or more certain useful peptide sequences. For example, the bioactive agent may contain an antibody Fc fragment. In one embodiment, the bioactive agent is a CTLA4 fusion protein. For example, the bioactive agent can be an Fc-CTLA4 fusion protein. In another embodiment, the bioactive agent is a Factor VIII fusion protein. For example, the bioactive agent can be an Fc-Factor VIII fusion protein.

In one particularly useful embodiment, the bioactive agent is a human protein or human polypeptide, for example, a heterologously produced human protein or human polypeptide. Numerous proteins and polypeptides are disclosed herein for which there is a corresponding human form (i.e., the protein or peptide is normally produced in human cells in the human body). Therefore, in one embodiment, the bioactive agent is the human form of each of the proteins and polypeptides disclosed herein for which there is a human form. Examples of such human proteins include, without limitation, human antibodies, human enzymes, human hormones and human cytokines such as granulocyte colony stimulation factor, granulocyte macrophage colony stimulation factor, interferons (e.g., alpha interferons and beta interferons), human growth hormone and erythropoietin.

Other examples of therapeutic proteins which may serve as bioactive agents include, without limitation, factor VIII, b-domain deleted factor VIII, factor VIIa, factor IX, anticoagulants; hirudin, alteplase, tpa, reteplase, tpa, tpa—3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-apha1, consensus ifn, ifn-beta, ifn-beta 1b, ifn-beta 1a, ifn-gamma (e.g., 1 and 2), ifn-lambda, ifn-delta, il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen cal 25, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diptheria toxin fusion protein, tnfr-lgg fragment fusion protein laronidase, dnaases, alefacept, darbepoetin alpha (colony stimulating factor), tositumomab, murine mab, alemtuzumab, rasburicase, agalsidase beta, teriparatide, parathyroid hormone derivatives, adalimumab (Igg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone. And any of these can be modified to have a site-specific conjugation point (a N-terminus, or C-terminus, or other location) using natural (for example, a serine to cysteine substitution) (for example, formylaldehyde per method of Redwood Biosciences) or non-natural amino acid.

Examples of therapeutic antibodies (or their respective scFv or Fab fragments) that may serve as bioactive agents include, but are not limited, to HERCEPTIN™ (Trastuzumab) (Genentech, Calif.) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/Medlmmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (DEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-α antibody (CATI-BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-$β_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

The spectrum of existing approaches to creating antibody drug conjugates depends on conjugation of single toxin-like molecules together with a linker to an antibody generally at one to eight sites. The approach outlined in this invention involves attachment of a random copolymer to the immunoglobulin via a cleavable or non-cleavable linkage chemistry. The copolymer is designed to have multiple copies of the small molecule bioactive moiety attached stoichiometrically via cleavable (including self-immolative) or non-cleavable linkage chemistry. Because of the additional flexibility inherent in the invention, more than one type of bioactive moiety and many more copies of each bioactive moiety can be included via conjugation or attachment to polymer comonomers, for example 10, 20, 50, 100, 250, or 500. The ability to include many more allows one to broaden the perspective of antibody drug conjugates beyond toxins to include other small molecule drugs with synergistic biologies (non-limiting examples include panitumumab and kras inhibitors; adalimumab and p38 or JAK inhibitors; bevacizumab and cMet inhibitors). The result is targeted distribution, focal delivery, tailored drug release kinetics which decrease off-target effects. Furthermore, the attachment of small molecule bioactives to the polymer backbone comonomers rescues bioactives with poor oral absorption, distribution, metabolism and/or elimination or other liabilities. All in, the result is a step change in efficacy due to multifunctionality, lower Cmax, increased drug loading, plus other benefits. Importantly, this approach to create combination therapeutics with the different bioactive agents attached to a common polymer core or scaffold results in local tissue therapeutic effects that can be synergistic and that can substantially increase efficacy while decreasing toxicity.

The antibodies of the present invention can also be linked to a therapeutic agent described within or known in the art to form an antibody drug conjugate (ADC). Targeted therapeutics provide several advantages over existing technologies, including reducing nonspecific toxicities and increasing efficacy. The targeting properties of antibodies, such as monoclonal antibodies (mABs) and mAB fragments (scFv and FAb'), enable delivery of a potent therapeutic agent that is coupled to the mAB. The therapeutic agent can be any useful drug, protein, peptide, or radionuclide. Antibody drug conjugates useful in combination with the random copolymers of the present invention are described in, for example, U.S. Pat. No. 7,745,394 (Seattle Genetics), U.S. Pat. No. 7,695,716 (Seattle Genetics), U.S. Pat. No. 7,662,387 (Seattle Genetics), U.S. Pat. No. 7,514,080 (ImmunoGen), U.S. Pat. No. 7,491,390 (Seattle Genetics), U.S. Pat. No. 7,501,120 (ImmunoGen), U.S. Pat. No. 7,494,649 (ImmunoGen), and U.S. Pat. No. 7,374,762 (ImmunoGen).

Proteins, Peptides and Amino Acids

Proteins and peptides for use as bioactive agents as disclosed herein can be produced by any useful method including production by in vitro synthesis and by production in biological systems. Typical examples of in vitro synthesis methods which are well known in the art include solid-phase synthesis ("SPPS") and solid-phase fragment condensation ("SPFC"). Biological systems used for the production of proteins are also well known in the art. Bacteria (e.g., *E. coli* and *Bacillus* sp.) and yeast (e.g., *Saccharomyces cerevisiae* and *Pichia pastoris*) are widely used for the production of heterologous proteins. In addition, heterologous gene expression for the production of bioactive agents for use as disclosed herein can be accomplished using animal cell lines such as mammalian cell lines (e.g., CHO cells). In one particularly useful embodiment, the bioactive agents are produced in transgenic or cloned animals such as cows, sheep, goats and birds (e.g., chicken, quail, ducks and turkey), each as is understood in the art. See, for example, U.S. Pat. No. 6,781,030, issued Aug. 24, 2004, the disclosure of which is incorporated in its entirety herein by reference.

Bioactive agents such as proteins produced in domesticated birds such as chickens can be referred to as "avian derived" bioactive agents (e.g., avian derived therapeutic proteins). Production of avian derived therapeutic proteins is known in the art and is described in, for example, U.S. Pat. No. 6,730,822, issued May 4, 2004, the disclosure of which is incorporated in its entirety herein by reference.

In embodiments where the bioactive agent is a protein or polypeptide, functional groups present in the amino acids of the protein polypeptide sequence can be used to link the agent to the random copolymer. Linkages to protein or polypeptide bioactive agents can be made to naturally occurring amino acids in their sequence or to naturally occurring amino acids that have either been added to the sequence or inserted in place of another amino acid, for example the replacement of a serine by a cysteine.

Protein or polypeptide bioactive agents may also comprise non-naturally occurring amino acids in addition to the common naturally occurring amino acids found in proteins and polypeptides. In addition to being present for the purpose of altering the properties of a polypeptide or protein, non-naturally occurring amino acids can be introduced to provide a functional group that can be used to link the protein or polypeptide directly to the random copolymer. Furthermore, naturally occurring amino acids, e.g., cysteine, tyrosine, tryptophan can be used in this way.

Non-naturally occurring amino acids can be introduced into proteins and peptides by a variety of means. Some of the techniques for the introduction of non-natural amino acids are discussed in U.S. Pat. No. 5,162,218, the disclosure of which is incorporated in its entirety herein by reference. First, non-naturally occurring amino acids can be introduced by chemical modification of a polypeptide or protein on the amino acid side chain or at either the amino terminus or the carboxyl terminus. Non-limiting examples of chemical modification of a protein or peptide might be methylation by agents such as diazomethane, or the introduction of acetylation at an amino group present in lysine's side chain or at the amino terminus of a peptide or protein. Another example of the protein/polypeptide amino group modification to prepare a non-natural amino acid is the use of methyl 3-mercaptopropionimidate ester or 2-iminothiolane to introduce a thiol (sulfhydryl, —SH) bearing functionality linked to positions in a protein or polypeptide bearing a primary amine. Once introduced, such groups can be employed to form a covalent linkage to the protein or polypeptide.

Second, non-naturally occurring amino acids can be introduced into proteins and polypeptides during chemical synthesis. Synthetic methods are typically utilized for preparing polypeptides having fewer than about 200 amino acids, usually having fewer than about 150 amino acids, and more usually having 100 or fewer amino acids. Shorter proteins or polypeptides having less than about 75 or less than about 50 amino acids can be prepared by chemical synthesis.

The synthetic preparation methods that are particularly convenient for allowing the insertion of non-natural amino acids at a desired location are known in the art. Suitable synthetic polypeptide preparation methods can be based on Merrifield solid-phase synthesis methods where amino acids are sequentially added to a growing chain (Merrifield (1963) J. Am. Chem. Soc. 85:2149-2156). Automated systems for synthesizing polypeptides by such techniques are now commercially available from suppliers such as Applied Biosystems, Inc., Foster City, Calif. 94404; New Brunswick Scientific, Edison, N.J. 08818; and Pharmacia, Inc., Biotechnology Group, Piscataway, N.J. 08854.

Examples of non-naturally occurring amino acids that can be introduced during chemical synthesis of polypeptides include, but are not limited to: D-amino acids and mixtures of D and L-forms of the 20 naturally occurring amino acids, N-formyl glycine, ornithine, norleucine, hydroxyproline, beta-alanine, hydroxyvaline, norvaline, phenylglycine, cyclohexylalanine, t-butylglycine (t-leucine, 2-amino-3,3-dimethylbutanoic acid), hydroxy-t-butylglycine, amino butyric acid, cycloleucine, 4-hydroxyproline, pyroglutamic acid (5-oxoproline), azetidine carboxylic acid, pipecolinic acid, indoline-2-carboxylic acid, tetrahydro-3-isoquinoline carboxylic acid, 2,4-diaminobutyricacid, 2,6-di-aminopimelic acid, 2,4-diaminobutyricacid, 2,6-di-aminopimelicacid, 2,3-diaminopropionicacid, 5-hydroxylysine, neuraminic acid, and 3,5-diiodotyrosine.

Third, non-naturally occurring amino acids can be introduced through biological synthesis in vivo or in vitro by insertion of a non-sense codon (e.g., an amber or ocher codon) in a DNA sequence (e.g., the gene) encoding the polypeptide at the codon corresponding to the position where the non-natural amino acid is to be inserted. Such techniques are discussed for example in U.S. Pat. Nos. 5,162,218 and 6,964,859, the disclosures of which are incorporated in their entirety herein by reference. A variety of methods can be used to insert the mutant codon including oligonucleotide-directed mutagenesis. The altered sequence is subsequently transcribed and translated, in vivo or in vitro in a system which provides a suppressor tRNA, directed against the nonsense codon that has been chemically or enzymatically acylated with the desired non-naturally occurring amino acid. The synthetic amino acid will be inserted at the location corresponding to the nonsense codon. For the preparation of larger and/or glycosylated polypeptides, recombinant preparation techniques of this type are usually preferred. Among the amino acids that can be introduced in this fashion are: formyl glycine, fluoroalanine, 2-Amino-3-mercapto-3-methylbutanoic acid, homocysteine, homoarginine and the like. Other similar approaches to obtain non-natural amino acids in a protein include methionine substitution methods.

Where non-naturally occurring amino acids have a functionality that is susceptible to selective modification, they are particularly useful for forming a covalent linkage to the protein or polypeptide. Circumstances where a functionality is susceptible to selective modification include those where the functionality is unique or where other functionalities that might react under the conditions of interest are hindered either stereochemically or otherwise.

Other antibodies, such as single domain antibodies are useful in the present invention. A single domain antibody (sdAb, called Nanobody by Ablynx) is an antibody fragment consisting of a single monomeric variable antibody domain. Like a whole antibody, the sdAb is able to bind selectively to a specific antigen. With a molecular weight of only 12-15 kDa, single domain antibodies are much smaller than common whole antibodies (150-160 kDa). A single domain antibody is a peptide chain of about 110 amino acids in length, comprising one variable domain (VH) of a heavy chain antibody, or of a common IgG.

Unlike whole antibodies, sdAbs do not show complement system triggered cytotoxicity because they lack an Fc region. Camelid and fish derived sdAbs are able to bind to hidden antigens that are not accessible to whole antibodies, for example to the active sites of enzymes.

A single domain antibody (sdAb) can be obtained by immunization of dromedaries, camels, llamas, alpacas or sharks with the desired antigen and subsequent isolation of the mRNA coding for heavy chain antibodies. Alternatively they can be made by screening synthetic libraries. Camelids are members of the biological family Camelidae, the only living family in the suborder Tylopoda. Camels, dromedaries, Bactrian Camels, llamas, alpacas, vicunas, and guanacos are in this group.

Peptides useful in the present invention also include, but are not limited to, a macrocyclic peptide, a cyclotide, an LDL receptor A-domain, a protein scaffold (as discussed in U.S. Patent No. 60/514,391, incorporated in its entirety herein), a soluble receptor, an enzyme, a peptide multimer, a domain multimer, an antibody fragment multimer, and a fusion protein.

Drugs

In another embodiment, the bioactive agents can also be selected from specifically identified drug or therapeutic agents, including but not limited to: tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutarnide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, vairubicin, vinblastine, vincristine, vindesine, vinorelbine, voriconazole, dolasetron, granisetron, formoterol, fluticazone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, and tyrphostines. Bioactive agents may also be selected from the group consisting of aminohippurate sodium, amphotericin B, doxorubicin, aminocaproic acid, aminolevulinic acid, arninosalicylic acid, metaraminol bitartrate, pamidronate disodium, daunorubicin, levothyroxine sodium, lisinopril, cilastatin sodium, mexiletine, cephalexin, deferoxamine, and amifostine in another embodiment.

Other bioactive agents useful in the present invention include extracellular matrix targeting agents, functional transport moieties and labeling agents. Extracellular matrix targeting agents include, but are not limited to, heparin binding moieties, matrix metalloproteinase binding moieties, lysyl oxidase binding domains, negatively charged moieties or positively charged moieties and hyaluronic acid. Functional transport moieties include, but are not limited to, blood brain barrier transport moieties, intracellular transport moieties, organelle transport moieties, epithelial transport domains and tumor targeting moieties (folate, other). In some embodiments, the targeting agents useful in the present invention target anti-TrkA, anti A-beta (peptide 1-40, peptide 1-42, monomeric form, oligomeric form), anti-IGF1-4, agonist RANK-L, anti-ApoE4 or anti-ApoA1, among others.

Diagnostic Agents

Diagnostic agents useful in the random copolymers of the present invention include imaging agents and detection agents such as radiolabels, fluorophores, dyes and contrast agents.

Imaging agent refers to a label that is attached to the random copolymer of the present invention for imaging a tumor, organ, or tissue in a subject. The imaging moiety can be covalently or non-covalently attached to the random copolymer. Examples of imaging moieties suitable for use in the present invention include, without limitation, radionuclides, fluorophores such as fluorescein, rhodamine, Texas Red, Cy2, Cy3, Cy5, Cy5.5, and the AlexaFluor (Invitrogen, Carlsbad, Calif.) range of fluorophores, antibodies, gadolinium, gold, nanomaterials, horseradish peroxidase, alkaline phosphatase, derivatives thereof, and mixtures thereof.

Radiolabel refers to a nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Radionuclides suitable for use in the present invention include, but are not limited to, fluorine 18 ($^{18}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for meta state. Additionally, naturally occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{17m}Sn$, $^{149}Pm$, $^{153}Sm$, $^{166}Ho$, and $^{188}Re$ are examples of beta-emitting radionuclides. $^{67}Ga$, $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{68}Ga$, $^{68}Ga$, $^{82}Rb$, and $^{86}Y$ are examples of positron-emitting radionuclides. $^{64}Cu$ is a beta- and positron-emitting radionuclide. Imaging and detection agents can also be designed into the random copolymers of the invention through the addition of naturally occurring isotopes such as deuterium, $^{13}C$, or $^{15}N$ during the synthesis of the initiator, linkers, linking groups, comonomers.

Nanoparticles

The functional agents can also include nanoparticles. Nanoparticles useful in the present invention include particles having a size ranging from 1 to 1000 nm. Nanoparticles can be beads, metallic particles or can in some cases be micelles and in some other be liposomes. Other nanoparticles include carbon nanotubes, quantum dots and colloidal gold. Nanoparticles can be packed with diagnostic and/or therapeutic agents.

Those skilled in the art will also recognize that the invention can be used to enable coincident detection of more than one agent of the same or different type. Also, the use of flexible linker chemistries can also be used to witness the loss of one fluorescent label, for example as the molecule is taken up into the cell and into a low pH environment.

In some embodiments, the random copolymer has the following formula:

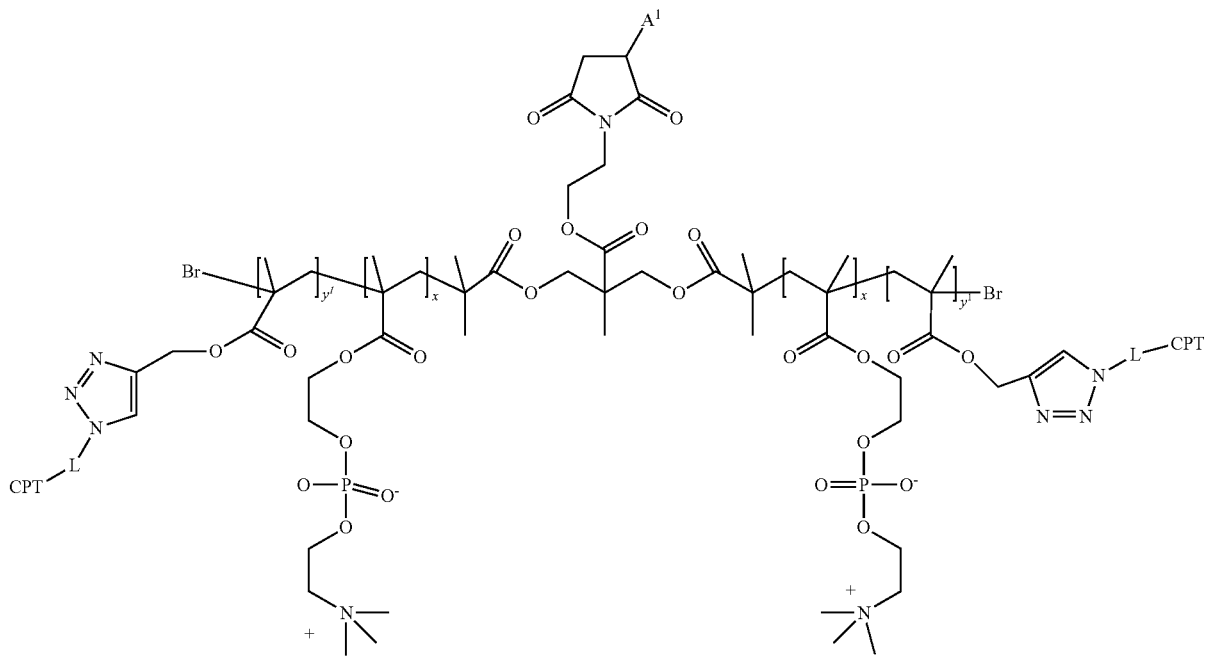

wherein subscripts x and $y^1$ are such that the Mn of the polymer portion is about 95,000 g/mol; $A^1$ is an antibody; and L-CTP has the formula:
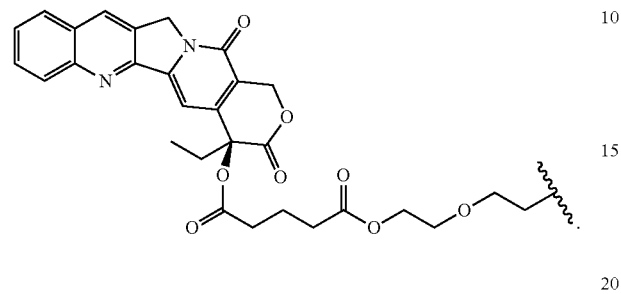
In other embodiments, the random copolymer has the formula:
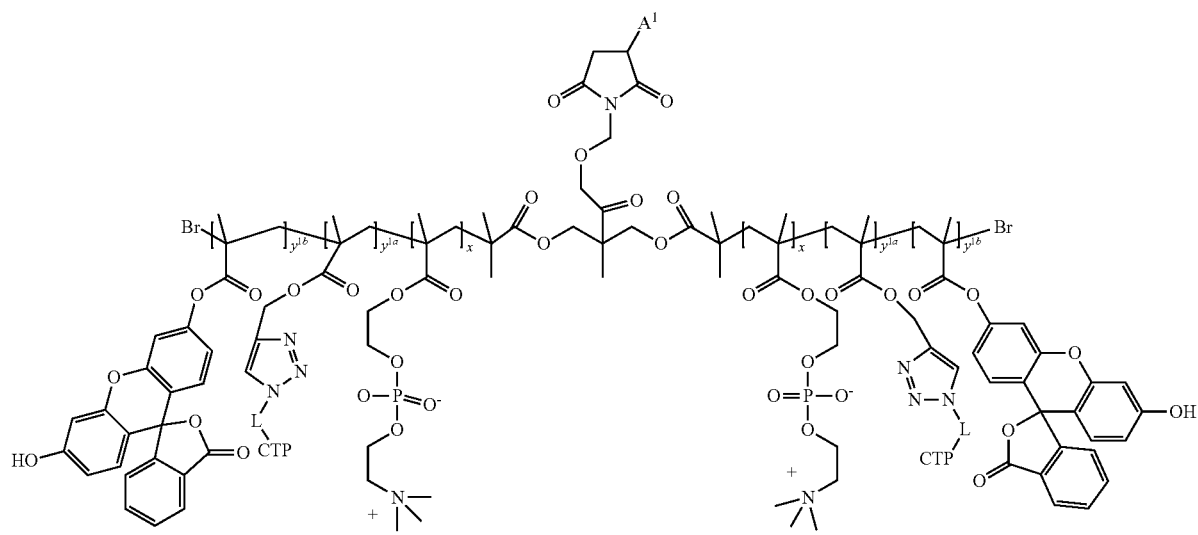
wherein subscripts x, $y^{1a}$ and $y^{1b}$ are such that the Mn of the polymer portion is about 107,100 g/mol; $A^1$ is an antibody; and L-CTP is as defined above.

In still other embodiments, the random copolymer has the formula:

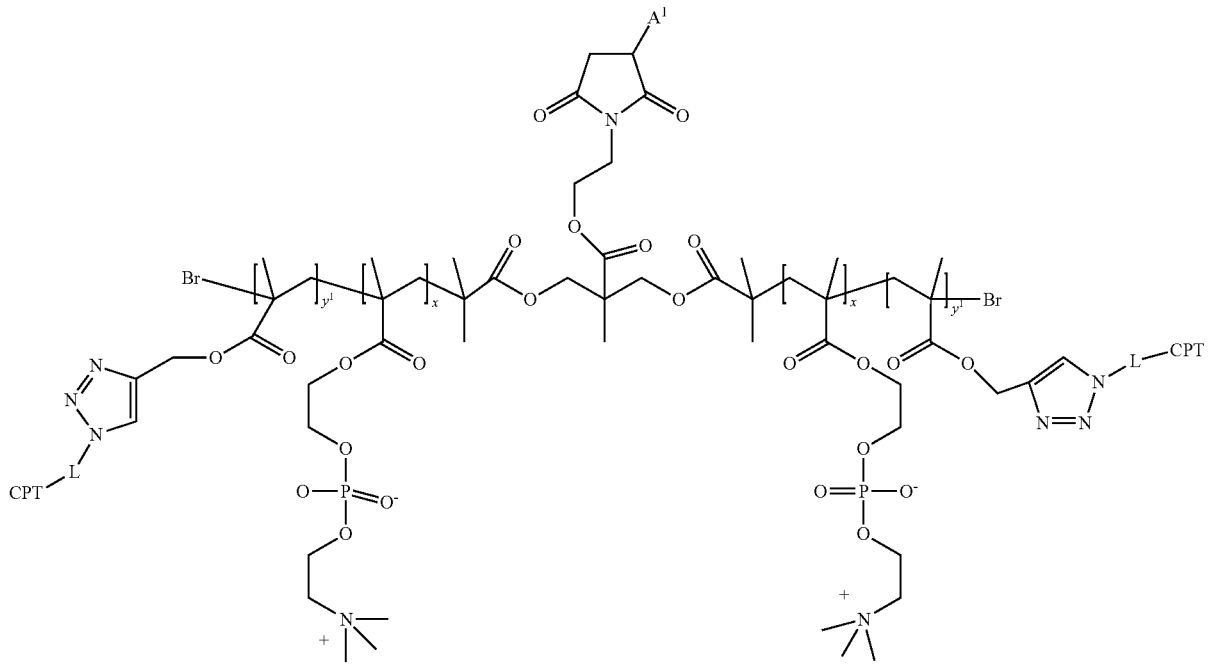

wherein subscripts x and $y^1$ are such that the Mn of the polymer portion is about 95,000 g/mol; $A^1$ is an IgG; and L-CTP is as defined above.

In some embodiments, each of $A^1$ and $A^2$ is independently an antibody, an antibody fragment, a Fab, IgG, a peptide, a protein, an enzyme, an oligonucleotide, a polynucleotide, nucleic acids, or an antibody drug conjugate (ADC).

In some embodiments, $A^1$ is independently selected from an antibody, an antibody fragment, a Fab, a scFv, an immunoglobulin domain, an IgG, and $A^2$ is independently selected from an anti-cancer agent, a toxin, a small molecule drug, a chemotherapy agent, a kinase inhibitor, an anti-inflammatory agent, and an antifibrotic agent.

In some embodiments, $R^1$ is $LG^1$, and $L^2$-$A^2$ is independently selected from an anti-cancer agent, a toxin, a small molecule drug, a chemotherapy agent, a kinase inhibitor, an anti-inflammatory agent, and an antifibrotic agent.

IV. Preparation of Zwitterion-Containing Random Copolymers

The random copolymers of the present invention can be prepared by any means known in the art. In some embodiments, the present invention provides a process for preparing a random copolymer of the present invention, the process including the step of contacting a mixture of a first monomer and a second monomer with an initiator, $I^1$, under conditions sufficient to prepare a random copolymer via free radical polymerization, wherein the first monomer comprises a phosphorylcholine, and each of the second monomer and initiator independently comprise at least one of a functional agent or a linking group for linking to the functional agent.

The mixture for preparing the random copolymers of the present invention can include a variety of other components. For example, the mixture can also include catalyst, ligand, solvent, and other additives. In some embodiments, the mixture also includes a catalyst and a ligand. Suitable catalysts and ligands are described in more detail below.

The mixture for preparing the random copolymers of the present invention can be prepared using a semi-continuous process to control the structure of the polymer when the reactivity ratio of the monomers are different in order to allow the final polymer to be an alternating copolymer, a periodic copolymer, a gradient copolymer, a block copolymer or a statistical copolymer.

Any suitable monomer can be used in the process of the present invention, such as those described above.

The random copolymers of the present invention can be prepared by any suitable polymerization method, such as by living radical polymerization. Living radical polymerization, discussed by Odian, G. in Principles of Polymerization, 4th Wiley-Interscience John Wiley & Sons: New York, 2004, and applied to zwitterionic polymers for example in U.S. Pat. No. 6,852,816. Several different living radical polymerization methodologies can be employed, including Stable Free Radical Polymerization (SFRP), Radical Addition-Fragmentation Transfer (RAFT) and Nitroxide-Mediated Polymerization (NMP). In addition, Atom Transfer Radical Polymerization (ATRP), provides a convenient method for the preparation of the random copolymers of the invention.

The preparation of polymers via ATRP involves the radical polymerization of monomers beginning with an initiator bearing one or more halogens. The halogenated initiator is activated by a catalyst (or a mixture of catalysts when $CuBr_2$ is employed) such as a transition metal salt (CuBr) that can be solubilized by a ligand (e.g., bipyridine or PMDETA). RAFT polymerization uses thiocarbonylthio compounds, such as dithioesters, dithiocarbamates, trithiocarbonates, and xanthates, to mediate the polymerization process via a reversible chain-transfer process. Other "living" or controlled radical processes useful in the preparation of the inventive random copolymers include NMP.

Initiators

Initiators useful for the preparation of the random copolymers of the present invention include any initiator suitable for polymerization via atom transfer radical polymerization (ATRP), such as those described above. Other useful initiators include those for nitroxide-mediated radical polymerization (NMP), or reversible addition-fragmentation-termination (RAFT or MADIX) polymerization. Still other techniques to control a free-radical polymerization process can be used, such as the use of iniferters, degenerative transfer or telomerization process. Moreover, the initiators useful in the present invention include those having at least one branch point, such as those described above.

Random copolymers of the present invention having complex architectures including branched compounds having multiple polymer arms including, but not limited to, comb and star structures. Comb architectures can be achieved employing linear initiators bearing three or more halogen atoms, preferably the halogens are chlorine, bromine, or iodine atoms, more preferably the halogens are chlorine or bromine atoms. Star architectures can also be prepared employing compounds bearing multiple halogens on a single carbon atom or cyclic molecules bearing multiple halogens. In some embodiments compounds having star architectures have 3 polymer arms and in other embodiments they have 4 polymer arms. See initiators described above.

Catalyst and Ligands

Catalyst for use in ATRP or group radical transfer polymerizations may include suitable salts of $Cu^{1+}$, $Cu^{2+}$, $Fe^{2+}$, $Fe^{3+}$, $Ru^{2+}$, $Ru^{3+}$, $Cr^{2+}$, $Cr^{3+}$, $Mo^{2+}$, $Mo.^{3+}$, $W^{2+}$, $W^{3+}$, $Mn^{2+}$, $Mn^{2+}$, $Mn^{4+}$, $Rh^{3+}$, $Rh^{4+}$, $Re^{2+}$, $Re^{3+}$, $Co^{1+}$, $Co.^{2+}$, $Co^{3+}$, $V^{2+}$, $V^{3+}$, $Zn.^{1+}$, $Zn^{2+}$, $Ni^{2+}$, $Ni^{3+}$, $Au^{1+}$, $Au^{2+}$, $Ag^{1+}$ and $Ag^{2+}$. Suitable salts include, but are not limited to: halogen, $C_1$-$C_6$-alkoxy, sulfates, phosphate, triflate, hexafluorophosphate, methanesulphonate, arylsulphonate salts. In some embodiments the catalyst is a Chloride, bromide salts of the above-recited metal ions. In other embodiments the catalyst is CuBr, CuCl or $RuCl_2$.

In some embodiments, the use of one or more ligands to solubilize transition metal catalysts is desirable. Suitable ligands are usefully used in combination with a variety of transition metal catalysts including where copper chloride or bromide, or ruthenium chloride transition metal salts are part of the catalyst. The choice of a ligand affects the function of the catalyst as ligands not only aid in solubilizing transition metal catalysts in organic reaction media, but also adjust their redox potential. Selection of a ligand is also based upon the solubility and separability of the catalyst from the product mixture. Where polymerization is to be carried out in a liquid phase soluble ligands/catalyst are generally desirable although immobilized catalysts can be employed. Suitable ligands include those pyridyl groups (including alkyl pyridines e.g., 4.4. dialkyl-2,2' bipyridines) and pyridyl groups bearing an alkyl substituted imino group, where present, longer alkyl groups provide solubility in less polar monomer mixtures and solvent media. Triphenyl phosphines and other phosphorus ligands, in addition to indanyl, or cyclopentadienyl ligands, can also be employed with transition metal catalysts (e.g., $Ru^{+2}$-halide or $Fe^{+2}$-halide complexes with triphenylphosphine, indanyl or cyclopentadienyl ligands).

An approximately stoichiometric amount of metal compound and ligand in the catalyst, based on the molar ratios of the components when the metal ion is fully complexed, is employed in some embodiments. In other embodiments the ratio between metal compound and ligand is in the range 1:(0.5 to 2) or in the range 1:(0.8 to 1.25).

Generally, where the catalyst is copper, bidentate or multidentate nitrogen ligands produce more active catalysts. In addition, bridged or cyclic ligands and branched aliphatic polyamines provide more active catalysts than simple linear ligands. Where bromine is the counter ion, bidentate or one-half tetradentate ligands are needed per $Cu^{+1}$. Where more complex counter ions are employed, such as triflate or hexafluorophosphate, two bidentate or one tetradentate ligand can be employed. The addition of metallic copper can be advantageous in some embodiments particularly where faster polymerization is desired as metallic copper and $Cu^{+2}$ may undergo redox reaction to form $Cu^{+1}$. The addition of some $Cu^{+2}$ at the beginning of some ATRP reactions can be employed to decrease the amount of normal termination.

In some embodiments, the amount of catalyst employed in the polymerization reactions is the molar equivalent of the initiator that is present. Since catalyst is not consumed in the reaction, however, it is not essential to include a quantity of catalyst as high as of initiator. The ratio of catalyst to each halogen contained in the initiator, based on transition metal compound in some embodiments is from about 1:(1 to 50), in other embodiments from about 1:(1 to 10), in other embodiments from about 1:(1 to 5), and in other embodiments from 1:1.

Polymerization Conditions

In some embodiments, the "living" or controlled radical polymerization process of the invention is preferably carried out to achieve a degree of polymerization in the range of 3 to about 2000, and in other embodiments from about 5 to about 500. The degree of polymerization in other embodiments is in the range 10 to 100, or alternatively in the range of about 10 to about 50. The degree of polymerization in group or atom transfer radical polymerization techniques, is directly related to the initial ratio of initiator to monomer. Therefore, in some embodiments the initial ratios of initiator to monomer are in the range of 1:(3 to about 2,000) or about 1:(5 to 500), or about 1:(10 to 100), or about 1:(10 to 50).

Polymerization reactions are typically carried out in the liquid phase, employing a single homogeneous solution. The reaction may, however, be heterogeneous comprising a solid and a liquid phase (e.g., a suspension or aqueous emulsion). The reaction may proceed in the solid state where the polymer is attached to a planar surface (wafer) or a non-planar surface (beads). In those embodiments where a non-polymerizable solvent is employed, the solvent employed is selected taking into consideration the nature of the zwitterionic monomer, the initiator, the catalyst and its ligand; and in addition, any comonomer that can be employed.

The solvent may comprise a single compound or a mixture of compounds. In some embodiments the solvent is water, and in other embodiments water is present in an amount from about 10% to about 100% by weight, based on the weight of the monomers present in the reaction. In those embodiments where a water insoluble comonomer is to be polymerized with a zwitterionic monomer, it can be desirable to employ a solvent or co-solvent (in conjunction with water) that permits solubilization of all the monomers present. Suitable organic solvents include, without limitation, formamides (e.g., N,N'-dimethylformamide), ethers (e.g., tetrahydrofuran), esters (ethyl acetate) and, most preferably, alcohols. In some embodiments where a mixture of water and organic solvent is to be employed, $C_1$-$C_4$ water miscible alkyl alcohols (methanol, ethanol, propanol, isopropanol, butanol, isobutanol, and tertbutanol) are useful organic solvents. In other embodiments, water and methanol combinations are suitable for conducting polymerization reactions. The reaction may also be conducted in supercritical solvents such as $CO_2$.

As noted above, in some embodiments it is desirable to include water in the polymerization mixture in an amount from about 10% to about 100% by weight based on the weight of monomers to be polymerized. In other embodiments the total non-polymerizable solvent is from about 1% to about 500% by weight, based on the weight of the monomers present in the reaction mixture. In other embodiments, the total non-polymerizable solvent is from about 10% to about 500% by weight or alternatively from 20% to 400%, based on the weight of the monomers present in the reaction mixture. It is also desirable in some cases to manipulate the solubility of an input reagent, such as initiator or monomer, for example by modifying temperature or solvent or other method so as to modify the reaction conditions in a dynamic fashion.

In some embodiments, contact time of the zwitterionic monomer and water prior to contact with the initiator and catalyst are minimized by forming a premix comprising all components other than the zwitterionic monomer and for the zwitterionic monomer to be added to the premix last.

The polymerization reactions can be carried out at any suitable temperature. In some embodiments the temperature can be from about ambient (room temperature) to about 120° C. In other embodiments the polymerizations can be carried out at a temperature elevated from ambient temperature in the range of about 60° to 80° C. In other embodiments the reaction is carried out at ambient (room temperature).

In some embodiments, the compounds of the invention have a polydispersity (of molecular weight) of less than 1.5, as judged by gel permeation chromatography. In other embodiments the polydispersities can be in the range of 1.2 to 1.4.

A number of workup procedures can be used to purify the polymer of interest such as precipitation, fractionation, reprecipitation, membrane separation and freeze-drying of the polymers.

Non-Halogenated Polymer Terminus

In some embodiments, it can be desirable to replace the halogen, or other radical scavenger I', with another functionality. A variety of reactions can be employed for the conversion of the aliphatic halogen. In some embodiments, the conversion of the aliphatic halogen can include reaction to prepare an alkyl, alkoxy, cycloalkyl, aryl, heteroaryl or hydroxy group. Halogens can also be subject to an elimination reaction to give rise to an alkene (double bond). Other methods of modifying the halogenated terminus are described in Matyjaszewski et al. *Prog. Polym. Sci.* 2001, 26, 337, incorporated by reference in its entirety herein.

Attachment of Functional agents

The coupling of functional agents to the random copolymers of the present invention can be conducted employing chemical conditions and reagents applicable to the reactions being conducted. Exemplary methods are described in *Bioconjugate Techniques*, Greg T. Hermanson, Academic Press, 2d ed., 2008 (incorporated in its entirety herein). Other bioconjugation techniques are described in Bertozzi et al. *Angewandte Chemie* 2009, 48, 6974, and Gauthier et al. *Chem. Commun.* 2008, 2591, each incorporated by reference in its entirety herein.

Where, for example, the coupling requires the formation of an ester or an amide, dehydration reactions between a carboxylic acid and an alcohol or amine may employ a dehydrating agent (e.g., a carbodiimide such as dicyclohexylcarbodiimide, DCC, or the water soluble agent 1-ethyl-3-(3-dimethyllaminopropyl)carbodiimide hydrochloride, EDC). Alternatively, N-hydroxysuccinimide esters (NHS) can be employed to prepare amides. Reaction to prepare amides employing NHS esters are typically conducted near neutral pH in phosphate, bicarbonate, borate, HEPES or other non-amine containing buffers at 4° to 25° C. In some embodiments, reactions employing EDC as a dehydrating agent, a pH of 4.5-7.5 can be employed; in other embodiments, a pH of 4.5 to 5 can be employed. Morpholinoethanesulfonic acid, MES, is an effective carbodiimide reaction buffer.

Thiol groups can be reacted under a variety of conditions to prepare different products. Where a thiol is reacted with a maleimide to form a thioether bond, the reaction is typically carried out at a pH of 6.5-7.5. Excess maleimide groups can be quenched by adding free thiol reagents such as mercaptoethanol. Where disulfide bonds are present as a linkage, they can be prepared by thiol-disulfide interchange between a sulfhydryl present in the bioactive group and an X functionality which is a disulfide such as a pyridyl disulfide. Reactions involving pyridyl disulfides can be conducted at pH 4-pH 5 and the reaction can be monitored at 343 nm to detect the released pyridine-2-thione. Thiol groups may also be reacted with epoxides' in aqueous solution to yield hydroxy thioethers. A thiol may also be reacted at slightly alkaline pH with a haloacetate such as iodoacetate to form a thioether bond.

The reaction of guanido groups (e.g., those of an arginine in a protein or polypeptide of interest) with a glyoxal can be carried out at pH 7.0-8.0. The reaction typically proceeds at 25° C. The derivative, which contains two phenylglyoxal moieties per guanido group, is more stable under mildly acidic conditions (below pH 4) than at neutral or alkaline pHs, and permits isolation of the linked materials. At neutral or alkaline pH values, the linkage decomposes slowly. Where an arginine residue of a protein or polypeptide is reacted with a phenylglyoxal reagent, about 80% of the linkage will hydrolyze to regenerate the original arginine residue (in the absence of excess reagent) in approximately 48 hours at 37° C. at about pH 7.

Imidoester reactions with amines are typically conducted at pH of 8-10, and preferably at about pH 10. The amidine linkage formed from the reaction of an imidoester with an amine is reversible, particularly at high pH.

Haloacetals can be reacted with sulfhydryl groups over a broad pH range. To avoid side reactions between histidine residues that can be present, particularly where the sulfhydryl group is present on a protein or polypeptide, the reaction can be conducted at about pH 8.3.

Aldehydes can be reacted with amines under a variety of conditions to form imines. Where either the aldehyde or the amine is immediately adjacent to an aryl group the product is a Schiff base that tends to be more stable than where no aryl group is present. Conditions for the reaction of amines with aldehydes to form an imine bond include the use of a basic pH from about pH 9 to about pH 11 and a temperature from about 0° C. to room temperature, over 1 to 24 hours. Alternatively, where preferential coupling to the N-terminal amine of a protein is desired, lower pHs from about 4-7 can be employed. Buffers including borohydride and tertiary amine containing buffers are often employed for the preparation of imines. Where it is desired imine conjugates, which are hydrolytically susceptible, can be reduced to form an amine bond which is not hydrolytically susceptible. Reduction can be conducted with a variety of suitable reducing agents including sodium borohydride or sodium cyanoborohydride.

The reaction conditions provided above are intended to provide general guidance to the artisan. The skilled artisan will recognize that reaction conditions can be varied as necessary to promote the attachment of the functional agent to the random copolymers of the present invention and that guidance for modification of the reactions can be obtained from standard texts in organic chemistry. Additional guidance can be obtained from texts such as Wong, S. S., "Chemistry of Protein Conjugation and Cross-Linking," (CRC Press 1991), which discuss related chemical reactions.

V. Compositions

The present invention includes and provides for pharmaceutical compositions comprising one or more compounds of the invention and one or more pharmaceutically acceptable excipients. The compounds of the invention may be present as a pharmaceutically acceptable salt, prodrug, metabolite, analog or derivative thereof, in the pharmaceutical compositions of the invention. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration.

Pharmaceutically acceptable carriers for use in formulating the random copolymers of the present invention include, but are not limited to: solid carriers such as lactose, terra alba, sucrose, talc, gelatin, agar, pectin, acacia, magnesium stearate, stearic acid and the like; and liquid carriers such as syrups, saline, phosphate buffered saline, water and the like. Carriers may include any time-delay material known in the art, such as glyceryl monostearate or glyceryl distearate, alone or with a wax, ethylcellulose, hydroxypropylmethylcellulose, methylmethacrylate or the like.

Other fillers, excipients, flavorants, and other additives such as are known in the art may also be included in a pharmaceutical composition according to this invention. The use of such media and agents for pharmaceutically active substances is well known in the art. Except insofar as any conventional media or agent is incompatible with the active compound, use thereof in the compositions of the invention is contemplated. Supplementary active compounds can also be incorporated into the compositions of the present invention.

The pharmaceutical preparations encompass all types of formulations. In some embodiments they are parenteral (including subcutaneous, intramuscular, intravenous, intradermal, intraperitoneal, intrathecal, intraventricular, intracranial, intraspinal, intracapsular, and intraosseous) formulations suited for injection or infusion (e.g., powders or concentrated solutions that can be reconstituted or diluted as well as suspensions and solutions). Where the composition is a solid that requires reconstitution or a concentrate that requires dilution with liquid media, any suitable liquid media may be employed. Preferred examples of liquid media include, but are not limited to, water, saline, phosphate buffered saline, Ringer's solution, Hank's solution, dextrose solution, and 5% human serum albumin.

Where a compound or pharmaceutical composition comprising a random copolymer of the present invention is suitable for the treatment of cell proliferative disorders, including but not limited to cancers, the compound or pharmaceutical composition can be administered to a subject through a variety of routes including injection directly into tumors, the blood stream, or body cavities.

While the pharmaceutical compositions may be liquid solutions, suspensions, or powders that can be reconstituted immediately prior to administration, they may also take other forms. In some embodiments, the pharmaceutical compositions may be prepared as syrups, drenches, boluses, granules, pastes, suspensions, creams, ointments, tablets, capsules (hard or soft) sprays, emulsions, microemulsions, patches, suppositories, powders, and the like. The compositions may also be prepared for routes of administration other than parenteral administration including, but not limited to, topical (including buccal and sublingual), pulmonary, rectal, transdermal, transmucosal, oral, ocular, and so forth.

In some embodiments, the pharmaceutical compositions of the present invention comprise one or more random copolymers of the present invention.

Other pharmaceutical compositions of the present invention may comprise one or more random copolymers of the present invention that function as biological ligands that are specific to an antigen or target molecule. Such compositions may comprise a random copolymer of the present invention, where the bioactive agent is a polypeptide that comprises the amino acid sequence of an antibody, or an antibody fragment such as a $FAb_2$ or FAb' fragment or an antibody variable region. Alternatively, the compound may be a random copolymer and the polypeptide may comprise the antigen binding sequence of a single chain antibody. Where a bioactive agent present in a random copolymer of the present invention functions as a ligand specific to an antigen or target molecule, those compounds may also be employed as diagnostic and/or imaging reagents and/or in diagnostic assays.

The amount of a compound in a pharmaceutical composition will vary depending on a number of factors. In one embodiment, it may be a therapeutically effective dose that is suitable for a single dose container (e.g., a vial). In one embodiment, the amount of the compound is an amount suitable for a single use syringe. In yet another embodiment, the amount is suitable for multi-use dispensers (e.g., containers suitable for delivery of drops of formulations when used to deliver topical formulations). A skilled artisan will be able to determine the amount a compound that produces a therapeutically effective dose experimentally by repeated administration of increasing amounts of a pharmaceutical composition to achieve a clinically desired endpoint.

Generally, a pharmaceutically acceptable excipient will be present in the composition in an amount of about 0.01% to about 99.999% by weight, or about 1% to about 99% by weight. Pharmaceutical compositions may contain from about 5% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90% excipient by weight. Other suitable ranges of excipients include from about 5% to about 98%, from about from about 15 to about 95%, or from about 20% to about 80% by weight.

Pharmaceutically acceptable excipients are described in a variety of well known sources, including but not limited to "Remington: The Science & Practice of Pharmacy", 19th ed., Williams & Williams, (1995) and Kibbe, A. H., Handbook of Pharmaceutical Excipients, $3^{rd}$ Edition, American Pharmaceutical Association, Washington, D.C., 2000.

VI. Methods

The random copolymers of the present invention are useful for treating any disease state or condition. By combining appropriate targeting agents, drugs and therapeutic proteins, along with a zwitterion such as phosphorylcholine, the random copolymers of the present invention can be used to address the panoply of mechanisms provided by any one disease state or condition. For example, the disease state or condition can be acute or chronic.

Disease states and conditions that can be treated using the random copolymers of the present invention include, but are not limited to, cancer, autoimmune disorders, genetic disorders, infections, inflammation, fibrotic disorders, and metabolic disorders.

Cancers that can be treated using the random copolymers of the present invention include, but are not limited to, ovarian cancer, breast cancer, lung cancer, bladder cancer, thyroid cancer, liver cancer, pleural cancer, pancreatic cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, osteogenic sarcomas, fibrosarcoma, neuroblastoma, glioma, melanoma, leukemia, and lymphoma.

Autoimmune diseases that can be treated using the random copolymers of the present invention include, but are not limited to, multiple sclerosis, myasthenia gravis, Crohn's disease, ulcerative colitis, primary biliary cirrhosis, type 1 diabetes mellitus (insulin dependent diabetes mellitus or IDDM), Grave's disease, autoimmune hemolytic anemia, pernicious anemia, autoimmune thrombocytopenia, vasculitides such as Wegener's granulomatosis, Behcet's disease, rheumatoid arthritis, systemic lupus erythematosus (lupus), scleroderma, systemic sclerosis, Guillain-Barre syndromes, fibrosis, hepatic fibrosis, post-transplant fibrosis, idiopathic pulmonary fibrosis, Hashimoto's thyroiditis spondyloarthropathies such as ankylosing spondylitis, psoriasis, dermatitis herpetiformis, inflammatory bowel diseases, pemphigus vulgaris and vitiligo.

Some metabolic disorders treatable by the random copolymers of the present invention include lysosomal storage disorders, such as mucopolysaccharidosis IV or Morquio Syndrome, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, hypophosphatasia, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders such as Pseudo-Hurler polydystrophy/Mucolipidosis IIIA, Hurler Syndrome, Scheie Syndrome, Hurler-Scheie Syndrome, Hunter syndrome, Sanfilippo syndrome, Hyaluronidase Deficiency, Maroteaux-Lamy, Sly Syndrome, Mucolipidosis I/Sialidosis, Mucolipidosis, and Mucolipidosis, Multiple sulfatase deficiency, Niemann-Pick Disease, Neuronal Ceroid Lipofuscinoses, Pompe disease/Glycogen storage disease type II, Pycnodysostosis, Sandhoff disease, Schindler disease, Salla disease/Sialic Acid Storage Disease, Tay-Sachs/GM2 gangliosidosis and Wolman disease.

Conjugates of the invention and compositions (e.g., pharmaceutical compositions) containing conjugates of the invention can be used to treat a variety of conditions. For example, there are many conditions for which treatment therapies are known to practitioners of skill in the art in which functional agents, as disclosed herein, are employed.

The invention contemplates that the conjugates of the invention (e.g., phosphorylcholine containing polymers conjugated to a variety of functional agents) and compositions containing the conjugates of the invention can be employed to treat such conditions and that such conjugates provide for an enhanced treatment therapy relative to the same functional agent not coupled to a phosphorylcholine containing polymer.

Therefore, the invention contemplates the treatment of a condition known to be treatable by a certain bioactive agent by treating the condition using the same certain bioactive agent conjugated to a phosphorylcholine containing polymer.

Another aspect of the present invention relates to methods of treating a condition responsive to a biological agent comprising administering to a subject in need thereof a therapeutically effective amount of a compound of the invention or of a pharmaceutically acceptable composition of the invention as described above. Dosage and administration are adjusted to provide sufficient levels of the bioactive agent(s) to maintain the desired effect. The appropriate dosage and/or administration protocol for any given subject may vary depending on various factors including the severity of the disease state, general health of the subject, age, weight, and gender of the subject, diet, time and frequency of administration, drug combination(s), reaction sensitivities, and tolerance/response to therapy. Therapeutically effective amounts for a given situation can be determined by routine experimentation that is within the skill and judgment of the clinician.

The pharmaceutical compositions described herein may be administered singly. Alternatively, two or more pharmaceutical compositions may be administered sequentially, or in a cocktail or combination containing two random copolymers of the present invention or one random copolymer of the present invention and another bioactive agent. Other uses of bioactive agents set forth herein may be found in standard reference texts such as the Merck Manual of Diagnosis and Therapy, Merck & Co., Inc., Whitehouse Station, N.J. and Goodman and Gilman's The Pharmacological. Basis of Therapeutics, Pergamon Press, Inc., Elmsford, N.Y., (1990).

The random copolymers of the present invention are useful for treating, detecting and imaging a variety of disease states and conditions. The random copolymers can be used as a chemotherapy agent in the treatment of cancer where the initiator fragment I is not functionalized and $R^2$ includes a cancer chemotherapeutic agent $A^2$ that is loaded onto the random copolymer via click chemistry or any suitable conjugation chemistry:

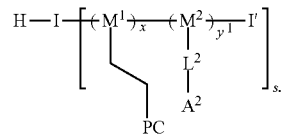

Additional cancer treatment agents using the random copolymers can include a targeting agent of an anti-angiogenic protein such as an anti-VEGF scFv fragment $A^1$ conjugated via a C-terminal cysteine to a maleimide initiator I. The random copolymer can also include a cancer chemotherapeutic agent $A^{2a}$ that is linked to the polymer backbone via a cleavable or self-immolative linker. Moreover, the cancer chemotherapeutic is loaded onto the random copolymer via click chemistry or any suitable conjugation chemistry. For example, in Ewing's sarcoma: the targeting agent can be an anti-cancer antibody fragment such as a Fab' or scFv fragment that binds to an angiogenic growth factor such as VEGF. In addition, bone targeting comonomer $A^{2b}$ can include an aspartate or glutamate rich peptide or a bisphosphonate. Other comonomers $A^{2c}$ can include Vincristine, Doxorubicin, and/or cyclophosphamide attached via cleavable or self-immolative linkers:

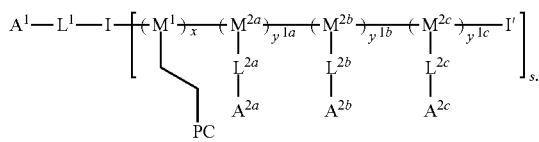

Random copolymers for more efficacious and longer residence time therapy for wet or dry macular degeneration can include an anti-inflammatory or anti-angiogenic protein such as anti-VEGF or anti-IL-6 scFv fragment $A^1$ conjugated via a C-terminal cysteine to a maleimide initiator I. The random copolymer prepared can be either a homopolymer of phosphorylcholine or a copolymer of phosphorylcholine stably attached to the polymer backbone, in combination with an anti-inflammatory small molecule or an anti-angiogenic small molecule $A^2$ linked to the polymer backbone via a cleavable linker $L^2$. Alternatively, the random copolymer can include another comonomer having a vitreous extracellular matrix (hyaluronic acid) binding moiety $A^2$ attached via a non-cleavable linker $L^2$ such as choline or a positively charged amino acid:

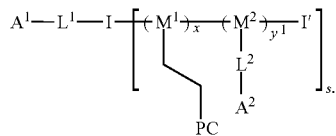

Random copolymers for real-time diagnostic estimate of tumor burden and imaging for oncology can include an anti-tumor-associated protein such as an anti-Carcino Embryonic Antigen (CEA) scFv fragment $A^1$ conjugated via a C-terminal cysteine to a maleimide initiator I. The random copolymer can include phosphorylcholine stably attached and an imaging reagent $A^{2a}$ such as a fluorescent dye (fluorescent probe detection) or gadolinium (for whole body imaging detection). Additional comonomers can be added having small molecule chemotherapy agents $A^{2b}$ attached via a cleavable linker $L^{2b}$ to add a therapeutic element. These structures provide both therapeutic and diagnostic functions, and are commonly referred to as theranostics:

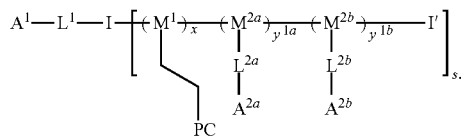

Random copolymers for use as a targeted platform for bone enzyme replacement therapies, specifically hypophosphatasia, can include recombinant alkaline phosphatase enzyme $A^1$ conjugated via aldehyde-modified initiator I through a stable linkage $L^1$. The random copolymer can include phosphorylcholine stably attached to the polymer, and a comonomer useful for targeting via a stably attached bone targeting moiety $A^2$ such as an aspartate or glutamate rich peptide sequence or a bisphosphonate such that more than five targeting moieties are present ($y^1$ is greater than 5). A1, of course, can be any protein such as a growth factor, for example human growth hormone, and the targeting peptide can be any peptide suitable for locating the conjugate in any tissue. These copolymers are useful for subcutaneous delivery:

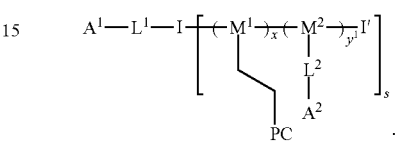

Other random copolymers are useful as a targeted platform for bone enzyme replacement therapies, specifically Morquio Syndrome (MPS type IVa). These types of random copolymers include a recombinant N-Acetylgalactosamine-6-sulfate sulfatase enzyme $A^1$ conjugated via site specific chemistry initiator I through a cleavable linker $L^1$. The random copolymer can include phosphorylcholine stably attached to the polymer, and a targeting comonomer containing a bone targeting moiety $A^2$ such as an aspartate or glutamate rich peptide sequence or a bisphosphonate linked via a non-cleavable linker $L^2$, such that more than five targeting moieties are present. These copolymers are useful for subcutaneous delivery:

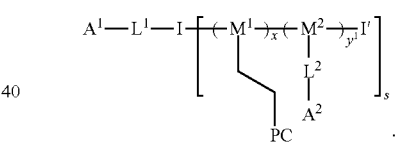

Random copolymers for targeted platforms for safer, more efficacious treatment of Rheumatoid Arthritis can include several different drugs, including an anti-TNFα biopharmaceutical such as an antibody fragment $A^1$ that is linked to the initiator I via a non-cleavable linker $L^1$, or an anti-VEGFR2, a small molecule $A^{2a}$, as a kinase inhibitor, and methotrexate $A^{2b}$, an antineoplastic antimetabolite with immunosuppressant properties both linked via cleavable linkers $L^{2a}$ and $L^{2b}$ respectively:

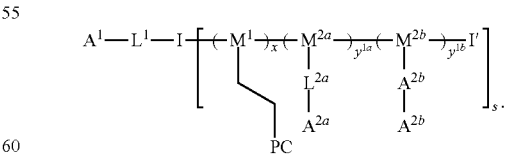

Similar random copolymers to those above can be prepared by replacing the anti-TNFα biopharmaceutical of $A^1$ with a small protein dual domain inhibitor such as an avimer or a scFv dimer that inhibits two proteins, for example TNFα and also VEGF, but without the small molecule inhibitor. In addition, the methotrexate $A^2$ can be substituted for cyclophosphamide:

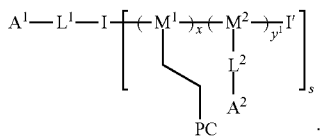

Finally, a random copolymer for targeted and protected RNAi can be prepared without a functionalized initiator I. The random copolymer can include phosphorylcholine stably attached to the polymer, and a comonomer having an siRNA $A^{2a}$ linked to the polymer via a cleavable bond $L^{2a}$, and another comonomer having a cell- or tissue-targeting group $A^{2b}$ attached via a non-cleavable linker $L^{2b}$. The siRNA containing comonomer can be prepared using a monomer having a linking group suitable for click chemistry or any suitable conjugation chemistry wherein the siRNA is linked to the linking group following polymerization. The comonomer having the targeting moiety can either already contain the targeting moiety, or link to the targeting moiety via a comonomer having a linking group suitable for click chemistry or any suitable conjugation chemistry via a different chemistry than for attachment of the siRNA. The cleavable linker is preferably a pH sensitive linker. The random copolymer can be prepared with a target stoichiometry of approximately five oligonucleotide moieties per drug $A^{2c}$ and five targeting moieties per drug (such that the ratio of $y^{1a}$:$y^{1b}$:$y^{1c}$ is about 5:5:1). Moreover, the phosphorylcholine polymer backbone can be optimized not for half-life, but to protect the siRNA in its journey from injection site to the targeted tissues. The siRNA can be replaced with microRNA:

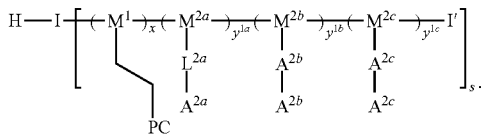

In addition, the initiator I can optionally be linked to a bioactive moiety $A^1$ such as an antibody fragment for targeting and therapy:

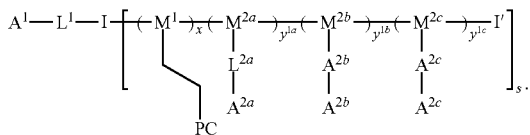

In some other embodiments, the engineering of novel multifunctional therapeutic systems can combine phosphorylcholine polymers with drug or gene targeting agents with imaging and/or sensing capabilities. Systems can have at least 3 components: (1) a targeting moiety or molecular signatures that can target delivery to specific sites, (2) the appropriate imaging agent/probe/tags for visualization or monitoring of the systems, and (3) one or more therapeutic agents to effectively treat a particular disease or disorder.

The following are examples of multifunctional systems that contain targeting, imaging, and drug/gene moieties. This list is not intended to be exclusive of a phosphorylcholine containing polymer system. Targeted systems that can be activated by internal processes such as pH, enzyme cleavage or external stimuli such as near IR light, ultrasound, heat, or magnetic field for therapeutic delivery and imaging are also suitable. First, our approach conceptually can be combined with all of the following:

Synthetic biodegradable polymer-based nanoparticles encapsulating a therapeutic gene, a gadolinium contrast agent for MRI analysis, and functionalized with antibodies to target specific disease sites.

Liposomes encapsulating small or large drug molecules, labeled with $^{18}$Fluorine for PET analysis, and functionalized with antibodies to target specific disease sites.

Polyplexes containing a siRNA molecule, an iron-oxide contrast agent for MRI analysis, and modified with cell binding ligands and cell-penetrating peptides for targeted cellular and intracellular delivery respectively.

Fluorescent quantum dots intercalated with a drug molecule for optical imaging and sensing of the delivery and functionalized with an RNA aptamer to target specific diseases.

Inorganic or organic nanoparticles containing an antisense oligonucleotide for gene therapy, a gadolinium contrast agent for MRI analysis, a fluorophore for optical imaging, and surface modified to target specific diseases.

pH sensitive polymeric nanocomposites with a drug molecule that is released as a function of pH, an iron oxide contrast agent for MRI imaging, CdTe quantum dots for optical imaging, and functionalized with antibodies to target specific diseases.

Nanoparticle-DNA aptamer conjugates containing a drug and a radiotracer such as $^{111}$In for SPECT imaging and functionalized with disease-specific membrane antibodies.

Second, the polymers of the present invention can be specifically combined with the above:

Phosphorylcholine polymer-based construct containing a therapeutic gene (bioactive 1), a gadolinium contrast agent for MRI analysis (functional 1), and a small protein (such as an antibody fragment) to target specific disease sites.

Imaging agent $^{18}$Fluorine for PET analysis, and functionalized with small protein (such as an antibody fragment) to target specific disease sites.

Phosphorylcholine polymers containing one or more siRNA molecules, an iron-oxide contrast agent for MRI analysis, and modified with cell binding ligands and cell-penetrating peptides for targeted cellular and intracellular delivery respectively.

Phosphorylcholine polymers containing fluorescent quantum dots (functional agent) intercalated with a drug molecule (functional agent) for optical imaging and sensing of the delivery and functionalized with an RNA aptamer or a small protein (such as an antibody fragment or scaffold derived protein) to target specific diseases.

Phosphorylcholine containing polymers containing an antisense oligonucleotide for gene therapy, a gadolinium contrast agent for MRI analysis, a fluorophore for optical imaging, and an additional functional agent for targeting specific diseases such as folate for tumor or choline for electrostatic interactions for targeting extracellular matrix.

pH sensitive phosphorylcholine polymer with a drug molecule that is released as a function of pH, an iron oxide contrast agent for MRI imaging, CdTe quantum dots for optical imaging, and functionalized with antibodies or other protein or aptamer to target and treat specific diseases.

Phosphorylcholine polymer with aptamer functional agent conjugates containing a drug and a radiotracer such as $^{111}$In for SPECT imaging and further functionalized with disease-specific membrane antibodies.

VII. Examples

Example 1

Preparation of N-(2-hydroxyethyl)-exo-3,6-epoxy-1,2,3,6-tetrahydrophthalimide

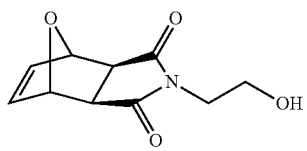 [SMILES: O=C1[C@@H]2C3C=CC(O3)[C@@H]2C(=O)N1CCO]

A 100-ml round-bottom flask equipped with a stir bar was charged with 50 ml ethanol and 2.0 grams of exo-3,6-epoxy-1,2,3,6-tetrahydrophthalic anhydride. The stirring mixture was cooled with an ice water bath, and a solution of 0.73 grams of ethanolamine in 20 ml of ethanol was added drop wise over 10 minutes. The reaction was heated at reflux for 4 hours, then refrigerated overnight. Filtration and rinsing with ethanol yielded 0.73 grams of the desired product as a white crystalline solid. The filtrate was concentrated and chilled again to obtain a second crystal crop. $^1$H NMR (400 MHz, CDCl$_3$): δ=2.90 (s, 2H, CH), 3.71 (m, 2H, OCH$_2$), 3.77 (t, J=5.0 Hz, NCH$_2$), 5.29 (t, J=1.0 Hz, 2H, OCH), 6.53 (t, J=1.0 Hz, 2H, CH=CH).

Example 2

Preparation of isopropylidene-2,2-bis(hydroxymethyl)propionic acid

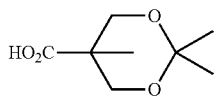

A 100 ml round-bottom flask equipped with a stir bar was charged with 50 ml of acetone, 13.8 ml of 2,2-dimethoxypropane, 10 grams of 2,2-bis(hydroxymethyl)propionic acid, and 0.71 grams p-toluenesulfonic acid monohydrate. The mixture was stirred for two hours at ambient temperature, then neutralized with 1 ml of 2M ammonia in methanol. The solvent was evaporated and the mixture dissolved in dichloromethane, then extracted twice with 20 ml of water. The organic phase was dried over magnesium sulfate and evaporated to give 10.8 grams of the product as a white crystalline solid. $^1$H NMR (400 MHz, CDCl$_3$): δ=1.20 (s, 3H, CH$_3$CC=O), 1.43 (s, 3H, CH$_3$), 1.46 (s, 3H, CH$_3$), 3.70 (d, J=12.4 Hz, 2H, OCH$_2$), 4.17 (d, J=12.4 Hz, 2H, OCH$_2$).

Example 3

Preparation of N,N-dimethylpyridinium p-toluenesulfonate (DPTS)

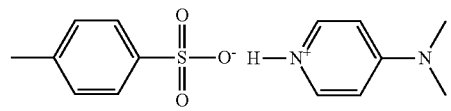

A solution of 1.9 grams of p-toluenesulfonic acid monohydrate in 10 ml benzene was dried by azeotropic distillation using a Dean-Stark trap, then 3.42 grams of 4-dimethylaminopyridine were added. Much solid formed, and an additional 25 ml of benzene were required to mobilize the reaction, which stirred slowly as it cooled to room temperature. The resulting solid was isolated by filtration, washed with 10 ml of benzene, and dried to yield 7.88 grams of the product as a white solid.

Example 4

Preparation of Protected Maleimide Bromopropionate Initiator

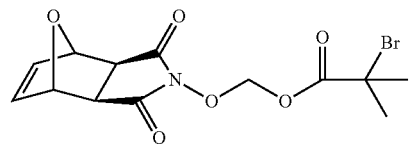 [SMILES: CC(C)(Br)C(=O)OCON1C(=O)[C@@H]2C3C=CC(O3)[C@@H]2C1=O]

A 100-ml round-bottom flask equipped with a stir bar was charged with 50 ml tetrahydrofuran, 2 grams of N-(2-hydroxyethyl)-exo-3,6-epoxy-1,2,3,6-tetrahydrophthalimide, and 2.0 ml triethylamine. The stirring mixture was cooled to 0 degrees, and a solution of 1.18 ml of 2-bromoisobutyryl bromide in 5 ml tetrahydrofuran was added drop wise over 30 minutes. The reaction was allowed to stir on ice for 3 hours followed by room temperature overnight. Concentration of the reaction mixture gave an oily residue, which was purified by silica gel flash chromatography with 30-50% ethyl acetate in hexane, giving 1.96 grams of the desired product as a white powder. $^1$H NMR (400 MHz, CDCl$_3$): δ=1.89 (s, 6H, CH$_3$), 2.87 (s, 2H, CH), 3.82 (t, J=5.4 Hz, 2H, NCH$_2$), 4.33 (t, J=5.4 Hz, 2H, OCH$_2$), 5.27 (t, J=1.0 Hz, 2H, OCH), 6.51 (t, J=1.0 Hz, 2H, CH$_{vinyl}$).

Example 5

Preparation of protected maleimide bis(bromopropionate) initiator

Protected Maleimide Isopropylidene Acid

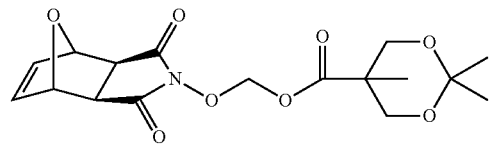

A solution of 2.00 grams of N-(2-hydroxyethyl)-exo-3,6-epoxy-1,2,3,6-tetrahydrophthalimide and 1.67 grams of isopropylidene-2,2-bis(hydroxymethyl)propionic acid in 30 ml of dry dichloromethane, together with 563 mg of DPTS was treated drop wise with a solution of 2.37 grams of N,N'-dicyclohexylcarbodiimide in 10 ml of dry dichloromethane. Much solid began to form as the reaction mixture was stirred at ambient temperature overnight. The reaction was filtered, and the precipitate was washed with a small amount of dichloromethane. The combined organic layers were concentrated to give a clear oil containing a small amount of solid. This oil was subjected to flash column chromatography on silica gel, using first 20-100% ethyl acetate in hexane. The fractions containing the desired product were combined and concentrated to give 3.17 grams of the final product as a white solid. $^1$H NMR (400 MHz, CDCl$_3$): δ=1.19 (s, 3H, CH$_3$CC=OO), 1.37 (s, 3H, CH$_3$), 1.41 (s, 3H, CH$_3$), 1.55 (s, 6H, (CH$_3$)$_2$C), 2.86 (s, 2H, C=OCHC HC=O), 3.58 (d, J=12 Hz, CH$_2$O), 3.78 (t, J=5.4 Hz, CH$_2$CH$_2$O), 4.14 (d, J=12H, CH$_2$O), 4.30 (t, J=5.4 Hz, CH$_2$CH$_2$O), 5.27 (t, 2H, CHOCH), 6.51 (s, 2H, CH=CH).

Protected Maleimide Diol

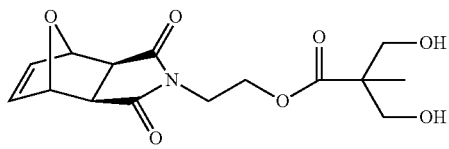 [SMILES: CC(CO)(CO)C(=O)OCCN1C(=O)[C@@H]2C3C=CC(O3)[C@@H]2C1=O]

A solution of the isopropylidene compound from above in 50 ml of methanol was treated with 1.0 grams of Dowex 50Wx8-100 ion exchange resin (H$^+$ form) and the reaction was stirred at room temperature overnight, at which time the reaction appeared complete by tlc (silica gel, ethyl acetate). The mixture was filtered, and the solid resin was washed with a small amount of methanol. The combined organics were concentrated and placed under high vacuum to give 1.55 grams of a slightly cloudy oil, which was used in the next reaction without further purification.

Protected Maleimide Bis(Bromopropionate) Initiator

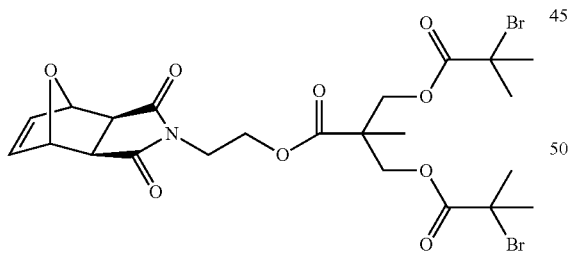

A solution of the crude product from above in 40 ml of anhydrous tetrahydrofuran (THF), together with 1.45 ml of triethylamine was cooled in an ice water bath, and a solution of 1.23 ml of 2-bromoisobutyryl bromide in 20 ml of anhydrous THF was added drop wise over a few minutes. The reaction was stirred in the cold for 30 minutes, then allowed to warm to room temperature over 6 hours. Another 600 µl of triethylamine were added, followed by another 0.5 ml of 2-bromoisobutyryl bromide. The reaction was acidic by pH paper, so another 200 µl of triethylamine were added to bring the pH of the solution to 9. The reaction was stirred overnight, concentrated, and the residue was partitioned between 50 ml of dichloromethane and 50 ml of water. The organic layer was dried over sodium sulfate, filtered and concentrated to give an oil. This was subjected to flash column chromatography on silica gel, first with 20%, then 30% and finally 40% ethyl acetate in hexane. The fractions containing product were combined and concentrated to give 1.63 g of an oil which solidified to a white solid. $^1$H NMR (400 MHz, CDCl$_3$): δ=1.32 (s, 3H, CH$_3$CC=O), 1.91 [s, 12H, (CH$_3$)$_2$CBr], 2.90 (s, 2H, CHC=O), 3.78 (t, 2H, NCH$_2$CH$_2$O), 4.28 (t, 2H, NCH$_2$CH$_2$O), 4.31 (app q, 4H, CH$_2$OC=O), 5.30 (s, 2H, CHOCH), 6.52 (s, 2H, CH=CH).

Example 6

Preparation of N-[2-(2-hydroxyethoxy)ethyl]-exo-3,6-epoxy-1,2,3,6-tetrahydrophthalimide

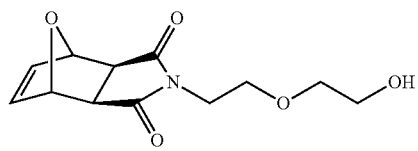 [SMILES: O=C1[C@@H]2C3C=CC(O3)[C@@H]2C(=O)N1CCOCCO]

A 250 ml round-bottom flask equipped with a stir bar was charged with 100 ml methanol and 20 grams of exo-3,6-epoxy-1,2,3,6-tetrahydrophthalic anhydride. The stirring mixture was cooled to 0 degrees, and a solution of 0.73 grams 2-(2-aminoethoxy)ethanol in 40 ml of methanol was added drop wise over 45 minutes. The reaction was stirred at room temperature for 2 hours, then heated at gentle reflux overnight. The solution was concentrated and the product was dissolved in 100 ml of dichloromethane, then washed with 100 ml brine. The organic layer was dried over sodium sulfate, concentrated, and purified by passage through a silica gel plug with 100 ml dichloromethane and 100 ml ethyl acetate. $^1$H NMR (400 MHz, CDCl$_3$): δ=2.90 (s, 2H, CH), 3.49 (m, 2H, OCH$_2$), 3.59 (m, 4H, OCH$_2$), 3.65 (m, 2H, NCH2), 5.15 (t, J=0.8 Hz, 2H, OCH), 6.55 (t, J=0.8 Hz, 2H, CH=CH).

Example 7

Preparation of bis 2,2[(2-bromoisobutyryl)hydroxymethyl]propionic acid

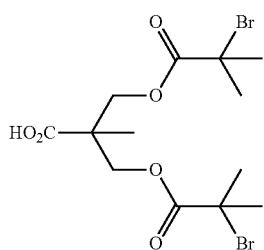 [SMILES: CC(C)(Br)C(=O)OCC(C)(COC(=O)C(C)(C)Br)C(=O)O]

To a solution of 17.5 ml of 2-bromoisobutyryl bromide in 100 ml of dichloromethane, cooled in an ice-water bath, was added dropwise over 30 minutes a solution of 10.0 grams of 2,2-bis(hydroxymethyl)propionic acid and 41 ml of triethylamine in 100 ml of dichloromethane. The reaction was allowed to stir in the cold for 1 hour, then allowed to warm to room temperature. The reaction mixture was then washed with 200 ml of IN HCl, then with 100 ml of 0.5N HCl, and finally with 50 ml of saturated NaCl. The organic layer was dried over anhydrous sodium sulfate, filtered and concentrated to give a yellow oil. This oil was taken up in 100 ml of 15% ethyl acetate in hexane using a heat gun to effect solution if necessary. The solution was then allowed to cool over 1 hour, adding a seed crystal as the solution neared room temperature. Crystallization was allowed to proceed for 2 hours, cooling first in an ice-water bath, then in the refrigerator overnight. The resulting solution had nearly solidified, so 25 ml of 10% ethyl acetate in hexane were added, the mixture was stirred, and the crystalline solid was recovered by filtration. It was washed with a minimum amount of hexane and dried under vacuum to give 14.55 grams of the desired product as a white solid. Additional product can be obtained from the mother liquors if desired. $^1$H NMR (400 MHz, CD$_3$OD): δ=1.33 (s, 3H, CCH$_3$), 1.90 (s, 12H, (C$\underline{H}_3$)$_2$CBr), 4.30 (d, J=5.4 Hz, 2H, NCH$_2$), 4.39 (d, J=5.4 Hz, 2H, OCH$_2$).

Example 8

Preparation of protected maleimide extended bis(bromopropionate) initiator

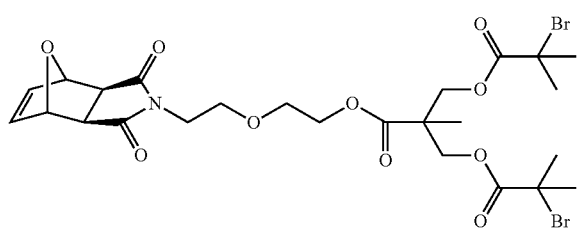 [SMILES: CC(C)(Br)C(=O)OCC(C)(COC(=O)C(C)(C)Br)C(=O)OCCOCCN1C(=O)[C@@H]2C3C=CC(O3)[C@@H]2C1=O]

A 250 ml round-bottom flask equipped with a stir bar was charged with 100 ml dichloromethane, 1.0 grams of N-[2-(2-hydroxyethoxy)ethyl]-exo-3,6-epoxy-1,2,3,6-tetrahydrophthalimide, 2.5 grams of the dibromo acid from Example 7, 0.5 grams of dimethylaminopyridine, and 0.35 grams DPTS. Nitrogen was bubbled through the solution briefly, and 1.6 grams DCC was added slowly. The reaction was allowed to stir at room temperature overnight. Filtration and evaporation gave a pink oily residue, which was purified by silica gel flash chromatography. $^1$H NMR (400 MHz, CD$_3$OD): δ=1.34 (s, 3H, CH$_3$), 1.90 (s, 6H, CH$_3$), 2.94 (s, 2H, CH), 3.64 (m, 6H, OCH$_2$), 4.22 (t, J=5.4 Hz, 2H, NCH$_2$), 4.35 (app q, 4H, OCH$_2$), 5.15 (t, J=1.0 Hz, 2H, OCH), 6.54 (t, J=1.0 Hz, 2H, CH=CH).

Example 9

Preparation of N-[2-(2-hydroxyethoxy)ethyl]-exo-3,6-epoxy-1,2,3,6-tetrahydrophthalimide, isopropylidene-2,2-bis(hydroxymethyl)propionate

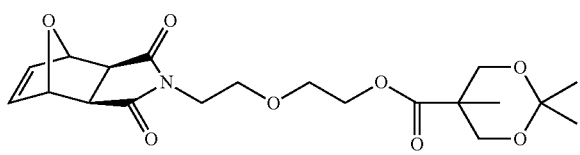

A solution of 11.0 grams of N-[2-(2-hydroxyethoxy)ethyl]-exo-3,6-epoxy-1,2,3,6-tetrahydrophthalimide and 8.22 grams of isopropylidene-2,2-bis(hydroxymethyl)propionic acid in 250 ml of dichloromethane, together with 1.3 grams of DPTS and 5.24 grams of DMAP was treated with 12.9 grams of DCC, and the reaction was stirred overnight. The reaction was filtered and concentrated to give a residue, which was subjected to flash column chromatography in two portions on silica gel with 40-50% ethyl acetate in hexane to give the desired product as a clear oil.

Example 10

Preparation of N-[2-(2-hydroxyethoxy)ethyl]-exo-3,6-epoxy-1,2,3,6-tetrahydrophthalimide, 2,2-bis(hydroxymethyl)propionate

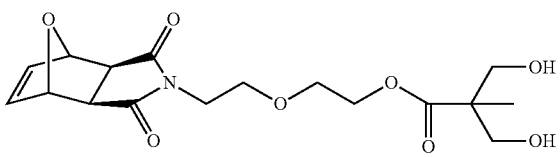 [SMILES: CC(CO)(CO)C(=O)OCCOCCN1C(=O)[C@@H]2C3C=CC(O3)[C@@H]2C1=O]

The product from above was dissolved in 100 ml of methanol and treated with 2.0 grams of Dowex 50Wx8-100 ion exchange resin (H$^+$ form) and the reaction was stirred at room temperature overnight. The reaction was filtered and concentrated to give the desired product as an oil which was used without further purification. NMR (CD$_3$OD): δ 6.546 (t, 2H, CH=CH, J=0.8 Hz), 5.158 (t, 2H, CH—O, J=0.8 Hz), 4.180 (m, 2H, CH$_2$—C$\underline{H}_2$—O—C=O, J=4.9 Hz), 3.63 (m, 10H, N—CH$_2$ and N—CH$_2$—C$\underline{H}_2$ and C$\underline{H}_2$—CH$_2$—O—C=O and CH$_2$—OH), 2.936 (s, 2H, CH—CH), 1.147 (s, 3H, CH$_3$).

Example 11

Preparation of N-[2-(2-hydroxyethoxy)ethyl]-exo-3,6-epoxy-1,2,3,6-tetrahydrophthalimide, 2,2-bis-[2,2-bis(2-bromoisobutyryloxymethyl) propionyloxymethyl] propionate initiator

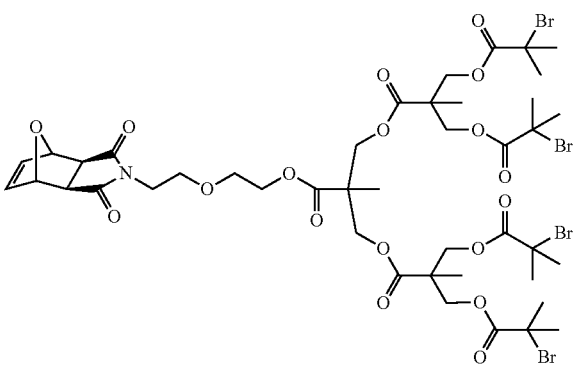

To a solution of 1.5 grams of the diol from the previous step and 3.72 grams of 2,2-bis[(2-bromoisobutyryloxy) methyl]propionic acid in 50 ml of dichloromethane, together with 500 mg of DPTS and 810 mg of DMAP, was treated with 1.40 grams of diisopropylcarbodiimide, and the reaction was stirred at room temperature overnight. The reaction was concentrated and the residue was chromatographed several times on silica gel with 40% ethyl acetate in hexane. The appropriate fractions in each case were combined and concentrated to give the desired product as an oil. NMR (CD$_3$OD): δ 6.55 (t, 2H, CH=CH, J=0.8 Hz), 5.17 (t, 2H, CH-O, J=0.8 Hz), 3.34 (m, 12H, CCH$_2$), 4.23 (m, 2H, CH$_2$—CH$_2$—O—C=O, J=4.7 Hz), 3.68 (m, 2H, N—CH$_2$, J=4.7 Hz), 3.64 (app q, 4H, N—CH$_2$—CH$_2$ and CH$_2$—CH$_2$—O—C=O), 2.95 (s, 2H, CH—CH), 1.907 (s, 24H, Br—C—CH$_3$), 1.34 (s, 6H, CH$_3$), 1.308 (s, 3H, CH$_3$).

Example 12

Preparation of N-(3-propionic acid)-exo-3,6-epoxy-3,6-dimethyl-1,2,3,6-tetrahydrophthalimide, ester with 2,2-bis[(2-bromoisobutyryloxy)methyl] propionic acid, 3-hydroxypropyl ester initiator

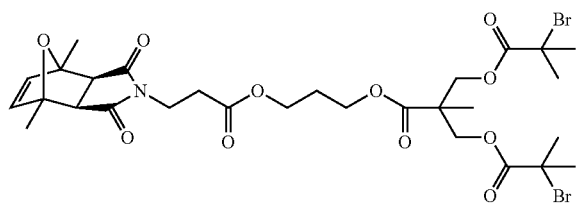 [SMILES: CC(C)(Br)C(=O)OCC(C)(COC(=O)C(C)(C)Br)C(=O)OCCCOC(=O)CCN1C(=O)[C@@H]2[C@H](C1=O)C1(C)C=CC2(C)O1]

A solution of 738 mg of 2,2-bis[(2-bromoisobutyryloxy) methyl]propionic acid, 3-hydroxypropyl ester and 399 mg of N-(3-propionic acid)-exo-3,6-epoxy-3,6-dimethyl-1,2,3,6-tetrahydrophthalimide in 20 ml of dry acetonitrile, together with 50 mg of DPTS and 100 mg of DMAP, was treated with 375 mg of DCC and the reaction was stirred at room temperature overnight. The reaction was filtered to give a residue, which was subjected to flash column chromatography on silica gel with 30-40% ethyl acetate in hexane. The appropriate fractions were combined and concentrated to give 1.02 grams of the desired product as a clear oil. By $^1$H NMR, it appeared that about 10% of the product had already undergone retro Diels-Alder reaction. NMR (CDCl$_3$): δ 6.19 (s, 2H, CH=CH), 4.37 (app q, 4H, CCH$_2$O, J=10.9, 29.7 Hz), 4.23 (t, 2H, CH$_2$CH$_2$O, J=6.3 Hz), 4.15 (t, 2H, CH$_2$CH$_2$O, J=6.3 Hz), 3.62 (t, 2H, NCH$_2$, J=7.4 Hz), 3.22 (s, 2H, CHC=O), 2.48 (t, 2H, CH$_2$C=O, J=7.4 Hz), 2.00 (m, 2H, CH$_2$CH$_2$CH$_2$, J=6.3 Hz), 1.92 (s, 12H, Br—C(CH$_3$)$_2$), 1.78 (s, 6H, CH$_3$), 1.35 (s, 3H, CH$_3$).

Example 13

Preparation of acetal bis(bromopropionate) initiator

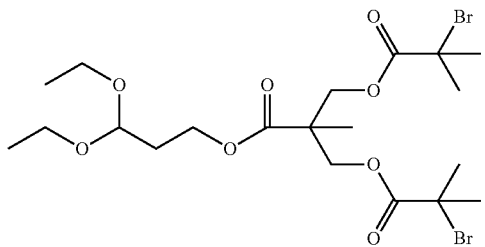 [SMILES: CCOC(CCOC(=O)C(C)(COC(=O)C(C)(C)Br)COC(=O)C(C)(C)Br)OCC]

To a solution of 1.03 grams of 3,3-diethoxy-1-propanol and 3.0 grams of 2,2-bis(2-bromoisobutyryloxymethyl)propionic acid in 50 ml of dichloromethane, together with 817 mg of N,N-dimethylpyridinium p-toluenesulfonate, was treated with 1.58 grams of N,N'-dicyclohexylcarbodiimide, and the reaction was stirred at ambient temperature overnight. The reaction was filtered, and the precipitate was washed with a small amount of dichloromethane. The combined organics were concentrated, and the residue was subjected to flash column chromatography on silica gel with 10-20% ethyl acetate in hexane. The fractions containing the desired product were combined and concentrated to give 2.87 grams of a clear, colorless oil. This material was still not pure by $^1$H NMR, so it was again subjected to flash column chromatography on silica gel using dichloromethane. The appropriate fractions were combined and concentrated to give 2.00 grams of the desired product as a viscous, clear oil. $^1$H NMR (400 MHz, CDCl$_3$): δ=1.20 (t, 6H, CH$_3$CH$_2$O), 1.34 (s, 3H, CH$_3$CC=O), 1.92 [s, 12H, (CH$_3$)$_2$CBr], 1.98 (app q, 2H, CHCH$_2$CH$_2$), 3.50 (m, 2H, OCH$_2$CH$_3$), 3.66 (m, 2H, OCH$_2$CH$_3$), 4.24 (t, 2H, CH$_2$CH$_2$OC=O), 4.37 (app q, 4H, CH$_2$OC=OCBr), 4.60 (t, 1H, O—CH—O).

Example 14

Preparation of vinyl bis(bromopropionate) initiator 1

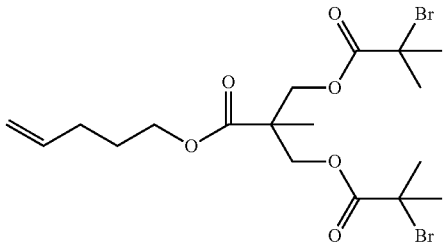 [SMILES: C=CCCCOC(=O)C(C)(COC(=O)C(C)(C)Br)COC(=O)C(C)(C)Br]

A 100 ml round-bottom flask equipped with a stir bar was charged with 30 ml of dichloromethane, 86 milligrams of 4-penten-1-ol, 432 milligrams of the dibromo acid from Example 7, and 88 milligrams of DPTS. Nitrogen was bubbled through the solution briefly, and 169 μl of N,N'-diisopropylcarbodiimide was added slowly. The reaction was allowed to stir at room temperature overnight, then another 0.1 grams DPTS was added and the reaction was again stirred overnight. Filtration and evaporation gave an oily residue, which was purified by flash chromatography on silica gel using 20-40% ethyl acetate in hexane. The solvent was removed from the first product to come off the column, yielding 0.13 grams of the desired product as a colorless oil. $^1$H NMR (400 MHz, CD$_3$OD): δ=1.34 (s, 3H, CH$_3$), 1.77 (m, 2H, CH$_2$CH$_2$CH$_2$), 1.90 (s, 12H, CH$_3$), 2.15 (q, J=7.2 Hz, 2H, CHCH$_2$CH$_2$), 4.16 (t, J=6.4 Hz, 2H, OCH$_2$), 4.36 (app q, 4H, CCH$_2$O), 5.02 (m, 2H, CH$_2$=CH), 5.82 (m, 1H, CH$_2$=CH).

Example 15

Preparation of vinyl bis(bromopropionate) initiator 2

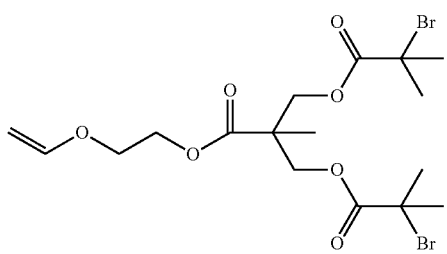 [SMILES: C=COCCOC(=O)C(C)(COC(=O)C(C)(C)Br)COC(=O)C(C)(C)Br]

A 100 ml round-bottom flask equipped with a stir bar was charged with 25 ml dichloromethane, 370 milligrams of ethylene glycol monovinyl ether, 432 milligrams of the dibromo acid from Example 7, and 590 grams of DPTS. The flask was flushed with nitrogen, and 681 µl of N,N'-diisopropylcarbodiimide was added slowly. The reaction was allowed to stir at room temperature overnight. The mixture was filtered and then dried onto silica gel for flash chromatography using 5-10% ethyl acetate in hexane, yielding the product as a colorless oil. $^1$H NMR (400 MHz, CDCl$_3$): δ=1.36 (s, 3H, CH$_3$), 1.92 (s, 12H, CH$_3$), 3.90 (app q, J=5.4 Hz, 2H, NCH$_2$CH$_2$O), 4.05 (dd, 1H, J=2.4, 6.8 Hz, =CH), 4.19 (dd, J=2.4, 14.4 Hz, 1H, =CH), 4.39 (m, 2H, NCH$_2$CH$_2$O), 4.40 (app q, 4H, OCH$_2$), 6.45 (dd, 1H, J=6.8, 14.4 Hz, =CHO).

Example 16

Preparation of Boc-amino bis(maleimide) initiator

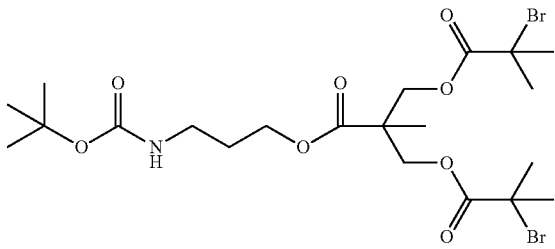 [SMILES: CC(C)(C)OC(=O)NCCCOC(=O)C(C)(COC(=O)C(C)(C)Br)COC(=O)C(C)(C)Br]

A solution of 2.19 grams of N-Boc-3-amino-1-propanol and 5.20 grams of 2,2-bis(2-bromoisobutyryloxymethyl) propionic acid in 50 ml of dichloromethane, together with 350 mg of DPTS, was treated with 3.0 grams of N,N'-dicyclohexylcarbodiimide and the reaction was stirred at ambient temperature overnight. The reaction mixture was filtered, and the precipitate was washed with a small amount of dichloromethane. Concentration gave a residue, which was subjected to flash column chromatography on silica gel with 5-20% ethyl acetate in hexane. The appropriate fractions were combined and concentrated to give an oil containing a little solid residue. This material was taken up in ethyl acetate and filtered. Concentration again gave an oil still containing a little solid, so the material was again taken up in ethyl acetate, filtered, and concentrated to give the desired product as a clear oil. $^1$H NMR (400 MHz, CDCl$_3$): δ=4.8 (br s, 1H, NH), 4.37 (app q, 4H, CH$_2$OC=OCBr), 4.22 (t, 2H, CH$_2$CH$_2$OC=O), 3.20 (app q, 2H, NHCH$_2$), 1.92 [s, 12H, (CH$_3$)$_2$CBr], 1.85 (t, 2H, CH$_2$CH$_2$CH$_2$), 1.43 (s, 9H, (CH$_3$)$_3$O), 1.35 (s, CH$_3$CC=O).

Example 17

Preparation of N-(3-Propionic acid, t-butyl ester)-2,2-Bis[(2-bromoisobutyryloxy) methyl] propionamide

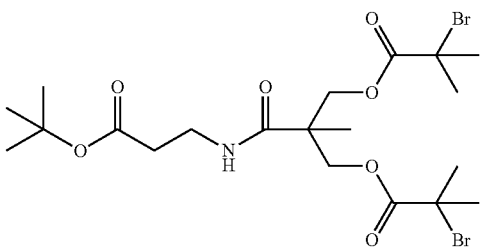 [SMILES: CC(C)(C)OC(=O)CCNC(=O)C(C)(COC(=O)C(C)(C)Br)COC(=O)C(C)(C)Br]

A solution of 1.00 grams of b-alanine t-butyl ester hydrochloride in 50 ml of dichloromethane was treated with 25 ml of saturated aqueous sodium bicarbonate, and the mixture was stirred for 15 minutes. The layers were separated, and the organics were dried over sodium sulfate. To this solution was added 2.38 grams of 2,2-bis[(2-bromoisobutyryloxy] methyl)propionic acid, followed by 1.92 ml of diisopropylethylamine and 2.1 grams of HBTU, and the reaction was stirred at room temperature overnight. The reaction mixture was then diluted with another 50 ml of dichloromethane, washed with 2 x 50 ml of water, and dried over sodium sulfate. Filtration and concentration gave an oil, which was subjected to flash column chromatography with 20-25% ethyl acetate in hexane. The appropriate fractions were combined and concentrated to give 730 mg of a white solid. NMR (CDCl$_3$): δ 6.70 (t, 1H, NH, J=5.4 Hz), 4.33 (app q, 4H, CH$_2$O, J=16.3, 11.4 Hz), 3.51 (q, 2H, NCH$_2$, J=6.0 Hz), 2.46 (t, 2H, CH$_2$CO, J=6.0 Hz), 1.93 (s, 12H, Br—C(CH$_3$)$_2$), 1.45 (s, 9H, C(CH$_3$)$_3$), 1.33 (s, 3H, CH$_3$).

Example 18

Preparation of protected maleimide 4-ol

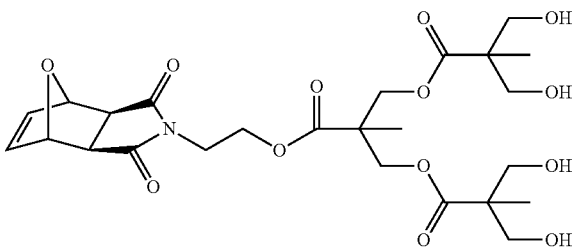 [SMILES: CC(CO)(CO)C(=O)OCC(C)(COC(=O)C(C)(CO)CO)C(=O)OCCN1C(=O)[C@@H]2C3C=CC(O3)[C@@H]2C1=O]

A 100 ml round-bottom flask equipped with a stir bar was charged with 30 ml of dichloromethane, 1.6 grams of the diol from Example 7, 1.71 grams of isopropylidene-2,2-bis (hydroxymethyl)propionic acid, and 0.5 grams of DPTS. Nitrogen was bubbled through the solution briefly, 1.70 ml of N,N'-diisopropylcarbodiimide was added slowly, and the reaction was allowed to stir at room temperature overnight. Filtration and evaporation gave an oily residue, which was purified by flash chromatography on silica gel using 10-40% ethyl acetate in hexane. A second purification by flash chromatography on silica gel using 2% methanol in dichloromethane yielded about 2 grams of colorless oil. This oil was dissolved in 25 ml of methanol and stirred for 60 hours at room temperature with Dowex 50WX8-100 resin (H$^+$ form). The reaction was filtered, concentrated, then passed through a silica gel plug with 150 ml of 15% methanol in dichloromethane. Evaporation yielded 1.3 grams of a nearly colorless hard foam. $^1$H NMR (400 MHz, CDCl$_3$): δ=1.13 (s, 6H, CH$_3$), 1.25 (s, 3H, CH$_3$), 2.96 (s, 2H, CHC=ON), 3.57-3.65 (m, 8H, CH$_2$OH), 3.64 (t, J=2.8 Hz, 2H, CH$_2$CH$_2$OC=O),4.22 (app q, 4H, C(CH$_3$)CH$_2$OC=O$_1$), 4.22 (t, J=2.8 Hz, CH$_2$CH$_2$OC=O), 5.21 (t, J=0.8 Hz, CHOCH), 6.55 (t, J=0.8 Hz, CH=CH).

Example 19

Preparation of protected maleimide tetra(bromopropionate) initiator

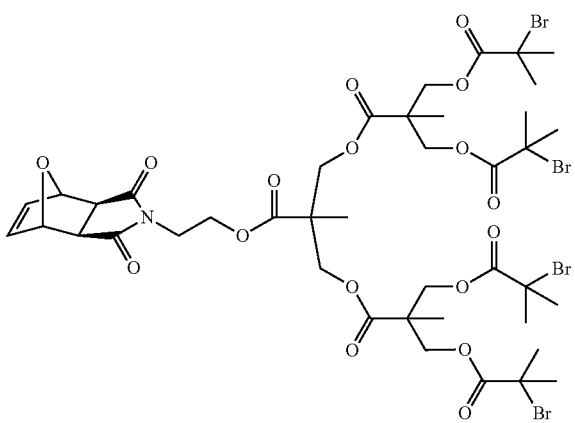 [SMILES: CC(C)(Br)C(=O)OCC(C)(COC(=O)C(C)(C)Br)C(=O)OCC(C)(COC(=O)C(C)(COC(=O)C(C)(C)Br)COC(=O)C(C)(C)Br)C(=O)OCCN1C(=O)[C@@H]2C3C=CC(O3)[C@@H]2C1=O]

A 100 ml round-bottom flask equipped with a stir bar was charged with 20 ml of dichloromethane, 0.55 grams of the tetraol from Example 13, and 1.69 ml of triethyl amine. The stirring mixture was cooled to 0 degrees, and a solution of 0.99 ml of 2-bromoisobutyryl bromide in 10 ml dichloromethane was added drop wise. The reaction was allowed to stir at room temperature overnight, then washed with 50 ml of half-saturated sodium bicarbonate. Concentration of the reaction mixture gave an oily brown residue, which was purified by flash chromatography on silica gel with 40% ethyl acetate in hexane. The brown residue was dissolved in methanol and treated with charcoal to remove color, yielding 0.68 grams of the desired product as a light brown oil. $^1$H NMR (400 MHz, CDCl$_3$): δ=1.26 (s, 3H, CH$_3$CC=O), 1.34 (s, 6H, CH$_3$CC=O), 1.90 (s, 24H, (CH$_3$)$_2$CBr), 2.95 (s, 2H, CH), 3.78 (t, J=5 Hz, 2H, NCH$_2$), 4.25 (m, 6H, OCH$_2$C (4H) and OCH$_2$CH$_2$N (2H)), 4.35 (app q, 8H, OCH$_2$), 5.23 (t, J=1 Hz, 2H, CHOCH), 6.55 (t, J=1 Hz, 2H, CH=CH).

Example 20

Preparation of 2,2-Bis[(2-bromoisobutyryloxy) methyl]propionic acid, 2-hydroxyethyl ester initiator

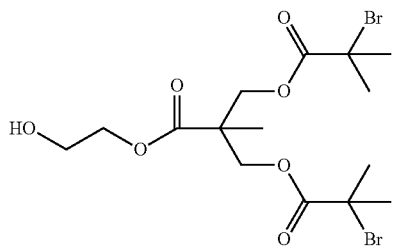 [SMILES: CC(C)(Br)C(=O)OCC(C)(COC(=O)C(C)(C)Br)C(=O)OCCO]

A solution of 4.32 grams of 2,2-bis[(2-bromoisobutyryloxy]methyl)propionic acid and 12.41 grams of ethylene glycol in 50 ml of dichloromethane, together with 883 mg of DPTS was treated with 1.39 grams of diisopropylcarbodiimide, and the reaction was stirred at room temperature overnight. The reaction mixture was concentrated, then partitioned between 150 ml of ethyl acetate and 70 ml of water. The organic layer was concentrated, and the residue was subjected to flash column chromatography on silica gel with 20%-40% ethyl acetate in hexane. The appropriate fractions were combined and concentrated to give 2.7 grams of the desired product as a clear oil. NMR (CD$_3$OD): δ 4.38 (app q, 4H, CCH$_2$, J=11.2, 30.2 Hz), 4.20 (t, 2H, CH$_2$OH, J=5.0 Hz), 3.75 (t, 2H, CH$_2$CH$_2$OH, J=5.0 Hz), 1.90 (s, 12H, Br—CCH$_3$), 1.36 (s, 3H, CH$_3$).

Example 21

Preparation of 2,2-Bis[(2-bromoisobutyryloxy) methyl]propionic acid, 3-hydroxypropyl ester initiator

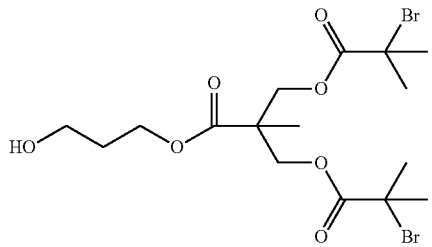 [SMILES: CC(C)(Br)C(=O)OCC(C)(COC(=O)C(C)(C)Br)C(=O)OCCCO]

A solution of 5.31 grams of 2,2-bis[(2-bromoisobutyryloxy)methyl]propionic acid and 4.68 grams of 1,3-propanediol in 80 ml of dichloromethane and 20 ml of acetonitrile was treated with 1.0 grams of DPTS, followed by 3.0 grams of DCC, and the reaction was stirred at room temperature for 2 hours. The reaction was then filtered, concentrated and the residue was subjected to flash column chromatography on silica gel with 30% ethyl acetate in hexane. The appropriate fractions were combined and concentrated to give a clear oil, which was not quite pure. Rechromatography on silica gel with 10-15% acetone in hexane gave the desired product as a clear, colorless oil. NMR (CDCl$_3$): δ 4.38 (app q, 4H, CCH$_2$O, J=11.2 Hz), 4.31 (t, 2H, CH$_2$CH$_2$O, J=6.3 Hz), 3.71

(q, 2H, CH$_2$OH, J=5.9 Hz), 1.92 (s, 12H, Br—C(CH$_3$)$_2$), 1.9 (m, 2H, CH$_2$CH$_2$CH$_2$), 1.35 (s, 3H, CH$_3$).

Example 22

2,2-Bis[(2-bromoisobutyryloxy)methyl]propionic acid, 11-hydroxy-3,6,9-trioxaundecanoate initiator

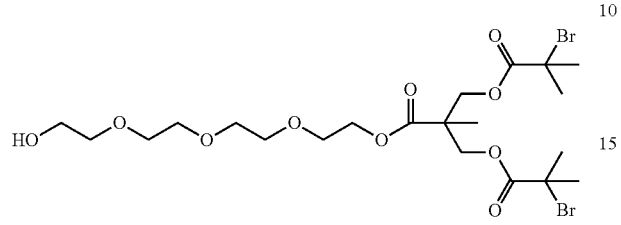

A solution of 1.86 grams of 2,2-bis[(2-bromoisobutyryloxy)methyl]propionic acid and 4.18 grams of tetraethylene glycol in 50 ml of dichloromethane, together with 250 mg of DPTS, was treated with 1.15 grams of DCC and the reaction was stirred at room temperature overnight. The reaction was filtered and the filtrate was diluted with 50 ml of dichloromethane and washed with 20 ml of water. The organics were dried over sodium sulfate, filtered and concentrated to give a residue, which was subjected to flash column chromatography on silica gel first with 50-70% ethyl acetate in hexane. The appropriate fractions were combined, filtered and concentrated to give 1.19 grams of the desired product as a clear, colorless oil. NMR (CDCl$_3$): δ 4.38 (app q, 4H, CCH$_2$O, J=31.8, 11.2 Hz), 4.31 (t, 2H, CH$_2$CH$_2$OC=O, J=5.0 Hz), 3.6-3.73 (m, 14H,CH$_2$O), 2.46 (t, 1H, OH, J=6.3 Hz), 1.92 (s, 12H, Br—C(CH$_3$)$_2$), 1.35 (s, 3H, CH$_3$).

Example 23

Preparation of 2,2-Bis[(2-bromoisobutyryloxy) methyl]propionic acid, 11-hydroxy-3,6,9-trioxaundecanoate, NHS carbonate initiator A solution of 630 grams of the above hydroxyl compound and 1.28 grams of disuccinimidyl carbonate in 3 ml of dry acetonitrile was treated with 610 mg of DMAP and the reaction was stirred at room temperature. The reaction was still heterogeneous, so 4 ml of dry THF were added, and after 2 hours the reaction turned yellow and became homogeneous, but contained several spots on tlc (silica gel, 50% ethyl acetate in hexane). The reaction was concentrated to give a residue which was subjected to flash column chromatography on silica gel with 50-60% ethyl acetate in hexane. Two fractions were isolated, and the fraction with a lower rf was concentrated to give 260 mg of the desired product as a clear oil. NMR (CDCl$_3$): δ 4.47 (m, 2H, CH$_2$O(C=O)O), 4.37 (app q, 4H, CCH$_2$O, J=11.2, 31.6 Hz), 4.30 (m, 2H, CH$_2$CH$_2$O(C=O)C), 3.79 (m, 2H, CH$_2$CH$_2$O(C=O)C), 3.71 (t, 2H, CH$_2$CH$_2$O(C=O)O, J=5.0 Hz), 3.67 (s, 4H,CH$_2$O), 3.65 (s, 4H, CH$_2$O), 2.84 (s, 4H, CH$_2$C=O), 1.92 (s, 12H, Br—C (CH$_3$)$_2$), 1.35 (s, 3H, CH$_3$).

Example 24

Preparation of 2,2-Bis[(2-bromoisobutyryloxy) methyl]propionic acid, solketal ester initiator

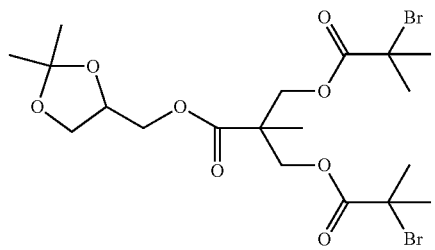

A solution of 918 mg of solketal and 3.0 grams of 2,2-bis[(2-bromoisobutyryloxy) methyl]propionic acid, together with 200 mg of DPTS was treated with 2.15 grams of DCC and the reaction was stirred at room temperature overnight. The reaction was filtered to give a residue, which was subjected to flash column chromatography on silica gel with 10% ethyl acetate in hexane. The appropriate fractions were combined and concentrated to give 1.85 grams of the desired product as a clear, colorless oil. NMR (CDCl$_3$): δ 4.38 (app q, 4H, CCH$_2$O), 4.32 (m, 1H, OCH), 4.19 (m, 2H, CHCH$_2$OC=O), 4.07 (d of d, 1H, OCH$_2$CH, J=6.7, 8.6 Hz), 3.76 (d of d, 1H, OCH$_2$CH, J=5.7, 8.6 Hz), 1.92 (s, 12H, Br—C(CH$_3$)$_2$), 1.43 (s, 3H, (CH$_3$)$_2$CO), 1.36 (s, 3H, CH$_3$), 1.35 (s, 3H, (CH$_3$)$_2$CO).

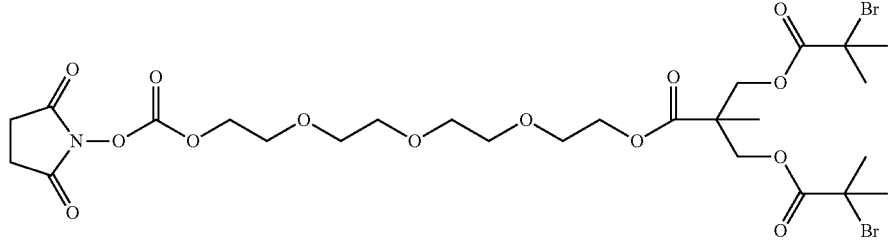 [SMILES: CC(C)(Br)C(=O)OCC(C)(COC(=O)C(C)(C)Br)C(=O)OCCOCCOCCOCCOC(=O)ON1C(=O)CCC1=O]

Example 25

Preparation of 2,2-Bis[(2-bromoisobutyryloxy) methyl]propionic acid, 2,3-dihydroxypropyl ester initiator

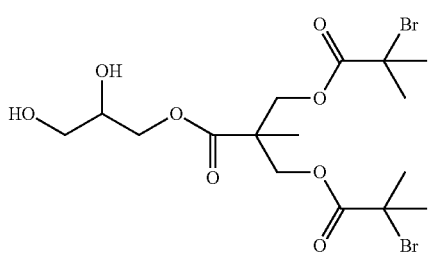 [SMILES: CC(C)(Br)C(=O)OCC(C)(COC(=O)C(C)(C)Br)C(=O)OCC(O)CO]

A solution of 1.0 grams of the previous ketal in 50 ml of methanol was treated with 750 mg of Dowex 50Wx8-100 and the reaction was stirred overnight. The reaction was then filtered, concentrated, and the residue was subjected to flash column chromatography on silica gel with 20-40% ethyl acetate in hexane. The appropriate fractions were combined and concentrated to give 630 mg of the desired product as a clear, colorless oil. NMR (CDCl$_3$+D$_2$O): δ 4.40 (app q of d, 4H, CCH$_2$O, J=2.8, 11.5, 30.2 Hz), 4.24 (app q of d, 2H, CHC$\underline{H}_2$OC=O, J=4.5, 6.6, 11.5 Hz), 3.96 (m, 1H, CH), 3.66 (app q of d, 2H, HOC$\underline{H}_2$CH, J=3.8, 5.6, 11.5, 37.9 Hz), 1.92 (s, 12H, Br—C(CH$_3$)$_2$), 1.37 (s, 3H, CH$_3$).

Example 26

Preparation of 2,2-Bis[(2-bromoisobutyryloxy) methyl]propionic acid, 2-(2,3-dihydroxypropoxy) ethyl ester initiator

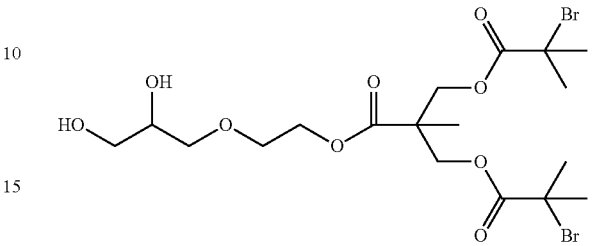

To a solution of 1.5 grams of 2-[(2-bromoisobutyryloxy) methyl]-2-hydroxymethylpropionic acid, 2-(allyloxy)ethyl ester in 15 ml of water and 15 ml of t-butanol was added 2.86 grams (3 eq) of potassium ferricyanide, 1.20 grams (3 eq) of potassium carbonate, 7.5 mg of potassium osmate dehydrate, 11 mg of quinuclidine, and 276 mg (1 eq) of methanesulfonamide, and the reaction mixture was stirred at room temperature overnight. The reaction appeared to be complete by TLC (silica gel, 50% ethyl acetate in hexane), so the reaction was poured into 100 ml of water, then extracted with 100 ml of dichloromethane. The combined organics were dried over sodium sulfate, filtered and concentrated to give an oily residue, which was subjected to flash column chromatography on silica gel with 30-40% ethyl acetate in hexane. The appropriate fractions were combined, treated with decolorizing carbon, filtered and concentrated to give 850 mg of the desired product as a nearly colorless oil. NMR (CDCl$_3$): δ 4.39 (app q of d, 4H, CCH$_2$O, J=4.1, 11.1, 3.0, 37.6 Hz), 4.31 (t, 2H, OCH$_2$C$\underline{H}_2$OC=O, J=4.7 Hz), 3.87 (m, 1H, C$\underline{H}$—OH), 3.54-3.77 (m, 2H, C$\underline{H}_2$—OH), 3.72 (m, 2H, OC$\underline{H}_2$CH), 3.58 (app t, 2H, OC$\underline{H}_2$CH$_2$OC=O), 2.68 (d, 1H, CH—OH, J=5.1 Hz), 2.15 (app t, 1H, CH$_2$—O$\underline{H}$, J=6.1 Hz), 1.92 (s, 12H, Br—C(CH$_3$)$_2$), 1.36 (s, 3H, CH$_3$).

Example 27

2,2-Bis[(2-bromoisobutyryloxy)methyl]propionic acid, 12-(allyloxy)-3,6,9,12-tetraoxadodecanoate initiator

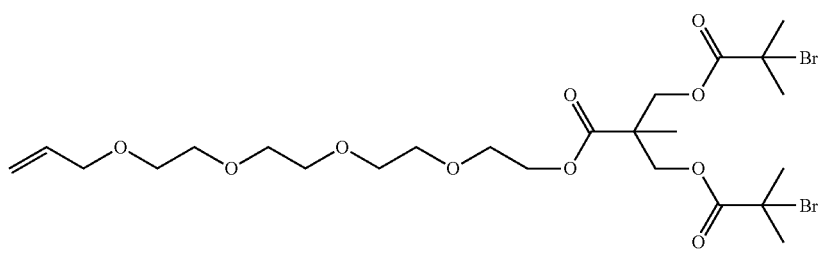 [SMILES: C=CCOCCOCCOCCOCCOC(=O)C(C)(COC(=O)C(C)(C)Br)COC(=O)C(C)(C)Br]

To a solution of 1.60 g of 2,2-bis[(2-bromoisobutyryloxy) methyl]propionic acid and 870 mg of 12-(allyloxy)-3,6,9, 12-tetraoxadodecane in 30 ml of dry acetonitrile, together with 218 mg of DPTS and 362 mg of DMAP, was added 917 mg of DCC and the reaction was stirred at room temperature overnight. The mixture was then filtered and concentrated, and the residue was subjected to flash column chromatography on silica gel first with 50-60% ethyl acetate in hexanes, and the product containing fractions were combined and concentrated to give 1.35 grams of the desired product as a clear, colorless oil. NMR (CDCl$_3$): δ 5.87-5.97 (m, 1H, CH$_2$C$\underline{H}$=CH$_2$), 5.28 (dq, 1H, $\underline{H}$—CH=CH), 5.18 (dq, 1H, $\underline{H}$—CH=CH), 4.37 (app q, C$\underline{H}_2$OC=O), 4.30 (dd, 2H, CH$_2$C$\underline{H}_2$OC=O), 4.02 (d, 2H, CH$_2$=CHC$\underline{H}_2$), 3.60-3.72 (m, 14H, CH$_2$C$\underline{H}_2$OCH$_2$), 1.92 (s, 12H, Br—C(CH$_3$)$_2$), 1.35 (s, 3H, CH$_3$).

Example 28

Preparation of 2,2-Bis[(2-bromoisobutyryloxy) methyl]propionic acid, 12-(2,3-dihydroxypropoxy)-3,6,9,12-tetraoxadodecyl ester initiator

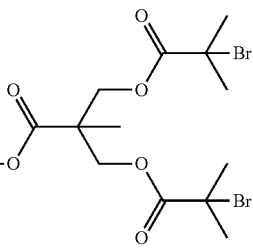

To a mixture of 1.29 grams of 2,2-bis[(2-bromoisobutyryloxy)methyl]propionic acid, 12-(allyloxy)-3,6,9,12-tetraoxadodecyl ester in 15 ml of water and 15 ml of t-butanol was added 1.98 grams (3 eq) of potassium ferricyanide, 829 mg (3 eq) of potassium carbonate, 8 mg of potassium osmate dehydrate, 11 mg of quinuclidine, and 190 mg (1 eq) of methanesulfonamide, and the reaction mixture was stirred at room temperature overnight. The reaction appeared to be complete by TLC (silica gel, 50% ethyl acetate in hexane), so the reaction was poured into 50 ml of water, then extracted with 100 ml of dichloromethane. The combined organics were dried over sodium sulfate, filtered and concentrated to give an oily residue, which was subjected to flash column chromatography on silica gel with 5% methanol in dichloromethane. The product containing fractions were combined and treated twice with two small spatulafuls of activated carbon, filtering between treatments. Filtration and concentration gave a light gray oil containing a small amount of solid, so it was taken up in ethyl acetate and filtered, then concentrated to give 1.06 grams of the desired product as a light gray oil, still containing a tiny amount of solid. NMR (CDCl$_3$): δ 4.38 (app q, 4H, CCH$_2$OC=O), 4.30 (t, 2H, CH$_2$C$\underline{H}_2$OC=O, J=5.0 Hz), 3.85 (p, 1H, C$\underline{H}$OH, J=5 Hz), 3.71 (t, 2H, OC$\underline{H}_2$CHOH, J=4.8 Hz), 3.72-3.55 (m, 16H, OC$\underline{H}_2$C$\underline{H}_2$O and C$\underline{H}_2$OH), 3.12 (s, 1H, CHO$\underline{H}$), 2.37 (s, 1H, CH$_2$O$\underline{H}$), 1.92 (s, 12H, Br—C(CH$_3$)$_2$), 1.35 (s, 3H, CH$_3$).

Example 29

Preparation of 2,2,5-Trimethyl-1,3-dioxane-5-carboxylic acid, 2-(allyloxy)ethyl ester

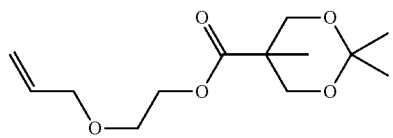

A solution of 1.4 grams of ethylene glycol monoallyl ether and 2.35 grams of 2,2,5-trimethyl-1,3-dioxane-5-carboxylic acid in 25 ml of anhydrous THF was treated with 500 mg of 4-dimethylaminopyridinium p-toluenesulfonate (DPTS) and 1.44 grams of dimethylaminopyridine (DMAP), followed by the addition of 3.38 grams of dicyclohexylcarbodiimide, and the reaction was stirred at room temperature for 3 days. The reaction mixture was filtered and concentrated to give a semisolid residue, which was subjected to flash column chromatography on silica gel with 20% ethyl acetate in hexane. The product containing fractions were combined, concentrated and filtered to give 2.83 grams (81%) of a clear oil containing a small amount of solid. $^1$H NMR (400 MHz, CDCl$_3$): δ=1.23 (s, 3H, C=OCCH$_3$), 1.39 (s, 3H, CH$_3$), 1.43 (s, 3H, CH$_3$), 3.66 (m, 4H), 4.02 (dd, 2H, CH$_2$=CHC$\underline{H}_2$), 4.20 (d, 2H), 4.31 (t, 2H, C=OOC$\underline{H}_2$), 5.18 (dd, 1H, =CH), 5.28 (dd, 1H, =CH), 5.89 (m, =CHC$\underline{H}_2$).

Example 30

2,2-Bis(hydroxymethyl)propionic acid, 2-(allyloxy)ethyl ester

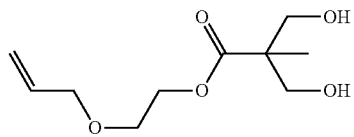

A solution of 2.72 grams of 2,2,5-trimethyl-1,3-dioxane-5-carboxylic acid, 2-(allyloxy)ethyl ester in 50 ml of methanol was treated with 1.0 gram of Dowex 50W-X8 resin (H+form) and the reaction was stirred at room temperature overnight. The reaction was filtered, and the filtrate was concentrated to give an oil, which was subjected to flash column chromatography on silica gel with 5% methanol in dichloromethane. The product containing fractions were combined and concentrated to give 2.23 grams of the product as a clear, light yellow oil. ¹H NMR (400 MHz, CDCl₃): δ=5.84-5.94 (ddt, 1H, H₂C=CHCH₂), 5.28 (dq, 1H, HHC=CHCH₂), 5.22 (dq, 1H, HHC=CHCH₂), 4.36 (app t, 2H, OCH₂CH₂), 4.02 (dt, 2H, H₂C=CHCH₂), 3.86 (dd, 2H, CH₂OH), 3.74 (dd, 2H, CH₂OH), 3.68 (app t, 2H, OCH₂CH₂), 2.90 (br d, 2H, OH), 1.11 (s, CH₃).

Example 31

Preparation of 2,2-Bis[(2-bromoisobutyryloxy)methyl]propionic acid, 2-(allyloxy)ethyl ester initiator

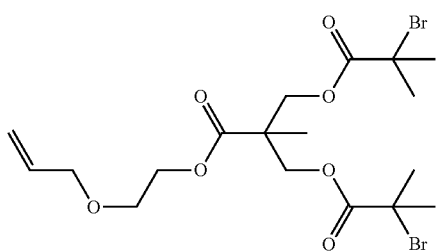 [SMILES: C=CCOCCOC(=O)C(C)(COC(=O)C(C)(C)Br)COC(=O)C(C)(C)Br]

A solution of 1.2 grams of allyloxyethanol, 5.0 grams of 2,2-bis(2-bromoisobutyryloxymethyl) propionic acid and 690 mg of DPTS in 100 ml of dichloromethane was stirred at room temperature as 2.86 grams of DCC were added as a solution in a small amount of dichloromethane. The reaction was stirred at room temperature overnight, then filtered and concentrated to give an oil. This was subjected to flash chromatography on silica gel with 10% ethyl acetate in hexane. The appropriate fractions were combined and concentrated to give a clear oil, which was not sufficiently pure. This oil was again subjected to flash chromatography on silica gel with 3-4% ethyl acetate in hexane. The product containing fractions were combined and concentrated to give 2.78 grams of the desired product as a clear, colorless oil. NMR (CDCl₃): δ 5.89 (m, 1H, CH₂CH=CH₂), 5.28 (d of q, 1H, H—CH=CH, J=17.2, 1.7 Hz), 5.20 (d of q, 1H, H—CH=CH, J=10.5, 1.5 Hz), 4.38 (app q, 4H, CH₂OC=O), 4.31 (t, 2H, OCH₂, J=4.7 Hz), 4.01 (d of t, 2H, OCH₂, J=5.6, 1.5 Hz), 3.65 (t, 2H, OCH₂, J=4.7 Hz), 1.91 (s, 12H, Br—C(CH₃)₂), 1.35 (s, 3H, CH₃).

Example 32

2,2-Bis-[2,2-bis(2-bromoisobutyryloxymethyl)propionyloxymethyl]propionic acid, 2-(allyloxy)ethyl ester initiator

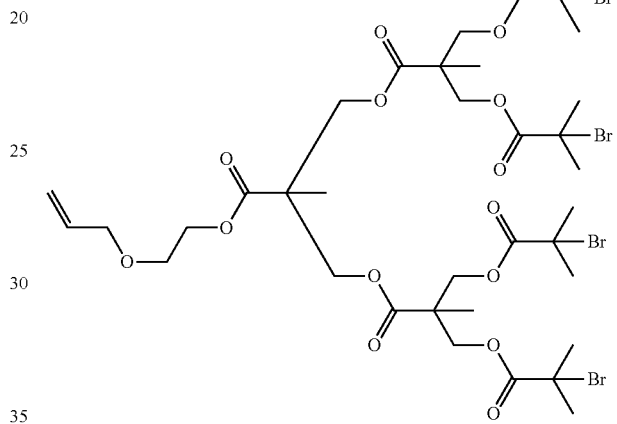

A solution of 2.42 grams of 2-[(2-bromoisobutyryloxy)methyl]-2-hydroxymethylpropionic acid, 2-(allyloxy)ethyl ester and 1.73 grams of 2,2-[bis-(2-bromoisobutyryloxy)methyl] propionic acid in 25 ml of dry acetonitrile, together with 200 mg of DPTS and 580 mg of DMAP, was treated with 1.03 grams of DCC, and the reaction was stirred at room temperature overnight. By TLC (silica gel, 30% ethyl acetate in hexane) it appeared that the reaction was incomplete, so another 812 mg of 2,2-[bis-(2-bromoisobutyryloxy)methyl]propionic acid and 400 mg of DCC were added, and the reaction was again stirred at room temperature overnight. The reaction mixture was filtered and concentrated, and the residue was subjected to flash column chromatography on silica gel first with 20%, and then with 30% ethyl acetate in hexanes. The product containing fractions were combined and concentrated to give 1.27 grams of the desired compound as a clear, colorless oil. NMR (CDCl₃): δ 5.88 (m, 1H, CH₂CH=CH₂), 5.28 (d of q, 1H, H—CH=CH, J=17.4, 1.6 Hz), 5.20 (d of q, 1H, H—CH=CH, J=10.3, 1.3 Hz), 4.24-4.44 (m, 14H, CH₂OC=O), 4.01 (d, 2H, CH₂=CHCH₂, J=5.6), 3.65 (t, 2H, CH₂CH₂OCH₂, J=4.7 Hz), 1.91 (s, 24H, Br—C(CH₃)₂), 1.33 (s, 6H, CH₃), 1.30 (s, 3H, CH₃).

Example 33

Preparation of 2,2-Bis[2,2-Bis[(2-Bromoisobutyryloxy) propionyloxymethyl]propionic acid], 2-[(2,3-dihydroxy)propoxy]ethyl ester initiator

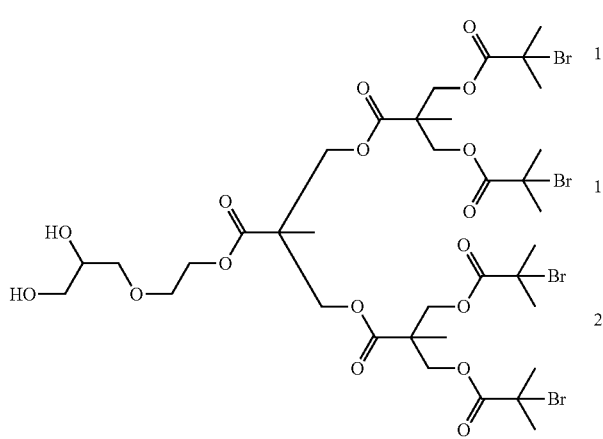

To a mixture of 1.21 grams of 2,2-bis[(2-bromoisobutyryloxy)methyl]propionic acid, 2-(allyloxy)ethyl ester in 15 ml of water and 15 ml of t-butanol was added 1.14 grams (3 eq) of potassium ferricyanide, 480 mg (3 eq) of potassium carbonate, 7.5 mg of potassium osmate dehydrate, 11 mg of quinuclidine, and 110 mg (1 eq) of methanesulfonamide, and the reaction mixture was stirred at room temperature overnight. The reaction appeared to be complete by tlc (silica gel, 50% ethyl acetate in hexane), so the reaction was poured into 50 ml of water, then extracted with 100 ml of dichloromethane, followed by another 50 ml of dichloromethane. The combined organics were dried over sodium sulfate, filtered and concentrated to give an oily residue, which was subjected to flash column chromatography on silica gel with 50% ethyl acetate in hexane, and the product containing fractions were combined and concentrated to give 620 mg of the desired product as a clear, colorless oil. NMR (CDCl$_3$): δ 4.28-4.41 (m, 14H, CCH$_2$OC=O), 3.86 (m, 1H, CH$_2$CHOHCH$_2$), 3.69-3.75 (m, 3H), 3.56-3.65 (m, 3H), 2.78 (dd, 11-1, OH), 2.23 (app t, 1H, OH), 1.92 (s, 24H, CH$_3$CBr), 1.34 (s, 6H, CH$_3$), 1.31 (s, 3H, CH$_3$).

Example 34

Preparation of 2,2-bis[(2-bromoisobutyryloxy) methyl]propionic acid, (2-azidoethoxy)ethyl ester initiator

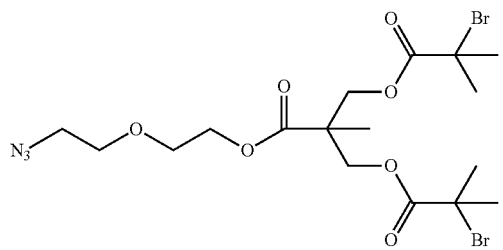 [SMILES: CC(C)(Br)C(=O)OCC(C)(COC(=O)C(C)(C)Br)C(=O)OCCOCCN=[N+]=[N-]]

To a solution of 3.30 grams of 2,2-bis[(2-bromoisobutyryloxy)methyl]propionic acid and 1.0 gram of 2-(2-azidoethoxy)ethanol in 20 mL of dry acetonitrile, together with 225 mg of DPTS, was added 1.89 grams of DCC and the reaction was stirred at room temperature overnight. The reaction was filtered and concentrated to give a residue, which was subjected to flash column chromatography on silica gel with 10-15% ethyl acetate in hexane. The appropriate fractions were combined and concentrated to give 2.06 grams of the desired product as a clear, colorless oil. NMR (CDCl$_3$): δ 4.39 (app q, 4H, CCH$_2$O, J=11.1, 33.8 Hz), 4.31 (t, 2H, OCH$_2$CH$_2$OC=O, J=5 Hz), 3.72 (t, 2H, CH$_2$N$_3$, J=5 Hz), 3.67 (t, 2H, CH$_2$CH$_2$N$_3$, J=5 Hz), 3.38 (t, 2H, OCH$_2$CH$_2$OC=O, J=5 Hz), 1.92 (s, 12H, Br—C(CH$_3$)$_2$), 1.36 (s, 3H, CH$_3$).

Example 35

Preparation of 3,5-bis-(2-bromoisobutyryloxy) benzaldehyde

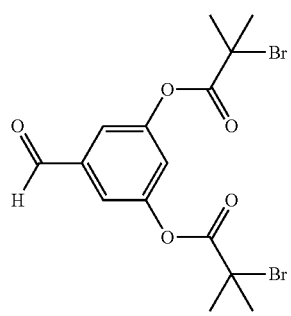 [SMILES: CC(C)(Br)C(=O)Oc1cc(C=O)cc(OC(=O)C(C)(C)Br)c1]

A solution of 1.0 gram of 3,5-dihydroxybenzaldehyde and 4.0 ml (4 eq) of triethylamine in 20 ml of dichloromethane was cooled with an ice-water bath, and a solution of 3.35 grams of 2-bromoisobutyryl bromide in 5 ml of dichloromethane was added dropwise over a few minutes as much solid formed. The reaction was stirred at room temperature for 1.5 hr, at which time the reaction appeared to be complete by TLC (silica gel, 30% ethyl acetate in hexane). The reaction was washed with 25 ml of water, then concentrated to give a residue, which was subjected to flash column chromatography on silica gel with 10% ethyl acetate in hexane. The appropriate fractions were combined, treated with a small amount of decolorizing carbon, filtered and concentrated to give 2.2 grams of an oil, which crystallized in the refrigerator to give a white solid. $^1$H NMR (400 MHz, CDCl$_3$): δ=2.08 (s, 12H, CH$_3$), 7.29 (t, 1H, J=2.4 Hz, ArH), 7.61 (d, J=2.4 Hz, 2H, ArH), 10.0 (s, 1H, CHO).

Example 36

Preparation of 7-(13-allyloxy-2,5,8,11-tetraoxatridecyl)-2,4,9-triphenyl-1,3,5-triazatricyclo[3.3.1.13, 7]decane

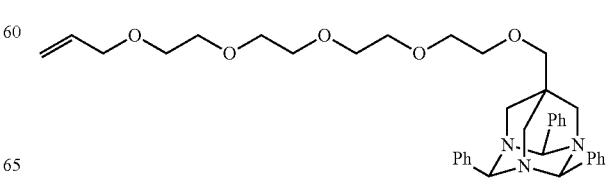

A solution of 870 mg of 11-allyloxy-3,6,9-trioxaundecan-1-ol methanesulfonate and 1.01 grams of 2,4,9-triphenyl-1,3,5-triazatricyclo[3.3.1.13,7]decane-7-methanol (WO2000/037658) in 10 ml of dry THF was treated with 410 mg of sodium hydride (60% in oil) and the reaction was heated at 80° C. for 20 hours. The reaction was then quenched carefully by the addition of a few ml of water, poured into 20 ml of sat NaCl, then extracted with 3×10 ml of dichloromethane. The organics were dried over sodium sulfate, filtered and concentrated to give a residue, which was subjected to flash chromatography on silica gel with 25-35% ethyl acetate in hexane. The appropriate fractions were combined and concentrated to give 920 mg of the desired product as a colorless oil. NMR (DMSO-$d_6$): δ 7.70-7.82 (m, 6H, PhH), 7.26-7.51 (m, 91-1, PhH), 3.69-3.75 (m, 3H), 3.56-3.65 (m, 3H), 2.78 (dd, 1H, OH), 2.23 (app t, 1H, OH), 1.92 (s, 24H, $CH_3CBr$), 1.34 (s, 6H, $CH_3$), 1.31 (s, 3H, $CH_3$).

Example 37

Preparation of 1-Amino-15-allyloxy-2,2-bis(aminomethyl)-4,7,10,13-tetraoxapentadecane trihydrochloride

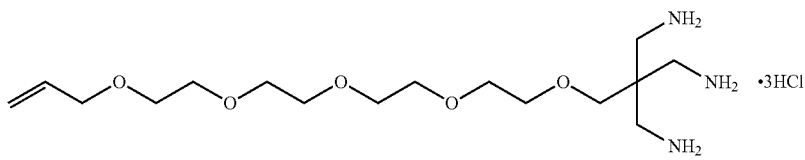 [SMILES: C=CCOCCOCCOCCOCCOCC(CN)(CN)CN]

The triazaadamantane compound from the previous reaction was taken up in 20 ml of ethanol and 4 ml of ether, then treated with 2 ml of concentrated hydrochloric acid. The reaction was mixed and then left to stand at 4° C. for 1.5 hours. Then 30 ml of ether were added and the mixture was cooled again for another 30 minutes. Then added 100 ml of ether and the solid product was recovered by filtration, washed with ether and dried under vacuum to give 564 mg of the product as a white solid. NMR (DMSO-$d_6$): δ 7.75 (m, 6H, CCH), 7.44 (m, 6H, CCHC$\underline{H}$), 7.30 (m, 3H, CCHCHC$\underline{H}$), 5.86 (m, 1H, $CH_2$=C$\underline{H}$), 5.70 (s, 1H, NCH (equatorial)), 5.250 (s, 2H, NCH(axial)), 5.23 (d of q, 1H, C$\underline{H}_2$=CH), 5.11 (d of q, 1H, C$\underline{H}_2$=CH), 3.93 (d of t, 2H, CH—C$\underline{H}_2$—O), 3.55-3.25 (m, 16H, OC$\underline{H}_2$C$\underline{H}_2$O), 3.26 (m, 2H, NC$\underline{H}_2$), 3.19 (d, 2H, NC$\underline{H}_2$), 2.88 (s, 2H, NC$\underline{H}_2$), 2.719 (s, 2H, CC$\underline{H}_2$O).

Example 38

Preparation of N-(2-Bromo-2-methylpropionyl)-1-Amino-15-allyloxy-2,2-bis[N-(2-bromo-2-methylpropionyl)aminomethyl]-4,7,10,13-tetraoxapentadecane initiator

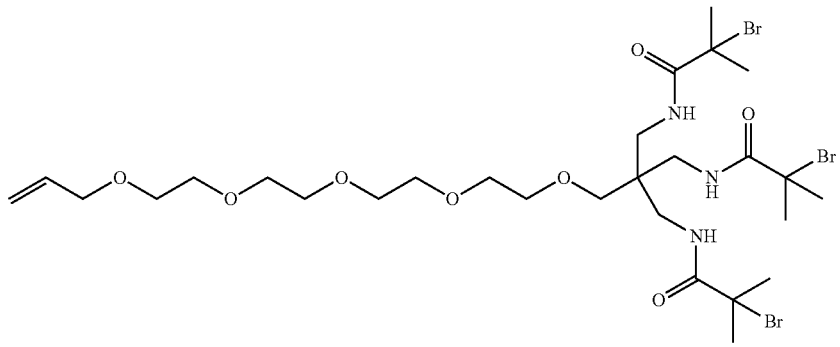 [SMILES: C=CCOCCOCCOCCOCCOCC(CNC(=O)C(C)(C)Br)(CNC(=O)C(C)(C)Br)CNC(=O)C(C)(C)Br]

The triamine hydrochloride from the previous procedure was taken up in 25 ml of dichloromethane, the solution was cooled with and ice water bath, and treated with 1.35 ml of triethylamine, followed by the addition of 0.46 ml of 2-bromoisobutyryl bromide. The reaction was then stirred as it was allowed to warm to room temperature over 2 hours. The reaction mixture was then washed with 3×10 ml of 1N HCl, 2×10 mL of sat NaHCO$_3$, 10 ml of sat NaCl, and dried over magnesium sulfate. The solution was filtered and concentrated to give a residue, which was flushed through a plug of silica gel with ethyl acetate. Concentration gave 989 mg of the desired product as a viscous oil. NMR (DMSO-d$_6$): δ 8.004 (t, 3H, NH), 5.87 (m, 1H, CH), 5.23 (d of q, 1H, C$\underline{H}_2$=CH), 5.12 (d of q, 1H, C$\underline{H}_2$=CH), 3.93 (d oft, 2H, C$\underline{H}_2$—CH), 3.6-3.45 (m, 16H, OC$\underline{H}_2$C$\underline{H}_2$O), 3.289 (s, 2H, CCH$_2$O), 3.12 (d, 6H, CCH$_2$N), 1.907 (s, 18H, CH$_3$).

Example 39

Preparation of N-(2-Bromo-2-methylpropionyl)-1-Amino-15-(2,3-dihydroxypropyl)-2,2-bis[N-(2-bromo-2-methylpropionyl)aminomethyl]-4,7,10,13-tetraoxapentadecane initiator

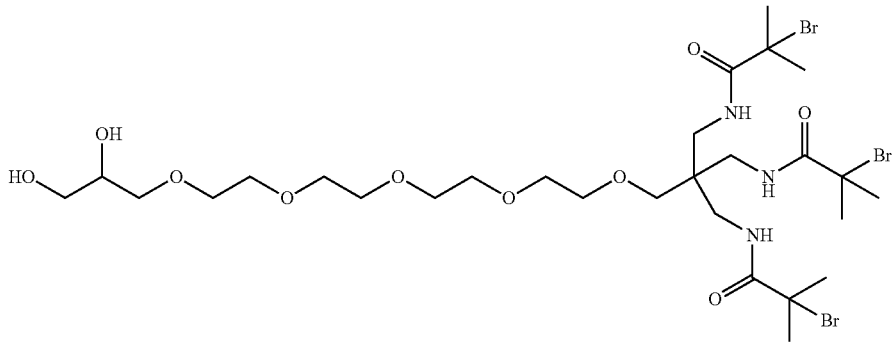 [SMILES: CC(C)(Br)C(=O)NCC(CNC(=O)C(C)(C)Br)(CNC(=O)C(C)(C)Br)COCCOCCOCCOCCOCC(O)CO]

To a mixture of 350 mg of the alkene from the previous procedure in 5 ml of t-butanol and 5 ml of water was added 433 mg (3 eq) of potassium ferricyanide, 182 mg (3 eq) of potassium carbonate, 42 mg (1 eq) of methanesulfonamide, 7.5 mg of quinuclidine, and 4 mg of potassium osmate dihydrate, and the solution was stirred at room temperature overnight. The reaction appeared to be complete by TLC (silica gel, 5% methanol in dichloromethane), so 50 ml of water were added and the solution was extracted with 50 ml of dichloromethane, followed by another 2×25 ml of dichloromethane. The combined extracts were dried over sodium sulfate, concentrated, and the dark gray residue was subjected to flash column chromatography on silica gel with 2-5% methanol in dichloromethane. The appropriate fractions were combined and concentrated to give 310 mg of the desired dihydroxy compound as a light gray oil. NMR (CDCl$_3$): δ 7.91 (t, 3H, NH), 3.88 (m, 1H, HOCH$_2$C$\underline{H}$OHCH$_2$), 3.55-3.72 (complex m, 21H), 3.35 (s, 1H, OC$\underline{H}_2$C(CH$_2$)$_3$), 3.19 (d, 6H, J=6.4 Hz, CH$_2$NH), 1.99 (s, 18H, CH$_3$).

Example 40

Preparation of 7-(7-Azido-2,5-dioxaheptyl)-2,4,9-triphenyl-1,3,5-triazatricyclo[3.3.1.1$^{3,7}$]decane

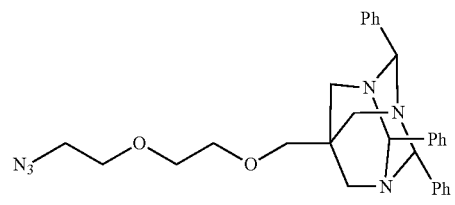 [SMILES: [N-]=[N+]=NCCOCCOCC12CN3C(c4ccccc4)N(C1)C(c1ccccc1)N(C2)C3c1ccccc1]

To a solution of 1.1 grams of 2,4,9-triphenyl-1,3,5-triazatricyclo[3.3.1.1$^{3,7}$]decane-7-methanol (WO2000/037658) and 585 mg of 2-(2-azidoethoxy)ethyl methanesulfonate in 15 ml of anhydrous THF was added 224 mg of NaH (60% in oil), and the solution was heated at 70° C. overnight. Another 245 mg of NaH and 600 mg of 2-(2-azidoethoxy)ethyl methanesulfonate were added, and heating was again continued overnight. The reaction mixture was cooled, diluted with 25 ml of water, and extracted with 50 ml of dichloromethane. The organic layer was washed with saturated NaCl, dried over sodium sulfate, filtered and concentrated to give a residue. This material was subjected to flash column chromatography on silica gel with 10-25% ethyl acetate in hexane. The appropriate fractions were combined and concentrated to give 1.15 grams of the desired product as an oil, which was not completely pure, but used in the next reaction without further purification. NMR(DMSO) extremely complex.

Example 41

Preparation of 1-Amino-9-azido-2,2-bis(aminomethyl)-4,7-dioxanonane trihydrochloride

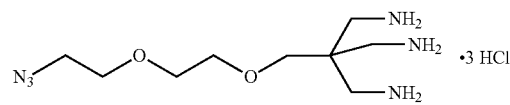

A solution of 1.15 grams of the triazaadamantane compound from the previous procedure in 20 ml of ethanol and 4 ml of ether was cooled with an ice water bath, and 3 ml of concentrated HCl were added. Solid product began to form immediately, and the reaction was allowed to stand in the cold for 10 minutes. Another 30 ml of ether were added, and the reaction was refrigerated overnight. The reaction mixture was diluted with another 100 ml of ether, and the solid product was isolated by filtration, washed with more ether and dried under vacuum to give 800 mg of the product as a white solid.

Example 42

Preparation of N-(2-Bromo-2-methylpropionyl)-1-Amino-9-azido-2,2-bis[N-(2-bromo-2-methylpropionyl)aminomethyl]-4,7-dioxanonane initiator

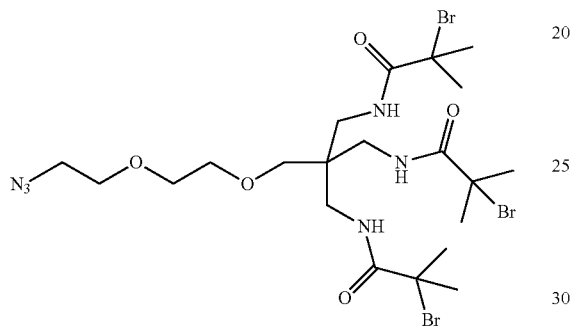

A solution of 800 mg of the trihydrochloride salt from the previous procedure in 25 ml of dichloromethane was cooled with an ice water bath, then treated with 3.5 ml of triethylamine. To this mixture was added dropwise 1.07 ml of 2-bromoisobutyryl bromide, and the reaction was stirred while warming to room temperature over 2 hours. The mixture was then washed with 3×10 ml of 1N HCl, 2×10 ml of saturated NaHCO3, and with 10 ml of saturated NaCl, then dried over magnesium sulfate. Filtration and concentration gave a residue, which was subjected to flash column chromatography on silica gel with 20-30% ethyl acetate in hexane. The appropriate fractions were combined and concentrated to give 630 mg of the desired product as an oil. NMR(CDCl$_3$): δ 7.76 (t, 3H, NH, J=6.3 Hz), 3.68 (m, 4H, OC$\underline{H}_2$C$\underline{H}_2$O), 3.63 (m, 2H, N$_3$CH$_2$C$\underline{H}_2$O), 3.40 (t, 2H, N$_3$CH$_2$, J=5.0 Hz), 3.37 (s, 2H, CCH$_2$O), 3.19 (d, 6H, CCH$_2$N, J=6.8 Hz), 1.99 (s, 18H, CH$_3$).

Example 43

13-Allyloxy-2,5,8,11-tetraoxatridecyl 6-arm initiator

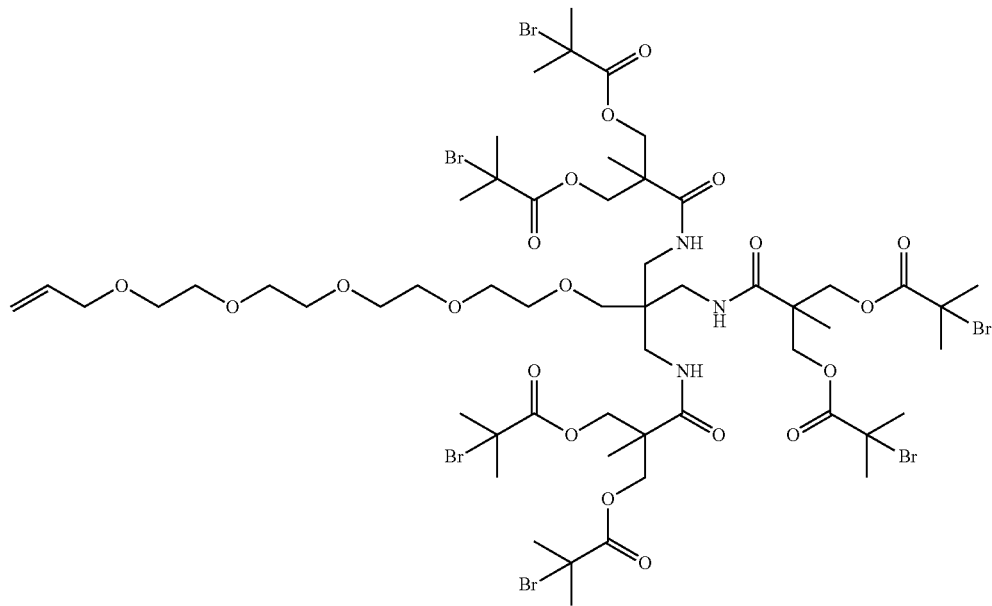 [SMILES: C=CCOCCOCCOCCOCCOCC(CNC(=O)C(C)(COC(=O)C(C)(C)Br)COC(=O)C(C)(C)Br)(CNC(=O)C(C)(COC(=O)C(C)(C)Br)COC(=O)C(C)(C)Br)CNC(=O)C(C)(COC(=O)C(C)(C)Br)COC(=O)C(C)(C)Br]

To a solution of 0.9 grams of 1-amino-15-allyloxy-2,2-bis(aminomethyl)-4,7,10,13-tetraoxapentadecane trihydrochloride and 3.89 grams of 2,2-bis[(2-bromoisobutyryloxy]methyl)propionic acid in 25 ml of dichloromethane, together with 530 mg of DPTS and 890 mg of DMAP, was added 2.7 grams of DCC and the reaction was stirred at room temperature overnight. The reaction was filtered and concentrated, and the residue was subjected to flash column chromatography on silica gel with 50-70% ethyl acetate in hexane. The appropriate fractions were combined and concentrated to give 1.9 grams of the desired product as a viscous oil. NMR (CDCl$_3$): δ 7.78 (t, 3H, NH, J=6.5 Hz), 5.91 (m, 1H, CH), 5.27 (d of q, 1H, C$\underline{H}_2$=CH, J=17.4, 1.6 Hz), 5.18 (d of q, 1H, C$\underline{H}_2$=CH, J=10.4, 1.4 Hz), 4.38 (app q, 12H, CH$_2$OC=O), 4.01 (d of t, 2H, CH—C$\underline{H}_2$, J=5.7, 1.4 Hz), 3.61 (two m, 16H, OC$\underline{H}_2$C$\underline{H}_2$O), 3.30 (s, 2H, CCH$_2$O), 3.14 (d, 6H, CH$_2$N, J=6.1 Hz), 1.92 (d, 36H, BrC(CH$_3$)$_2$, J=1.2 Hz), 1.38 (s, 9H, CH$_3$).

Example 44

13-(2,3-Dihydroxypropyl)-2,5,8,11-tetraoxatridecyl 6-arm initiator

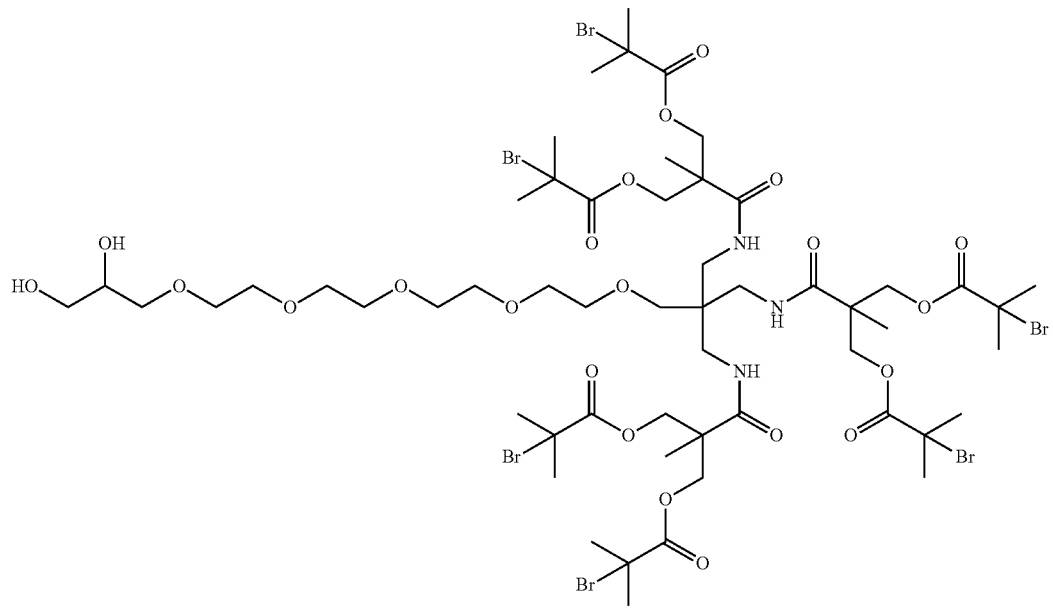 [SMILES: CC(C)(Br)C(=O)OCC(C)(COC(=O)C(C)(C)Br)C(=O)NCC(CNC(=O)C(C)(COC(=O)C(C)(C)Br)COC(=O)C(C)(C)Br)(CNC(=O)C(C)(COC(=O)C(C)(C)Br)COC(=O)C(C)(C)Br)COCCOCCOCCOCCOCC(O)CO]

To a mixture of 1.0 gram of the alkene from the previous procedure in 10 ml of water and 10 ml of t-butanol was added 638 mg (3 eq) of potassium ferricyanide, 268 mg (3 eq) of potassium carbonate, 10 mg of potassium osmate dehydrate, 12 mg of quinuclidine, and 61 mg (1 eq) of methanesulfonamide, and the reaction mixture was stirred at room temperature overnight. The reaction was poured into 50 ml of water, then extracted with 50 ml of dichloromethane, followed by another 25 ml of dichloromethane. The combined organics were dried over sodium sulfate, filtered and concentrated to give an oily residue, which was subjected to flash column chromatography on silica gel with 2-4% methanol in dichloromethane, and the product containing fractions were combined and concentrated to give 417 mg of the desired product as a viscous oil. NMR (CDCl$_3$): δ 7.78 (t, 3H, NH, J=6.0 Hz), 4.39 (app q, 12H, CH$_2$OC=O), 3.86 (broad s, 1H, OH—C$\underline{H}$), 3.62 (m, 20H, OC$\underline{H}_2$C$\underline{H}_2$O and OHCHC$\underline{H}_2$O and OH—C$\underline{H}_2$), 3.27 (s, 2H, CCH$_2$O), 3.13 (s, 6H, NC$\underline{H}_2$), 2.40 (s, 2H, OH), 1.92 (s, 36H, BrC(CH$_3$)$_2$), 1.38 (s, 9H, CH$_3$).

Example 45

Preparation of Hexaglutamic acid amide with 9-Azido-4,7-dioxanononanoic acid

Preparation of t-Butyl 9-hydroxy-4,7-dioxanonanoate methane sulfonate

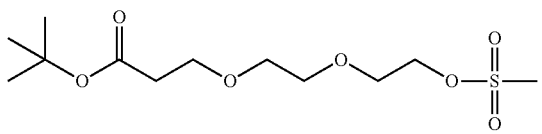 [SMILES: CC(C)(C)OC(=O)CCOCCOCCOS(C)(=O)=O]

A solution of 3.0 grams of t-Butyl 9-hydroxy-4,7-dioxanonanoate (Bioconjugate Chem, 2004, 15, 1349) in 50 ml of dichloromethane was cooled with an ice water bath, treated with 2.5 ml of triethylamine followed by the addition of 1.60 grams of methanesulfonyl chloride. The reaction was stirred in the cold for 10 minutes, then allowed to stir while warming to room temperature over 1 hour. The reaction was diluted with 50 ml of dichloromethane, washed with 50 ml of water and dried over sodium sulfate. Filtration and concentration gave an oil, which was subjected to flash column chromatography on silica gel with 50% ethyl acetate in hexane. The appropriate fractions were combined and concentrated to give 3.99 grams of the product as a clear, colorless oil. NMR (CDCl$_3$): δ 4.38 (m, 2H), 3.76 (m, 2H), 3.70 (t, 2H, J=6.4 Hz, C=OC$\underline{H}_2$), 3.61-3.66 (m, 4H), 3.08 (s, 3H, OSO$_2$CH$_3$), 2.49 (t, 2H, J=6.4 Hz, C=OCH$_2$C$\underline{H}_2$), 1.45 (s, 9H, CH$_3$).

Preparation of t-Butyl 9-azido-4,7-dioxanonanoate

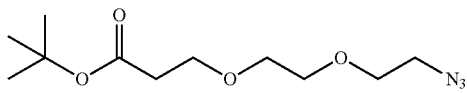 [SMILES: CC(C)(C)OC(=O)CCOCCOCCN=[N+]=[N-]]

A solution of 2.0 grams of the mesylate from the previous procedure in 25 ml of DMF, together with 1.25 grams (3 eq) of sodium azide, was heated at 85° C. overnight. The reaction mixture was poured into 100 ml of water, then extracted with 4×50 ml of ether. The combined organic layers were dried over sodium sulfate, filtered and concentrated to give a clear oil. This oil was flushed through a plug of silica gel with 200 ml of 50% ethyl acetate in hexane, and the filtrate was concentrated to give 1.63 grams of the product as a clear, colorless oil. NMR (CDCl$_3$): δ 3.73 (t, 2H, J=6.4 Hz, C=OC$\underline{H}_2$), 3.63-3.69 (m, 6H), 3.39 (app t, 2H, C$\underline{H}_2$N$_3$), 2.51 (t, 2H, J=6.4 Hz, C=OCH$_2$C$\underline{H}_2$), 1.45 (s, 9H, CH$_3$).

Preparation of 9-Azido-4,7-dioxanononanoic acid

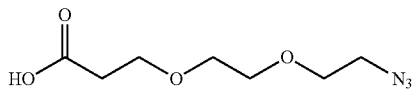

A solution of 1.63 grams of the azido ester from the previous procedure in 5 ml of 88% formic acid was stirred at room temperature overnight. The reaction mixture was diluted with 50 ml of water, then extracted with 4×25 ml of ether. The combined organics were dried over sodium sulfate, filtered and concentrated to give 1.14 grams of the product as a clear oil. NMR (CDCl$_3$): δ 3.79 (t, 2H, J=6.4 Hz, C=OC$\underline{H}_2$), 3.68 (app t, 2H), 3.67 (s, 4H), 3.39 (app t, 2H, C$\underline{H}_2$N$_3$), 2.66 (t, 2H, J=6.4 Hz, C=OCH$_2$C$\underline{H}_2$).

Preparation of 9-Azido-4,7-dioxanononanoic acid, N-hydroxysuccinimide ester

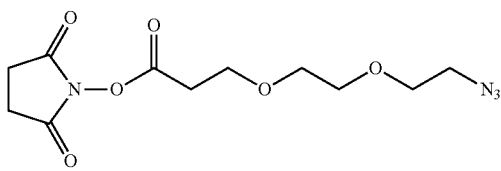 [SMILES: [N-]=[N+]=NCCOCCOCCC(=O)ON1C(=O)CCC1=O]

A solution of 1.14 grams of the acid from the previous procedure and 650 mg of N-hydroxysuccinimide in 15 ml of dry acetonitrile, together with 150 mg of DMAP, was treated with 1.4 grams of DCC and the reaction was stirred at room temperature for 3 hours. The reaction was filtered and concentrated to give a residue, which was subjected to flash column chromatography on silica gel with 10-30% ethyl acetate in hexane. The appropriate fractions were combined and concentrated to give 960 mg of the product as a clear oil containing a small amount of solid. NMR (CDCl$_3$): δ 3.87 (t, 2H, J=6.4 Hz, C=OC$\underline{H}_2$), 3.68 (app t, 2H), 3.67 (s, 4H), 3.39 (app t, 2H, C$\underline{H}_2$N$_3$), 2.91 (t, 2H, J=6.4 Hz, C=OCH$_2$C$\underline{H}_2$), 2.84 (br s, 4H, CH$_2$CH$_2$).

Preparation of Hexaglutamic acid amide with 9-Azido-4,7-dioxanononanoic acid

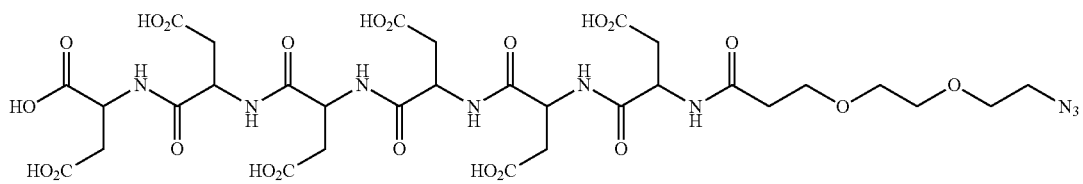 [SMILES: [N-]=[N+]=NCCOCCOCCC(=O)NC(CC(=O)O)C(=O)NC(CC(=O)O)C(=O)NC(CC(=O)O)C(=O)NC(CC(=O)O)C(=O)NC(CC(=O)O)C(=O)NC(CC(=O)O)C(=O)O]

A mixture of 17 mg of hexaglutamic acid in 1 ml of 25 mM HEPES buffer pH 7 was prepared, adding 350 μL of DMF to improve solubility. Then was added 7 mg of the above NHS ester in DMF solution, and checked the pH, which was about 5. A total of 240 μL of 0.5 M NaOH were added to bring the pH back to about 7.5, and added another 13 mg of the NHS ester. The reaction was followed by reverse phase HPLC using a Waters HPLC system with a 2695 Alliance Solvent delivery system equipped with a Waters 2685 Dual Wavelength Detector. Samples were chromatographed using a Jupitor C18 HPLC column (8×260 mm) from Phenomenex at 1.2 ml/min with pump A buffer as 0.08% TFA in water and pump B buffer as 0.1% TFA in acetonitrile for 25 min. Following sample injection, the column was washed for 1 min. with isocratic 100% A, then increased to 20% B over 10 min. with a linear gradient followed by a linear increase to 50% B over 6 min. The column was stripped with 95% B for 2 min. before regeneration using an isocratic 100% A for 2 min. The chromatogram was monitored at OD220 nm. The native peptide and the azide modified peptide eluted as sharp peaks at 5.6 min. and 9.6 min., respectively. Following the overnight reaction, the peptide peak was gone and the product peak was at its maximum. Product purity was confirmed by anion exchange chromatography using a Waters HPLC system with 2695 Alliance Solvent delivery system equipped with a Waters 2685 Dual Wavelength Detector. Samples were chromatographed using a weak anion exchange DEAE-825 HPLC column (8×75 mm) from Shodex at 1 ml/min. with pump A buffer as 20 mM Tris pH 7.5 and pump B buffer as buffer A containing 0.5M NaCl for 16 min. Following sample injection, the column was first washed for 5 min. with isocratic 30% B, then increased to 100% B over 10 min. with a linear gradient and then maintained at 100% B for 2 min. The column was then regenerated using isocratic 30% B for 3 min. prior to the next injection. The chromatogram was monitored at OD220 nm. The native peptide eluted as a single sharp peak at 10.1 min while the modified peptide eluted as a single sharp peak at 10.6 min. The reaction was concentrated using a vacuum pump on the rotary evaporator to remove all solvent, and the residue was triturated with 100 μL of 2.5 M HCl, resulting in a white solid. This mixture was

Example 46

Preparation of Camptothecin PC-Copolymer

Synthesis of 2-(2-Azidoethoxy)ethanol

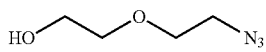

A solution of 10.0 grams of 2-(2-chloroethoxy)ethanol in 50 ml of deionized water was treated with 10.4 grams (2 eq) of sodium azide, and the reaction mixture was heated at 80° C. for 48 hours. The solution was cooled to room temperature, saturated with sodium chloride and extracted with 3×50 ml of ether. The combined organics were dried over anhydrous sodium sulfate, filtered and concentrated to give 7.25 grams (69%) of the desired product as a clear, colorless oil. $^1$H NMR (400 MHz, CDCl$_3$): δ=2.05 (t, J=6.4 Hz, 1H, OH), 3.42 (t, J=5 Hz, 2H), 3.63 (dd, J=4.4, 5.6 Hz), 3.71 (dd, J=4.4, 4.8 Hz, 2H), 3.77 (dt, J=4.4, 6 Hz, 2H).

Synthesis of 5-[2-(2-Azidoethoxy)ethoxy]-4-oxopentanoic acid

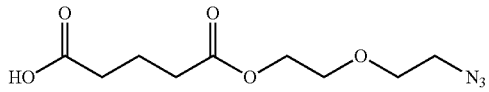

A solution of 3.0 grams of 2-(2-azidoethoxy)ethanol in 50 ml of dichloromethane was treated with 280 mg of 4-(dimethylamino)pyridine and 64 ml (2 eq) of triethylamine, and the solution was cooled with an ice bath. A solution of 2.61 grams (1.0 eq) of glutaric anhydride in 5 ml of dichloromethane was then added dropwise over a few minutes. The reaction was stirred, then heated at gentle reflux overnight. The reaction was cooled to room temperature, washed with 2×25 ml of 1N HCl and 25 ml of H$_2$O, then dried over sodium sulfate. Filtration and concentration gave 4.66 grams (83%) of the desired product as a clear, colorless oil. $^1$H NMR (400 MHz, CDCl$_3$): δ=1.97 (quintet, J=7.2 Hz, 2H), 2.45 (t, J=7.2 Hz, 4H), 3.39 (t, J=4.8 Hz, 2H), 3.66-3.72 (m, 4H), 4.26 (app t, J=4.6 Hz, 2H).

Synthesis of Camptothecin Azide Conjugate

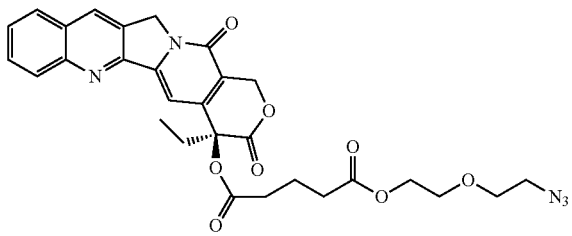 [SMILES: CC[C@@]1(OC(=O)CCCC(=O)OCCOCCN=[N+]=[N-])C(=O)OCc2c1cc1n(c2=O)Cc2cc3ccccc3nc2-1]

A solution of 70 mg of 5-[2-(2-azidoethoxy)ethoxy]-4-oxopentanoic acid in 10 ml of dichloromethane was cooled in an ice-water bath, and treated with 55 mg of EDC, followed by 35 mg of DMAP and 50 mg of camptothecin. The reaction was then allowed to warm to room temperature and stirred overnight as the solution slowly became homogeneous. The reaction mixture was then concentrated and applied to a silica gel column, which was eluted first with 1-2% methanol in dichloromethane. The appropriate fractions were then concentrated to give the desired conjugate as a yellow solid. $^1$H NMR (400 MHz, CDCl$_3$): δ=0.98 (t, J=7.6H), 1.98 (quintet, J=7.2 Hz, 2H), 2.13-2.32 (complex m, 2H), 2.45 (t, J=7.6 Hz, 2H), 2.51-2.65 (complex m, 2H), 3.35 (t, J=5 Hz, 2H), 3.63-3.68 (m, 4H), 4.21-4.25 (m, 2H), 5.30 (br s, 2H), 5.41 (d, J=17.2 Hz, 1H), 5.68 (d, J=17.2 Hz, 1H), 7.21 (s, 1H), 7.68 (t, J=6.8 Hz, 1H), 7.84 (app t, J=8.4 Hz, 1H), 7.95 (d, J=8 Hz, 1H), 8.23 (d, J=8 Hz, 1H), 8.40 (s, 1H).

Synthesis of Copolymer of Methacryloyloxyethyl Phosphorylcholine and Trimethylsilyl (TMS)-Protected Propargyl Methacrylate Ethyl α-bromoisobutyrate (18.84 mg, 0.096 mmol), bipyridine (30.1 mg, 0.192 mmol) and 450 mg of DMSO were initially loaded into a Schlenk tube. The mixture was carefully degassed and the tube filled with nitrogen. CuBr was then added to the tube under inert conditions (13.8 mg, 0.096 mmol). The reaction mixture was sealed and cooled at −78° C. A mixture of trimethylsilyl-protected propargyl methacrylate (TMS-PgMA) (66 mg, 0.336 mmol) and methacryloyloxyethyl phosphoryl choline (0.9, 3.04 mmol) were dissolved in 4 mL of degassed 200 proof ethanol. The solution was added drop wise under inert conditions to the cooled reaction vessel. The mixture was thoroughly degassed under vacuum for 15 min at 0° C. and filled with inert gas. Polymerization was allowed to proceed for 15 hours.

127

-continued

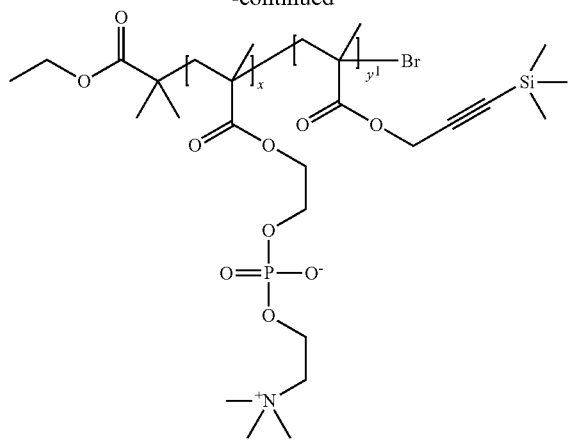

After 15 hours, the reaction mixture was found to be very homogeneous with no apparent crosslinking. The reaction was quenched by exposure to air and the mixture turned from dark brown to green. GPC analysis of a crude sample before purification performed on a Shodex column (OH806) calibrated with polyethylene oxide standards indicated the formation of a polymer as a single peak of narrow distribution (molecular weight at peak Mp was found to be 13200 g/mol). Analysis by light scattering showed a Mn of 22900 g/mol, Mp of 25000 g/mol and PDi of 1.14. The crude reaction was passed through silica gel, concentrated and precipitated carefully into diethyl ether. The solid was isolated by filtration and washed several times with diethyl ether. Copolymer was dried inside an oven at 50° C. overnight, yielding 0.9 g of copolymer. Analysis by $^1$H NMR spectroscopy showed no TMS group. As a precautionary step, 0.5 g of the copolymer was further treated by 100 mg of tetrabutyl ammonium fluoride trihydrate and purified by precipitation.

Grafting of Camptothecin Azide Conjugate onto the Alkyne-Functionalized Copolymer CuBr (13 mg) was loaded inside a degassed Schlenk tube followed by the addition of 15 mg of N, N, N', N'', N''-pentamethyl diethylenetriamine. 240 mg of copolymer was dissolved into 2 g of 200 proof degassed ethanol and 50 mg of camptothecin azide conjugate (CPT-L-N3) were dissolved into 1.5 g of DMF. The solution of CPT-L-N3 was added dropwise under inert conditions to the Schlenk tube while stirring, followed by the addition of the solution of alkyne-functionalized copolymer. The mixture was degassed by three cycles of vacuum-nitrogen and was allowed to react at room temperature for 3 hours.

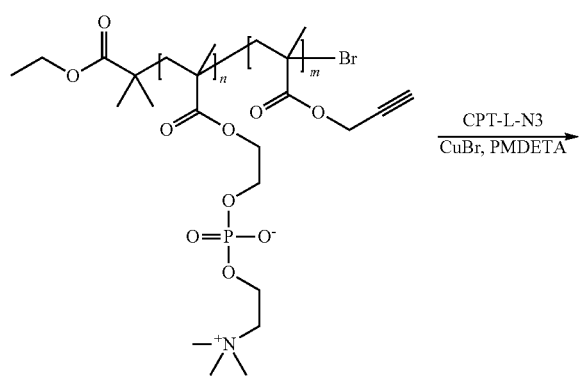

128

-continued

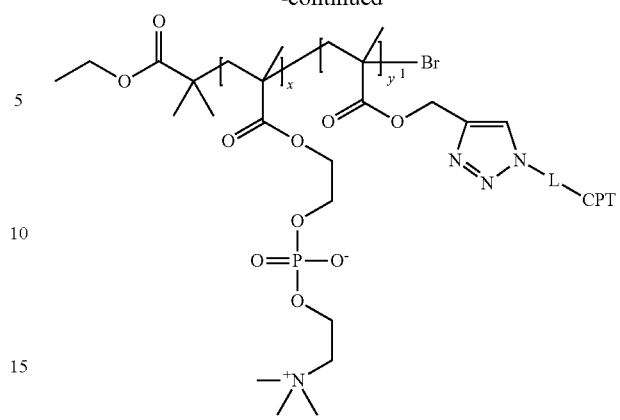

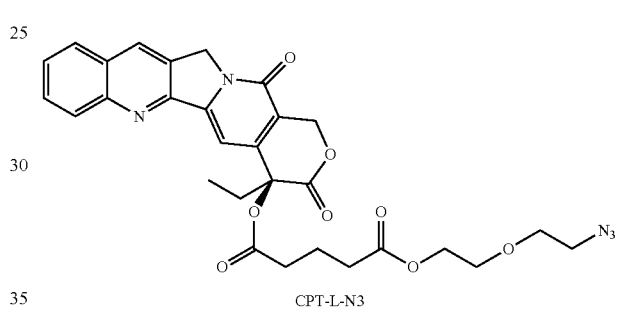

CPT-L-N3

After 3 hours, an aliquot was taken from the crude mixture and analyzed by GPC at 370 nm which showed the disappearance of the free camptothecin peak and a high molecular weight peak which corresponded to the camptothecin copolymer conjugate.

The reaction mixture was exposed to air, concentrated to half its volume, passed through silica gel to remove the copper catalyst and then precipitated carefully into diethyl ether. The polymer was washed with an excess of diethyl ether. The solid was isolated by filtration and washed several times with diethyl ether. The polymer was dried in an oven at 50° C. overnight and was isolated as a light-brown powder. $^1$HNMR spectroscopy analysis performed on the camptothecin grafted copolymers (CD$_3$OD) showed weak and broad aromatic signals in the 7-9 ppm area, characteristic of protons from the incorporated camptothecin.

Example 47

Camptothecin Release Study from Camptothecin Grafted Copolymer

Samples of camptothecin grafted copolymer were prepared at approximately 10 mg/ml in Tris Buffer, pH=8.0. Liver esterase from rabbit liver (Sigma-Aldrich E0887-IKU, Lot #061K74451) was added to the sample and the sample was incubated at 37° C. for up to 65 hours.

GPC analysis of the samples was made using an HPLC system consisting of a Waters Alliance 2995 with Waters 2410 Refractive Index Detector, Waters 2996 Photodiode Array Detector, and a Shodex Protein KW-803 column. The mobile phase used for the elution was phosphate buffered saline containing 10% absolute ethanol. The flow rate was set to 1 ml/min and the presence of camptothecin monitored at 370 nm. Ten microliter injections of the samples were made at each time point.

| Time (h) | Camptothecin Released (mg/ml) |
|---|---|
| 0 | 0.059 |
| 1 | 0.079 |
| 2 | 0.132 |
| 3 | 0.130 |
| 4 | 0.128 |
| 17 | 0.208 |
| 26 | 0.251 |
| 41 | 0.335 |
| 65 | 0.427 |

Example 48

Preparation of Maleimide-Functionalized PC-Copolymer Containing Camptothecin

Polymerization

The polymerization protocol followed was essentially the same as that described in Example 46 except that the protected maleimide functionalized initiator described in Example 5 was used in lieu of ethyl α-bromoisobutyrate. The amounts of reagents utilized were as described in the following table:

| Initiator (mol) | HEMA-PC (g) | TMS-PgMA (mg) | CuBr (mg) | Bipyridyl (mg) | Ethanol (ml) | DMF (mg) |
|---|---|---|---|---|---|---|
| $2.214 \times 10^{-5}$ | 1.116 | 40.1 | 6.38 | 13.8 | 4 | 42.5 |

The polymerization reaction mixture was thoroughly degassed at −78° C. and the reaction allowed to proceed at room temperature for 17 hours. The polymerization was quenched upon exposure to air. A solution of 100 mg of tetrabutyl ammonium fluoride dissolved in 1 ml of methanol was added to the reaction mixture. The crude reaction was passed through silica gel, concentrated and precipitated carefully into diethyl ether. The solid was isolated by filtration and washed several times with diethyl ether. Polymer was dried inside an oven at 40° C. overnight. Analysis by light scattering showed a Mn of 73000 g/mol, Mp of 74000 g/mol and PDi of 1.15. Analysis by $^1$H NMR spectroscopy showed no TMS group.

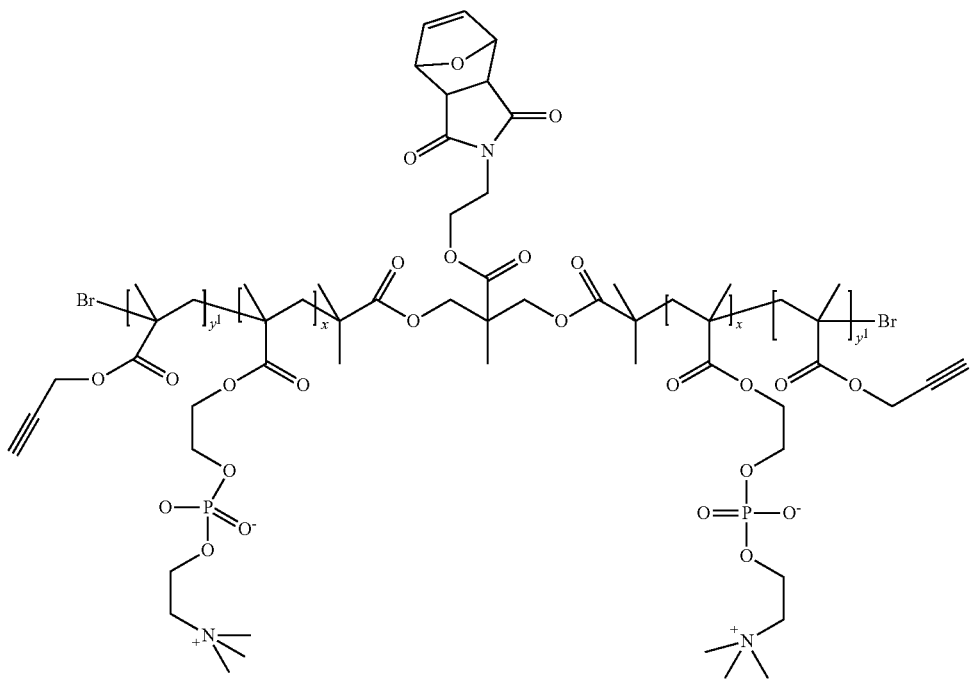

Deprotection of the Protected Maleimide Functional Group

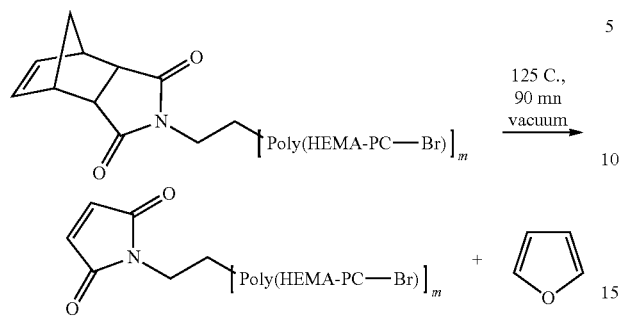

The polymer from the previous step was sprayed as a thin layer of powder on the bottom of a wide crystallizing dish. The dish was placed in a vacuum oven preheated at 125° C. and vacuum applied. Heating at 125° C. was carried out for 1 hour and vacuum was gradually discontinued once the temperature reached room temperature. The resulting solid/powder was collected on a frit/filtration device, washed several times with diethyl ether and dried in a vacuum oven at room temperature.

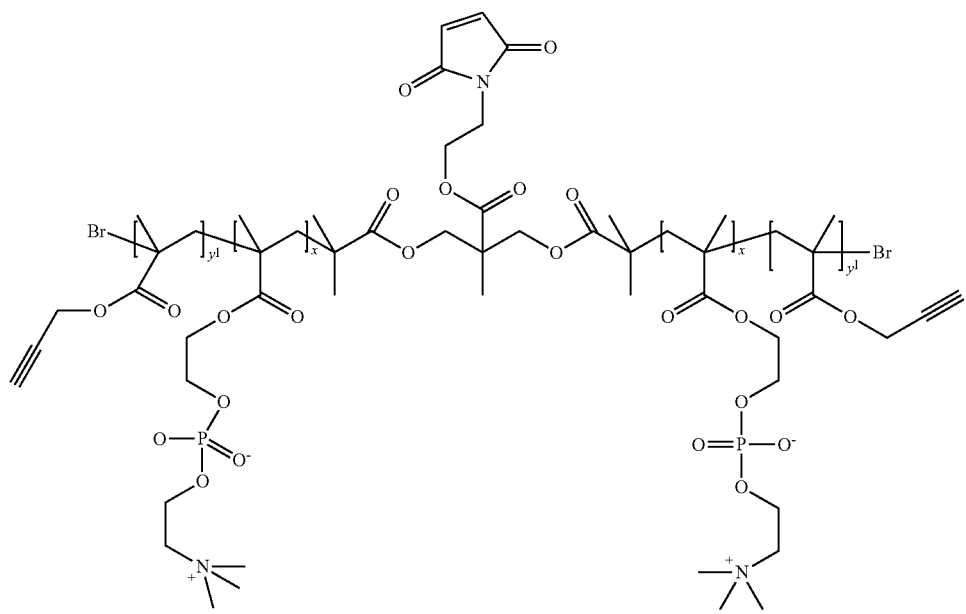

$^1$H NMR analysis showed disappearance of signals at 5.2 and 6.6 ppm (representing the furan group) and the appearance of a new signal at 6.95 ppm (representing the CH from maleimide). Analysis by light scattering showed a Mn of 77000 g/mol, Mp of 69000 g/mol and PDi of 1.1.

Preparation of Maleimide-Functionalized PC-Copolymer Containing Camptothecin

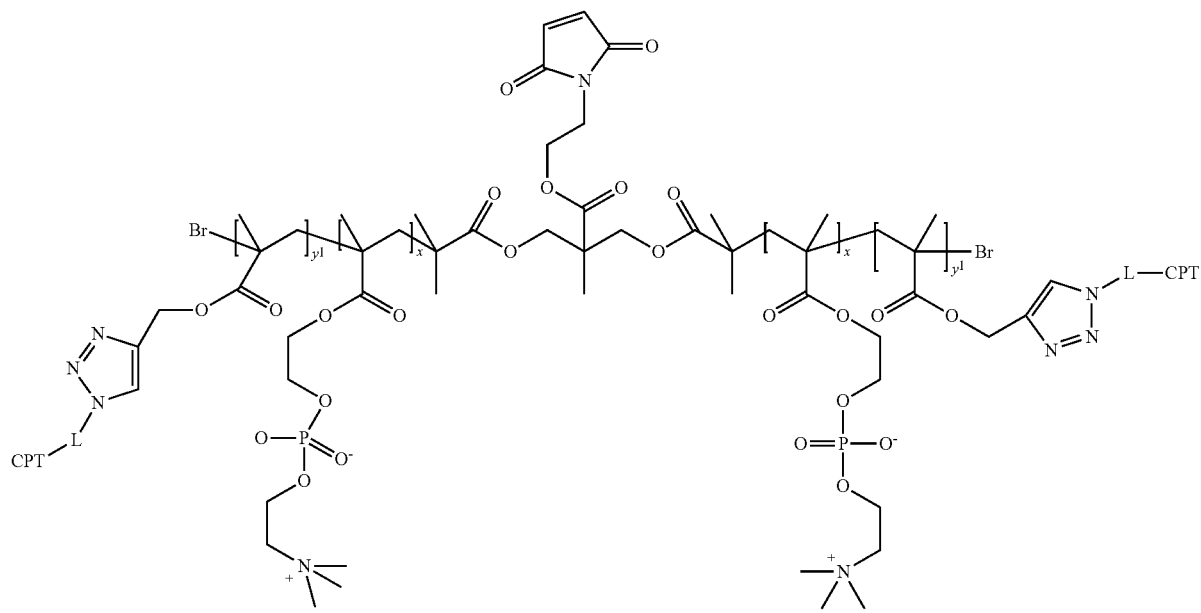

The attachment of camptothecin to the maleimide functionalized polymer from the previous step was essentially as described in Example 43. 170 mg of the polymer from the previous step was dissolved in 0.5 ml of 200 proof ethanol in a Schlenk tube. To the solution was added 50 µL of a PMDETA solution in dry DMF (5 mg in 504.), followed by the addition of a 2004, of a solution of camptothecin azide conjugate dissolved in DMF (125 mg of CPT-L-N3 per ml of DMF). To the mixture was added an additional 210 mg of dry DMF to ensure the homogeneity of the reaction mixture. The mixture was briefly degassed and 4 mg of CuBr were added under inert conditions. The mixture was degassed and the reaction allowed to proceed at room temperature overnight. The crude mixture was dissolved in methanol and passed through a short column of silica gel and purified by precipitation and washing in THF. The solid was finally washed with diethyl ether and dried overnight at 35-40° C. Analysis by light scattering showed a 20% increase in molecular weight (Mp), with Mn of 95000 g/mol, Mp of 84000 g/mol and PDi of 1.14. $^1$H NMR analysis of the resulting polymer in $CD_3OD$ showed weak aromatic signals in the 7-9 ppm range. A rough estimate based on CH from camptothecin at 8.4 ppm and methylene groups from HEMA-PC in the 4-4.5 ppm region gave a camptothecin incorporation of 1.5-2%.

Example 49

Deprotection of Protected Maleimide
Functionalized PC-Copolymer Following
Attachment of Camptothecin Azide Conjugate

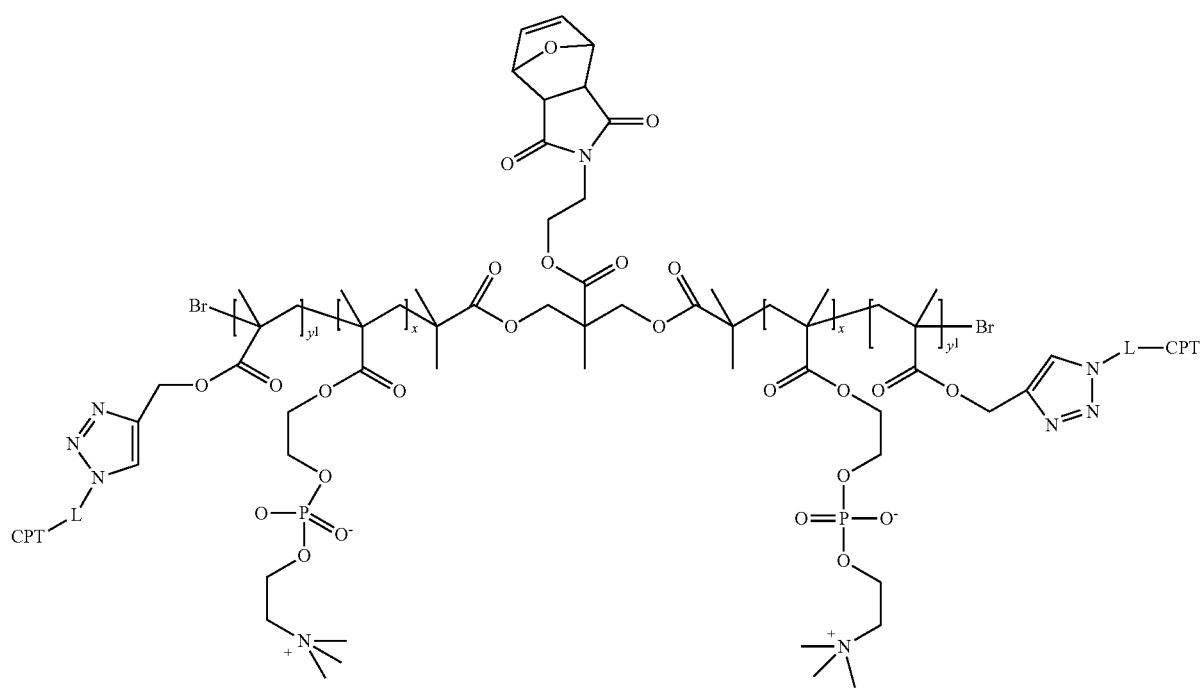

To 100 mg of the protected maleimide functionalized copolymer from Example 46 in 300 μL of ethanol was added 29.4 μL of a stock solution of PMDETA dissolved in DMF (10 mg/ml), followed by the addition of 117 μL of a stock solution of camptothecin azide conjugate in DMF (30 mg in 240 μL of DMF), 85 μL of DMF and 2.1 mg of CuBr. The reaction mixture was thoroughly degassed and stirred overnight. Deprotection of the maleimide functionality was performed as described in Example 48.

Example 50

Preparation of Maleimide-Functionalized PC-Copolymer Containing Camptothecin and Fluorescein Polymerization

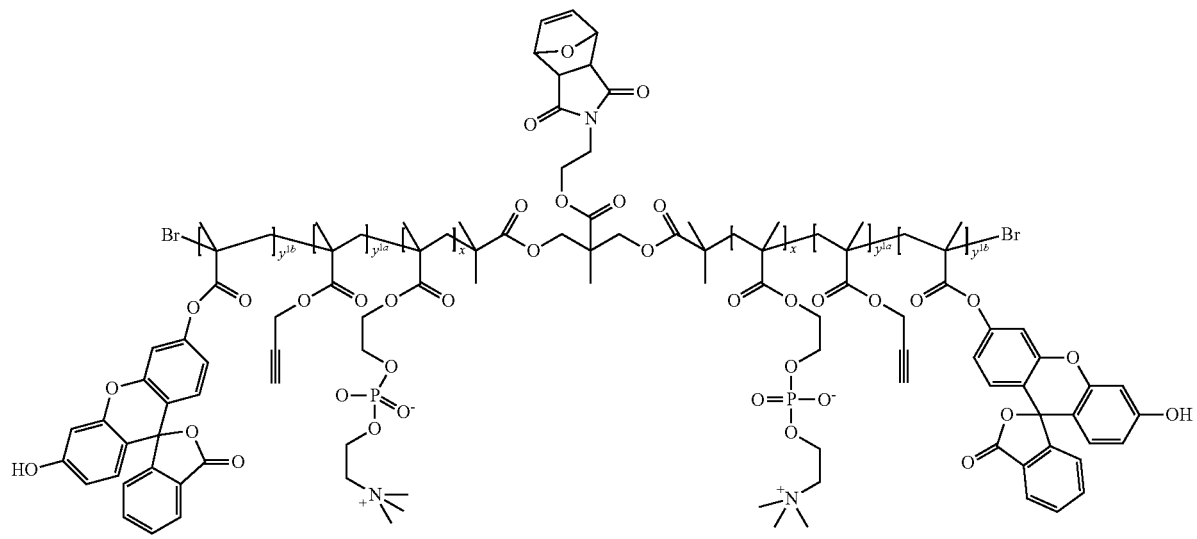

The polymerization protocol followed was essentially the same as that described in Example 46 except that a third comonomer, fluorescein methacrylate (FLMA), was added:

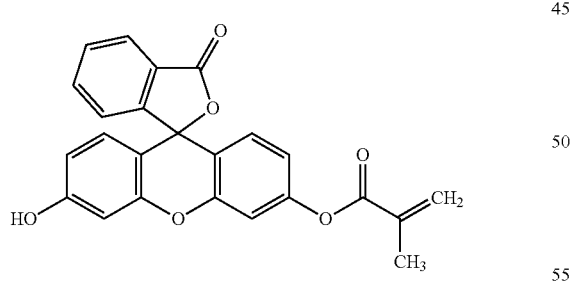

The amounts of reagents utilized were as described in the following table:

| Initiator (mol) | HEMA-PC (g) | TMS-PgMA (mg) | FLMA (mg) | CuBr (mg) | Bipyridyl (mg) | Ethanol (ml) | DMF (mg) |
|---|---|---|---|---|---|---|---|
| $2.133 \times 10^{-5}$ | 1.005 | 35.5 | 14.46 | 6.12 | 13.33 | 4 | 42.5 |

The polymerization reaction mixture was thoroughly degassed at −78° C. and the reaction allowed to proceed at room temperature for 17 hours. The polymerization was quenched upon exposure to air. A solution of 100 mg of tetrabutyl ammonium fluoride dissolved in 1 ml of methanol was added to the reaction mixture. The crude reaction was passed through silica gel, concentrated and precipitated carefully into diethyl ether. The solid was isolated by filtration and washed several times with diethyl ether. The copolymer was dried inside an oven at 40° C. overnight. Analysis by light scattering showed a Mn of 69000 g/mol, Mp of 70000 g/mol and PDi of 1.15. $^1$H NMR spectroscopy of the dry polymer showed no TMS group.

Deprotection of the Protected Maleimide Functional Group

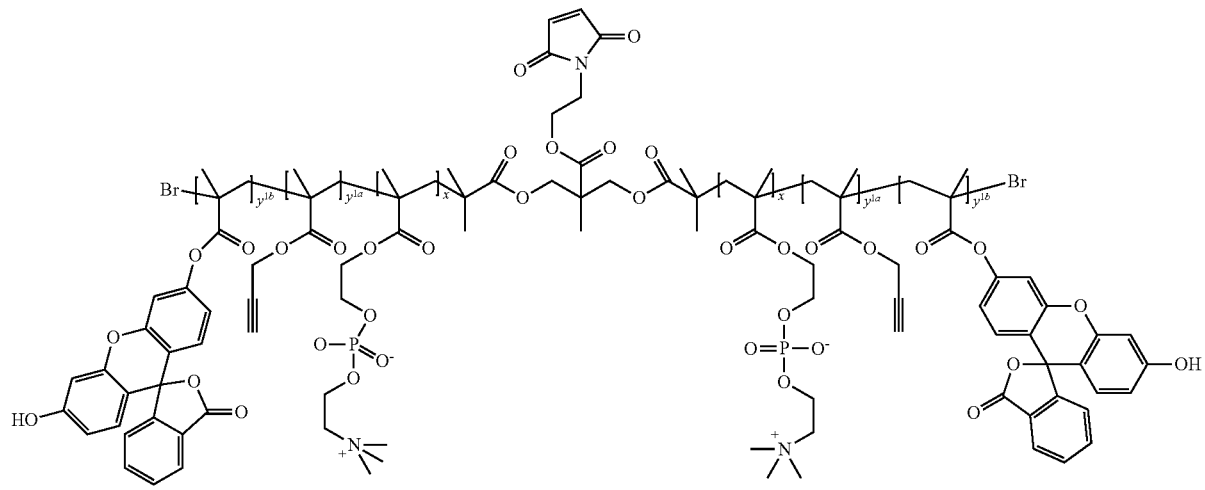

The protected maleimide functional group of the polymer from the previous step was deprotected using the protocol detailed in Example 46. $^1$H NMR analysis showed disappearance of signals at 5.2 and 6.6 ppm (representing the furan group) and the appearance of a new signal at 6.95 ppm (representing the CH from maleimide). Analysis by light scattering showed a Mn of 72,200 g/mol, Mp of 63,700 g/mol and PDi of 1.1.

Preparation of Maleimide-Functionalized PC-Copolymer Containing Camptothecin and Fluorescein

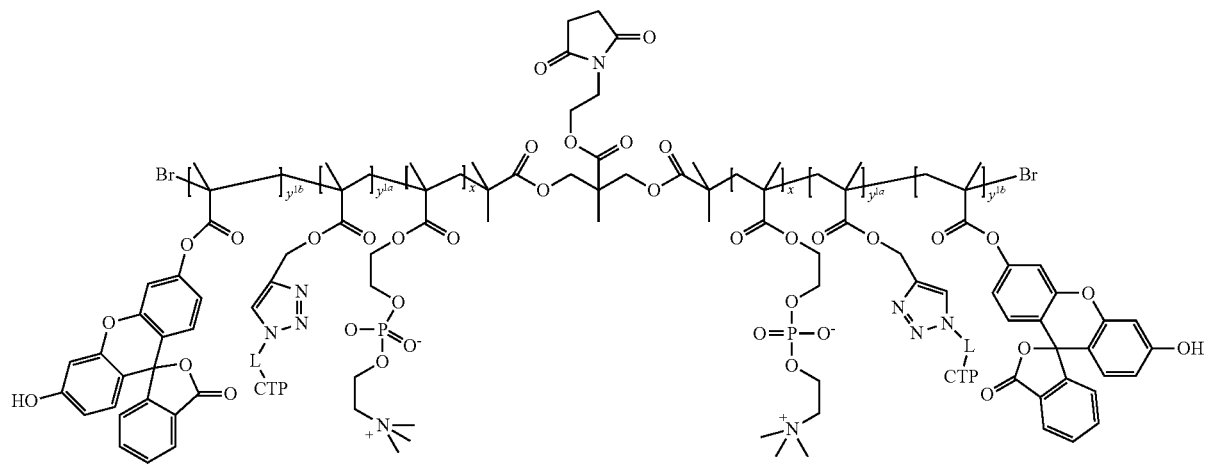

The attachment of camptothecin to the maleimide functionalized polymer from the previous step was essentially as described in Example 46. 170 mg of the polymer from the previous step was dissolved in 0.5 ml of 200 proof ethanol in a Schlenk tube. To the solution was added 50 μL of a PMDETA solution in dry DMF (5 mg in 50 μL), followed by the addition of a 200 μL of a solution of camptothecin azide conjugate dissolved in DMF (125 mg of CPT-L-N3 per ml of DMF). To the mixture was added an additional 210 mg of dry DMF to ensure the homogeneity of the reaction mixture. The mixture was briefly degassed and 4 mg of CuBr were added under inert conditions. The mixture was degassed and the reaction allowed to proceed at room temperature overnight. The crude mixture was dissolved in methanol and passed through a short column of silica gel and purified by precipitation and washing in THF. The solid was finally washed with diethyl ether and dried overnight at 35-40° C. Analysis by light scattering showed a 20% increase in molecular weight (Mp), with Mn of 107,100 g/mol, Mp of 98100 g/mol and PDi of 1.14. $^1$H NMR analysis of the resulting polymer in CD$_3$OD showed weak aromatic signals in the 7-9 ppm range. A rough estimate based on CH from camptothecin at 8.4 ppm and methylene groups from HEMA-PC in the 4-4.5 ppm region gave a camptothecin incorporation of 2.5-5%.

Example 51

Deprotection of Protected Maleimide Functionalized Fluorescein PC-Copolymer Following Attachment of Camptothecin Azide Conjugate reaction mixture was thoroughly degassed and stirred overnight. Deprotection of the maleimide functionality was performed as described in Example 43.

Example 52

Preparation of 4-Arm Maleimide Functionalized HEMA-PC Choline Block Copolymer

Preparation of 4-Arm Protected Maleimide Functionalized PC-Polymer

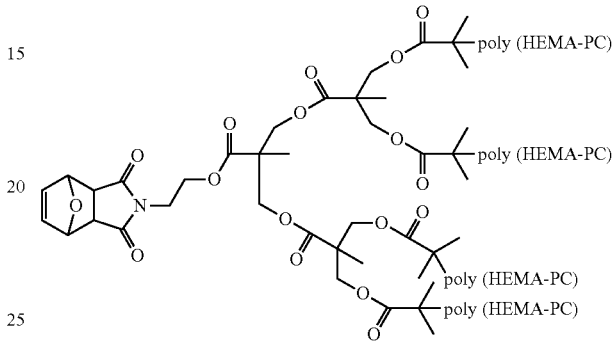

The 4-arm protected maleimide functionalized initiator from Example 11 and the ligand 2,2'-bipyridyl were introduced into a Schenk tube. Dimethyl formamide was introduced drop wise so that the weight percent of initiator and ligand was approximately 20%. The resultant solution was cooled to −78° C. using a dry ice/acetone mixture, and was

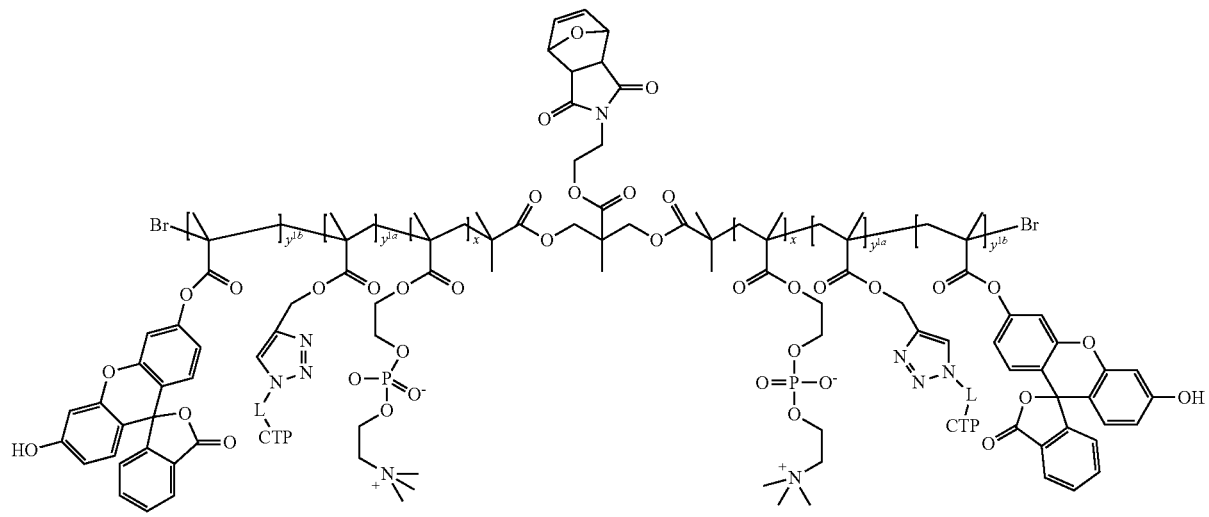

To 100 mg of the protected maleimide functionalized copolymer from Example 50 in 300 μL of ethanol was added 29.4 μL of a stock solution of PMDETA dissolved in DMF (10 mg/ml), followed by the addition of 117 μL of a stock solution of camptothecin azide conjugate in DMF (30 mg in 240 μL of DMF), 85 μL of DMF and 2.1 mg of CuBr. The degassed under vacuum for 10 min. The tube was refilled under nitrogen and the catalyst CuBr, kept under nitrogen, was introduced into the Schlenck tube (the Molar ratio of bromine/catalyst/ligand was kept at 1/1/2). The solution became dark brown immediately. The Schlenk tube was sealed and kept at −78° C. The solution was purged by applying a vacuum/nitrogen cycle three times. A solution of HEMA-PC was prepared by mixing a defined quantity of monomer, kept under nitrogen, with 200 proof degassed ethanol. The monomer solution was added drop wise into the Schlenk tube and homogenized by light stirring. The temperature was maintained at −78° C. A thorough vacuum was applied to the reaction mixture for at least 10 to 15 min. until bubbling from the solution ceased. The tube was then refilled with nitrogen and warmed to room temperature. The solution was stirred, and as the polymerization proceeded, the solution became viscous. After 38 hours, the reaction was quenched by direct exposure to air in order to oxidize Cu (I) to Cu (II), the mixture became blue-green in color, and was passed through silica gel, concentrated and precipitated carefully into diethyl ether. The solid was isolated by filtration and washed several times with diethyl ether. Polymer was dried inside an oven at 40° C. overnight. The amounts of reagents utilized were as described in the following table:

| Initiator (mol) | HEMA-PC (g) | CuBr (mg) | Bipyridyl (mg) | Ethanol (ml) | DMF (mg) |
|---|---|---|---|---|---|
| $3.66 \times 10^{-5}$ | 2.203 | 2.1 | 4.58 | 5 | 42.5 |

Analysis by light scattering showed a Mn of 550,000 g/mol, Mp of 640,000 g/mol and PDi of 1.18.

Preparation of 4-Arm Maleimide Functionalized HEMA-PC Choline Block Copolymer

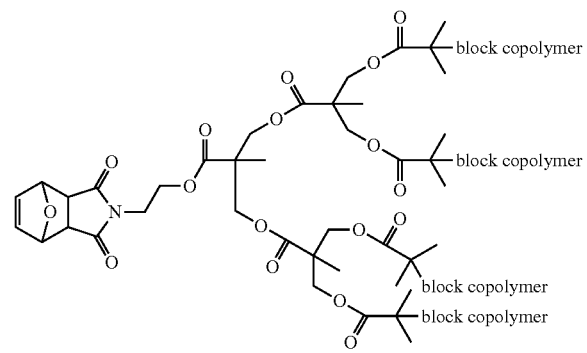

wherein the block copolymer has the formula:

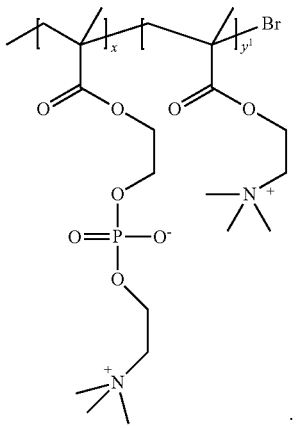

To a mixture of 300 mg of the polymer from the previous step in 0.7 ml of ethanol was added, under inert conditions, 1 mg of PMDETA dissolved in 42 mg of DMF followed by 1mg of CuBr. The reaction mixture was immediately cooled to −78° C. and degassed thoroughly. 2(Methacryloyloxy) ethyltrimethyl ammonium chloride (MC) as an aqueous solution (72% w/w) was preliminary passed through a short column to remove the stabilizer. 177 mg of the solution was added to the reaction mixture, and the mixture was thoroughly degassed at −78° C. for 30 min. until no bubbling was seen. The reaction mixture was replenished with nitrogen and the reaction allowed to proceed at room temperature for 44 hours. Conversion estimated by $^1$H NMR indicated that 15% of MC was converted into a polymer. Crude mixture was purified by dialysis to remove any low molecular weight impurities (MWCO 15 kDa) followed by lyophilization. $^1$H NMR analysis indicated a new peak in the 4.5 ppm region ($CH_2O$) from choline group next to the three peaks from phosphorylcholine (from 4 ppm to 4.5 ppm). $^1$H NMR analysis of the final polymer in $CD_3OD$ showed a Molar ratio of 5-10% of MC versus HEMA-PC. The maleimide functional group was generated by deprotection as described in Example 43. Similar chain extensions have been observed in a one step process where the MC was added at the end of the HEMA-PC polymerization.

Example 53

Preparation of 3-Arm Diol Functionalized HEMA-PC Fluorescein Block Copolymer

Polymerization

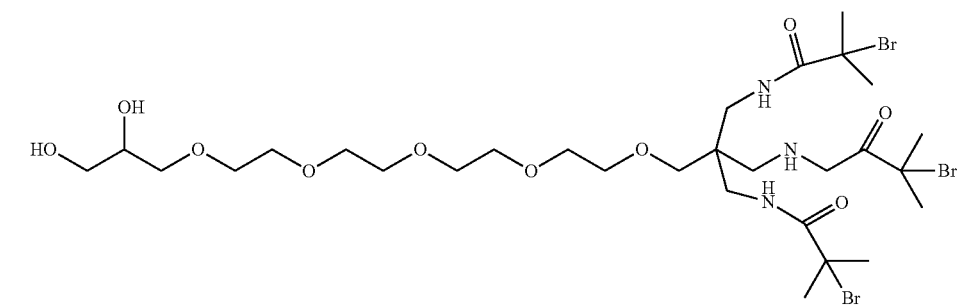

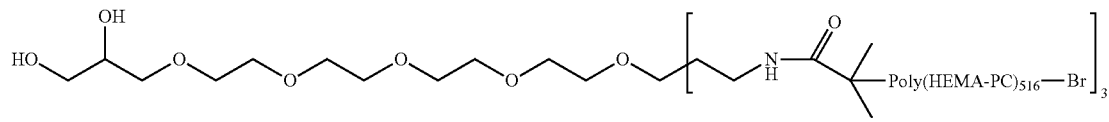

4.66 mg of 2,2'bipyridyl were added to a Schlenk tube followed by 41.3 μL of a stock solution of the initiator from Example 37 in DMF (10 mg/100 mL of DMF) and by 83.4 μL of a stock solution of CuBr$_2$ in DMF (10 mg/ml of DMF). The mixture was degassed under vacuum at −78° C. To the reaction mixture was added 1.6 mg of CuBr under inert conditions, followed by an addition of 2 g of HEMA-PC dissolved in 3.75 ml of 200 proof ethanol dropwise. The vessel was sealed and degassed at −78° C. under vacuum until no bubbling was seen. The reaction mixture was placed under inert conditions and the reaction allowed to proceed at room temperature for 48 hours. Conversion was estimated by $^1$14 NMR to be above 98%. Analysis by light scattering showed a Mp of 457 kDa, Mn of 407 kDa and PDi of 1.13. The crude mixture was passed through a plug of silica gel and purified by precipitation into THF followed by washing with THF and then a final washing with diethyl ether.

Preparation of 3-Arm Diol Functionalized HEMA-PC Fluorescein Block Copolymer

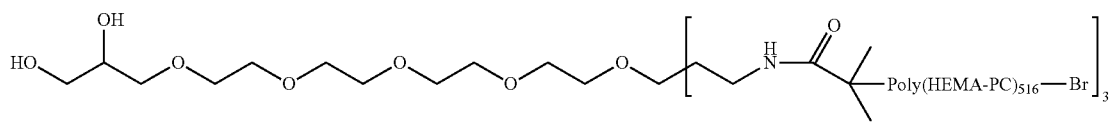

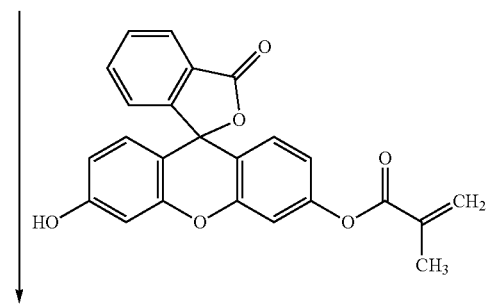

147

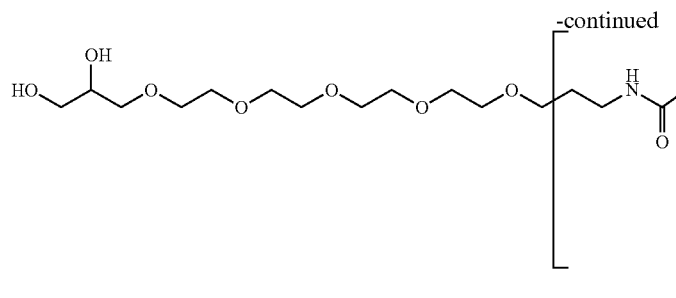 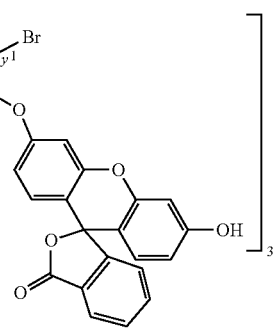

-continued

148

1.409 g of the polymer from the previous step were dissolved in 4 ml of 200 proof ethanol. To the reaction mixture was added a solution of 14 mg of FLMA dissolved in 182 mg of DMF, 510 mg of DMF and 3 mg of 2,2'bipyridyl. The reaction mixture was thoroughly degassed before the addition of 1.34 mg of CuBr and 1 mg of Cu(0). The reaction mixture was thoroughly degassed and allowed to proceed at room temperature for 8 hours. The crude mixture was passed through a plug of silica gel and purified by precipitation in THF, followed by a washing with THF and another washing with diethyl ether. Final polymer was isolated as a yellow powder. The presence of fluorescein was demonstrated by $^1$H NMR in methanol and absorbance at 370 nm. Molecular weight analysis performed on the polymer by light scattering indicated an increase in molecular weight to Mp of 501 kDa and a PDi of 1.28.

Example 54

Preparation of Aldehyde Functionalized PC Copolymer Containing Alkyne Groups

Polymerization

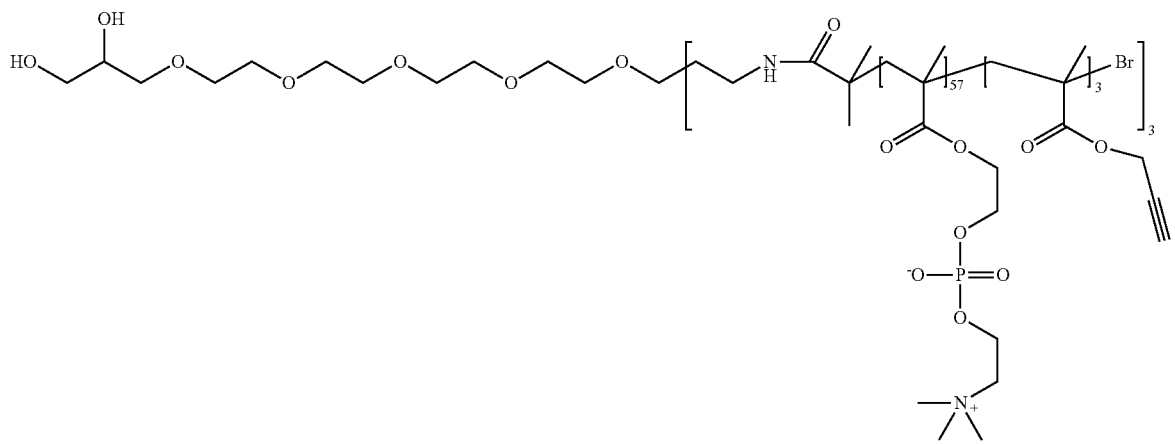

The amounts of reagents utilized were as described in the following table:

| Initiator (mol) | HEMA-PC (g) | TMS-PgMA (mg) | CuBr$_2$ (mg) | CuBr (mg) | Bipyridyl (mg) | Ethanol (ml) | DMF (μl) |
|---|---|---|---|---|---|---|---|
| 2.133 × 10$^{-5}$ | 2.005 | 30 | 1.7 | 3.27 | 9.53 | 3.8 | 555 |

The initiator from Example 39 was utilized. The polymerization reaction mixture was thoroughly degassed at −78° C. and allowed to proceed at room temperature for 64 hours. The reaction was quenched upon exposure to air. A solution of 100 mg of tetrabutyl ammonium fluoride dissolved in 1 ml of methanol was added to the reaction mixture. The crude reaction mixture was passed through silica gel, concentrated and precipitated carefully into diethyl ether. The solid was isolated by filtration and washed several times with diethyl ether. The polymer was dried in an oven at 40° C. overnight. Analysis by light scattering showed a Mn of 71,000 g/mol, Mp of 64000 g/mol and PDi of 1.15. $^1$H NMR spectroscopy of the dry polymer showed no TMS group.

Generation of Aldehyde Functional Group by Periodate Oxidation

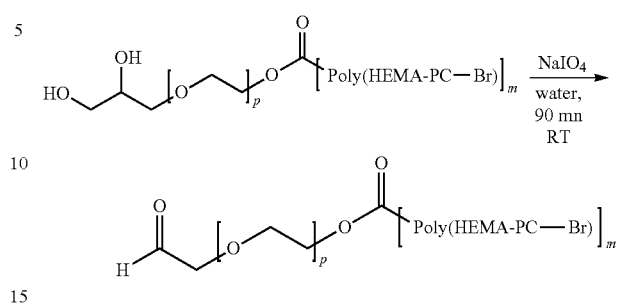

To a solution of diol functionalized polymer in distilled water (10 wt. %) was introduced a large excess of sodium periodate dissolved in distilled water. The reaction was allowed to proceed at room temperature for 90 min. in the dark. The reaction was quenched with an aqueous solution of glycerol (1.5× vs. NaIO$_4$) to remove any unreacted sodium periodate. The mixture was stirred at room temperature for 15 min. and placed in a dialysis bag (MWCO 14 to 25 kDa) for purification at room temperature for one day. Water was removed by lyophilization and the polymer was collected as a dry powder.

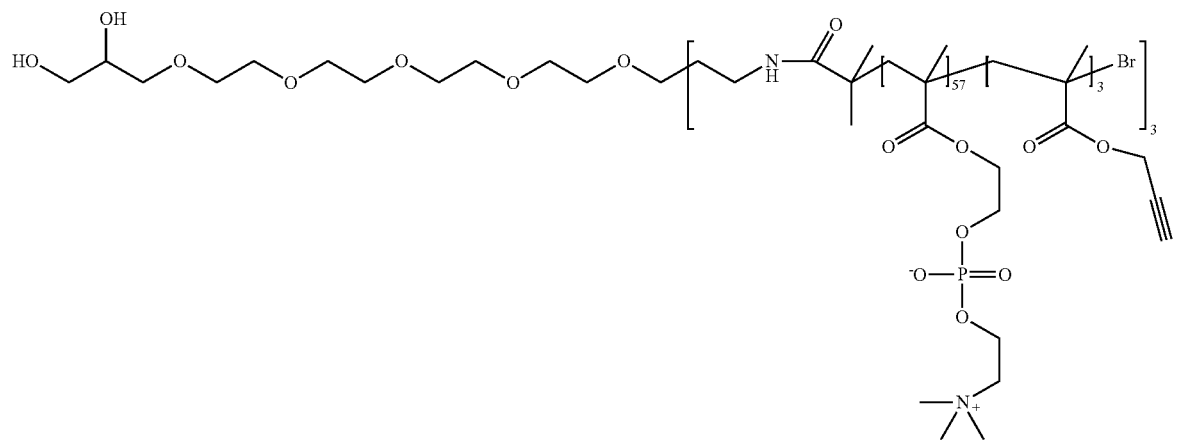

Example 55

Preparation of Diol Functionalized PC Copolymer Containing Epoxide Groups

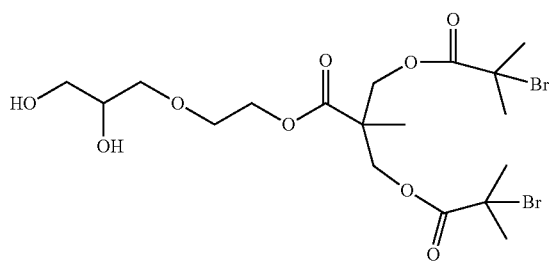

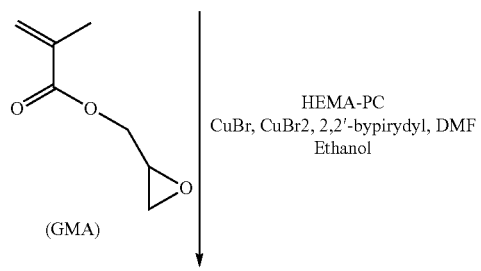

(GMA)

HEMA-PC
CuBr, CuBr2, 2,2'-bypirydyl, DMF
Ethanol

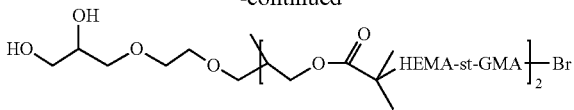

9.13 mg of 2,2'bipyridyl were added to a Schlenk tube followed by 80 µl of a stock solution of the initiator from Example 26 in DMF (10 mg/100 ml of DMF). The mixture was degassed under vacuum at −78° C. To the reaction mixture was added 4.2 mg of CuBr under inert conditions, followed by an addition of a mixture of 1 g of HEMA-PC and 234, of purified glycidyl methacrylate (GMA) (passed through a stabilizer remover, to remove the MEHQ stabilizer) which was dissolved in 2 ml of 200 proof ethanol was added by drop wise addition. The vessel was sealed and degassed at −78° C. under vacuum until no bubbling was seen. The reaction mixture was placed under inert conditions and allowed to proceed at room temperature for 3 hours. The crude mixture was passed through a plug of silica gel and purified by precipitation into THF followed by a washing with THF and then a final washing with diethyl ether. Analysis by light scattering showed a Mp of 92 kDa, Mn of 83 kDa and PDi of 1.1.

Example 56

Preparation of Protected Maleimide Functionalized PC Copolymer Containing Epoxide Groups

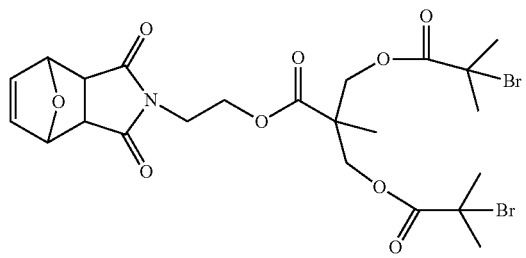

CuBr, 2,2'-bypirydyl
DMSO, Ethanol

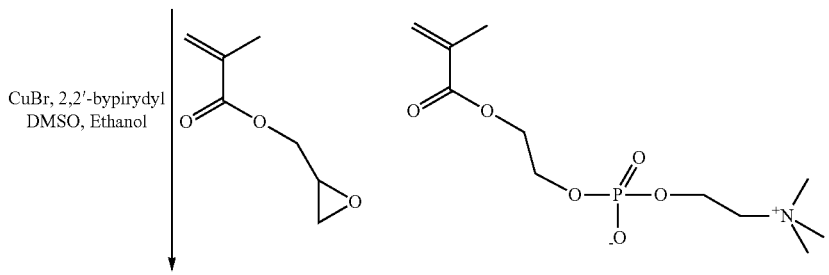

-continued

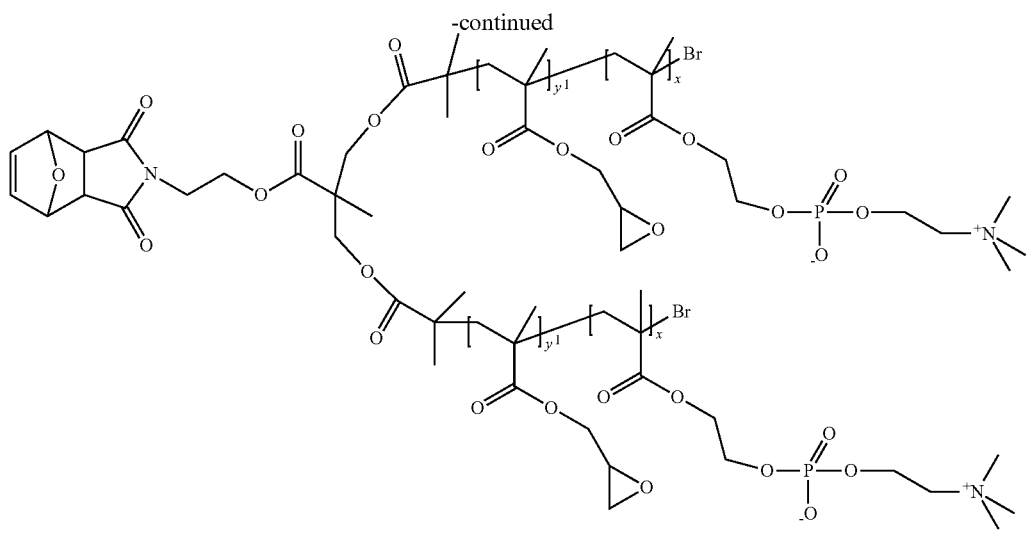

13.55 mg of 2,2'bipyridyl were added to a Schlenk tube followed by 13.52 mg of the initiator from Example 26. The solids were dissolved in 142 mg of DMSO. The mixture was degassed under vacuum at −78° C. To the reaction mixture was added 6.22 mg of CuBr under inert conditions, followed by an addition of a mixture of 1 g of HEMA-PC and 78 μL of purified GMA (passed through a stabilizer remover, to remove the MEHQ stabilizer) which was dissolved in 2 ml of 200 proof ethanol was added by drop wise addition. The vessel was sealed and degassed at −78° C. under vacuum until no bubbling was seen. The reaction mixture was placed under inert conditions and allowed to proceed at room temperature for 3 hours. The crude mixture was passed through a plug of silica gel and purified by precipitation into THF followed by a washing with THF and then a final washing with diethyl ether. Analysis by light scattering showed a Mp of 71 kDa, Mn of 65 kDa and PDi of 1.13.

Example 57

Preparation of Protected Maleimide Functionalized PC Copolymer Containing Acetoacetate Groups

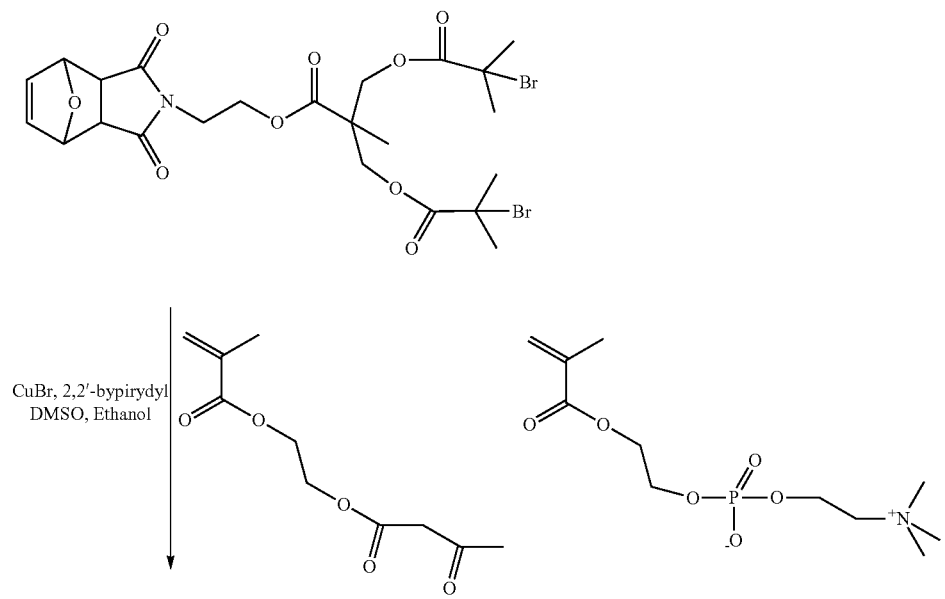

-continued

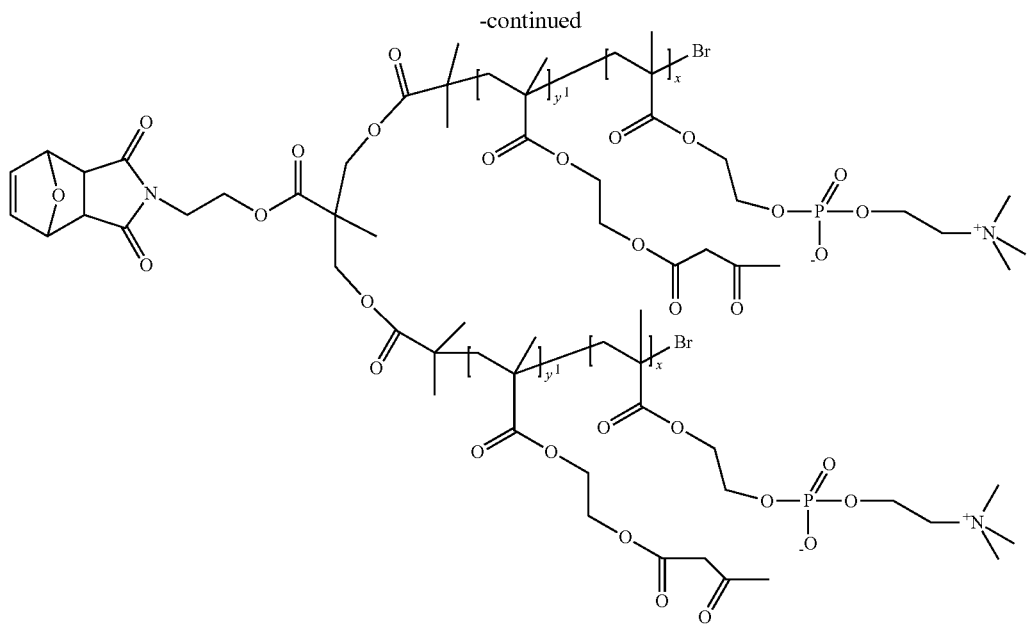

13.55 mg of 2,2'bipyridyl were added to a Schlenk tube followed by 13.52 mg of the initiator from Example 26. The solids were dissolved in 142 mg of DMSO. The mixture was degassed under vacuum at −78° C. To the reaction mixture was added 6.22 mg of CuBr under inert conditions, followed by an addition of a mixture of 1 g of HEMA-PC and 110 µL of purified 2-(acetoacetyloxy)ethyl 2-methacrylate (MEA) (passed through a stabilizer remover, to remove the MEHQ stabilizer) which was dissolved in 2 ml of 200 proof ethanol was added by drop wise addition. The vessel was sealed and degassed at −78° C. under vacuum until no bubbling was seen. The reaction mixture was placed under inert conditions and allowed to proceed at room temperature for 3 hours. The crude mixture was passed through a plug of silica gel and purified by precipitation into THF followed by a washing with THF and then a final washing with diethyl ether. Analysis by light scattering showed a Mp of 85 kDa, Mn of 79 kDa and PDi of 1.15.

Example 58

Preparation of Protected Maleimide Functionalized PC Copolymer Containing Alkyne and Acetoacetate Groups

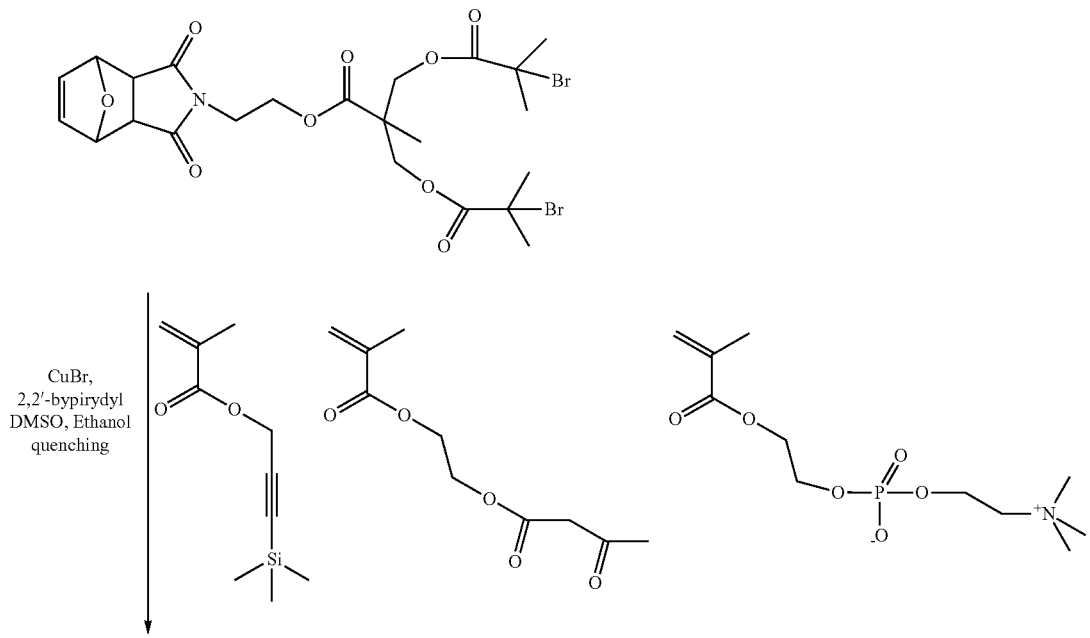

-continued

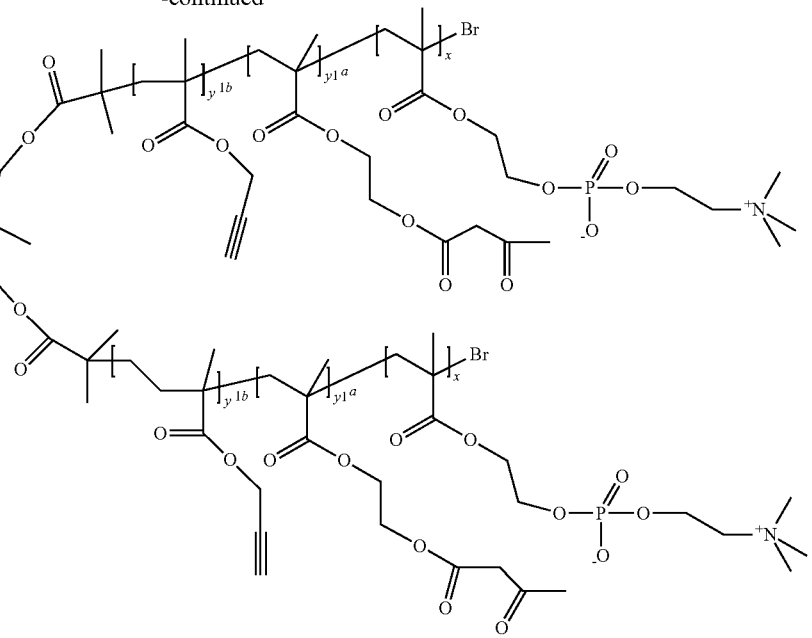

13.55 mg of 2,2'bipyridyl were added to a Schlenk tube followed by 13.52 mg of the initiator from Example 26. The solids were dissolved in 142 mg of DMSO. The mixture was degassed under vacuum at −78° C. To the reaction mixture was added 6.22 mg of CuBr under inert conditions, followed by an addition of a mixture of 1 g of HEMA-PC, 56.3 mg of TMS-PgMA and 554, of purified MEA (passed through a stabilizer remover, to remove the MEHQ stabilizer) which was dissolved in 2 ml of 200 proof ethanol was added by drop wise addition. The vessel was sealed and degassed at −78° C. under vacuum until no bubbling was seen. The reaction mixture was placed under inert conditions and allowed to proceed at room temperature for 3 hours. The crude mixture was passed through a plug of silica gel and purified by precipitation into THF followed by a washing with THF and then a final washing with diethyl ether. Analysis by light scattering showed a Mp of 78 kDa, Mn of 72 kDa and PDi of 1.13.

Example 59

Preparation of Diol Functionalized PC Copolymer Containing Alkyne Groups

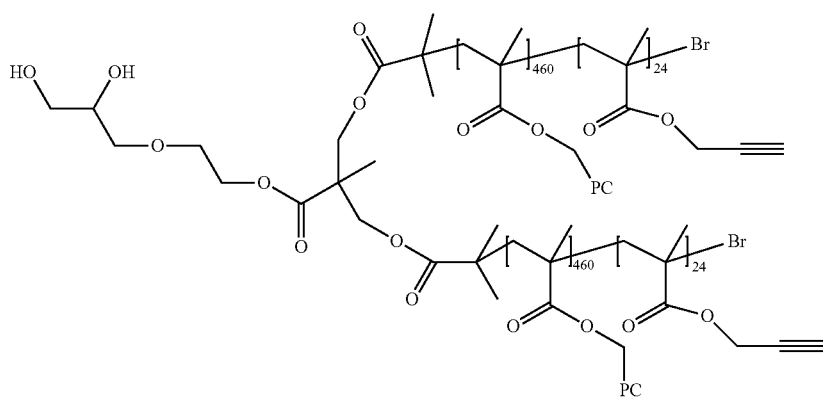

The amounts of reagents utilized were as described in the following table:

| Initiator (mol) | HEMA-PC (g) | TMS-PgMA (mg) | CuBr (mg) | Bipyridyl (mg) | Ethanol (ml) | DMF (μl) |
|---|---|---|---|---|---|---|
| 2.37 × 10⁻⁵ | 1.983 | 69.2 | 6.76 | 14.71 | 8 | 35.2 |

The initiator from Example 26 was utilized. The polymerization reaction mixture was thoroughly degassed at −78° C. and allowed to proceed at room temperature for 14 hours. The reaction was quenched upon exposure to air. A solution of 100 mg of tetrabutyl ammonium fluoride dissolved in 1 ml of methanol was added to the reaction mixture. The crude reaction mixture was passed through silica gel, concentrated and precipitated carefully into diethyl ether. The solid was isolated by filtration and washed several times with diethyl ether. The polymer was dried in an oven at 40° C. overnight. Analysis by light scattering showed a Mn of 222,000 g/mol, Mp of 277,000 g/mol and PDi of 1.2. $^1$H NMR spectroscopy of the dry polymer showed no TMS group.

Example 60

Attachment of hexaglutamic acid amide with 9-azido-4,7-dioxanonanoic acid to diol functionalized PC copolymer containing alkyne groups and subsequent generation of aldehyde functional groups from diol precursors

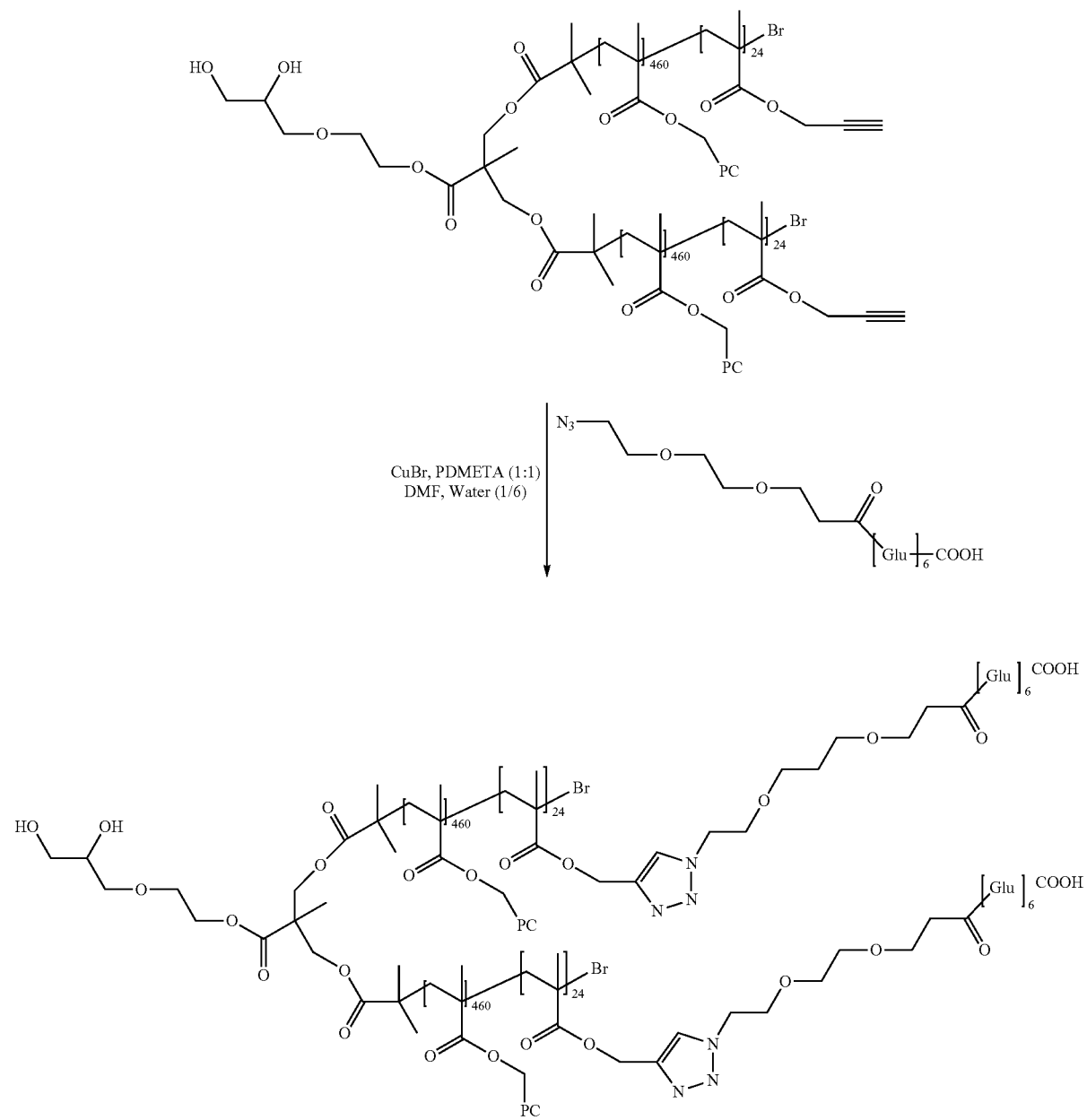

45 mg of the diol functionalized PC copolymer with alkyne groups from [0368] 13.55 mg of 2,2'bipyridyl were added to a Schlenk tube followed by 13.52 mg of the initiator from Example 26. The solids were dissolved in 142 mg of DMSO. The mixture was degassed under vacuum at −78° C. To the reaction mixture was added 6.22 mg of CuBr under inert conditions, followed by an addition of a mixture of 1 g of HEMA-PC, 56.3 mg of TMS-PgMA and 554 of purified MEA (passed through a stabilizer remover, to remove the MEHQ stabilizer) which was dissolved in 2 ml of 200 proof ethanol was added by drop wise addition. The vessel was sealed and degassed at −78° C. under vacuum until no bubbling was seen. The reaction mixture was placed under inert conditions and allowed to proceed at room temperature for 3 hours. The crude mixture was passed through a plug of silica gel and purified by precipitation into THF followed by a washing with THF and then a final washing with diethyl ether. Analysis by light scattering showed a Mp of 78 kDa, Mn of 72 kDa and PDi of 1.13. Example 59 were dissolved in 800-900 mg of de-ionized water. 13.5 μl of PDMETA (from stock solution of 10 mg in 100 μl of DMF) were added to the reaction mixture in a round bottom flask. 7 mg of hexaglutamic acid amide with 9-azido-4,7-dioxanononanoic acid from Example 45 were dissolved in 70 μl of DMF and added to the reaction mixture, along with 2.1 mg of CuBr. The mixture was degassed thoroughly, placed under inert conditions and stirred overnight at room temperature.

Reaction efficiency was monitored by anion exchange chromatography at OD220 nm as described in Example 45. Injection at time zero showed the presence of unreacted polymer in the flow-through, and the unreacted peptide at 10.6 min. Following the overnight reaction, the polymer peak disappeared, and a new peak, corresponding to the polymer modified peptide, appeared at 11.6 min. This peak was broad indicating the presence of multiple polymer-peptide species due to the fact that each polymer has multiple alkyne groups for potential attachment of the azide modified peptide.

Purification by Anion Exchange Chromatography

Based upon the analytical anion exchange chromatography experience, the polymer modified peptide was purified using anion exchange chromatography on an Akta Prime Plus system using a Hitrap DEAE FF column (5 ml) from GE Healthcare. Buffer A was 20 mM Tris pH7.5, and Buffer B was Buffer A containing 0.5M NaCl. The column was equilibrated with Buffer A, followed by three column volumes of Buffer B, and then sufficient Buffer A to return the column eluate to the same conductivity as Buffer A. 700 μg of the crude polymer modified peptide was loaded onto the column in Buffer A, and the column was washed with sufficient Buffer A to return the column eluate to the same conductivity as Buffer A. Elution was performed in a stepwise fashion using 20% B, 30% B, 50% B, 70% B, and 100% B. Fractions of 10 ml were collected and fractions 17 and 18 were pooled (20 ml) to form a 40% B pool, and fractions 19 and 20 were pooled to form a 70% B pool (20 ml). Both pools were concentrated to a volume of 0.5-1 ml using an Amicon Ultra 30 kDa MWCO concentrator. Analysis was performed using the analytical anion exchange method from Example 45 which indicated that the 70% B pool contained a single broad peak as described previously. The 40% B pool also contained a single broad peak which eluted slightly earlier than the 70% B peak indicating the presence of polymer modified peptide with fewer peptides per polymer. Further analysis was performed using size exclusion chromatography on a Waters HPLC system with a 2695 Alliance Solvent Delivery system equipped with a Waters 2685 Dual Wavelength Detector. Samples were chromatographed using a Superdex 200 column (10×300 mm) from GE Healthcare at 1 ml/min. with 1×PBS pH 7.4 for 25 min. The chromatogram was monitored at OD220 nm and OD280 nm. Both the 40% B and 70% B pools from anion exchange purification eluted with peak retention times at around 9 min. equating to a molecular weight in the 500 kDa-600 kDa range. The peaks were visible at 220 nm and 280 nm indicating the presence of polymer and peptide. Unreacted polymer eluted in a similar position, but was only visible at 220 nm, while unreacted peptide eluted with a retention time of 18 min, but was only visible at 280 nm.

Conversion of Terminal Diol Functional Groups into Aldehyde Functional Groups by Periodate Oxidation on the Hexaglutamic Acid Modified PC Copolymer The terminal diol functional groups on the anion exchange purified and concentrated 70% B elution pool of the polymer modified peptide from the previous step were converted into aldehyde functional groups using periodate oxidation as described in Example 54.

Example 61

Conjugation of Alkaline Phosphatase to Aldehyde Functionalized PC Polymer Containing Hexaglutamic Acid Alkaline phosphatase (Sigma-Aldrich) was buffer exchanged into 25 mM Hepes pH 7 (conjugation buffer) and concentrated to 5-8 mg/ml. Conjugation reactions were carried out at 3-5× molar excess of the aldehyde functionalized PC copolymer containing hexaglutamic acid from Example 60 to protein in the presence of 40 mM sodium cyanoborohydride with a final protein concentration of ~1 mg/ml. All the reactions were carried out in crimp sealed glass vials overnight at room temperature. The diol form of the polymer was used as a negative control. 400 of each reaction were fractionated on a Superdex 200 column (10/300 mm) at 1 ml/min. in 1×PBS pH 7.4. Fractions of 1 ml were collected and tested for alkaline phosphatase activity as follows. 50 of the SEC fractions were diluted 5× with 20 mM Tris pH 7.5, and 100 μl of the PNPP substrate was added and the samples were incubated at 37° C. for 20 min. OD405 nm was measured using a SpectraMax Plus 384 plate reader from Molecular Devices. As expected, no conjugation was observed when the diol functionalized polymer was used. However, in the case of the aldehyde functionalized polymer, alkaline phosphatase activity was determined in the 8-10 min. retention time range, corresponding with free polymer and higher molecular weight species, as well as in the 12-13 min. range corresponding with free alkaline phosphatase.

Example 62

Conjugation of Human Fab to Maleimide Functionalized PC Copolymer Containing Camptothecin Human Fab was prepared by pepsin digestion of whole human IgG (Innovative Research) to yield Fab$_2$, followed by subsequent reduction with TCEP to yield Fab. Pepsin digestion of IgG was performed in 0.1M sodium acetate pH 4.5 at 4° C. overnight to obtain over 90% digestion efficiency. The Fab$_2$ fraction was then further purified using cation exchange chromatography with a MacroCap SP column.

The pure Fab$_2$ fraction was eluted with 100-200 mM NaCl at pH 5 while the free pepsin and all other contaminants eluted in the unbound fraction. The purified Fab$_2$ was then reduced with a 2× molar ratio of TCEP at 37° C. for 30 min., and gel filtration chromatography was used to purify the Fab from unreduced Fab$_2$ and free TCEP. The Fab fraction was then pooled and buffer exchanged into the conjugation buffer. The conjugation experiment described below is for conjugation of 1 mg of Fab to a 13× molar excess of the 84 kDa maleimide functionalized PC copolymer containing camptothecin from Example 48. The conjugation reaction was performed in 10 mM sodium acetate pH 5 with 2 mM EDTA. The final Fab concentration was 2.7 mg/ml in the presence of a 13× molar excess of polymer dissolved in the conjugation buffer and 3× molar excess of TCEP as reducing agent. The polymer was dissolved in conjugation buffer at a concentration of 100-300 mg/ml followed by addition of the TCEP and Fab. The reaction mixture was gently mixed, and the conjugation carried out in the dark at room temperature overnight.

The conjugation status can be monitored with SDS-PAGE where under non-reducing conditions, the accumulation of high MW species larger than the free Fab is a good indication of the conjugation event. Such high MW conjugate species are characterized to be: (1) fluorescent under UV illumination due to the presence of camptothecin; (2) the conjugate bands should be stainable by Coomassie Blue due to the presence of protein (the polymer does not stain); (3) the high MW species does not shift under reducing conditions which is a good indication that they are not due to disulfide mediated aggregates.

Alternatively, the conjugation event can be monitored with analytical SEC using a Superdex 200 (10/300 mm) column from GE Healthcare at 1 ml/min in 1×PBS pH 7.4. Under such running conditions, the free Fab elutes at 15.3 min. and the free polymer elutes at 10.6 min.

To further characterize the presence of Fab-polymer-camptothecin conjugate as described above, the reaction mixture was further fractionated using a 1 ml cation exchange chromatography (CEX) or MacroCap SP column from GE Healthcare at pH 5. The column was connected to an AKTA Prime Plus chromatography system equipped with an OD280 nm detector, conductivity meter and fraction collector. Buffer A was 10 mM sodium acetate pH 5 and buffer B was Buffer A containing 0.5M NaCl. The eluted fractions were further analyzed using SDS-PAGE.

As the Fab is protonated at pH 5, together with the low ionic strength at 10 mM NaCl, Fab-conjugate and free Fab bind to the cation exchange column while the unconjugated polymer should not interact with the CEX and therefore should remain in the flow through fraction. The unbound fraction was collected for analysis. After washing with at least 15 column volumes (CV) of buffer A, the column was eluted stepwise with 8%, 12%, 20%, 40% and 100% buffer B which are equivalent to buffer A containing 40 mM, 60 mM, 100 mM, 200 mM and 500 mM NaCl, respectively. In each elution step, at least 10 CV of each elution buffer was passed through the column and 1.5 ml fractions were collected and the OD280 nm trace was monitored continuously until the baseline dropped to at least 5% of the initial buffer background before the higher salt elution gradient was initiated.

The peak fractions of each step elution were collected and concentrated with an Amicon Ultrafree concentrator with 10 kDa MW cutoff (MWCO) membrane. The concentrate was analyzed with SDS-PAGE under non-reducing and reducing conditions using a 1 mm NuPAGE Novex 4-12% gradient gel, and electrophoresis was performed according to the manufacturer's specifications (Invitrogen Corp). Samples for SDS-PAGE analysis include the initial reaction mixture, MacroCap SP column unbound fraction, column wash fractions, and concentrated fractions of 8%, 12%, 20% and 40% elution pools. Once the electrophoresis was completed, the PAGE was disassembled from the cassette and placed on the UV illuminator to review the fluorescence which is due to the camptothecin containing polymer and conjugate. A picture was taken immediately before the gel was subjected to Coomassie Blue stain using the SimplyBlue stain system from Invitrogen to review the protein containing bands.

The results based on the SDS-PAGE analysis indicate the following:

The bulk of the unbound MacroCap SP fraction contained no protein based on Coomassie Blue staining but exhibited an extensive fluorescent signal at the high MW range of the well ($\geq$160 kDa). In addition, when the fraction was analyzed by Bradford protein assay, it showed no protein signal at all compared to the MacroCap SP column-load; this is additional evidence to confirm that the unbound fraction is devoid of any protein including Fab and Fab-polymer conjugate. However, it contained mostly free polymer but no free camptothecin as the camptothecin is too small to migrate at this MW range.

Fractions at 8% and 12% B contain two major species that were stained by Coomassie Blue, one was the free Fab and the other a higher MW diffused band with MW spanning between 110-260 kDa, only the latter band showed fluorescence but not free Fab. Based on the previous evidence that the polymer cannot be stained by Coomassie Blue and the fact that the unbound fraction contains mostly polymer and showed no Coomassie Blue stain, we can conclude that the high MW species is the conjugate that contains both Fab and polymer with camptothecin.

No fluorescence was observed in the 20% and 40% eluted fractions as these corresponded to the free Fab and Fab$_2$ fraction. These two fractions constitute the majority of the eluted protein (>80%) which is a good indication that the conjugate was enriched in the low salt eluted fractions as expected (due to the expected shielding effect of the polymer).

The eluted fraction pools were also subjected to reducing conditions using DTT, and the Fab band was shifted down to the 25 kDa position which is a good indication of light chain and half-heavy chain dissociation due to reduction of inter-chain disulfide linkages. Under such conditions, the fluorescent signal at high MW as described above was not shifted and was also stained by Coomassie Blue. This observation confirms that the high MW species is covalently attached to the polymer rather than non-covalent association or connection through disulfide linkages.

In addition to the SDS-PAGE analysis, the MacroCap SP eluted fractions were subjected to analytical SEC using a Superdex 200 (10×300 mm) column from GE Healthcare and a Waters HPLC system with 2695 Alliance Solvent delivery system with a Diode Array detector 2669. The analysis was performed in 1×PBS pH 7.4 at a flow rate of 1 ml/min. The chromatogram was monitored using OD220 nm, OD280 nm and OD355 nm where OD220 nm detects protein, polymer and camptothecin, OD280 nm detects only protein and camptothecin, and OD355 nm detects only the camptothecin. The results are as follows:

| Fraction | Fraction contains | | OD peak signal (nm) | | |
|---|---|---|---|---|---|
| elution % | Fab-polymer conjugate | Fab | 220 | 280 | 355 |
| 8 | Yes | Yes | Yes | Yes | Yes |
| 12 | Yes | Yes | Yes | Yes | Yes |
| 20 | No | Yes | Yes | Yes | No |
| 40 | No | Yes | Yes | Yes | No |

Example 63

Conjugation of Human Fab to Maleimide Functionalized PC Copolymer Containing Camptothecin and Fluorescein The conjugation reaction conditions, purification, analyses and conclusions were essentially the same as for Example 62, except for the following:

The 98 kDa maleimide functionalized PC copolymer containing camptothecin and fluorescein from Example 50 was used.

For MacroCap SP elution, an additional 4% B elution preceded the 8% B elution. Therefore, the 4% B elution pool was included in both the SDS-PAGE and SEC analysis. The 4% B pool also showed fluorescence, a good indication that this fraction contains conjugate also.

SEC/MALS analysis of the unbound MacroCap SP fraction confirmed that this fraction was composed of free polymer only.

Example 64

Conjugation of Traut's Reagent Modified Human Whole IgG to Maleimide Functionalized PC Copolymer Containing Camptothecin and Fluorescein In this example, whole human IgG (Innovative Research) was first modified with Traut's reagent at a 3 fold molar excess ratio in 1×PBS pH 7.4. The reaction setup included 10 mg/ml IgG and 3 mg/ml Traut's reagent in 1×PBS pH 7.4, the reaction volume was 300 μl and the reaction was carried out for 1 hour at room temperature in the dark with mixing. Upon completion of the reaction, the reaction mixture was buffer exchanged into 10 mM sodium acetate pH 5 with 2 mM EDTA using a 10 ml BioGel P30 desalting column. At pH 5 and in the presence of EDTA, oxidation of sulfhydryl groups to form disulfide linkages was prevented. The column was connected to an AKTA Prime Plus equipped with an OD280 nm detector, conductivity meter, and fraction collector. Protein fractions were collected and concentrated to 4.45 mg/ml. The sample was now ready for conjugation to the polymer. SDS-PAGE analysis showed that modification of IgG with Traut's reagent under these conditions did not result in protein aggregation.

Conjugation of the Traut's modified IgG to polymer was performed in 10 mM sodium acetate pH 5 with 20 fold polymer molar excess. The final concentration of IgG and polymer was 3.8 mg/ml and 44 mg/ml, respectively. The reaction was carried out at room temperature overnight. Upon completion of the reaction, the conjugation reaction was subjected to cation exchanger chromatography as described in Example 62 without modification. The eluted fraction pools at 8% B, 12% B, 20% B and 40% B were analyzed by SDS-PAGE and subjected to UV illumination. The results indicate that only the 8% B eluted fraction contained high MW species larger than the IgG monomer and the free polymer. In addition, the band stained with Coomassie blue and exhibited fluorescence, indicating presence of conjugate. Under reducing conditions, the band did not shift down again indicating the presence IgG-polymer conjugate as described in Examples 62 and 63.

Example 65

Preparation of 2-(Acryloyloxyethyl-2'-(trimethylammonium)ethyl phosphate, inner salt 1$^{st}$ Intermediate

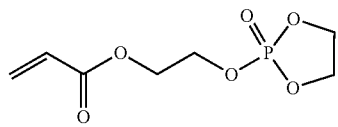

A solution of 11.6 grams of 2-hydroxyethylacrylate and 14.0 ml of triethylamine in 100 ml of dry acetonitrile, under a nitrogen atmosphere, was cooled to −20° C., and a solution of 14.2 grams of 2-chloro-2-oxo-1,3,2-dioxaphospholane in 10 ml of dry acetonitrile was added dropwise over about 30 minutes. The reaction was stirred in the cold for 30 minutes, then filtered under a nitrogen atmosphere. The precipitate was washed with 10 ml of cold acetonitrile, and the filtrate was used directly in the next reaction.

2-(Acryloyloxyethyl-2'-(trimethylammonium)ethyl phosphate, inner salt

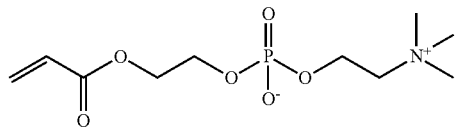 [SMILES: C=CC(=O)OCCOP(=O)([O-])OCC[N+](C)(C)C]

To the solution from the previous procedure was added 14.0 ml of trimethylamine (condensed using a dry ice-acetone condenser under nitrogen), the reaction mixture was sealed into a pressure vessel, and stirred at 65° C. for 4 hours. The reaction mixture was allowed to stir while cooling to room temperature, and as it reached about 30° C., a solid began to form. The vessel was then placed in a 4° C. refrigerator overnight. Strictly under a nitrogen atmosphere, the solid was recovered by filtration, washed with 20 ml of cold dry acetonitrile, then dried under a stream of nitrogen for 15 minutes. The solid was then dried under high vacuum overnight to give 12.4 grams of product as a white solid. NMR (CDCl$_3$): δ 6.41 (dd, 1H, J=1.6, 17.2 Hz, vinyl CH), 6.18 (dd, 1H, J=10.6, 17.2 Hz, vinyl CH), 5.90 (dd, 1H, J=1.6, 10.4 Hz, vinyl CH), 4.35 (m, 2H), 4.27 (m, 2H), 4.11 (m, 2H), 3.63 (m, 2H), 3.22 (s, 9H, N(CH$_3$)$_3$).

Example 66

Preparation of 3-Trimethylsilylpropargyl methacrylate

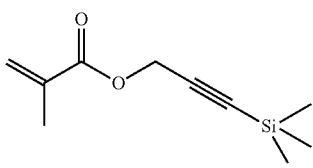

A solution of 3.0 grams of 3-(trimethylsilyl)propargyl alcohol and 4.2 ml of triethylamine in 50 ml of ether was cooled to −10° C. with a dry ice/acetonitrile/ethylene glycol bath, and a solution of 2.9 grams of methacryloyl chloride in 25 mL of ether were added dropwise over 30 minutes. The reaction mixture was stirred while warming to room temperature over 4 hours, then filtered and concentrated to give an oily residue, which subjected to flash column chromatography on silica gel with 1% ether in hexane. The product containing fractions were combined, concentrated, and subjected to a second chromatography as before to give 2.46 g of the product as a clear, colorless oil.

NMR(CDCl$_3$): δ 6.18 (t, 1H, CCH$_2$, J=1.2 Hz), 5.62 (p, 1H, CCH$_2$, J=1.6 Hz), 4.76 (s, 2H, CH$_2$), 1.97 (d of d, 3H, CCH$_3$, J=1.0, 1.6 Hz), 0.187 (s, 9H, Si(CH$_3$)$_3$).

Example 67

Preparation of N-Iodoacetylpropargylamine

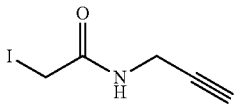

A solution of 1.05 grams of propargylamine hydrochloride in 20 ml of dry acetonitrile was treated with 4.0 ml of diisopropylethylamine, followed by the addition of 4.29 grams of iodoacetic anhydride in 20 ml of dry acetonitrile. The reaction was stirred at room temperature for 1.5 hours, then concentrated to give a residue, which was partitioned between 100 ml of ethyl acetate and 100 ml of water. The organic phase was washed with 50 ml of saturated sodium chloride, then dried over sodium sulfate. Concentration gave a dark solid, which was subjected to flash column chromatography on silica gel with 30-40% ethyl acetate in hexane. The product containing fractions which were clean were combined and concentrated to give a solid, which was triturated with a small amount of hexane and air-dried to give 940 mg of the product as a very light yellow solid. NMR(CDCl$_3$): δ 6.25 (s, 1H, CH), 4.08 (app d of d, 2H, NCH$_2$, J=2.6, 5.3), 3.72 (s, 2H, ICH$_2$), 2.28 (t, 1H, NH, J=2.6 Hz).

Example 68

Preparation of 4-Pentyn-1-ol, NHS ester

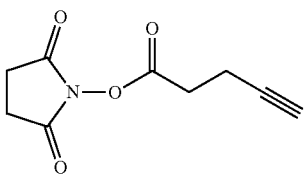

A solution of 1.02 grams of 4-pentynoic acid and 1.20 grams of N-hydroxysuccinimide in 20 ml of dry acetonitrile was treated with 300 mg of DPTS, followed by 2.8 grams of DCC, and the reaction was stirred at room temperature overnight. The reaction was filtered and concentrated to give a residue, which was subjected to flash column chromatography on silica gel with 30% ethyl acetate in hexane. The product containing fractions were combined and concentrated to give a 1.62 grams of the desired product as a white solid. NMR(CDCl$_3$): δ 2.89 (d of d, 2H, CH$_2$C=O, J=7.9, 6.4 Hz), 2.85 (s, 4H, O=CCH$_2$CH$_2$C=O), 2.62 (app d of d of d, 2H, CHCCH$_2$, J=8.6, 6.9, 2.7 Hz), 2.06 (t, 1H, CH, J=2.7 Hz).

Example 69

Preparation of N-Propargylmaleimide

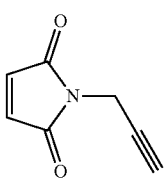

A solution of 1.08 grams of propargylamine hydrochloride in 50 ml of saturated sodium bicarbonate was cooled with an ice water bath, and 2.0 grams of N-carboethoxymaleimide were added portionwise over a few minutes. The reaction was stirred in the cold for 30 min., then while warming to room temperature over 25 min. The reaction was then extracted with 3×25 ml of dichloromethane, which was dried over sodium sulfate, filtered and concentrated. The residue was taken up in 10 ml of ethyl acetate and heated at 50° C. for two hours to complete the cyclization. The reaction was concentrated and the residue was which was subjected to flash column chromatography on silica gel with 30% ethyl acetate in hexane. A second chromatography as before gave 1.24 g of the product as a very light yellow oil. NMR(CDCl$_3$): δ 6.77 (s, 2H, CHC=O), 4.30 (d, 2H, NCH$_2$, J=2.4 Hz), 2.22 (t, 1H, CCH, J=2.5 Hz).

Example 70

Preparation of 5-Hexyn-1-al

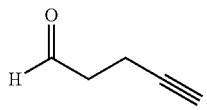

A solution of 694 mg of 5-hexyn-1-ol in 20 ml of dichloromethane was treated at room temperature with 3.0 grams of Dess-Martin periodinane, and the solution was stirred at room temperature for 2 hr. The reaction was filtered and the filtrate was concentrated to give a residue, which was subjected to flash column chromatography on silica gel with ethyl acetate in hexane. Concentration of the appropriate fractions gave the product as a very light yellow oil. NMR(CDCl$_3$): δ 9.81 (t, 1H, C$\underline{H}$=O, J=2.6 Hz), 2.61 (t of d, 2H, C$\underline{H_2}$CH=O, J=7.1, 1.2 Hz), 2.28 (t of d, 2H, CCH$_2$, J=7.1, 2.6 Hz), 1.99 (t, 1H, CC$\underline{H}$, J=2.6 Hz), 1.86 (p, 2H, CCH$_2$C$\underline{H_2}$, J=7.0 Hz).

Example 71

Conjugation of Recombinant Human Erythropoietin to Aldehyde Functionalized PC Polymer Containing Hexaglutamic Acid Recombinant human erythropoietin (R&D Systems) was buffer exchanged into 25 mM Hepes pH 7 (conjugation buffer) and concentrated to 5 mg/ml. Conjugation reactions were carried out at 3-5× molar excess of the aldehyde functionalized PC copolymer containing hexaglutamic acid from Example 60 to protein in the presence of 40 mM sodium cyanoborohydride with a final protein concentration of ~1 mg/ml. All the reactions were carried out in crimp sealed glass vials overnight at room temperature. The diol form of the polymer was used as a negative control. 40 µl of each reaction were fractionated on a Superdex 200 column (10/300 mm) at 1 ml/min. in 1×PBS pH 7.4. Fractions of 1 ml were collected and analyzed at OD220 nm and OD280 nm. As expected, no conjugation was observed when the diol functionalized polymer was used. However, in the case of the aldehyde functionalized polymer, the presence of erythropoietin-polymer conjugate was observed because the OD280 nm:OD220 nm ratio was much higher than for the free polymer alone in the 8-10 min. retention time range, where free polymer and higher molecular weight species elute. Free erythropoietin eluted in the 14-15 min. range.

Example 72

Preparation of 9-(Methacryloyloxy)-4,7-dioxanonanoic acid, 4-sulfo-2,3,5,6-tetrafluorophenyl ester, sodium salt

Preparation of 9-(Methacryloyloxy)-4,7-dioxanonanoic acid, t-butyl ester

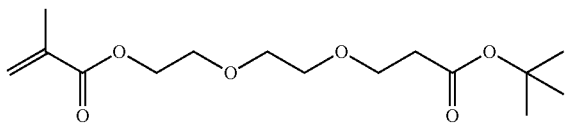 [SMILES: C=C(C)C(=O)OCCOCCOCCC(=O)OC(C)(C)C]

A solution of 5.0 grams of t-butyl 4,7-dioxa-9-hydroxynonanoate in 100 ml of ether, together with 5.9 ml (2 eq) of triethylamine, was cooled with an ice water bath, and a solution of 2.3 grams of methacryloyl chloride in 5 ml of ether was added dropwise over a few minutes. The reaction was stirred in the cold for 30 minutes, then allowed to warm to room temperature. By TLC (silica gel, 50% ethyl acetate in hexane) the reaction appeared to be incomplete, so another 1.0 g of methacryloyl chloride was added dropwise. After another 2 hours, the reaction appeared complete, so the reaction mixture was washed with 50 ml of water, then dried over sodium sulfate. Filtration and concentration gave an oily residue, which was subjected to flash column chromatography on silica gel with 20-30% ethyl acetate in hexane. The appropriate fractions were combined and concentrated to give 4.07 grams of the desired product as a clear, nearly colorless oil. NMR (CDCl$_3$): δ 6.13 (br m, 1H, C=C$\underline{H}$H), 5.57 (br app t, 1H, J=1.6 Hz, C=CH$\underline{H}$), 4.29 (app t, 2H, J=4.8 Hz, C=OOC$\underline{H_2}$), 3.70-3.76 (m, 4H), 3.61-3.67 (m, 4H), 2.50 (t, 2H, J=6.4 Hz, C=OC$\underline{H_2}$), 1.95 (app t, 3H, CH$_2$=CC$\underline{H_3}$), 1.45 (s, 9H, C(CH$_3$)$_3$).

Preparation of 9-(Methacryloyloxy)-4,7-dioxanonanoic acid

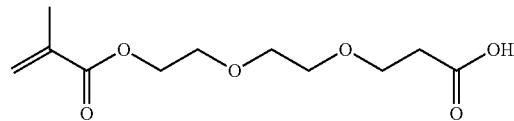 [SMILES: C=C(C)C(=O)OCCOCCOCCC(=O)O]

A solution of 3.70 grams of t-butyl 9-(methacryloyloxy)-4,7-dioxanonanoate in 15 ml of 88% formic acid was stirred at room temperature for 5 hours, at which time the reaction was complete by TLC (silica gel, 50% ethyl acetate in hexane). Concentration gave an oil, which was partitioned between 100 ml of dichloromethane and 50 ml of water, and the organic layer was dried over sodium sulfate. Filtration and concentration gave an oil, which was subjected to flash column chromatography on silica gel with 40% ethyl acetate in hexane. The appropriate fractions were combined and concentrated to give 2.01 grams of the desired product as a clear, colorless oil. NMR (CDCl$_3$): δ 6.14 (br m, 1H, C=C$\underline{H}$H), 5.58 (br app t, 1H, J=1.6 Hz, C=CH$\underline{H}$), 4.31 (app t, 2H, J=4.8 Hz, C=OOC$\underline{H_2}$), 3.73-3.80 (overlapping tm, 4H, J=6 Hz), 3.66 (m, 4H), 2.65 (t, 2H, J=6 Hz, C=OC$\underline{H_2}$), 1.95 (app t, 3H, CH$_2$=CC$\underline{H_3}$).

Preparation of 9-(Methacryloyloxy)-4,7-dioxanonanoic acid, 4-sulfo-2,3,5,6-tetrafluorophenyl ester, sodium salt

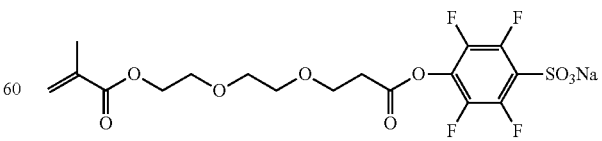

A mixture of 970 mg of 9-(methacryloyloxy)-4,7-dioxanonanoic acid and 1.06 grams of 4-sulfo-2,3,5,6-tetrafluorophenyl, sodium salt in 20 ml of dry acetonitrile was treated with 1.06 grams of DCC, and the reaction was stirred at room temperature for 1.5 hours. Filtration and concentration nearly to dryness gave a residue, which was subjected to flash column chromatography on silica gel with 5% methanol in dichloromethane. The appropriate fractions were combined and concentrated to give a solid, which was placed under high vacuum overnight to afford 783 mg of the desired product as a slightly sticky solid. NMR ($^1$H, CD$_3$OD): δ 6.10 (h, 1H, CR$_2$, J=0.9 Hz), 5.61 (p, 1H, CH$_2$, J=1.6 Hz), 4.27 (m, 2H, CH$_2$OC=O), 3.87 (t, 2H, CH$_2$CH$_2$C=O, J=6.0 Hz), 3.75 (m, 2H, CH$_2$CH$_2$OC=O), 3.67 (s, 4H, OCH$_2$CH$_2$O), 2.98 (t, 2H, CH$_2$C=O, J=6.0 Hz), 1.92 (d of d, 3H, CH$_3$, J=1.6, 0.9 Hz). NMR ($^{19}$F, CD$_3$OD): δ−140.92 (m, 2F, SCCF), 155.00 (m, 2F, OCCF).

Example 73

Preparation of (2-Mercaptoethyl)methacrylate, S-sulfate

Preparation of (2-Bromoethyl)methacrylate

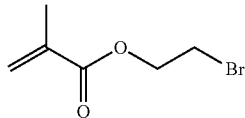

A solution of 6.25 grams of bromoethanol and 8.36 ml of triethylamine in 50 ml of dichloromethane was cooled with an ice water bath, and a solution of 5.0 grams of methacryloyl chloride in 5 ml of dichloromethane was added dropwise. The reaction was stirred at room temperature for 4 hours, then another 50 ml of dichloromethane were added and the reaction was washed with 2×25 mL of water, then with 25 ml of saturated sodium chloride. The organics were dried over sodium sulfate, filtered and concentrated to give an orange residue, which was subjected to flash column chromatography on silica gel with 10% ethyl acetate in hexane. The appropriate fractions were combined and concentrated to give 3.15 grams of the product as a clear oil, which was pure enough to use in the next reaction. NMR (CDCl$_3$): δ 6.18 (app p, 1H, J=1.1 Hz, C=CHH), 5.62 (p, 1H, C=CHH, J=1.6 Hz), 4.46 (t, 2H, J=6.0 Hz, CH$_2$OC=O), 3.56 (t, 2H, CH$_2$Br, J=6.0 Hz), 1.97 (dd, 3H, J=1.4, 1.1 Hz, CH$_3$C=C).

Preparation of (2-Mercaptoethyl)methacrylate, S-sulfate

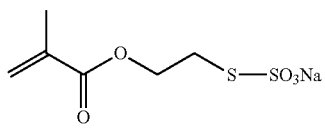

To a solution of 5.25 grams of sodium thiosulfate pentahydrate and 10 mg of hydroquinone in 45 ml of water and 30 ml of isopropanol was added 3.0 grams of (2-bromoethyl) methacrylate and the reaction was stirred at room temperature overnight. Concentration gave a residue, which was taken up in 20 ml of ethanol and 20 ml of methanol. Filtration and concentration gave a white solid, which was slurried with 45 ml of isopropanol. After stirring vigorously for 4 hours, the solid was recovered by filtration washed with a small amount of isopropanol and dried under high vacuum to give 940 mg of the desired product as a white solid. NMR (CD$_3$OD): δ 6.11 (h, 1H, CH$_2$, J=0.9 Hz), 5.62 (p, 1H, CH$_2$, J=1.6 Hz), 4.47 (t, 2H, OCH$_2$, J=6.9 Hz), 3.31 (t, 2H, SCH$_2$, J=6.9 Hz), 1.93 (d of d, 3H, CH$_3$, J=1.5, 1.0 Hz).

Example 74

Preparation of PC Copolymer Containing Trimethoxysilane Functional Groups

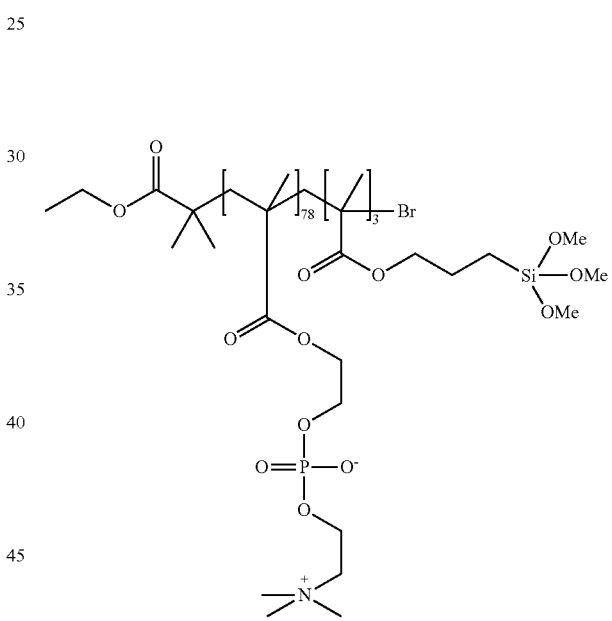

32.18 mg of 2,2'bipyridyl were placed in a Schlenk tube followed by 20.1 mg of the initiator ethyl α-bromo isobutyrate and dissolved in 160 mg of DMSO. The mixture was degassed under vacuum for 10 min. 14.78 mg of CuBr were added under inert conditions, and the reaction mixture was cooled to −78° C., degassed and refilled with inert gas. 1.033 g of HEMA-PC and 46 mg of 3-(trimethoxysilyl) propyl methacrylate were dissolved in 4 ml of 200 proof ethanol and added to the reaction mixture dropwise. The vessel was sealed and thoroughly degassed at −78° C. under vacuum until no bubbling was seen. The reaction mixture was placed under inert conditions and allowed to proceed at room temperature for 2 hours. Analysis by light scattering showed a Mp of 24 kDa, Mn of 22 kDa and PDi of 1.05.

Example 75

Preparation of PC Copolymer Containing Protected Thiol Functional Groups

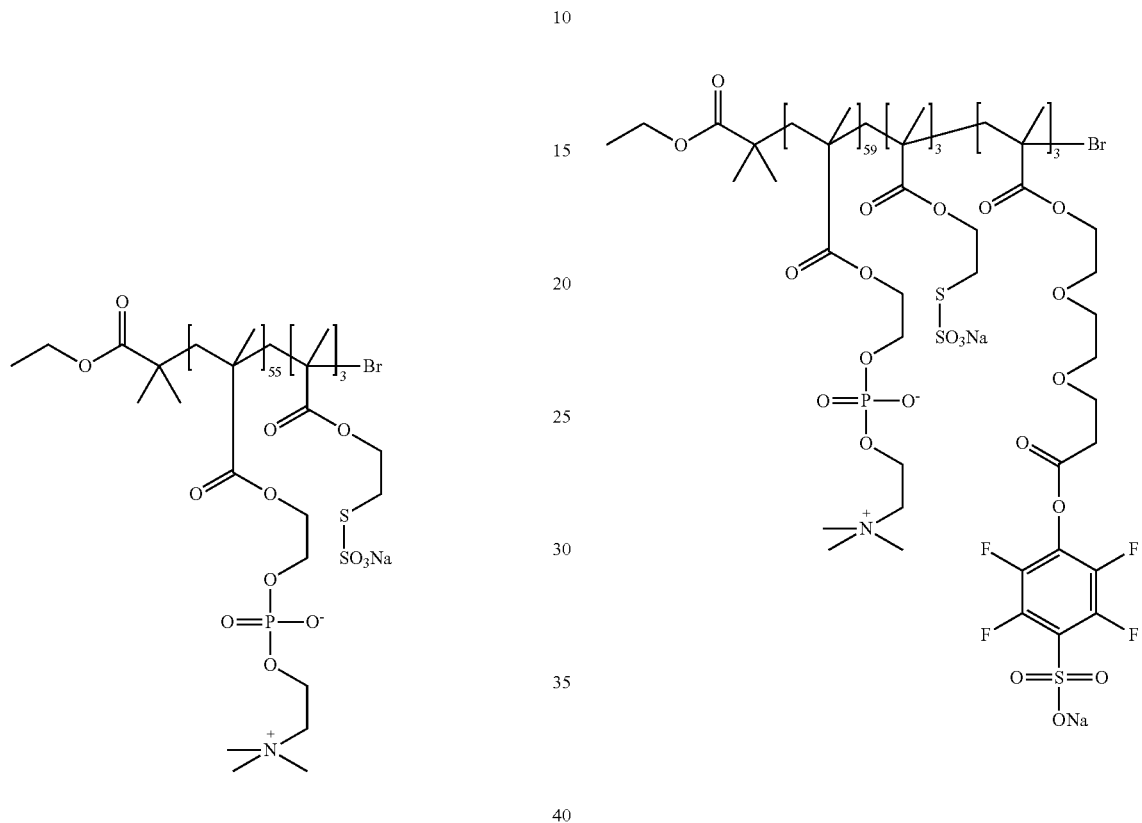

74.8 mg of 2,2'bipyridyl were placed in a Schlenk tube followed by 46.58 mg of the initiator ethyl α-bromo isobutyrate and dissolved in 520 mg of DMSO. The mixture was degassed under vacuum for 10 min. 34.26 mg of CuBr were added under inert conditions, and the reaction mixture was cooled to −78° C., degassed and refilled with inert gas. 1.601 g of HEMA-PC and 70.8 mg of S-Sulfo-(2-thioethyl)methacrylate, sodium salt (from Example 73) were dissolved in 6.2 ml of 200 proof ethanol and added to the reaction mixture dropwise. The vessel was sealed and thoroughly degassed at −78° C. under vacuum until no bubbling was seen. The reaction mixture was placed under inert conditions and allowed to proceed at room temperature for 3 hours. Analysis by light scattering showed a Mp of 17 kDa, Mn of 16 kDa and PDi of 1.05.

Example 76

Preparation of PC Copolymer Containing Protected Thiol Functional Groups and Tetrafluorophenol Ester Functional Groups 64 mg of 2,2'bipyridyl were placed in a Schlenk tube followed by 40 mg of the initiator ethyl α-bromo isobutyrate and dissolved in 300 mg of DMSO. The mixture was degassed under vacuum for 10 min. 29.4 mg of CuBr were added under inert conditions, and the reaction mixture was cooled to −78° C., degassed and refilled with inert gas. 1.8 g of HEMA-PC, 6.77×10-4 mol of S-Sulfo-(2-thioethyl)methacrylate, sodium salt (from Example 73), and 6.77×10-4 mol of 4,7-Dioxa-9-(methacryloyloxy)nonanoic acid, 4-sulfo,2,3,5,6-tetrafluorophenyl ester, sodium salt (from Example 72) were dissolved in 7.5 ml of 200 proof ethanol and added to the reaction mixture dropwise. The vessel was sealed and thoroughly degassed at −78° C. under vacuum until no bubbling was seen. The reaction mixture was placed under inert conditions and allowed to proceed at room temperature for 2 hours. Analysis by light scattering showed a Mp of 24 kDa, Mn of 25 kDa and PDi of 1.05.

Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A random copolymer comprising a first monomer and a second monomer, wherein the first monomer comprises a phosphorylcholine, and the second monomer is linked to a first functional agent, wherein the first and the second monomer are each independently selected from the group consisting of acrylates, methacrylates, acrylamides, methacrylamides, styrenes, vinyl-pyridine and vinyl-pyrrolidone, and are distributed randomly throughout the polymer, and the random copolymer has multiple polymer arms extending from a branched initiator fragment.

2. The random copolymer of claim 1, wherein the branched initiator fragment is linked to a second functional agent.

3. The random copolymer of claim 2, wherein the first functional agent is different from the second functional agent.

4. The random copolymer of claim 1, wherein the branched initiator fragment is selected from the group consisting of an alkane, a cycloalkane, an alkyl carboxylic acid, an ester of an alkyl carboxylic acid, a cycloalkylcarboxylic acid, an ester of a cycloalkylcarboxylic acid, an ether, a cyclic alkyl ether, an alkyl aryl group, an alkyl amide, an alkyl-aryl carboxylic acid, and an ester of an alkyl-aryl carboxylic acid.

5. The random copolymer of claim 1, wherein the first monomer comprises 2-(methacryloyloxy)ethyl (2-(trimethylammonio)ethyl) phosphate.

6. The random copolymer of claim 1, wherein the polymer has 2, 3, 4, 5, 6, 7, 8 or 9 polymer arms.

7. The random copolymer of claim 1, which comprises from about 100 to about 1,000 first monomers, and from about 100 to about 1,000 second monomers.

8. The random copolymer of claim 1, which comprises from about 10 to about 5,000 first monomers, and from about 10 to about 5,000 second monomers.

9. The random copolymer of claim 8, wherein the second monomers are present relative to the first monomers in a ratio of 100:1, 50:1, 40:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:40, 1:50 or 1:100.

10. The random copolymer of claim 8, which has a weight average molecular weight of from about 1000 to about 1,500,000 Daltons, as determined by a light scattering technique.

11. The random copolymer of claim 10, which has a polydispersity less than about 1.5, as determined by gel permeation chromatography.

12. The random copolymer of claim 1, wherein the second monomer is linked to the first functional agent through a cleavable linker.

13. The random copolymer of claim 12, wherein the cleavable linker is selected from the group consisting of a hydrolyzable linker, an enzymatically cleavable linker, a pH sensitive linker, a disulfide linker, and a photolabile linker.

14. The random copolymer of claim 1, wherein the second monomer is linked to the first functional agent through a non cleavable linker.

15. The random copolymer of claim 1, wherein the second monomer is linked to the first functional agent through the linker which comprises a triazole ring.

16. The random copolymer of claim 1, wherein the first functional agent is selected from the group consisting of a bioactive agent, a detection agent, an imaging agent, a labeling agent, and a diagnostic agent.

17. The random copolymer of claim 1, wherein the first functional agent is a bioactive agent.

18. The random copolymer of claim 17, wherein the bioactive agent is a therapeutic protein.

19. The random copolymer of claim 17, wherein the bioactive agent is an antibody or antibody fragment.

20. The random copolymer of claim 17, wherein the bioactive agent is a drug.

21. A method of making a random copolymer of claim 1, the method comprising the step of contacting a mixture of a first monomer and a second monomer with a branched initiator under conditions sufficient to prepare a multiple arms random copolymer via free radical polymerization, wherein the first monomer comprises a phosphorylcholine, and the second monomer is linked to a functional agent.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: synthetic hexaglutamic acid amide with
      9-azido-4,7-dioxanononanoic acid
<220> FEATURE:
<221> NAME/KEY: MOD_RES
<222> LOCATION: (6)...(6)
<223> OTHER INFORMATION: Glu modified by 9-azido-4,7-dioxanononanoic
      acid

<400> SEQUENCE: 1

Glu Glu Glu Glu Glu Glu
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic hexaglutamic acid, [Glu]-6

<400> SEQUENCE: 2

Glu Glu Glu Glu Glu Glu
1               5
```